US006843854B2

(12) United States Patent
Farrenburg et al.

(10) Patent No.: US 6,843,854 B2
(45) Date of Patent: Jan. 18, 2005

(54) METHOD AND APPARATUS FOR SEPARATING A COMPONENT FROM A MIXTURE

(75) Inventors: Chad Farrenburg, Sikeston, MO (US); Nien-Hwa Linda Wang, West Lafayette, IN (US); Yi Xie, West Lafayette, IN (US); Benjamin J. Hritzk, Groton, CT (US)

(73) Assignee: Purdue Research Foundation, West Lafayette, IN (US)

( * ) Notice: Subject to any disclaimer, the term of this patent is extended or adjusted under 35 U.S.C. 154(b) by 12 days.

(21) Appl. No.: 10/159,313

(22) Filed: May 31, 2002

(65) Prior Publication Data

US 2003/0229213 A1 Dec. 11, 2003

(51) Int. Cl.$^7$ .................................................. A23N 1/00
(52) U.S. Cl. ............................ 127/24; 536/7.2; 536/127
(58) Field of Search ....................... 127/24, 9; 536/7.2, 536/127

(56) References Cited

U.S. PATENT DOCUMENTS

| | | | |
|---|---|---|---|
| 3,291,726 | A | 12/1966 | Broughton |
| 4,331,803 | A | 5/1982 | Watanabe et al. |
| 4,668,776 | A | 5/1987 | Yamada et al. |
| 4,670,549 | A | 6/1987 | Morimoto et al. |
| 4,672,109 | A | 6/1987 | Watanabe et al. |
| 4,680,386 | A | 7/1987 | Morimoto et al. |
| 4,990,602 | A | 2/1991 | Morimoto et al. |
| 5,274,085 | A | 12/1993 | Amano et al. |
| 6,284,200 | B1 | 9/2001 | Hotier |
| 6,306,306 | B1 | 10/2001 | Voigt et al. |

FOREIGN PATENT DOCUMENTS

WO    WO 00/71539 A1    11/2000

OTHER PUBLICATIONS

Z. Ma, R. D. Whitley, and N.–H. L. Wang. Pore and Surface Diffusion in Multicomponent Adsorption and Liquid Chromatography Systems. *AIChE J.*, 42: 1244–1262, 1996.
T. Mallmann, B. D.Burris, Z. Ma, and N.–H. L. Wang. "Standing Wave Design of Nonlinear SMB Systems for Fructose Purification", *AIChE J.*, 44:2628–2646, 1998.
M. Mazzotti, R. Baciocchi, G. Storti, and M. Morbidelli. "Vapor–Phase SMB Adsorptive Separation of Linear /Nonlinear Paraffins". *Ind. Eng. Chem. Res.*, 35:2313–2321, 1996.
M. Mazzotti, G. Storti, and M. Morbidelli. "Robust Design of Countercurrent Adsorption Separation Processes: 2. Multicomponent Systems". *AIChE J.*, 40:1825–1842, 1994.
M. Mazzotti, G. Storti, and M. Morbidelli. "Robust Design of Countercurrent Adsorption Separation: 3. Nonstoichiometric Systems". *AIChE J.*, 42:2784–2796, 1996.
M. Mazzotti, G. Storti, and M. Morbidelli. "Robust Design of Countercurrent Adsorption Separation Processes: 4. Desorbent in the Feed". *AIChE J.*, 43:64–72, 1997.

H.–K. Rhee, R. Aris, and N. R. Amundson. "Multicomponent Adsorption in Continuous Countercurrent Exchangers". *Phil. Trans. Roy. Soc. London A*, 269:187–215, 1971.
G. Storti, R. Baciocchi, M. Mazzotti, and M. Morbidelli. "Design of Optimal Operating Conditions of Simulated Moving Bed Adsorptive Separation Units". *Ind. Eng. Chem. Res.*, 34:288–301, 1995.
G. Storti, M. Masi, S. Carra, and M. Morbidelli. "Optimal Design of Multicomponent Countercurrent Adsorption Separation Processes Involving Nonlinear Equilibria". *Chem Eng. Sci.*, 44:1329–1345, 1989.
G. Storti, M. Mazzotti, M. Morbidelli, and S. Carra. "Robust Design of Binary Countercurrent Adsorption Separation Processes". *AIChE J.*, 39:471–492, 1993.
D.–J. Wu, Z. Ma, B. W. Au, and N.–H. L. Wang. "Recovery and Purification of Paclitaxol Using Low Pressure Chromatography". *AIChE J.*, 43:232–242, 1997.
T. Yun, G. Zhong, and G. Guiochon. "Experimental Study of the Influence of the Flow Rates in SMB Chromatography". *AIChE J.*, 43:2970–2983, 1997.
G. Zhong and G. Guiochon. "Analytical Solution for the Linear Ideal Model of Simulated Moving Bed Chromatography". *Chem. Eng. Sci.*, 51:4307–4319, 1996.
J. A. Berninger, R. D. Whitley, and N.–H. L. Wang. "A Versatile Model for Simulation of Reaction and Non–Equilibrium Dynamics in Multi–Component Fixed–Bed Adsorption Processes". *Comp. Chem. Eng.*, 15:749–768, 1991.
A. S. T. Chiang. "Complete Separation Conditions for a Local Equilibrium TCC Adsorption Unit". *AIChE J.*, 44:332–340, 1998.
A. S. T. Chiang. "Continuous Chromatographic Process Based on SMB Technology". *AIChE J.*, 44:1930–1932, 1998.

(List continued on next page.)

*Primary Examiner*—Elli Peselev
(74) *Attorney, Agent, or Firm*—Bose McKinney & Evans LLP

(57) ABSTRACT

The present invention comprises the optimization of a four zone simulated moving bed system configured to separate a first component from a mixture containing the first component and a second component wherein the first component exhibits non-linear adsorption and non-negligible mass transfer resistances. In one example, the four zone simulated moving bed is optimized to separate Clarithromycin from a mixture containing Clarithromycin and 6,11-O-methyl erythromycin A. The present invention further comprises a four zone or a five zone apparatus having a first portion and a second portion and the optimization of the four zone or five zone apparatus to separate a first component from a mixture containing the first component and a second component and the method of using the same. In one example, the four zone and five zone simulated moving beds are optimized to separate Clarithromycin from a mixture containing Clarithromycin and 6,11-O-methyl erythromycin A. The present invention further comprises a batch elution system configured to separate Clarithromycin from a mixture containing Clarithromycin and 6,11-O-methyl erythromycin A.

20 Claims, 71 Drawing Sheets

OTHER PUBLICATIONS

C. B. Ching and D. M. Ruthven. "Analysis of th Performance of a Simulated Countercurrent Chromatographic System from Fructose–Glucose Separation". *Can J. Chem. Eng.*, 62:399–403, 1984.

S. F. Chung and C. Y. Wen. "Longitudinal Dispersion of Liquid Flowing Through Fixed and Fluidized Beds", *AIChE J.*, 14:857–866, 1968.

M. V. Ernest Jr., J. P. Bibler, R. D. Whitley, and N.–H. L. Wang. "Development of a Carousel Ion Exchanger Process for Removal of Cesium–137 from Alkaline Nuclear Waste". *Ind. Eng. Chem. Res.*, 36:2775–2788, 1997.

E. Francotte, P. Richert, M. Mazzotti, and M. Morbidelli. "Simulated Moving Bed Chromatographic Resolution of a Chiral Antitussive". *J. Chromatogr. A*, 796:239–248, 1998.

C. R. Wilke and Pin Chang. "Correlation of Diffusion Coefficients in Dilute Solutions". *AIChE J.*, pp. 264–270, 1955.

Z. Ma and N.–H. L. Wang. "Standing Wave Analysis of SMB Chromotagraphy: Linear Systems". *AIChE J.*, 43:2488–2508, 1997.

Z. Ma, A. Katti, B. Lin, and G. Guiochon. "Simple Wave Effects in Two–Component Nonlinear Liquid Chromatography. Application to the Measurement of Competitve Adsorption Isotherms". *J. Phy. Chem.*, 94:6911–6922, 1990.

Xie, Y, B. Hritizko, C. Farrenburg, and N.–H. L. Wang. "Comparison of Standing Wave Analysis with the Triangle Theory for the Design of Simulated Moving Bed Processes" http://www.aiche.org/conferences/techprogram/paperdetail.asp?PapaerID=3556&DSN=annual101, pp.1–3, Nov. 8, 2001.

J. S. Mackie and P. Meares. "The Diffusion of Electrolytes in a Cation–Exchange Resin Membrane". Proc. Roy. Soc. London, Ser. A., 232:498–509, 1955.

H.–K. Rhee, R. Aris, and N. R. Amundson. "On the Theory of Multicomponent Chromatography". *Phil. Trans. Roy. Soc. London A*, 267:419–455, 1970.

J.–H. Koh, P. C. Wankat, and N.–H. L. Wang. "Pore and Surface Diffusion and Bulk–Phase Mass Transfer in Packed and Fluidized Beds". *Ind. Eng. Chem. Res.*, 37:228–239, 1998.

E. J. D. Lee, C. B. Ching, B. G. Lim, and S. C. Ng. "Preparative Resolution of Praziquantal by Simulated Counter–Current Chromatography". *J. Chromatography*, 624:215–219, 1993.

R. D. Whitely. *Dynamics of Nonlinear Multi–component Chromatography—Interplay of Mass Transfer, Intrisic Sorption Kinetics, and Reaction*. PhD Thesis, Purdue University, 1990.

E. J. Wilson and C. J. Geankoplis. "Liquid Mass Transfer at Very Low Reynolds Numbers in Packed Beds". *Ind. Eng. Chem. Fund*, 5:9–14, 1966.

G. Zhong, M. S. Smith, and G. Guichon. "Effect of the Flow Rates in Linear, Ideal, Simulated Moving–Bed Chromatography". *AIChE J.*, 43: 2960–2969, 1997.

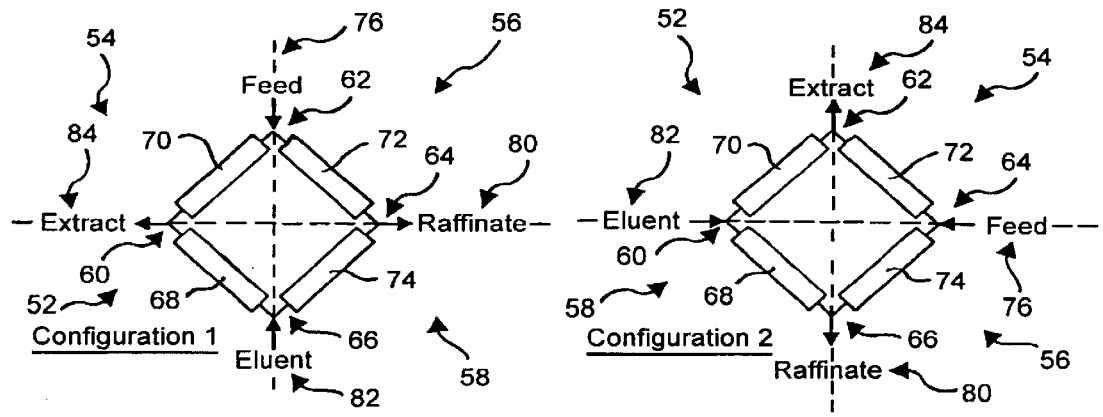
FIG. 3a
(PRIOR ART)
FIG. 3b
(PRIOR ART)
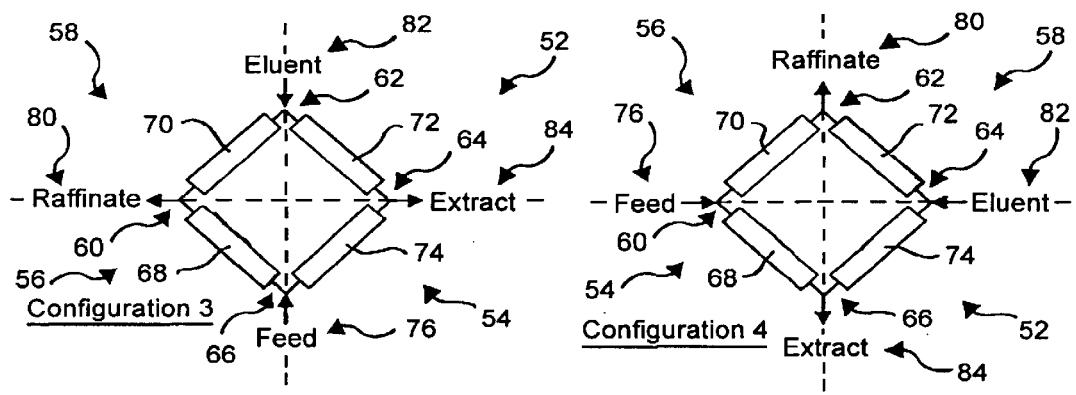
FIG. 3c
(PRIOR ART)
FIG. 3d
(PRIOR ART)

Column profiles for optimal design of small particle, eight-column system.

Position 1

Position 2

Position 3

Position 4

Position 5

Position 6

Position 7

Position 8

Position 9

Raffinate profile from 80% methanol/Dow L-323 gradient SMB experiment #4. Lines show simulation of original design.

ME THOD AND APPARATUS FOR
SEPARATING A COMPONENT FROM A
MIXTURE

FIELD OF THE INVENTION

The present invention relates to methods for separating a component from a mixture, in particular for separating a component from a mixture wherein the component and at least one other component of the mixture have similar chemical structures or adsorption properties, such as separating from a mixture a first component of 6-O-methyl erythromycin A (Clarithromycin) from a second component of 6,11-O-methyl erythromycin A.

BACKGROUND OF THE INVENTION

One method of separating chemical compounds is chromatography wherein the compounds are separated based upon their different adsorption properties. However, chemical compounds, which have similar chemical structures, are difficult to separate with chromatography due to their similar properties such as adsorption. One example of this is exhibited in the difficulty in purifying a viable product, 6-O-methyl erythromycin A (Clarithromycin) from the impurity, 6,11-O-methyl erythromycin A. Clarithromycin is an effective antibiotic obtained by the chemical methylation of erythromycin, a naturally occurring antibiotic.

U.S. Pat. No. 4,990,602 to Morimoto et al. discloses the preferred commercial method for producing Clarithromycin by the chemical methylation of erythromycin. The methylation process used to produce Clarithromycin produces several by-products. A major by-product is 6,11-O-methyl erythromycin A (6, 11) which differs from Clarithromycin by the addition of an extra methyl group at the #11 carbon atom. The similar chemical structure between Clarithromycin and 6,11 increases the difficulty in separating the product, Clarithromycin and the by-product, 6,11. Therefore, in order to produce a high purity of Clarithromycin, a significant portion of Clarithromycin is left behind with the 6,11 resulting in a loss of Clarithromycin yield. Approximately seven percent of Clarithromycin is left behind in a mixture from the commercial process with the 6,11.

The mixture of Clarithromycin and 6,11 may be recovered in a nearly one-to-one solid mixture of Clarithromycin and 6,11. This solid mixture may contain up to 23% other impurities. These additional impurities are easily separated from Clarithromycin by crystallization.

Additional methods for the production of Clarithromycin are disclosed in U.S. Pat. No. 4,331,803 to Watanabe et al; U.S. Pat. No. 4,668,776 to Yamada et al.; U.S. Pat. No. 4,670,549 to Morimoto et al.; U.S. Pat. No. 4,672,109 to Watanabe et al.; U.S. Pat. No. 4,680,386 to Morimoto et al.; and U.S. Pat. No. 5,274,085 Amano et al.

A need exists for a method and apparatus to recover a high purity of Clarithromycin from the mixture of Clarithromycin and 6,11 left over from the commercial process in order to increase overall product yield of Clarithromycin.

SUMMARY OF THE INVENTION

The present invention relates to the separation of a first component from a second component given a mixture of the two.

In a first exemplary embodiment an apparatus for separating a first component from a mixture containing the first component and a second component comprises at least one column packed with a stationary phase having a greater affinity for the second component. The at least one column further comprising a first and second inlet coupled to the column and a first and second outlet coupled to the column. The at least one column being separated into a first portion and a second portion wherein the first portion includes a first and a second zone connected together in series and the second portion includes at least a third zone and a fourth zone connected together in series. The apparatus further comprises a first pump coupled to the first inlet and configured to provide the mixture to the second portion and a second pump coupled to the second inlet and configured to provide at least one solution to the first portion to remove the second component from the stationary phase. The apparatus further comprising a processor configured to control the flow rates of the first pump, the second pump, and the zones within the first portion and the second portion to facilitate the separation of the first component and the second component so that the first component exits the first outlet which is coupled to the second portion and the second component exits the second outlet which is coupled to the first portion.

In one variation of the first exemplary embodiment the second portion includes a fifth zone and the apparatus comprises at least five columns, a first column located in the first zone, a second column located in the second zone, a third column located in the third zone, a fourth column located in the fourth zone and a fifth column located in the fifth zone.

In another variation of the first exemplary embodiment the first inlet is coupled to the fourth column located in the fourth zone, the second inlet is coupled to the second column located in the second zone, the first outlet is coupled to the fourth column located in the fourth zone, and the second outlet is coupled to the second column located in the second zone.

In yet another variation of the first exemplary embodiment the processor after a first predetermined switching interval changes of the position of each column so that the first column is located in the fifth zone, the second column is located in the first zone, the third column is located in the second zone, the fourth column is located in the third zone, and the fifth column is located in the fourth zone and wherein the first inlet is coupled to the fifth column located in the fourth zone, the second inlet is coupled to the third column located in the second zone, the first outlet is coupled to the fifth column located in the fourth zone, and the second outlet is coupled to the third column located in the second zone. After a second predetermined switching interval the processor changes of the position of each column so that the first column is located in the fourth zone, the second column is located in the fifth zone, the third column is located in the first zone, the fourth column is located in the second zone, and the fifth column is located in the third zone and wherein the first inlet is coupled to the first column located in the fourth zone, the second inlet is coupled to the fourth column located in the second zone, the first outlet is coupled to the first column located in the fourth zone, and the second outlet is coupled to the fourth column located in the second zone.

In still another variation of the first exemplary embodiment and the foregoing variations, the first component and the second component exhibit non-linear adsorption isotherms and non-negligible mass transfer resistances, such as when the first component is Clarithromycin and the second component is 6,11-O-methyl erythromycin A.

In a first exemplary method of the present invention for separating a first component from a mixture including at least the first component and a second component an apparatus is provided. The apparatus including at least one column packed with a stationary phase and having a first portion and a second portion, the first portion including a first and a second zone connected together in series and the second portion including a third zone, a fourth zone, and a fifth zone connected together in series. The method further comprises feeding the mixture into the second portion of the apparatus and optimizing a flow rate for each of the zone of the second portion and a switching time to facilitate the separation of the first component and the second component. The method further comprises collecting the first component from an outlet of the second portion of the apparatus and treating the first portion of the apparatus to remove the second component from the apparatus.

In one variation of the first exemplary method the first component and the second component exhibit non-linear adsorption isotherms and non-negligible mass transfer resistances. In a further variation the first component is Clarithromycin and the second component is 6,11-O-methyl erythromycin A.

In another variation of the first exemplary method, the method further comprises the step of controlling the zone flow rates and switching time. In yet another variation of the first exemplary method, the method further comprises the steps of monitoring the outlet of the second portion and controlling the zone flow rates and switching time based at least on the monitoring of the outlet of the second portion. The zone flow rates and switching time, in one example, are controlled by a feedback system.

In a second exemplary method of the present invention for separating a first component from a mixture including at least the first component and a second component, wherein the first and second component having non-linear adsorption properties and non-negligible mass transfer resistances a simulated moving bed apparatus is provided. The simulated moving bed apparatus including at least one column packed with an adsorbent and having four zones, a first zone, a second zone, a third zone, and a fourth zone, a first inlet positioned between a first pair of the four zones and configured to receive the mixture, a first outlet positioned between a second pair of the four zones and configured to pass a solution predominately including the first component, and a second outlet positioned between a third pair of the four zones and configured to pass a solution predominately including the second component. The second exemplary method further comprising feeding the mixture into the simulated moving bed at a predetermined flow rate in the first inlet and optimizing a flow rate for each of the four zones and a switching time. The flow rates for each zone and switching time being optimized by the following relationships wherein $u_o^I$ is the flow rate for the first zone, $u_o^{II}$ is the flow rate for the second zone, $u_o^{III}$ is the flow rate of the third zone, and $u_o^{IV}$ is the flow rate of the fourth zone:

$$u_0^I = (1 + P\delta'^I)v + \beta_2^I \left( \frac{E_{b_2}^I}{L^I} + \frac{Pv^2(\delta'^I)^2}{K_{f_2}^I L^I} \right)$$

$$u_0^{II} = (1 + P\delta'^{II})v + \beta_1^{II} \left( \frac{E_{b_1}^{II}}{L^{II}} + \frac{Pv^2(\delta'^{II})^2}{K_{f_1}^{II} L^{II}} \right)$$

$$u_0^{III} = (1 + P\delta'^{III})v - \beta_2^{III} \left( \frac{E_{b_2}^{III}}{L^{III}} + \frac{Pv^2(\delta'^{III})^2}{K_{f_2}^{III} L^{III}} \right)$$

-continued $$u_0^{IV} = (1 + P\delta'^{IV})v - \beta_1^{IV} \left( \frac{E_{b_1}^{IV}}{L^{IV}} + \frac{Pv^2(\delta'^{IV})^2}{K_{f_1}^{IV} L^{IV}} \right); \text{ and}$$

$$u_0^{III} - u_0^{II} = \frac{F^{feed}}{S\varepsilon_b}$$

wherein $F^{feed}$ corresponds to the flow rate of the mixture into the simulated moving bed, S corresponds to the cross-sectional area of the column and $\varepsilon_b$ corresponds to the interparticle porosity of the adsorbent. The method further comprising controlling the zone flow rates and switching time.

In one variation of the second exemplary method, the first component is Clarithromycin and the second component is 6,11-O-methyl erythromycin A. In another variation of the second exemplary method, the method further comprises the steps of monitoring the at least one of the first and second outlets and controlling the zone flow rates and switching time based on at least the monitoring of the at least one of the first and second outlets. In a further variation the zone flow rates and switching time are controlled by a processor.

In a third exemplary method of the present invention a method is provided for separating Clarithromycin from 6,11-O-methyl erythromycin A, comprising the steps of preparing a mixture of the Clarithromycin and 6,11-O-methyl erythromycin A in a mobile phase containing at least one organic solvent and of providing a batch elution system having at least one column, a first inlet and a first outlet. The at least one column of the batch elution system being packed with a stationary phase having a higher affinity for the 6,11-O-methyl erythromycin A than the Clarithromycin. The method further comprises the steps of introducing the mixture into the batch elution system through the first inlet and retrieving the Clarithromycin from the batch elution system at the first outlet.

In one variation of the third exemplary embodiment the organic solvent is selected from the group consisting of: methanol, ethanol and isopropyl alcohol. In another variation, the stationary phase is selected from the group consisting of: Dow Optipore L-323, Amberlite XAD-16 and Macronet-200. In a yet another variation, the mobile phase includes about 75 percent by volume to about 85 percent by volume of methanol and the stationary phase is Dow Optipore L-323.

In a fourth exemplary method of the present invention a method is provided for separating Clarithromycin from 6,11-O-methyl erythromycin A, comprising the steps of preparing a mixture of the Clarithromycin and 6,11-O-methyl erythromycin A in a mobile phase containing at least one organic solvent and providing a four zone simulated moving bed system having at least one column, a first inlet and a first outlet. The at least one column being packed with a stationary phase having a higher affinity for the 6,11-O-methyl erythromycin A than the Clarithromycin. The method further comprises the steps of introducing the mixture into the four zone simulated moving bed system through the first inlet and retrieving the Clarithromycin from the four zone simulated moving bed system at the first outlet.

In one variation of the fourth exemplary method, the organic solvent is selected from the group consisting of: methanol, ethanol and isopropyl alcohol. In another variation, the stationary phase is selected from the group consisting of: Dow Optipore L-323, Amberlite XAD-16 and Macronet-200. In yet another variation, the mobile phase includes about 75 percent by volume to about 85 percent by volume of methanol and the stationary phase is Dow Optipore L-323.

In a fifth exemplary method of the present invention, a method is provided for separating Clarithromycin from 6,11-O-methyl erythromycin A, comprising the steps of preparing a mixture of the Clarithromycin and 6,11-O-methyl erythromycin A in a mobile phase containing at least one organic solvent and providing a five zone simulated moving bed system having at least one column, a first inlet and a first outlet. The at least one column being packed with a stationary phase having a higher affinity for the 6,11-O-methyl erythromycin A than the Clarithromycin. The method further comprises the steps of introducing the mixture into the five zone simulated moving bed system through the first inlet and retrieving the Clarithromycin from the five zone simulated moving bed system at the first outlet.

In one variation of fifth exemplary method of the present invention, the organic solvent is selected from the group consisting of: methanol, ethanol and isopropyl alcohol. In another variation, the stationary phase is selected from the group consisting of: Dow Optipore L-323, Amberlite XAD-16 and Macronet-200. In yet another variation, the mobile phase includes about 75 percent by volume to about 85 percent by volume of methanol and the stationary phase is Dow Optipore L-323.

Additional objects, features and advantages of the invention will become apparent to those skilled in the art upon consideration of the following detailed descriptions of exemplary embodiments exemplifying the best mode of carrying out the invention presently perceived.

BRIEF DESCRIPTION OF THE DRAWINGS

FIG. 3a is the simulated moving bed of FIG. 2 in a first configuration;

FIG. 3b is the simulated moving bed of FIG. 2 in a second configuration;

FIG. 3c is the simulated moving bed of FIG. 2 in a third configuration;

FIG. 3d is the simulated moving bed of FIG. 2 in a fourth configuration;

DETAILED DESCRIPTION

The present invention is related to the separation of a first component from a mixture including the first component and a second component. In a first embodiment of the present invention, a novel method for utilizing a four zone simulated moving bed system is provided to separate a first component and a second component wherein the first and second components each exhibit non-linear adsorption isotherms and exhibit non-negligible mass transfer resistances. In a first example, the four zone simulated moving bed of the first embodiment is used to separate Clarithromycin from 6,11-O-methyl erythromycin (6,11). However, it will be apparent to those skilled in the art that the first embodiment of the present invention can be used to separate a variety of solutes, wherein the solutes exhibit non-linear adsorption isotherms and non-negligible mass transfer resistances.

In a second embodiment of the present invention, a novel five zone simulated moving bed and method of utilizing the same is provided to separate a first component from a mixture including the first component and the second component. As explained in more detail in connection with FIGS. 26–49 below, the five zone simulated moving bed consists of a first portion including a two zone carousel process and a second portion including three zones. In one variation the second portion is a 3-zone simulated moving bed ring. The two zone carousel process replaces one of the four zones of the four zone simulated moving bed. The two zone carousel reduces the amount of solvent that is consumed during a separation procedure. In one variation of the second embodiment, a novel four zone simulated moving bed having a first portion and a second portion and method of utilizing the same is provided to separate a first component from a mixture. The five zone simulated moving bed and four zone simulated moving bed are capable of separating a variety of components including components exhibiting linear adsorption isotherms and negligible mass transfer resistances, exhibiting linear adsorption isotherms and non-negligible mass transfer resistances, exhibiting non-linear adsorption isotherms and negligible mass transfer resistances, and exhibiting non-linear adsorption isotherms and non-negligible mass transfer resistances. In a first example, five zone simulated moving bed or four zone simulated moving bed of the second embodiment is used to separate Clarithromycin from 6,11-O-methyl erythromycin (6,11). However, it will be apparent to those skilled in the art that the five zone simulated moving bed can be used for the separation of a first component from a mixture including at least the first component and a second component when adsorption properties of the first component and the second component are similar.

In a third embodiment of the present invention, a novel method of utilizing a batch elution system to separate Clarithromycin and 6,11.

Figure 1:
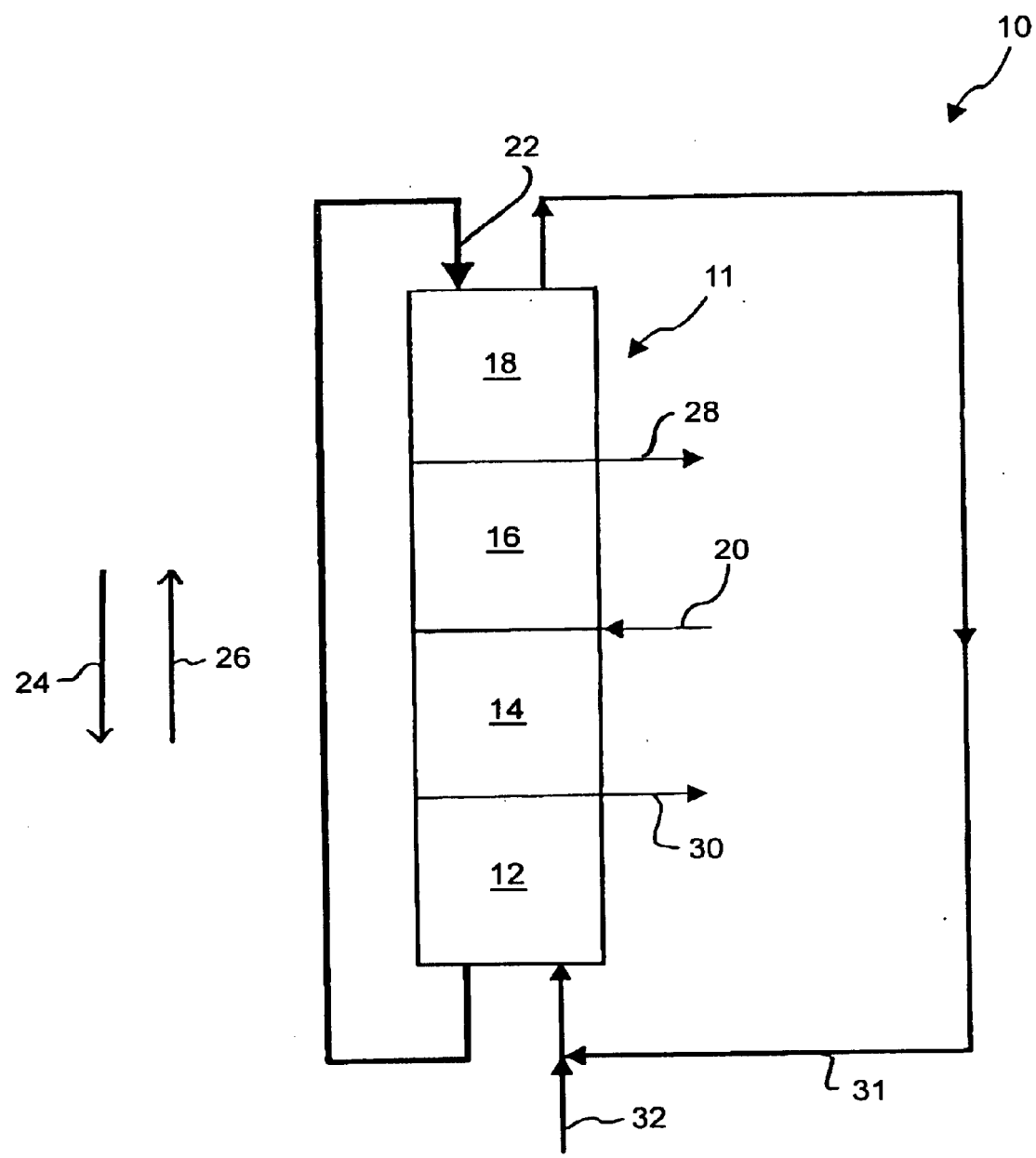
FIG. 1 is a diagrammatic representation of a conventional continuous moving bed chromatography system.

Conventional simulated moving bed systems are similar to continuous moving bed chromatography (CMB) systems in respect to the theory of operation. An example CMB system 10 is shown in FIG. 1. CMB system 10 has a column 11 that contains four zones 12, 14, 16 and 18 divided by inlet and outlet ports. Column 11 can be a single column or multiple columns. A feed 20 consisting of a mixture including at least a first component and a second component and a carrier fluid or mobile phase is continuously fed into CMB 10 between zones 14 and 16. An adsorbent 22 is fed into CMB 10 at zone 18 as a recycle from zone 12.

CMB 10 uses countercurrent movement of the mobile phase and adsorbent 22 to separate the first component and the second component. Adsorbent 22 flows in a direction 24 through CMB 10 while the fluid flow from feed 20 flows in a direction 26, opposite to direction 24. If the flow of adsorbent 22 in direction 24 is ignored then both the first component and the second component would flow in direction 26 through zones 16 and 18, exiting zone 18 and re-entering CMB 10 at zone 12 through connection 31.

However, the relative adsorption properties and migration velocities of the first component and the second component when exposed to adsorbent 22 allow for CMB 10 to move the first component and the second component in different directions through CMB 10. By choosing appropriate values for the flow rates of adsorbent 22 and feed 20, the first component and the second component are separated. The component of either the first component or the second component whose movement is less slowed by adsorbent 22, the less retained component, moves in direction 26 with the feed flow while the component whose flow is more slowed by adsorbent 22, the more retained component, moves in direction 24 with the adsorbent 22.

The less retained of either the first component or the second component is removed at an outlet port 28, known as the Raffinate, between zones 16 and 18. The fluid velocity in zone 18 is reduced relative to the fluid velocity in zone 16 enough as to cause the less retained solute to move downward in zone 18 and to be removed at Raffinate 28. The more retained of either the first component or the second component is removed at an outlet port 30, known as the Extract, between zones 12 and 14. The fluid velocity in zone 12 is increased relative to the fluid velocity of zone 14 enough to cause the more retained solute to move upward in zone 12 and to be removed at Extract 30. Additional mobile phase is added at the inlet port 32, the Mobile Phase, between zones 12 and 18 to make up the difference in the flow rates of zones 12 and 18.

CMB systems like CMB 10 are very difficult to implement because of the requirement that adsorbent 22 is mobile. Simulated moving bed chromatography (SMB) was developed to mimic the operation of CMB system without the requirement that the adsorbent be mobile. In a SMB, a series of packed columns are used as opposed to the mobile adsorbent of CMB. The movement of the adsorbent in the SMB is simulated by periodically changing the positions of the inlet and outlet ports for the Feed, the Extract, the Raffinate, and the Mobile Phase in relation to packed columns or portions of columns.

Figure 2:
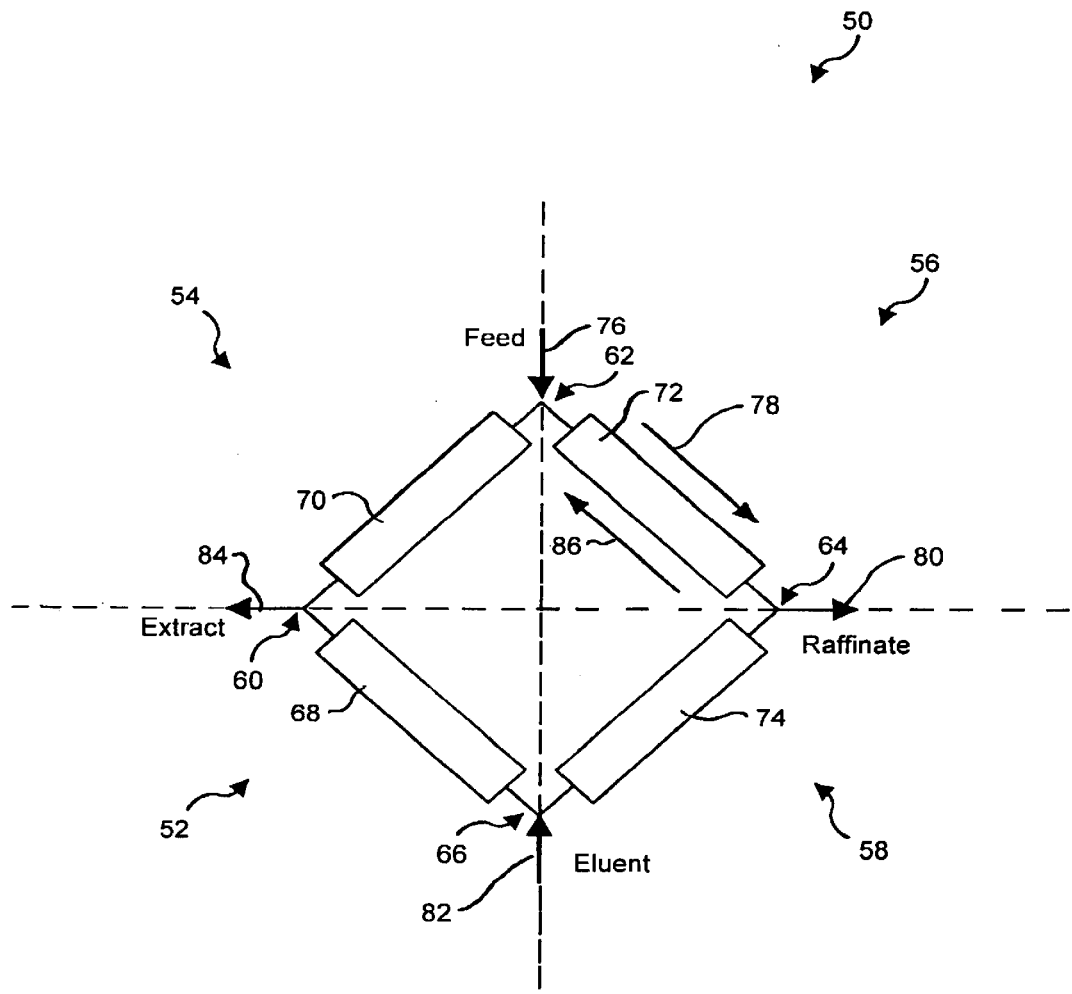
FIG. 2 is a diagrammatic representation of a conventional simulated moving bed system having four zones, each zone having at least one column.

A conventional SMB system 50 is shown in FIG. 2. SMB system 50 consists of four zones 52, 54, 56, and 58 divided by a series of ports 60, 62, 64, and 66 having both an inlet and an outlet. Between ports 60, 62, 64, and 66 is one or more packed columns. Alternatively, the ports are positioned at distribution plates within the column. The packed columns are packed with a stationary phase, such as an adsorbent which has a greater affinity for either the first component or the second component of the feed mixture. The movement of the stationary phase in a SMB is simulated by switching the location of the inlets and the outlets at designated switching times.

An example SMB system has four columns, one column per zone. Referring to FIG. 2, zones 52, 54, 56 and 58 are shown with one column each, columns 68, 70, 72, and 74, respectively. It is to be understood that SMB 50 can include a fewer or greater number of columns. The function of each port 62, 64, 66, and 68 varies depending upon the configuration of SMB 50. All ports 62, 64, 66, and 68 include at least one inlet and at least one outlet.

FIG. 2 shows a first configuration of SMB 50. A feed 76 containing a mixture including the first component and the second component enters SMB 50 through an inlet at port 62 between zones 54 and 56. Feed 76 flows in a clockwise direction 78 into zone 56. The less retained component of either the first component or the second component is removed through Raffinate 80 which is connected to an outlet of port 64 in the first configuration. A Mobile Phase 82 is added through an inlet at port 66. Mobile Phase 82 provides additional mobile phase to SMB 50 to make up the difference in flows between zones 52 and 58. The more retained component of either the first component or the second component is removed through an Extract 84, which is connected to an outlet of port 60, between zones 52 and 54.

While SMB 50 is in the first configuration Feed 76 and flow from zone 54 combine and flow into zone 56. Flow from zone 56 splits into Raffinate 80 and flow into zone 58. Flow from zone 58 and Mobile Phase 82 combine and flow into zone 52. Flow from zone 52 splits into Extract 84 and flow into zone 54.

As explained above, the movement of the stationary phase in SMB 50 is simulated by periodically switching the inlet ports to which Feed 76 and Mobile Phase 82 are connected and changing the outlet ports to which Raffinate 80 and Extract 84 are connected in relation to columns 68, 70, 72, 74. Referring to FIGS. 3a–d, a complete cycle or four configurations of the four column SMB 50 are shown. Configuration 1 shown in FIG. 3a corresponds to the first configuration shown in FIG. 2. The desired result of the four configurations is to simulate the movement of the stationary phase in a counterclockwise direction 86, as shown in FIG. 2. In alternative embodiments, wherein the SMB has more than four columns, more configurations are possible, equal to the number of columns. For example, if the SMB has eight columns, eight configurations are possible. Further, the number of configurations possible can be unequal to the number of columns if any one of the columns includes a distribution plate. For example, a single column including three distribution plates is capable of having four configurations.

Turning to FIG. 3a, in configuration 1 Feed 76 enters SMB 50 at an inlet associated with port 62, Raffinate 80 leaves SMB 50 at an outlet associated with port 64, Mobile Phase 82 enters SMB 50 at an inlet associated with port 66, and Extract 84 leaves SMB 50 at outlet associated with port 60. After a predetermined time interval, $t_{sw}$, the ports corresponding to Feed 76, Raffinate 80, Mobile Phase 82 and Extract 84 are rotated counterclockwise one column length. Turning to FIG. 3b, in configuration 2 corresponding to the elapsing of a first time interval, $t_{sw}$, Feed 76 enters SMB 50 at an inlet associated with port 64, Raffinate 80 leaves SMB 50 at an outlet associated with port 66, Mobile Phase 82 enters SMB 50 at an inlet associated with port 60, and Extract 84 leaves SMB 50 at an outlet associated with port 62. Turning to FIG. 3c, in configuration 3 corresponding to the elapsing of a second time interval, $2t_{sw}$, Feed 76 enters SMB 50 at an inlet associated with port 66, Raffinate 80 leaves SMB 50 at an outlet associated with port 60, Mobile Phase 82 enters SMB 50 at an inlet associated with port 62, and Extract 84 leaves SMB 50 at an outlet associated with port 64. Turning to FIG. 3d, in configuration 4 corresponding to the elapsing of a third time interval, $3t_{sw}$, Feed 76 enters SMB 50 at an inlet associated with port 60, Raffinate 80 leaves SMB 50 at an outlet associated with port 62, Mobile Phase 82 enters SMB 50 at an inlet associated with port 64, and Extract 84 leaves SMB 50 at an outlet associated with port 66. After a fourth time interval, $4t_{sw}$, SMB 50 returns to configuration 1 shown in FIG. 3a.

When correctly designed, SMB 50 is capable of continuously separating two solutes such as the first component and the second component by taking advantage of their different adsorption behavior. Periodic movement of ports 60, 62, 64, 66 at a designated switching time, $t_{sw}$, gives the stationary phase an average velocity in direction 86 counter to the direction 78 of fluid flow. If the average velocity of the stationary phase is greater than the velocity of the slower moving or more retained solute, the more retained solute will travel backwards relative to ports 60, 62, 64, 66 in the ring until the more retained solute reaches zone 52. At zone 52 the slower solute is allowed to pass back into zone 54 by adjusting the flow rate of zone 52, with a fraction of the more retained solute exiting SMB 50 through Extract 84. The faster moving or less retained solute is allowed to flow out of zone 56 to zone 58, with a fraction of the less retained solute exiting SMB 50 through Raffinate 80. The velocity of the less retained solute in zone 58 is chosen so that the less retained solute will not travel on to zone 52 before the next port switch, at time, $nt_{sw}$, wherein n is the cycle number.

Four Zone SMB System for Non-linear, Non-ideal Solutes

In the first embodiment of the present invention, a novel method of optimizing SMB system 50 is configured to separate a first component from a second component wherein the first component and the second component exhibit non-linear adsorption isotherms and non-negligible mass transfer resistances. The novel method of utilizing SMB system 50 for the separation of solutes having non-linear adsorption isotherms and non-negligible mass transfer resistances, is based upon the ability to optimize the flow rates required for Feed 76, Raffinate 80, Extract 84, Mobile Phase 82, the four zone flow rates and the switching time interval. In order to achieve separation of the first component and the second component and achieve the required yield and purity requirements it is imperative that the flow rates and switching time be optimized. Further, the optimization of the flow rates and switching time reduces the amount of Mobile Phase consumed during separation and therefore the overall cost of separation. The cost associated with the mobile phase is the predominant cost of operating SMB 50 for the separation of components with non-linear adsorption properties.

Equations for the zone flow rates and switching time for SMB 50 for the separation of solutes exhibiting non-linear adsorption isotherms and non-negligible mass transfer resistances are determined based upon the development of equations for other types of SMB systems. Equations for determining the flow rates and switching time interval for SMB systems have been derived in the past for various solutes using either a triangular theory or a standing wave analysis. Using standing wave analysis, equations have been developed for SMB systems to separate solutes which exhibit linear adsorption isotherms and negligible mass transfer resistances by Ma and Wang, "Standing Wave Analysis of SMB Chromatography: Linear Systems," *AIChE Journal,* October 1997, the disclosure of which is hereby incorporated by reference; for SMB systems to separate solutes which exhibit linear adsorption isotherms and non-negligible mass transfer resistances by Ma and Wang, 1997, the disclosure of which is hereby incorporated by reference, and for SMB systems to separate solutes which exhibit non-linear adsorption isotherms and negligible mass transfer resistances by Mallmann et al., "Standing Wave Design of Nonlinear SMB Systems for Fructose Purification," AIChE Journal, December 1998, the disclosure of which is hereby incorporated by reference.

Figure 4:
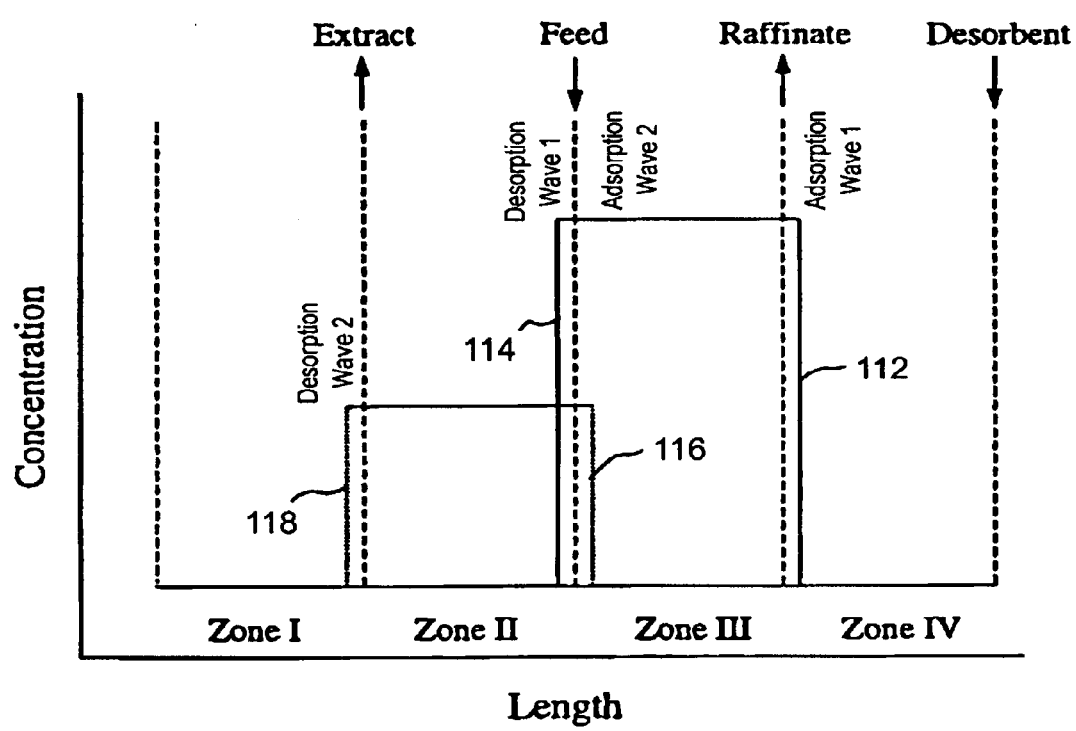
FIG. 4 shows a representation of the adsorption and desorption frontals of a first component and a second component exhibiting linear adsorption isotherms and negligible mass transfer resistances in a simulated moving bed system.

From standing wave theory, the separation of at least a first component from a second component in a mixture, is achieved by the standing of the adsorption waves and desorption waves of the first component and the second component within designated zones of the SMB system. As shown in FIG. 4, wherein the first component is the less retained solute and the second component is the more retained solute, an adsorption wave 112 for a first component stands in zone IV between the Raffinate outlet and the Mobile Phase inlet, a desorption wave 114 for a first component stands in zone II between the Extract outlet and the Feed inlet, an adsorption wave 116 for a second component stands in zone III between the Feed inlet and the Raffinate outlet and a desorption wave 118 stands in zone I between the Mobile Phase inlet and the Extract outlet. The zone flow rates, u, and port movement velocity, should be determined under these conditions:

$$u_{s2}^I = v \quad (1a)$$

$$u_{s1}^{II} = v \quad (1b)$$

$$u_{s2}^{III} = v \quad (1c)$$

$$u_{s1}^{IV} = v \quad (1d)$$

where v is the solid movement velocity or bed velocity, s1 is the first component or solute, s2 is the second component or solute and I, II, III, IV designate the zones of the SMB system. For a simulated moving bed system, v becomes the average solid movement velocity determined by the switching time and column length used:

$$v = \frac{L}{t_{sw}} \quad (2)$$

where L is the column length and $t_{sw}$ is the switching time.

For the separation of solutes exhibiting linear adsorption isotherms and negligible mass transfer resistances, Ma and Wang 1997 derived the zone flow rates from equations 1a–d as:

$$u_0^I = (1 + P\delta_2)v \quad (3a)$$

$$u_0^{II} = (1 + P\delta_1)v \quad (3b)$$

$$u_0^{III} = (1 + P\delta_2)v \quad (3c)$$

$$u_0^{IV} = (1 + P\delta_1)v \quad (3d)$$

where $$\delta_i = \varepsilon_p + (1 - \varepsilon_p)a_i \quad (4)$$

$$P = \frac{1 - \varepsilon_b}{\varepsilon_b} \quad (5)$$

$a_i$ is the linear isotherm coefficient, $\delta$ is the capacity factor, $\varepsilon_p$ is the intraparticle porosity of the adsorbent, $\varepsilon_b$ is the interparticle porosity of the adsorbent, and P is the porosity factor. For a given flow rate of the feed into the simulated moving bed, $F^{feed}$, an additional condition must be met:

$$u_0^{III} - u_0^{II} = \frac{F^{feed}}{S\varepsilon_b} \quad (6)$$

where S is cross-sectional area of the column. The above equations for zone flow rates and feed rates are then combined to find the average bed moving velocity for a given feed flow rate:

$$v = \frac{F^{feed}}{S\varepsilon_b P(\delta_2 - \delta_1)} \quad (7)$$

Using equation 2, the switching time $t_{sw}$, is determined from the average bed velocity given in equation 7. The optimal zone flow rates in equations 3a–d are also determined from the average bed velocity given in equation 7.

For the separation of solutes exhibiting linear adsorption isotherms and non-negligible mass transfer resistances, additional terms are added to the linear, ideal equations, 3a–d, to account for the mass transfer resistances of the solutes:

$$u_o^I = (1 + P\delta_2)v + \beta_2^I\left(\frac{E_{b2}^I}{L^I} + \frac{Pv^2\delta_2^2}{K_{f_2}^I L^I}\right) \quad (8a)$$

$$u_o^{II} = (1 + P\delta_1)v + \beta_1^{II}\left(\frac{E_{b1}^{II}}{L^{II}} + \frac{Pv^2\delta_1^2}{K_{f_1}^{II} L^{II}}\right) \quad (8b)$$

$$u_o^{III} = (1 + P\delta_2)v - \beta_2^{III}\left(\frac{E_{b2}^{III}}{L^{III}} + \frac{Pv^2\delta_2^2}{K_{f_2}^{III} L^{III}}\right) \quad (8c)$$

$$u_o^{IV} = (1 + P\delta_1)v - \beta_1^{IV}\left(\frac{E_{b1}^{IV}}{L^{IV}} + \frac{Pv^2\delta_1^2}{K_{f_1}^{IV} L^{IV}}\right) \quad (8d)$$

where $$\frac{1}{K_f} = \frac{R^2}{15\varepsilon_p D_p} + \frac{R}{3k_f} \quad (9)$$

The $K_f$ term is the lumped mass transfer term, which includes the average particle radius, R, the film mass transfer coefficient, $k_f$, and the pore diffusivity, $D_p$. The $E_b$ term in the zone flow rate equations 8a–d is the axial dispersion coefficient, as determined from the Chung and Wen correlation, provided in Chung and Wen, "Longitudinal Dispersion of Liquid Flowing Through Fixed and Fluidized Beds," *AIChE Journal,* November 1968, the disclosure of which has been incorporated by reference. The β terms relate to the highest concentration and the lowest concentration of a standing wave.

Figure 5:
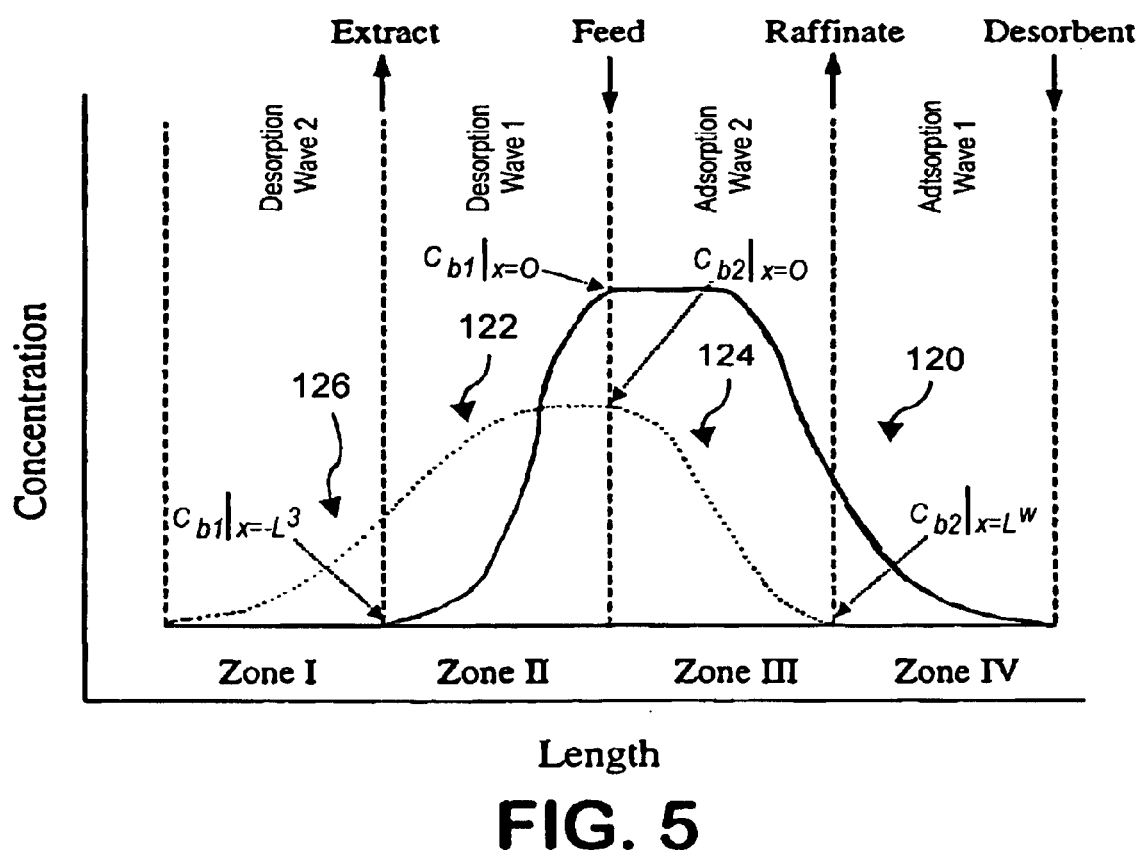
FIG. 5 shows a representation of the adsorption and desorption frontals of a first component and a second component exhibiting linear adsorption isotherms and non-negligible mass transfer resistances in a simulated moving bed system.

The effect of non-negligible mass transfer resistances is to spread the adsorption waves of the zone toward the following zones and spread the desorption waves of the solutes toward the prior zones. FIG. 5 shows an adsorption wave 120 and a desorption wave 122 of the first component or solute and an adsorption wave 124 and a desorption wave 126 of the second component or solute. If this spreading is not accounted for in the determination of the SMB operating conditions, large contamination of the product streams can occur.

In equations, 8a–d, the zone flow rates in zones III and IV are decreased to prevent the spreading solute adsorption waves from passing beyond their designated zones. At the same time, velocities in zones I and II are increased to prevent the spreading desorption waves from passing behind their designated zones.

The β terms are related to the ratio of the highest concentration and the lowest concentration of a designated standing wave.

$$\beta_2^{III} \equiv \ln\left(\frac{c_{b2}|_{x=0}}{c_{b2}|_{x=L^{III}}}\right) \quad (10)$$

$$\beta_1^{II} \equiv \ln\left(\frac{c_{b1}|_{x=0}}{c_{b1}|_{x=-L^{II}}}\right) \quad (11)$$

FIG. 5 shows the positions of the concentration values used to calculate the four β terms. The term $\beta_2^{III}$ is the natural log of the concentration of the second component at the feed port over the concentration of the second component in the Raffinate. The concentration of the second component in the Raffinate is the level of impurity in the Raffinate. Therefore, the $\beta_2^{III}$ term determines both the purity of the Raffinate and the yield of the Extract. The term $\beta_1^{II}$ is the natural log of the concentration of the first component in the feed over the concentration of the first component in the Extract. The concentration of the first component in the Extract is the level of impurity in the Extract. Therefore, the $\beta_1^{II}$ term determines the purity of the Extract and the yield of the Raffinate.

For a given feed flow rate, the average bed moving velocity, v, can be found by substituting equations 8b and 8c into equation 6 to arrive at equation 12 and then solving for v, equation 13:

$$\left(\frac{P\beta_2^{III}\delta_2^2}{K_{f2}^{III}L^{III}} + \frac{P\beta_1^{II}\delta_1^2}{K_{f1}^{II}L^{II}}\right)v^2 - P(\delta_2 - \delta_1)v + \frac{F^{feed}}{\varepsilon_b S} + \frac{\beta_2^{III}E_{b_2}^{III}}{L^{III}} + \frac{\beta_1^{II}E_{b_1}^{II}}{L^{II}} = 0 \quad (12)$$

$$v = \frac{P(\delta_2 - \delta_1) \pm \left[P^2(\delta_2 - \delta_1)^2 - 4\left(\frac{P\beta_2^{III}\delta_2^2}{K_{f2}^{III}L^{III}} + \frac{P\beta_1^{II}\delta_1^2}{K_{f1}^{II}L^{II}}\right)\left(\frac{F^{feed}}{\varepsilon_b S} + \frac{\beta_2^{III}E_{b_2}^{III}}{L^{III}} + \frac{\beta_1^{II}E_{b_1}^{II}}{L^{II}}\right)\right]^{1/2}}{\left(\frac{P\beta_2^{III}\delta_2^2}{K_{f2}^{III}L^{III}} + \frac{P\beta_1^{II}\delta_1^2}{K_{f1}^{II}L^{II}}\right)2} \quad (13)$$

Equation 13 only provides a meaningful solution for v if:

$$P^2(\delta_2 - \delta_1)^2 - 4\left(\frac{P\beta_2^{III}\delta_2^2}{K_{f2}^{III}L^{III}} + \frac{P\beta_1^{II}\delta_1^2}{K_{f1}^{II}L^{II}}\right)\left(\frac{F^{feed}}{\varepsilon_b S} + \frac{\beta_2^{III}E_{b_2}^{III}}{L^{III}} + \frac{\beta_1^{II}E_{b_1}^{II}}{L^{II}}\right) \geq 0 \quad (14)$$

As seen in equation 14, there is an inter-dependence between the purities of the Raffinate, $\beta_2^{III}$, and the Extract, $\beta_1^{II}$, and the feed flow rate, $F^{feed}$, for systems with non-negligible mass transfer resistances. Therefore, the maximum feed flow rate, $F^{feed}$, of a given system is dependent on and limited by the purity requirements of the Raffinate and the Extract.

For the separation of solutes exhibiting non-linear adsorption isotherms and negligible mass transfer resistances, equations 15a–d provide the zone flow rates derived by Mallmann et al [1998], the disclosure of which is hereby incorporated by reference Equations 19a–d assume that the adsorption isotherms are in Langmuirian form:

$$u_0^I = (1 + P\varepsilon_p + P(1 - \varepsilon_p)\frac{DQ_2}{DC_2}\Big|_{(0,0)})v \quad (15a)$$

$$u_0^{II} = (1 + P\varepsilon_p + P(1 - \varepsilon_p)\frac{DQ_1}{DC_1}\Big|_{(0,C_{p2})})v \quad (15b)$$

$$u_0^{III} = (1 + P\varepsilon_p + P(1 - \varepsilon_p)\frac{\Delta Q_2}{\Delta C_2}\Big|_{(C_{s1},C_{s2})})v \quad (15c)$$

$$u_0^{IV} = (1 + P\varepsilon_p + P(1 - \varepsilon_p)\frac{\Delta Q_1}{\Delta C_1}\Big|_{(C_{p1},0)})v \quad (15d)$$

where DQ/DC is the substantial derivative of the adsorption isotherm at the designated point, ΔQ/ΔC is the slope of the tangent at the designated point along the isotherm curve, $C_s$ is the concentration at the Feed, and $C_p$ is a secondary plateau concentration. In non-linear systems, the first and second components compete for adsorption along with other adsorbing components present in the mixture. This competition alters the shape of the adsorption and desorption profiles of the first component and the second component due to changes in the steady-state concentration of each. The degree to which each adsorption equilibrium is altered is dependent upon the concentration of the competing components.

Figure 6:
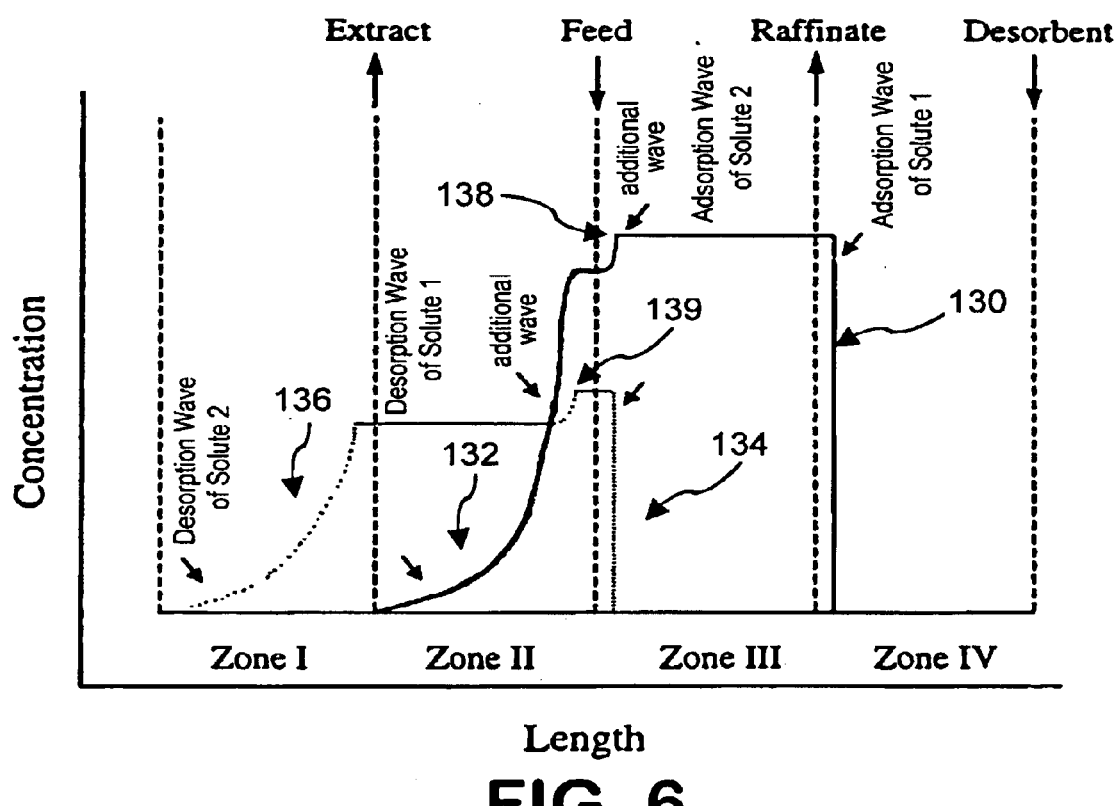
FIG. 6 shows a representation of the adsorption and desorption frontals of a first component and a second component exhibiting non-linear adsorption isotherms and negligible mass transfer resistances in a simulated moving bed system.

Referring to FIG. 6, an adsorption wave 130 and desorption wave 132 for the first component and an adsorption wave 134 and desorption wave 136 for a second component are shown. Further, additional waves 138, 139 occur in the concentration profiles for both the first component and the second component, respectively, as shown in FIG. 6, because of non-linear effects. This increases the number of concentration plateaus to four. $C_{s1}$ and $C_{s2}$ are the concentrations at the feed port, and $C_{p1}$ and $C_{p2}$ are the additional concentration plateaus created by the nonlinear behavior, as seen in FIG. 6.

The switching time for the SMB system is calculated by substituting equations 15b and 15c into equation 6 to get equation 16

$$v = \frac{F^{feed}}{S(1 - \varepsilon_b)(1 - \varepsilon_p)\left[\frac{\Delta Q_2}{\Delta C_2}\Big|_{(C_{s1},C_{s2})} - \frac{DQ_1}{DC_1}\Big|_{(0,C_{p2})}\right]} \quad (16)$$

The solutions to equations 15a–d and 16 give the optimal system for a given feed flow rate, $F^{feed}$.

In the present invention a novel method is provided to optimize the zone flow rates and switching time for use with SMB 50 in the separation of components exhibiting non-linear adsorption isotherms and non-negligible mass transfer resistances. The developed method is then used to optimize the zone flow rates and switching time for SMB 50 when Clarithromycin is to be separated from 6,11 given a mixture of the two.

In a first example method for optimizing the zone flow rates and switching time for use with SMB 50 in the separation of components exhibiting non-linear adsorption isotherms and non-negligible mass transfer resistances, the equations provided above for the zone flow rates for the separation of solutes exhibiting linear adsorption isotherms, negligible mass transfer resistances, for the separation of solutes exhibiting linear adsorption isotherms, non-negligible mass transfer resistances, and for the separation of solutes exhibiting non-linear adsorption isotherms, negligible mass transfer resistances, and the switching time for the separation of solutes exhibiting non-linear adsorption isotherms and negligible mass transfer resistances are combined in a novel way to approximate the zone flow rates and switching time for the separation of solutes or components exhibiting both non-linear adsorption isotherms and non-negligible mass transfer resistances. Based upon the estimated values, an iterative process is used to optimize the zone flow rates and switching time.

In the first method it is assumed that the terms added to equations 8a–d to account for the mass transfer resistances of the solutes exhibiting linear adsorption isotherms is a reasonable estimate for the mass transfer resistances of the solutes exhibiting non-linear adsorption isotherms. As such, a first estimate of the flow rates for the four zones of SMB 50 for the separation of solutes exhibiting non-linear adsorption isotherms and non-negligible mass transfer resistances are:

$$u^I_{0,non-linear,non-equil} = u^I_{0,non-linear,equil} + u^I_{0,linear,non-equil} - u^I_{0,linear,equil} \quad (17a)$$

$$u^{II}_{0,non-linear,non-equil} = u^{II}_{0,non-linear,equil} + u^{II}_{0,linear,non-equil} - u^{II}_{0,linear,equil} \quad (17b)$$

$$u^{III}_{0,non-linear,non-equil} = u^{III}_{0,non-linear,equil} + u^{III}_{0,linear,non-equil} - u^{III}_{0,linear,equil} \quad (17c)$$

$$u^{IV}_{0,non-linear,non-equil} = u^{IV}_{0,non-linear,equil} + u^{IV}_{0,linear,non-equil} - u^{IV}_{0,linear,equil} \quad (17d)$$

A similar estimation is used to optimize the equation for the average bed velocity, v. It is known that the average bed velocity, v, increases for linear systems when the solutes exhibit non-negligible mass transfer resistances compared to linear systems wherein the mass transfer resistances of the solutes are negligible. As such, a reasonable first estimate for the average bed velocity, v, for SMB systems configured to separate solutes exhibiting non-linear adsorption isotherms and non-negligible mass transfer resistances is to multiply the average bed velocity, v, for solutes exhibiting non-linear adsorption isotherms and negligible mass transfer resistances, equation 16 by the ratio of zone III flow rates for solutes exhibiting non-linear adsorption isotherms and negligible mass transfer resistances, equation 15c and solutes exhibiting non-linear adsorption isotherms and non-negligible mass transfer resistances, equation 17c. Therefore, a first estimate of the average bed velocity, for SMB system 50 configured to separate solutes exhibiting non-linear adsorption isotherms and non-negligible mass transfer resistances is:

$$v_{non-linear,non-equil} = \frac{u^{III}_{0,non-linear,equil}}{u^{III}_{0,non-linear,non-equil}} v_{non-linear,equil} \quad (18)$$

Equation 18 is an estimate that is optimized upon through an iteration process in the following manner. First, the SMB system derived from equations 17a–d is simulated with the first estimate for v. Next, the SMB system is simulated with a slightly changed value of v. Based on the results of these two simulations, a new value for v is chosen for a third simulation. If the second simulation provides a more optimal design, the third value for v will be further away from the first estimate of v. Subsequent iterations are carried out until an optimal point is found. If the second simulation provides a less optimal point, the third value for v will be slightly changed from the first estimated value for v in the opposite direction from the second value. Subsequent iterations are carried out until an optimal point is established. For a given set of flow rates, this optimal point is defined by the purity and yield required. An increase in v will increase yield but decrease purity. A decrease in v will decrease yield but increase purity.

Figure 7:
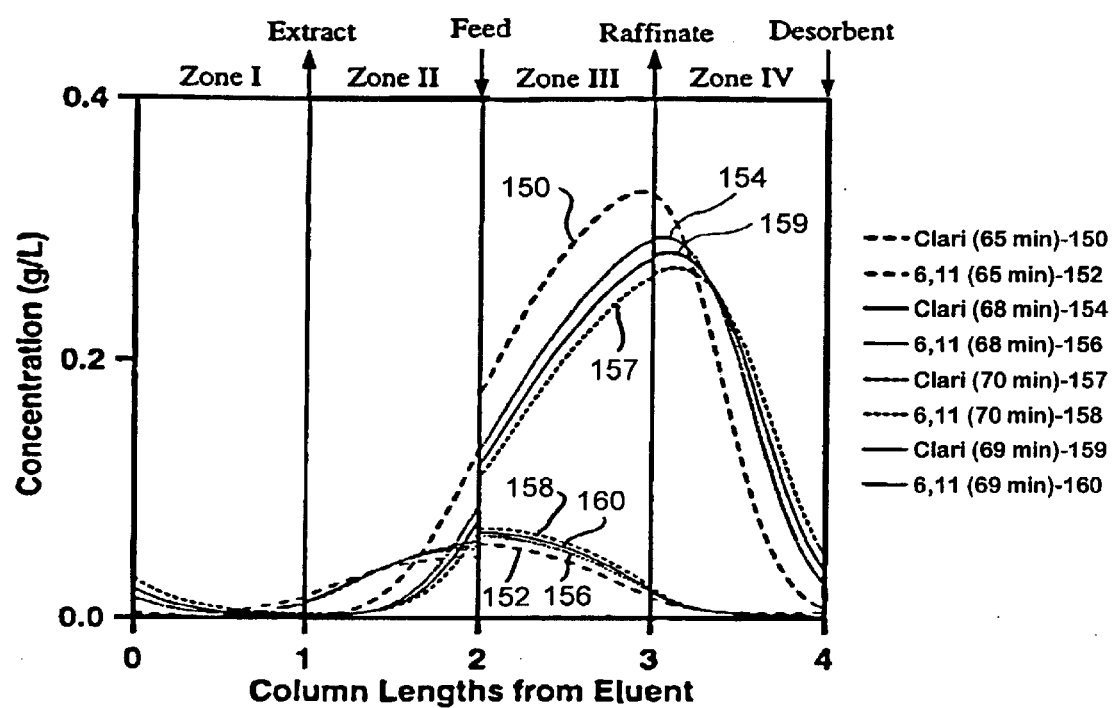
FIG. 7 shows a representation of a first example of simulations of an iteration process to optimize the switching time for the separation of a first component and a second component exhibiting non-linear adsorption isotherms and non-negligible mass transfer resistances in a simulated moving bed system.

A first example iteration to optimize the average bed velocity for a SMB system configured to separate Clarithromycin and 6,11 in a Optipore adsorbent available from Dow Chemical Company located in Midland, Michigan and a 60% (by volume) Ethanol/Water mixture is shown in FIG. 7 and Table A. FIG. 7 shows the simulated column profiles at the end of 25 switching cycles. An initial estimate of the switching time of, 65 minutes, was found using Equation 18 based upon the solution to equations 17a–d. Referring to FIG. 7, curve 150 shows the concentration curve for Clarithromycin with a 65 minute switching time and curve 152 shows the concentration curve for 6,11 with a 65 minute switching time. The second estimate for the switching time chosen was 68 minutes. The 68-minute switching time gave a slightly higher purity and a much higher yield. Curve 154 shows the concentration curve for Clarithromycin with a 68 minute switching time and curve 156 shows the concentration curve for 6,11 with a 68 minute switching time.

Since 68 minutes provided better results than 65 minutes the next iteration simulation was for a switching time of 69 minutes. Compared to 68 minutes, the purity showed minimal change while the yield increased approximately 3%. Referring to FIG. 7, curve 157 shows the concentration curve for Clarithromycin with a 69 minute switching time and curve 158 shows the concentration curve for 6,11 with a 69 minute switching time. As such, a fourth estimate of the switching time of 70 minutes was simulated (curve 159 for Clarithromycin and curve 160 for 6,11). Compared to the switching time of 69 minutes, the purity of the Clarithromycin decreased and the yield of the Clarithromycin increased. Based on these four iterations, a switching time of 69 minutes was chosen as the optimal switching time.

TABLE A

Purity and Yield for Clarithromycin during the Iterative Solution for the Switching Time

| Switching Time (minutes) | Percent Purity | Percent Yield |
|---|---|---|
| 65 | 96.5% | 60.6% |
| 68 | 97.0% | 82.1% |
| 69 | 97.0% | 85.0% |
| 70 | 96.8% | 87.2% |

In a second method for determining the zone flow rates and switching time for use with SMB 50 in the separation of components exhibiting non-linear adsorption isotherms and non-negligible mass transfer resistances, equations are developed with the assumption that the δ' terms in equations 19a–d, which describe the relative adsorption or retention for the standing wave in each zone, are constant when the SMB system reaches steady state. If the δ' terms are constant, they can be substituted for the δ terms in the linear adsorption isotherms, non-negligible mass transfer resistance system equations 8a–d and 12.

First, a feed flow rate, $F^{feed}$, and purity requirements of the two outlet streams, the Raffinate and the Extract, (represented by the β terms in equations 10 and 11) are chosen. Next, the separation zone plateau concentrations, which are the steady-state maximum concentrations at the feed port $C_{s1}$ and $C_{s2}$ are estimated. From the two plateau concentrations at the Feed port, the other two plateau concentrations, $C_{p1}$ and $C_{p2}$ are calculated as described in Mallmann et al [1998] the disclosure of which has been incorporated by reference. The next step is to calculate the δ' values of each zone. These terms can be derived by comparing the equations for systems with solutes exhibiting linear adsorption isotherms and negligible mass transfer resistances, equations 3a–d, with the equations for systems with solutes exhibiting non-linear adsorption isotherms and negligible mass transfer resistances, equations 15a–d. The δ' values for each zone are:

$$\delta'^I = \varepsilon_p + (1-\varepsilon_p)\frac{Dq_2}{Dc_2}\bigg|_{(0,0)} \quad (19a)$$

$$\delta'^{II} = \varepsilon_p + (1-\varepsilon_p)\frac{Dq_1}{Dc_1}\bigg|_{(0,c_{p2})} \quad (19b)$$

$$\delta'^{III} = \varepsilon_p + (1-\varepsilon_p)\frac{\Delta q_2}{\Delta c_2}\bigg|_{(c_{s1},c_{s2})} \quad (19c)$$

$$\delta'^{IV} = \varepsilon_p + (1-\varepsilon_p)\frac{\Delta q_1}{\Delta c_1}\bigg|_{(c_{p1},c_0)} \quad (19d)$$

The calculated values for δ' are substituted for the δ terms in the equations 8a–d and 13. These new terms still describe the relative retention of the adsorption and desorption waves in each zone as they did with the linear system. But they are concentration dependent and must be calculated differently for each zone. $\delta_2$ from equation 8a is replaced by $\delta'^I$, $\delta_1$ from equation 8b is replaced by $\delta'^{II}$, $\delta_2$ from equation 8c is replaced by $\delta'^{III}$, and $\delta_1$ from equation 8d is replaced by $\delta'^{IV}$. Using the resultant equations, the zone flow rates and solid movement velocity for systems with solutes exhibiting non-linear adsorption isotherms and non-negligible mass transfer resistances are optimized. The first step, however, is to determine if these equations will give meaningful solutions for the given feed flow rate, purity conditions, and estimated plateau concentrations. Therefore, $\delta'^{III}$ and $\delta'^{IIII}$ should be plugged into Equation 12 for $\delta_1$ and $\delta_2$, respectively:

$$\left(\frac{P\beta_2(\delta'^{IIII})^2}{K_{f_2}^{III}L^{III}} + \frac{P\beta_1(\delta'^{III})^2}{K_{f_1}^{II}L^{II}}\right)v^2 - \quad (20a)$$

$$P(\delta'^{IIII} - \delta'^{III})v + \frac{F^{feed}}{\varepsilon_b S} + \frac{\beta_2 E_{b_2}^{III}}{L^{III}} + \frac{\beta_1 E_{b_1}^{II}}{L^{II}} = 0$$

Because equation 20a is a quadratic equation, a meaningful solution is attained only if:

$$P^2(\delta'^{IIII} - \delta'^{III})^2 - \quad (20b)$$

$$4\left(\frac{P\beta_2(\delta'^{IIII})^2}{K_{f_2}^{III}L^{III}} + \frac{P\beta_1(\delta'^{III})^2}{K_{f_1}^{II}L^{II}}\right)\left(\frac{F^{feed}}{\varepsilon_b S} + \frac{\beta_2 E_{b_2}^{III}}{L^{III}} + \frac{\beta_1 E_{b_1}^{II}}{L^{II}}\right) \geq 0$$

If equation 20b is not satisfied, a change must be made to the the feed flow rate, $F^{feed}$, purity conditions, and/or the estimated plateau concentrations. Once a reasonable v has been found from Equation 20a, the δ' terms are substituted into Equations 8a–d to find the four zone flow rates:

$$u_0^I = (1+P\delta'^I)v + \beta_2^I\left(\frac{E_{b_2}^I}{L^I} + \frac{Pv^2(\delta'^I)^2}{K_{f_2}^I L^I}\right) \quad (21a)$$

$$u_0^{II} = (1+P\delta'^{II})v + \beta_1^{II}\left(\frac{E_{b_1}^{II}}{L^{II}} + \frac{Pv^2(\delta'^{II})^2}{K_{f_1}^{II} L^{II}}\right) \quad (21b)$$

$$u_0^{III} = (1+P\delta'^{III})v - \beta_2^{III}\left(\frac{E_{b_2}^{III}}{L^{III}} + \frac{Pv^2(\delta'^{III})^2}{K_{f_2}^{III} L^{III}}\right) \quad (21c)$$

$$u_0^{IV} = (1+P\delta'^{IV})v - \beta_1^{IV}\left(\frac{E_{b_1}^{IV}}{L^{IV}} + \frac{Pv^2(\delta'^{IV})^2}{K_{f_1}^{IV} L^{IV}}\right) \quad (21d)$$

The switching time found from equation 20a, can potentially be improved through an iterative process. This is because the plateau concentrations used to derive the operating parameters may not be the actual values that occur in the system along with the other estimation used in the calculation of equation 20a. The iteration process is the same process as used with the first method above. The zone flow rates are calculated from the first estimate for the switching time, provided by equation 20a and subsequent iterations are carried out until an optimal set of flow rates and switching time is determined. This optimal condition, is defined in one embodiment, as either the maximum yield for a given minimum purity or the maximum purity for a given minimum yield.

A third method for determining the optimal zone flow rates and optimal switching time is described in detail in connection with the second embodiment of the present invention, the five zone SMB system as the third method for determining the optimal zone flow rates and optimal switching time. All three methods can be used for either the four zone SMB system of the first embodiment or the five zone SMB system and the four zone SMB system of the second embodiment.

Either the first method or the second method or the third method provides a determination of optimal zone flow rates and optimal switching time to use with SMB 50 for the separation of a first component from a second component when the first and second components exhibit non-linear adsorption isotherms and non-negligible mass transfer resistances. The following is the application of either the first method or the second method or the third method to separate Clarithromycin from 6,11 given a solid mixture of the two. The Clarithromycin and 6,11 used in the experiments throughout this disclosure are pure, HPLC-grade Clarithromycin and 6,11 provided by Abbott Laboratories located in Chicago, Ill.

Several parameters must be determined, in order to simulate SMB 50 to optimize the zone flows rates and switching time. For example, an appropriate stationary phase, such as an adsorbent, to use as packing for the columns and the mobile phase to use as a carrier fluid must be determined. Also, the adsorption isotherms and mass transfer effects of the solutes to be separated, such as Clarithromycin and 6,11 need to be determined.

The stationary phase used in SMB 50 is chosen based upon the mobile phase to be used and the characteristics of the components in the mixture to be separated. It is within the scope of the present invention to employ sorbents as the stationary phase, including adsorbents and absorbents. Example adsorbents include adsorbents having one or more of the following mechanisms: hydrophobic interactions, ionic interactions, hydrogen bonds, π—π interactions, complex formation or ligand exchange, dipole interactions, and affinity interactions or guest-host interactions.

The mobile phase used in the SMB 50 is chosen based upon the stationary phase to be used and the characteristics of the components in the mixture to be separated. Example mobile phases include water or aqueous solutions, at least one organic solvent, supercritical fluids, or combinations thereof.

For the example of the separation of Clarithromycin from 6,11, the stationary phase used in the SMB system must be able to facilitate the separation of the Clarithromycin from the 6,11 based on the difference in the relative affinity of the Clarithromycin and 6,11 for the stationary phase contained in the column or columns. The separation of the first and second components must happen before the first and second components pass out of the separation zone, the region between Raffinate 80 and Extract 84, such as zones 54 and 56 in FIG. 2. A further parameter to consider is the strength of the stationary phase. When the component or components to be separated are weakly adsorbed, for example when the components are chemically inert compounds such as hydrocarbons, such as Clarithromycin and 6,11, strong stationary phases are usually preferred to facilitate separation.

The structures of Clarithromycin and 6,11 suggest the use of a hydrophobic adsorbent, because both are hydrocarbons and differ by a single methyl group that has replaced a hydroxyl group. 6,11 is expected to be more hydrophobic due to the additional methyl group than Clarithromycin, resulting in a higher relative affinity for a hydrophobic polymeric adsorbent.

The Mobile Phase 82 used in SMB 50 is an additional factor in the effectiveness of SMB 50 to separate Clarithromycin and 6,11. Several factors should be considered in choosing a mobile phase including: compatibility with the stationary phase, ability to dissolve the first and second solutes or components (Clarithromycin and 6,11), low viscosity to reduce pressure drop in the column, ability to maximize the rate of mass transfer, purity, recoverability, commercial availability, cost, and ability to facilitate adsorption or desorption. The Mobile Phase used can have a large impact on the adsorption isotherms of both the Clarithromycin and 6,11. The affinity of Clarithromycin and 6,11 for an stationary phase is strongly affected by the affinity of Clarithromycin and 6,11 for a Mobile Phase.

Clarithromycin and 6,11 are known to dissolve in a mobile phase consisting of a mixture of organic and aqueous solvents. The mobile phase selected should balance the solubility of the Clarithromycin and 6,11 and the selectivity of the stationary phase for Clarithromycin and 6,11. Example mobile phases include a mixture of water and an alcohol, such as Ethanol, Methanol or Isopropyl.

In one exemplary embodiment, an Ethanol/water solution was chosen for the mobile phase for separation of Clarithromycin and 6,11. Ethanol is an organic solvent, which will assist in dissolving the Clarithromycin and the 6,11. The water in the Ethanol/water solution facilitates the adsorption of the solutes to the hydrophobic adsorbent. In alternate embodiments, other organic solvents are used in combination with water as the mobile phase, such as methanol and isopropyl alcohol.

The preferred percentage makeup of the Ethanol/water solution for use as the mobile phase in an SMB system is based on the solubilities of Clarithromycin and 6,11 in the mobile phase and the interaction of the mobile phase with the adsorbent. The relative solubilities of Clarithromycin and 6,11 at various percentages of Ethanol in the Ethanol/water solution provide a solubility curve for both Clarithromycin and 6,11. The Ethanol used is 200 proof and is available from McCormick Distilling Co. in Weston, Mass. The water used is distilled deionized water obtained from a MILLI-Q™ system available from Millipore located in Bedford, Mass. The solubilities of Clarithromycin and 6,11 are determined by adding an excess amount of the component being tested to the tested Ethanol/water solution and stirring the mixture for four hours at approximately room temperature (24 C.). The resultant solution is then filtered and assayed for concentration using HPLC (high performance liquid chromatography).

Figure 8:
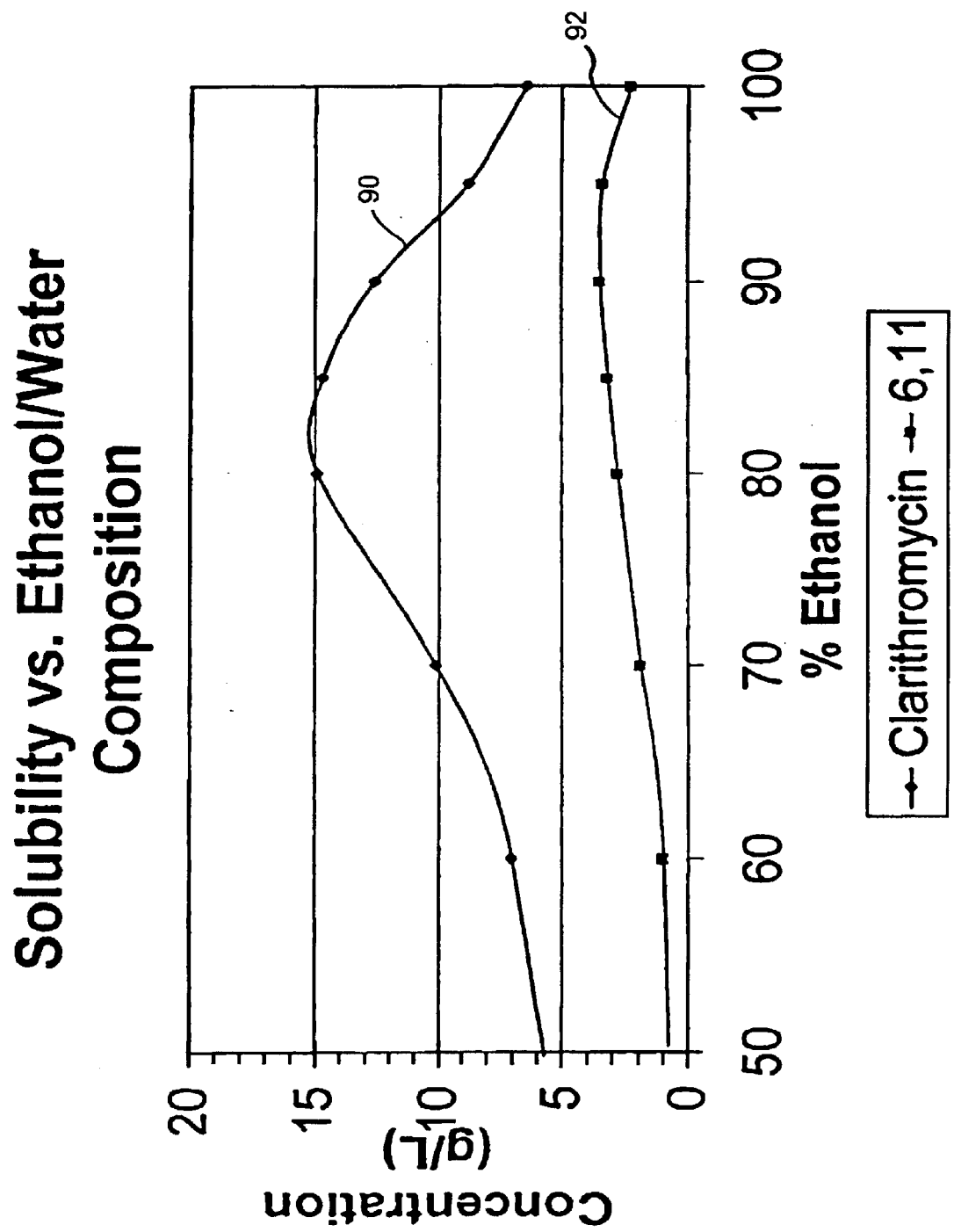
FIG. 8 shows experimental solubility data and fitted curves for Clarithromycin and 6,11 for various mobile phases comprising mixtures of Ethanol and water.

FIG. 8 depicts the experimental data and fitted solubility curves for both Clarithromycin and 6,11, 90 and 92, respectively, in various solutions of Ethanol and water. Clarithromycin solubility curve 90 was found using pure Clarithromycin. 6,11 solubility curve 92 was found using a binary mixture of Clarithromycin and 6,11. However, it was assumed that the Clarithromycin concentration present was well below its solubility limit and therefore should have little effect on the 6,11 solubility data.

Referring to FIG. 8, the 6,11 solubility was very low at all Ethanol/water mixtures, reaching a maximum for an Ethanol/water solution comprised of about 90% Ethanol. Clarithromycin solubility curve 90 exhibited a maximum generally around an Ethanol/water solution comprised of about 80% Ethanol. Clarithromycin showed a higher degree of solubility than 6,11. The less soluble 6,11 is expected to adsorb more strongly onto a hydrophobic adsorbent.

A preferred Ethanol/water solution provides a large relative difference in the solubilities of the first component, Clarithromycin, and the second component, 6,11. Based on the solubility curve data, a preferred Ethanol/water mobile phase for Clarithromycin and 6,11 generally contains from about 60% to about 80% Ethanol. At Ethanol percentages above about 80%, the Clarithromycin and 6,11 solubilities decline rapidly and the difference between the solubilities decreases. Further, at Ethanol percentages above about 80%, strong hydrophobic adsorption of 6,11 to the adsorbent becomes less likely. At Ethanol percentages below about 60%, the solubilities of both Clarithromycin and 6,11 become very small. As such, at Ethanol percentages below about 60%, a larger amount of the mobile phase is required to completely dissolve the Clarithromycin and the 6,11.

The final percentage makeup of the Ethanol/water solution is determined in conjunction with the determination of the preferred stationary phase to use in the column or columns of the SMB because of the interdependence between the mobile phase and the stationary phase. Three different hydrophobic adsorbents were tested: Dow Optipore Hydrophobic XUS-40323 adsorbent ("Optipore adsorbent") available from Dow Chemical located in Midland, Mich.; Amberlite XAD-16 adsorbent ("Amberlite adsorbent") available from Rohm and Haas located in Philadelphia, Pa.; and Macronet-200 adsorbent ("Macronet adsorbent") available from Purolite located in Philadelphia, Pa.

Two methods were used to determine the adsorption isotherms of Clarithromycin and 6,11 in the presence of the various adsorbents: batch and frontal. The batch method was used for initial screening experiments. The frontal method was used to distinguish the more preferred candidate adsorbents. The adsorption isotherm describes the relationship at equilibrium between the adsorbed solute concentration, Q, and the solute concentration in the solvent, C. The adsorption isotherm is unique for a given solute, a given mobile phase, the ambient temperature, and a given adsorbent. Any change in one of the above parameters results in a different isotherm. The adsorption isotherm is valuable for predicting the separation potential of a packed column.

In a batch method, a known mass of dry adsorbent is mixed with a known volume of solution composed of the proposed mobile phase and a known concentration of a solute or component. The mixture is sonicated to ensure that any air trapped within the pores of the adsorbent is released and to ensure an adsorption equilibrium is reached. A sample of the supernatant is taken and analyzed for solute concentration using HPLC analysis. The initial and final concentrations are used to determine the amount of solute adsorbed to the adsorbent. By knowing the mass of adsorbent before the introduction of the solute and after the introduction of the solute, the mass of solute adsorbed per mass of adsorbent is calculated. The calculated packed bed or column volume per mass of adsorbent is used to calculate the mass adsorbed per packed bed or column volume, Q. By conducting several batch tests at different concentrations, a Q vs. C isotherm curve is achieved.

Batch tests were carried out on the three different types of adsorbent with Clarithromycin: Optipore adsorbent, Amberlite adsorbent, and Macronet adsorbent. The objective of the batch tests is to detect fairly strong adsorption of Clarithromycin, because adsorbents that adsorb Clarithromycin strongly are likely to adsorb 6,11 strongly enough to achieve separation of the two.

For the batch tests, the particle size of the adsorbent is less of a concern, so adsorbent particles larger than 400 micrometers are used. Because of the large particle size, the solution and adsorbent are mixed for at least 12 hours to assure that equilibrium had been reached.

Figure 9:
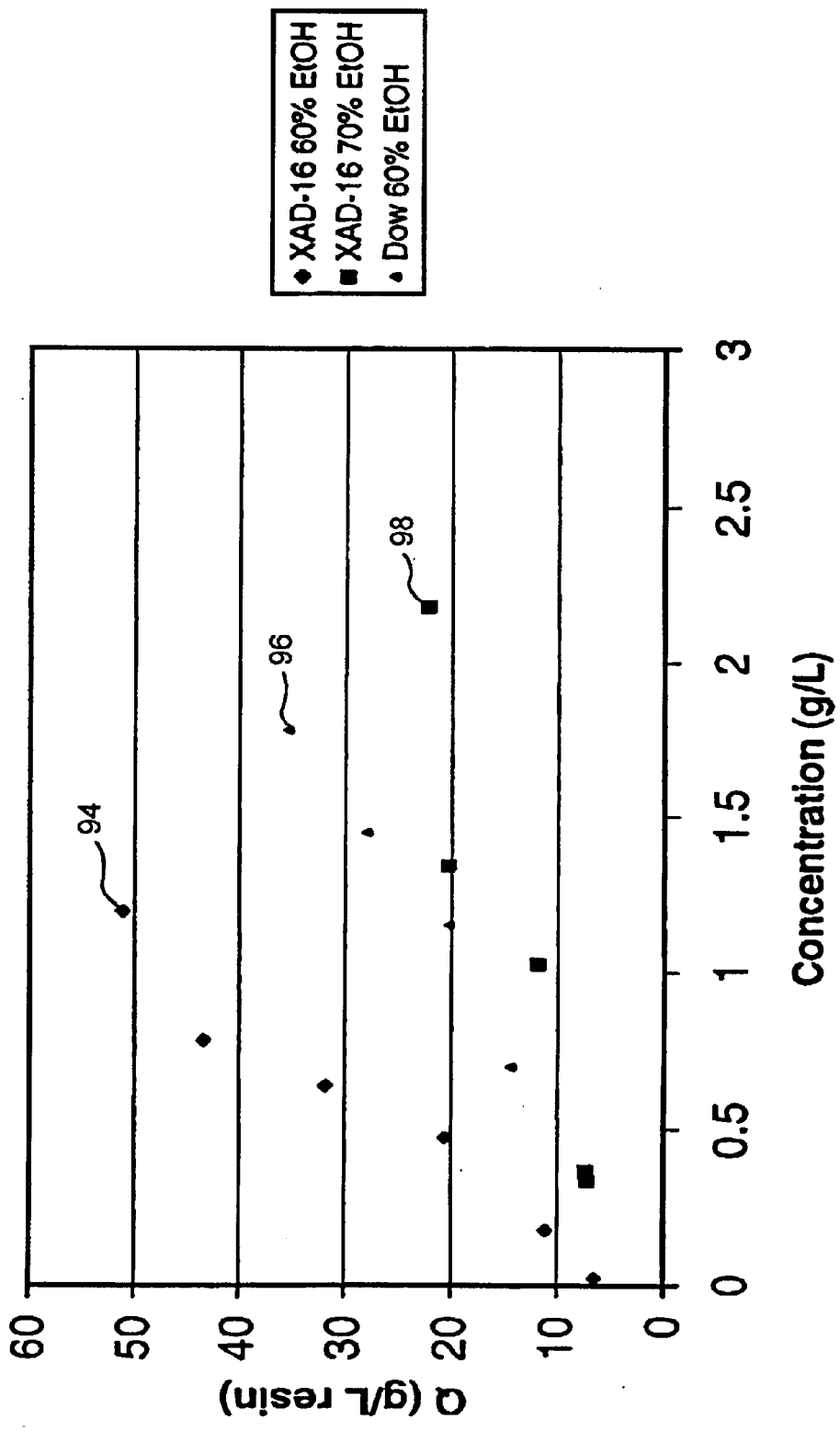
FIG. 9 shows experimental data for the adsorption isotherm for Clarithromycin in various adsorbents from batch method tests.

The batch test data showed that the Optipore and Amberlite adsorbents showed much more adsorption of Clarithromycin than the Macronet adsorbent. Based on these results, the Macronet adsorbent was eliminated from the candidates of potential adsorbents. The batch test results for the Optipore and Amberlite adsorbents are shown in FIG. 9. Further as expected, adsorption was significantly stronger in mobile phase solutions containing a larger proportion of water due to the hydrophobic nature of Clarithromycin. As shown in FIG. 9, the Amberlite adsorbent, data point sets 94 and 96, has a higher Q factor, a measure of the adsorption capacity of the adsorbent, than the Optipore adsorbent, data point set 98. Further, the Amberlite adsorbent Q factor is higher for Clarithromycin dissolved in a 60% Ethanol/water solution, data point set 94, than for Clarithromycin dissolved in a 70% Ethanol/water solution, data point set 96.

An additional factor in selecting the adsorbent is safety. The adsorbent is packed in a column usually made of glass. As such, a significant expansion of the adsorbent due to the introduction of the mobile phase could shatter the glass damaging the column and possibly causing injury. As such, expansion tests were conducted on both the Optipore and Amberlite adsorbents in the presence of several Ethanol/water solutions.

Figure 10:
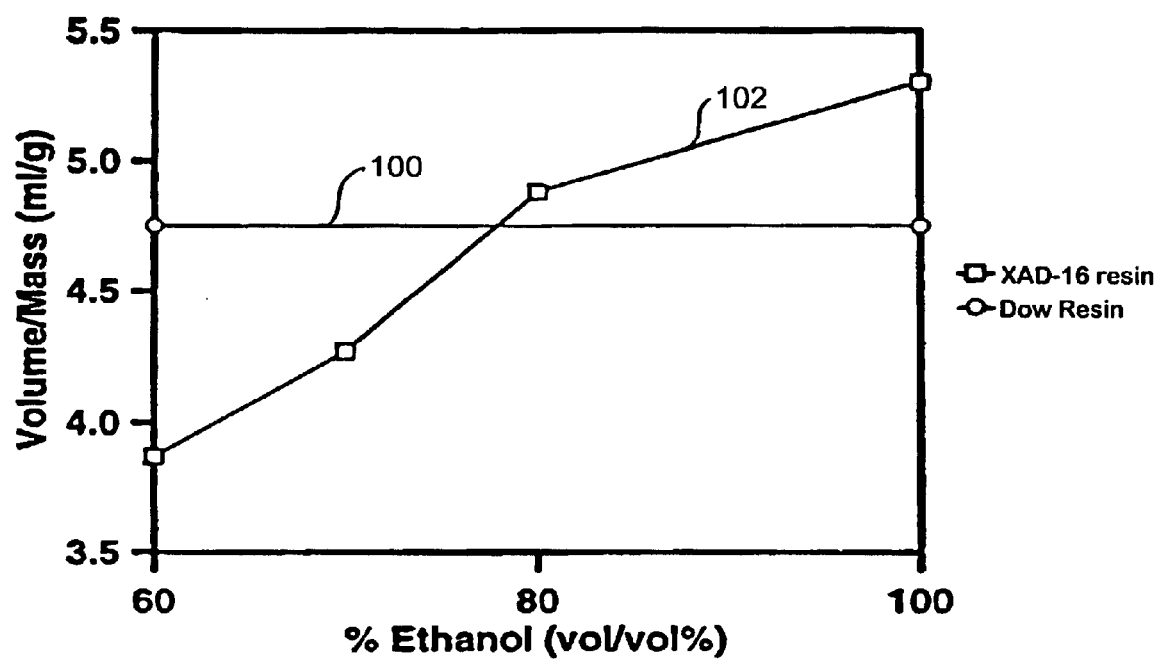
FIG. 10 shows the expansion characteristics for the Optipore and Amberlite adsorbents in the presence of various mixtures of Ethanol and water.

The packed bed volume per mass of both the Optipore and Amberlite adsorbents is shown in FIG. 10 as a function of the percentage of Ethanol in the ethanol/water solution. Both adsorbents expanded significantly in the presence of Ethanol. However, in the range between about 60% and about 100% Ethanol, as shown in FIG. 10, the Optipore adsorbent, data set 100, showed little or no change in packed density, while the Amberlite adsorbent, data set 102, showed significant changes in packed density versus Ethanol percentage in this range. Due to the expansion problems associated with the Amberlite adsorbent, the Optipore adsorbent is selected for further study using frontal method tests to find the best match between adsorbent and mobile phase.

In frontal method tests, a series of solute concentration increases are introduced into a packed, well-equilibrated column. After each concentration increase, the resulting frontal is allowed to completely breakthrough before the next increase in concentration is introduced. The resulting elution profile is a series of fronts, one for each concentration increase. The retention time, $t_r$, for each frontal is found. The mass adsorbed per solid adsorbent volume, Q, is calculated using the following equation for frontal wave velocity, u, which assumes the isotherm to be Langmuirian:

$$u = \frac{v}{1 + \frac{1-\varepsilon_b}{\varepsilon_b}\varepsilon_p K_d + \frac{1-\varepsilon_b}{\varepsilon_b}(1-\varepsilon_p)\frac{\Delta Q}{\Delta C}} \quad (22)$$

where $$u = \frac{L}{t_r}, \quad (23)$$

and $\mu$ is the frontal wave velocity, L is the column length, $K_d$ is the size exclusion factor, v is the interstitial velocity, $\Delta Q$ is the change in adsorption, $\Delta C$ is the change in concentration of the influent, $\epsilon_b$ is the interparticle porosity of the adsorbent, and $\epsilon_p$ is the intraparticle porosity of the adsorbent.

Frontal tests were performed for a first mobile phase having 60% by volume Ethanol and a second mobile phase 80% by volume Ethanol, both with the Optipore adsorbent. Several different concentrations of Clarithromycin and 6,11 were used in order to develop a full adsorption isotherm for both the 60% Ethanol and 80% Ethanol mobile phase.

Figure 11:
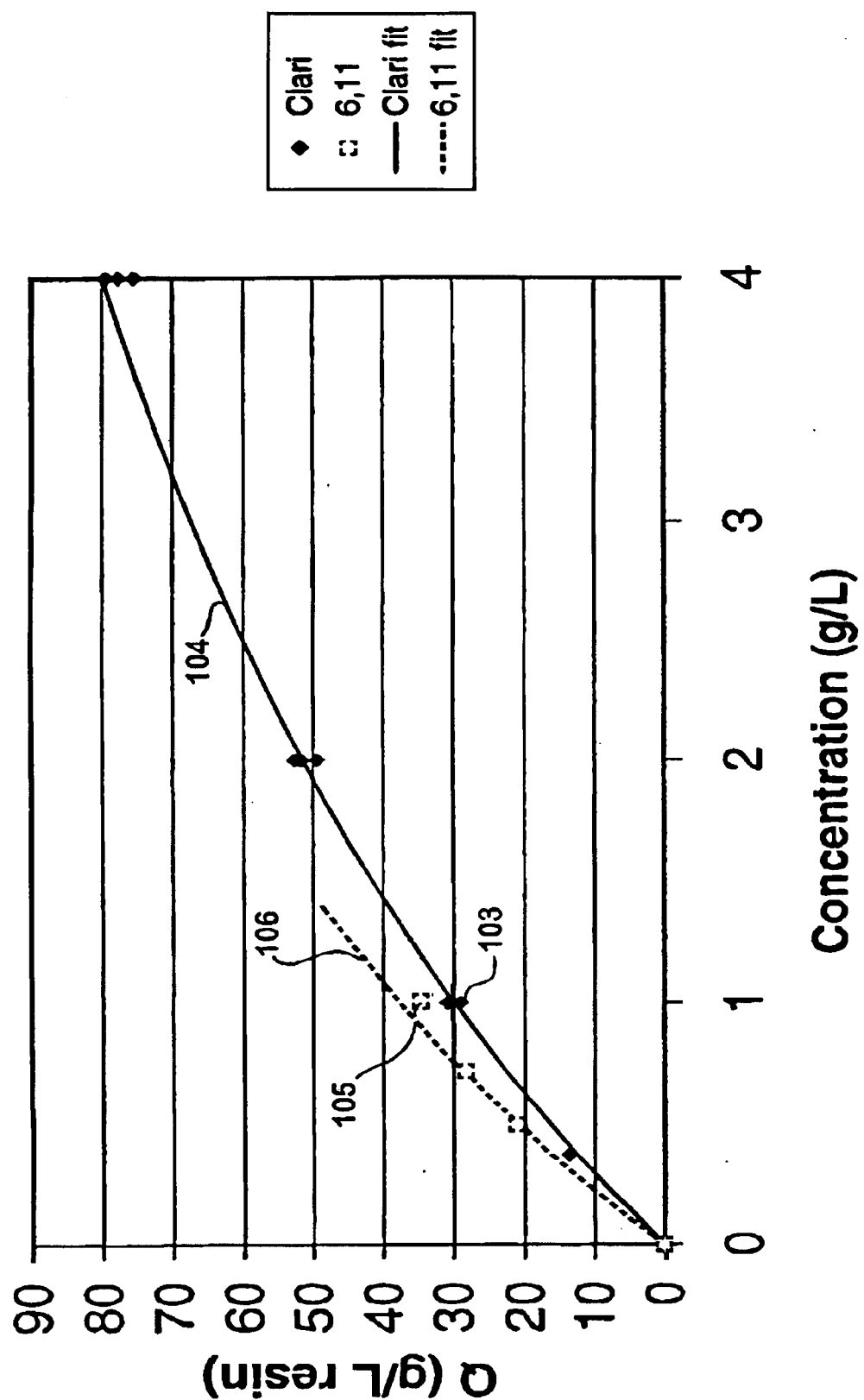
FIG. 11 shows experimental and fitted adsorption isotherms for Clarithromycin and 6,11 in the Optipore adsorbent and a 60% Ethanol/Water mixture mobile phase.

FIG. 11 depicts experimental data 103 of the Clarithromycin isotherm, a fitted adsorption isotherm 104 for Clarithromycin, experimental data 105 of the 6,11 isotherm and 6,11 fitted adsorption isotherm 106 in 60% Ethanol. The 6,11 adsorption was about 30% higher than the adsorption of the Clarithromycin and the overall adsorption was strong. This difference in adsorption is sufficient to provide separation of Clarithromycin and 6,11 in an SMB system.

Figure 12:
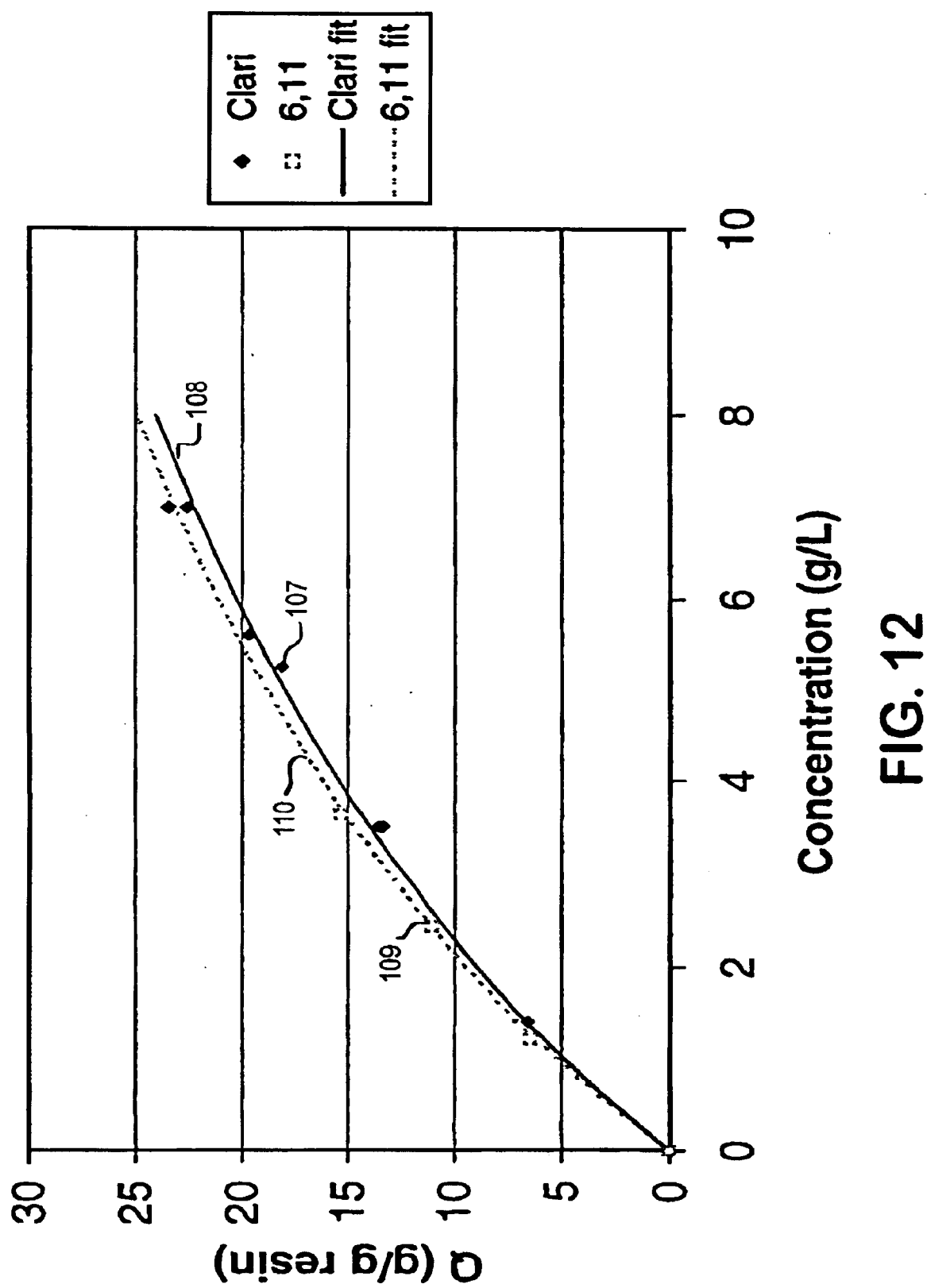
FIG. 12 shows experimental and fitted adsorption isotherms for Clarithromycin and 6,11 in the Optipore adsorbent and a 80% Ethanol/Water mixture mobile phase.

FIG. 12 depicts experimental data 107 of the Clarithromycin adsorption isotherm, the fitted absorption isotherm 108 for Clarithromycin, experimental data 109 of the 6,11 adsorption isotherm and 6,11 fitted adsorption isotherm 110 in 80% Ethanol. The extent of the experimental data 109 for the 6,11 isotherm was limited by the solubility of 6,11 in 80% volume Ethanol. However, the isotherm curve for 6,11 110 was extrapolated. The 80% Ethanol mobile phase exhibited less difference in the adsorption of Clarithromycin and 6,11. Therefore, the 60% Ethanol mobile phase is preferred to the 80% Ethanol mobile phase.

The experimental data 103 of Clarithromycin in 60% Ethanol mobile phase showed significant convex nonlinearity. As such, the Clarithromycin isotherm data 103 was fit to a Langmuir equation to produce the following equation for Clarithromycin curve 104.

$$Q_{Clari} = \frac{a_i C}{1 + b_i C} = \frac{35.95 C}{1 + 0.20 C} \quad (24)$$

It should be noted that at low concentrations the experimental data 103 appeared to be fairly linear. The experimental data 105 of 6,11 was limited because of the low solubility of 6,11 in the solvent or mobile phase. As such, the complete isotherm for 6,11 was estimated from the available data and an assumption that both Clarithromycin and 6,11 have the same adsorption capacity, $Q_{max}$. The adsorption capacity of Clarithromycin was calculated by plugging an infinite concentration into its Langmuir isotherm curve 104:

$$Q_i = \frac{a_i C}{1 + b_i C} \stackrel{C \to \infty}{\approx} Q_{max} = \frac{a_i}{b_i} = \frac{35.95}{0.20} \quad (25)$$

Using this value and the experimental data set 105 available, a Langmuir equation for 6,11 produced the following equation for 6,11 curve 106:

$$Q_{6,11} = \frac{47.58C}{1 + 0.265C} \quad (26)$$

The characteristics of the Optipore adsorbent must be determined to properly optimize the zone flow rates and switching time for the SMB system. The Optipore adsorbent was separated based upon particle size for further study. Four columns were packed with Optipore adsorbent having particle size in the range of 300–420 micrometers. Four additional columns were packed with Optipore adsorbent having particle size in the range of 38–150 micrometers.

When an adsorbent is packed into a column, there is a certain amount of space between the adsorbent particles, which is characterized by the interparticle porosity, $\epsilon_b$, which is the volumetric fraction that is void space between the particles. Another characteristic of the column is the intraparticle porosity, $\epsilon_p$, which is the volumetric fraction of the solid particle that is pores. These two properties of an adsorbent packed in a column are combined to give the total void fraction of the column, $\epsilon_t$, as shown by the following equation:

$$\epsilon_t = \epsilon_b + (1 - \epsilon_b)\epsilon_p \quad (27)$$

where $\epsilon_t$ is the total void fraction of the column, $\epsilon_b$ is the interparticle porosity, and $\epsilon_p$ is the intraparticle porosity.

The porosity characteristics for the two size ranges of the Optipore adsorbent are provided in Table B. The small particle columns had a smaller interparticle porosity due to the smaller particle's wider particle size distribution (the smaller particle size varies by 60% from its median while the larger particle size varies by 17%).

TABLE B

| Adsorbent Characteristics | | |
|---|---|---|
| Particle Size | 300–420 μm | 38–150 μm |
| $\epsilon_b$ | .428 | .370 |
| $\epsilon_p$ | .664 | .664 |
| $\epsilon_t$ | .808 | .788 |

The mass transfer properties of both Clarithromycin, 6,11, and the Optipore adsorbent packed columns are also estimated. The estimated mass property parameters include a Brownian diffusivity, $D_{oo}$, particle diffusivity, $D_p$, the film mass transfer coefficient, $k_f$, and an axial dispersion coefficient, $E_b$. The Brownian diffusivities, $D_{oo}$, of Clarithromycin and 6,11 in 60% ethanol was estimated to be 0.00023 cm²/min using a correlation from Wilke and Chang, "Correlation of Diffusion Coefficients in Dilute Solutions," *AIChE Journal*, June 1955, the disclosure of which is hereby incorporated by reference. The film mass transfer coefficient, $k_f$, was estimated to be (0.12–0.15) cm/min using a correlation from Wilson and Geankoplis, "Liquid mass transfer at very low Reynolds numbers in packed beds," *Ind. Eng. Chem. Fund.*, 1966, the disclosure of which is hereby incorporated by reference, and the axial dispersion coefficient, $E_b$, was estimated to be (0.006–0.011) cm²/min using a correlation from Chung and Wen, the disclosure of which is hereby incorporated by reference. Finally, the particle diffusivity, $D_p$, was estimated to be 0.000035 cm²/min using the Mackie-Meares equation discussed in Mackie and Meares, "The diffusion of electrolytes in a cation-exchange resin membrane," *Proc. Roy. Soc. London*, Ser. A., 1955 the disclosure of which is hereby incorporated by reference.

To validate the mass transfer parameters, the isotherms, and the column characteristics, simulations of several frontal experiments were done. To insure consistency, simulations were run for all four cases: Clarithromycin using large adsorbent particles (300–420 μm), 6,11 using large adsorbent particles (300–420 μm), Clarithromycin using small adsorbent particles (38–150 μm), and 6,11 using small adsorbent particles (38–150 μm).

All computer simulations in the present invention, unless otherwise noted, are performed using the VERSE (VErsatile Reaction SEparation model) computer simulation program, developed by Whitley and Wang and available from Purdue University located in West Lafayette, Ind. VERSE is a detailed simulation package used to solve the general rate model equations for liquid chromatography systems. The rate model equations in VERSE include several mass transfer effects: axial dispersion, film mass transfer, intraparticle diffusion, surface diffusion, and convection.

VERSE is capable of simulating many types and modes of chromatography including simulated moving beds. The VERSE simulation package assumes that: the column is packed with homogeneous spherical particles with uniform particle and pore size, the column has uniform packing and flow distribution, all processes are isothermal, concentration gradients in the radial direction of the column are negligible, concentration gradients in the angular direction of a particle are negligible, intraparticle diffusion can occur via pore diffusion, surface diffusion, or parallel diffusion, and mass transfer coefficients are constant and independent of other components.

Figure 13A:
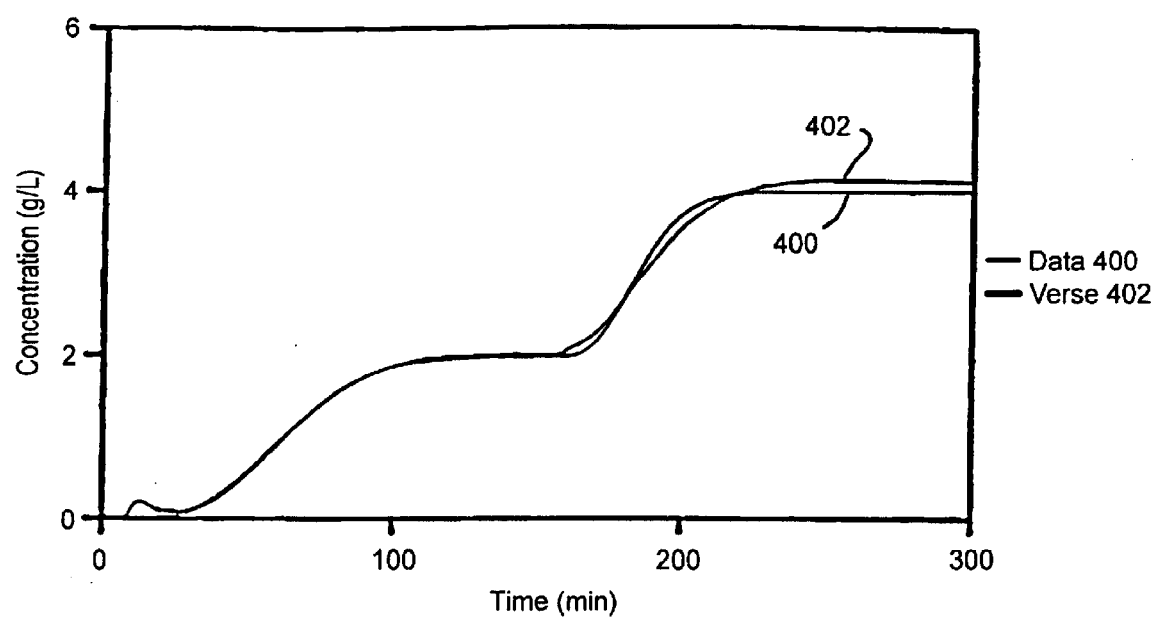
FIG. 13a shows a comparison of experimental frontals and computer simulation frontals for 2 g/L of Clarithromycin followed by 4 g/L of Clarithromycin in a column packed with 360 micrometer adsorbent particles.
Figure 13B:
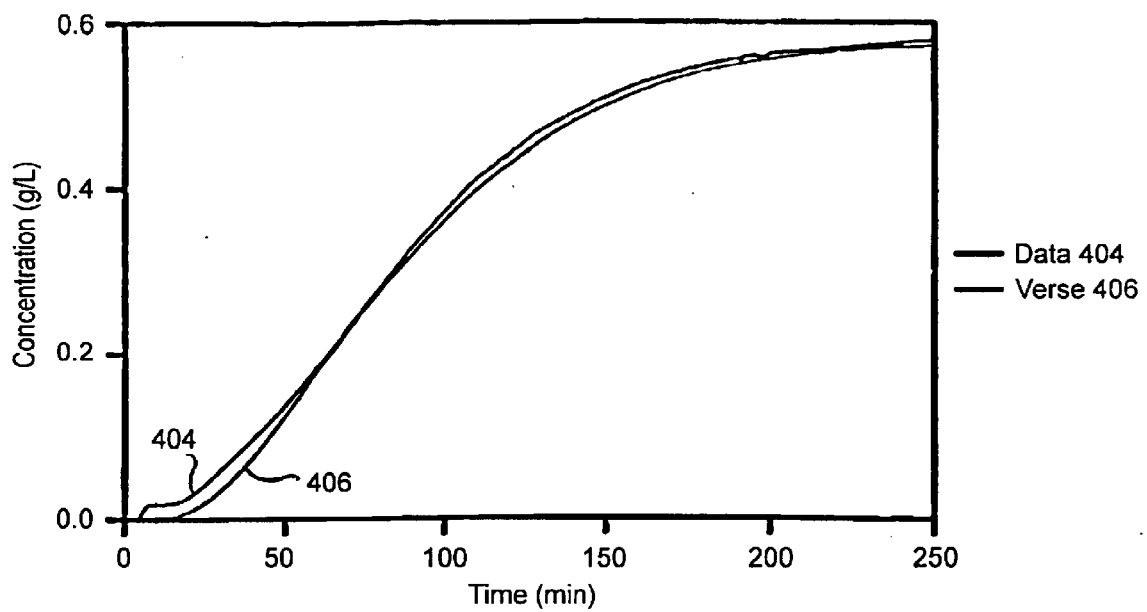
FIG. 13b shows a comparison of experimental frontals and computer simulation frontals for 0.58 g/L of 6, 11 in a packed column with 360 micrometer adsorbent particles.
Figure 13C:
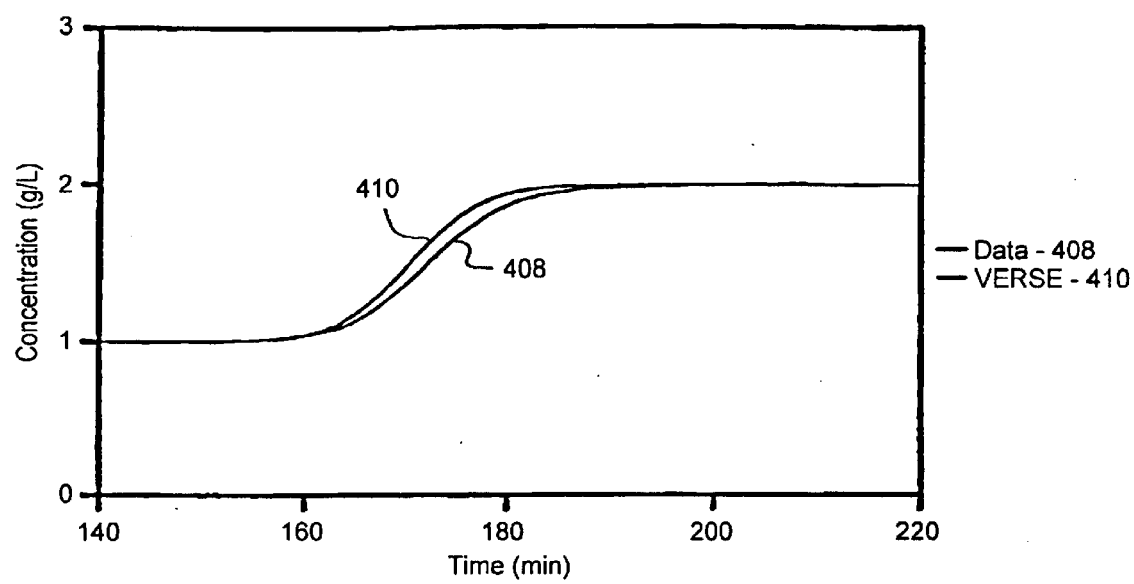
FIG. 13c shows a comparison of experimental frontals and computer simulation frontals for 2.00 g/L of Clarithromycin in a packed column with 100 micrometer adsorbent particles.
Figure 13D:
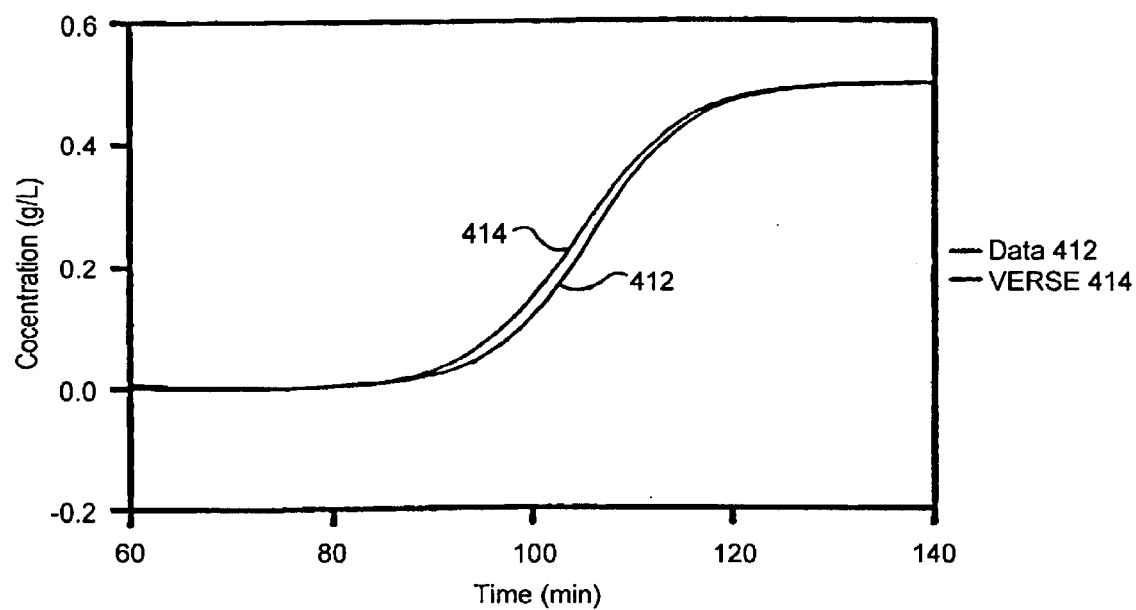
FIG. 13d shows a comparison of experimental frontals and computer simulation frontals for 0.50 g/L of 6, 11 in a packed column with 100 micrometer adsorbent particles.

The results of the frontal simulations are shown in FIGS. 13a–d. FIG. 13a shows a comparison of experimental frontals 400 and VERSE simulation frontals 402 for 2 g/L of Clarithromycin in a column packed with 360 μm adsorbent particles. FIG. 13b shows a comparison of experimental frontals 404 and VERSE simulation frontals 406 for 0.58 g/L of 6,11 in a packed column with 360 μm adsorbent particles. FIG. 13c shows a comparison of experimental frontals 408 and VERSE simulation frontals 410 for 2 g/L of Clarithromycin in a packed column with 100 μm adsorbent particles. FIG. 13d shows a comparison of experimental frontals 412 and VERSE simulation frontals 414 for 0.5 g/L of 6,11 in a packed column with 100 μm adsorbent particles. The simulations and the experimental data had good agreement. As such, the mass transfer parameters are validated. Further, these tests support the use of VERSE simulations to predict simulated moving bed experimental results.

Figure 14:
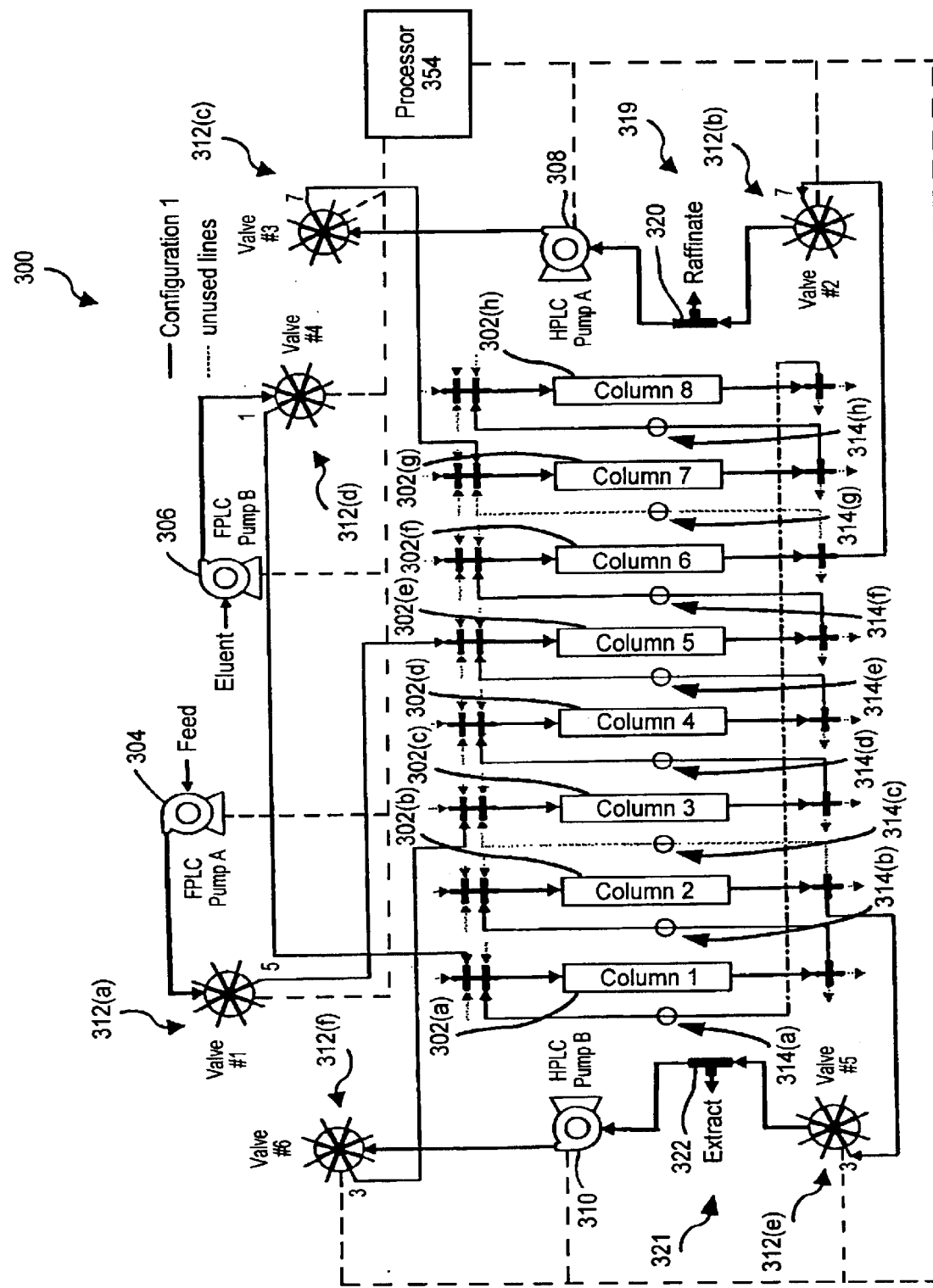
FIG. 14 shows a diagrammatic representation of a lab scale simulated moving bed system having four zones.

A comparison was carried out to compare the optimized zone flow rates and switching time between equations assuming solutes exhibiting linear adsorption and negligible mass transfer resistances, equations assuming solutes exhibiting linear adsorption and non-negligible mass transfer resistances, equations assuming solutes exhibiting non-linear adsorption and negligible mass transfer resistances, and equations assuming solutes exhibiting non-linear adsorption and non-negligible mass transfer resistances for the separation of Clarithromycin and 6,11 with a lab-scale SMB 300, shown in FIG. 14. As shown below in Table D, the comparison showed that the equations assuming non-linear adsorption and non-negligible mass transfer resistances provided superior estimates of the zone flow rates and switching time than the other systems.

Referring to FIG. 14, simulated moving bed 300 includes eight columns, 302a–h. Columns 302a–h are each Omnifit Model No. 6412 glass columns. These columns are 12.2 centimeters in bed length and 1.5 centimeters in diameter. Simulated moving bed 300 further includes four pumps, 304, 306, 308, 310. Pumps 304 and 306 are Pharmacia Biotech Model P-500 pumps. Pumps 308 and 310 are Waters Model No. 510 pumps. Simulated moving bed 300 further includes six eight way rotary valves 312a–f. Valves 312a–f are Pharmacia Model No. MV-8 valves. Simulated moving bed 300 further includes eight manual valves 314a–h. In one embodiment, a controller 354 controls the positioning of the valves and the flow rates of the pumps in simulated moving bed 300. An example controller for use in a simulated moving bed 300 is a Pharmacia Biotech Controller Model LCC-501.

Each column 302a–h is connected to each rotary valve 312a–f. By having each column 302a–h connected to valves 312a–f, eight different configurations are possible for simulated moving bed 300. Referring to FIG. 14, a first configuration of simulated moving bed 300 is shown. Referring to Table C, the valve position for each rotary valve and each manual valve is given for the eight configurations of simulated moving bed 300.

In the first configuration shown in FIG. 14, a feed solution is introduced to column 302e through valve 312a. The feed solution is pumped into column 302e by pump 304. As the feed solution flows into columns 302e it combines with the outlet flow from column 302d. The solution that exits column 302e enters column 302f through manual valve 314f. The solution exiting column 302f enters valve 312b. The solution exiting valve 312b splits into the outlet stream called the Raffinate 319 and solution to pump 308. An air trap is positioned at a splitting point 320 just before pump 308 to allow air bubbles to exit SMB 300. The solution from pump 308 enters valve 312c and is then fed into column 302g. The solution exiting column 302g enters column 302h through manual valve 314h. Solution exiting 302h flows through manual valve 314a and is combined with a Mobile Phase (Eluent) and flows into column 302a. The Mobile Phase is pumped through valve 312d by pump 306. The Mobile Phase is provided to make up for the loss of column flow due to the loss of flow to the Raffinate. The solution upon exiting column 302a enters column 302b through manual valve 314b. Upon exiting column 302b the solution is fed through valve 312e and splits into an outlet stream called the Extract 321 and solution to pump 310. An air trap is provided at a splitting point 322 between valve 312e and pump 310 to allow air bubbles to exit SMB 300 before entering pump 310. The solution upon exiting pump 310 enters valve 312f and is fed into column 302c. The solution exiting 302c enters column 302d through manual valve 314d. Upon exiting column 302d the solution flows through manual valve 314e and combines with the feed solution from pump 304 and enters column 302e.

Prior to operation SMB 300 is cleaned with the mobile phase which is going to be used in the particular experiment. Any air present in columns 302a–h or the lines connecting columns 302a–h and the various valves and pumps is removed. Pumps 308 and 310 are primed and calibrated. Next, pumps 304 and 306 are connected to the rest of the system. Pump 304 is primed with feed solution. Pump 306 is primed with mobile phase. The manual valves are placed in either the open or closed position based upon the starting configuration of SMB 300.

Valves 312a–f in a preferred embodiment are controlled by controller 354 and are positioned according to a software program configured to control the operation of SMB 300. Once SMB 300 is set up, the feed and eluent pumps 304 and 306 begin pumping and pumps 308 and 310 are set to their optimized flow rates derived with either the first method, equations 17a–d or the second method for estimating the zone flow rates for separating solutes exhibiting non-linear adsorption isotherms and non-negligible mass transfer

TABLE C

Valve Settings for the Eight Configurations of SMB 300

Rotary Valves

| Config. # | Valve #1 | Valve #2 | Valve #3 | Valve #4 | Valve #5 | Valve #6 |
|---|---|---|---|---|---|---|
| 5 | 5 | 7 | 7 | 1 | 3 | 3 |
| 6 | 6 | 8 | 8 | 2 | 4 | 4 |
| 7 | 7 | 1 | 1 | 3 | 5 | 5 |
| 8 | 8 | 2 | 2 | 4 | 6 | 6 |
| 1 | 1 | 3 | 3 | 5 | 7 | 7 |
| 2 | 2 | 4 | 4 | 6 | 8 | 8 |
| 3 | 3 | 5 | 5 | 7 | 1 | 1 |
| 4 | 4 | 6 | 6 | 8 | 3 | 2 |

Manual Valves

| Config. # | Valve #1 | Valve #2 | Valve #3 | Valve #4 | Valve #5 | Valve #6 | Valve #7 | Valve #8 |
|---|---|---|---|---|---|---|---|---|
| 1 | Open | Open | Closed | Open | Open | Open | Closed | Open |
| 2 | Open | Open | Open | Closed | Open | Open | Open | Closed |
| 3 | Closed | Open | Open | Open | Closed | Open | Open | Open |
| 4 | Open | Closed | Open | Open | Open | Closed | Open | Open |
| 5 | Open | Open | Closed | Open | Open | Open | Closed | Open |
| 6 | Open | Open | Open | Closed | Open | Open | Open | Closed |
| 7 | Closed | Open | Open | Open | Closed | Open | Open | Open |
| 8 | Open | Closed | Open | Open | Open | Closed | Open | Open | resistances, equations 21a–d. SMB 300 remains in configuration 1 until the designated switching time calculated with the iterative process of either the first method or the second method. Once the switching time is reached valves 312a–f and 314a–h are changed to their corresponding configuration 2 positions provided in Table B. Followed by their corresponding configuration 3 positions after a second switching interval and so forth through the number of configurations of the SMB system.

SMB 300 was simulated using the VERSE program to compare the equations assuming solutes exhibiting linear adsorption and negligible mass transfer resistances, the equations assuming solutes exhibiting linear adsorption and non-negligible mass transfer resistances, the equations assuming solutes exhibiting non-linear adsorption and negligible mass transfer resistances, and the equations assuming solutes exhibiting non-linear adsorption and non-negligible mass transfer resistances for the various methods. Each simulation had a target purity of 95%. The feed concentration was assumed to be 2.0 g/L Clarithromycin and 0.55 g/L 6,11. Each simulation was run for 30 cycles using the VERSE program. Table D shows the results of the simulations. As seen in Table D the equations assuming solutes exhibiting non-linear adsorption and non-negligible mass transfer resistances was the only group to provide zone flow rates and switching time that achieved the target purity.

TABLE D

Comparison of the equations assuming solutes exhibiting non-linear adsorption and non-negligible mass transfer resistances other systems

| System | 8 Column Simulated Moving Bed in (2-2-2-2) | |
|---|---|---|
| | Purity | Yield |
| Linear Adsorption, Negligible Mass Transfer Resistances | | |
| Raffinate | 76.2% | 60.1% |
| Extract | 13.1% | 24.3% |
| Linear Adsorption, Non-Negligible Mass Transfer Resistances | | |
| Raffinate | 91.5% | 93.9% |
| Extract | 71.2% | 60.8% |
| Non-Linear Adsorption, Negligible Mass Transfer Resistances | | |
| Raffinate | 86.7% | 90.9% |
| Extract | 61.0% | 50.5% |
| Non-Linear Adsorption, Non-Negligible Mass Transfer Resistances | | |
| Raffinate | 95.0% | 90.4% |
| Extract | 63.3% | 77.8% |

Feed: 2.0 g/L Clarithromycin, 0.55 g/L 6, 11, 0.2 ml/min

A series of simulated moving bed experiments were carried out with SMB 300 to validate the mass transfer parameters and to determine the ability of the VERSE model to simulate a simulated moving bed system configured to separate two solutes having non-linear adsorption isotherms and non-negligible mass transfer resistances. A feed solution was created with a mixture of Clarithromycin and 6,11 in a Ethanol/water solution comprising 60% Ethanol. The resulting concentrations were 1.78 g/L Clarithromycin and 1.37 g/L 6,11.

In each experiment at least one of the expected purity and yield of Clarithromycin and 6,11 or the experimental purity and yield of Clarithromycin and 6,11 are reported. The purities of Clarithromycin and 6,11 are calculated as:

$$Purity_{Clari} = \frac{R_C}{R_C + R_{6,11}} \quad (28)$$

where $R_C$ is the weight of Clarithromycin recovered in the Raffinate and $R_{6,11}$ is the weight of 6,11 present in the Raffinate. Note that this does not take into account any other impurities present.

$$Purity_{6,11} = \frac{E_{6,11}}{E_C + E_{6,11}} \quad (29)$$

where $E_{6,11}$ is the weight of 6,11 recovered in the Extract and $E_C$ is the weight of Clarithromycin present in the Extract. The yields of Clarithromycin and 6,11 are calculated as:

$$Yield_{Clari} = \frac{R_C}{Feed_C} \quad (30)$$

where $R_C$ is the weight of Clarithromycin recovered in the Raffinate and $Feed_C$ is the weight of Clarithromycin present in the Feed.

$$Yield_{Clari} = \frac{R_C}{Feed_C} \quad (31)$$

where $E_{6,11}$ is the weight of 6,11 recovered in the Extract and $Feed_{6,11}$ is the weight of 6,11 present in the Feed. Both the purities and the yields can be calculated based on the concentrations of Clarithromycin and 6,11 at the Raffinate, the Extract and the Feed.

Four Zone SMB Experiment #1

Figure 15A:
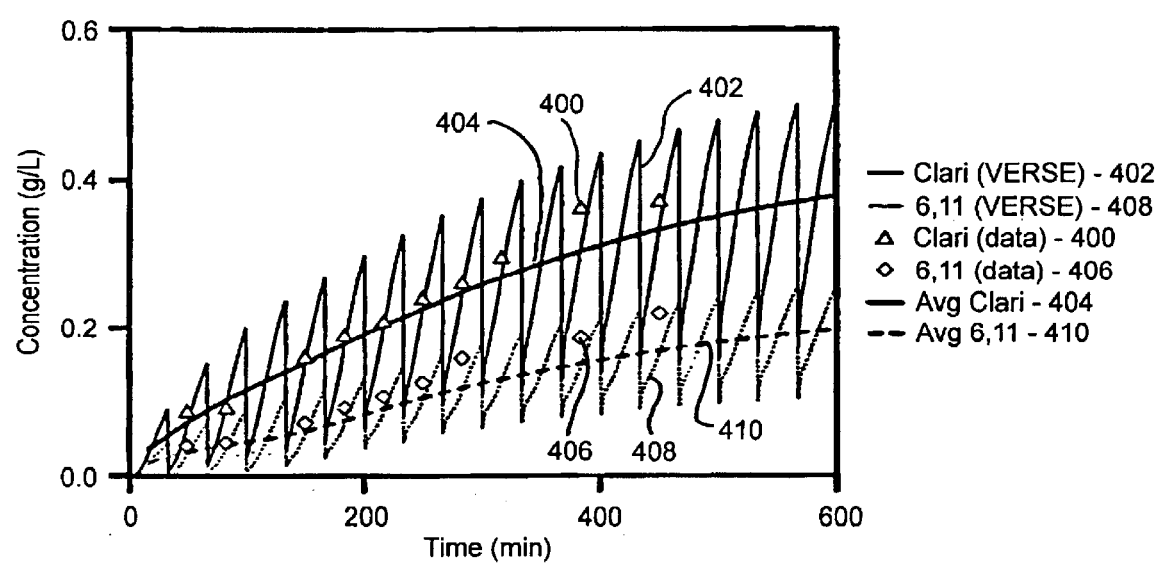
FIG. 15a shows the experimental and simulated Raffinate histories for Experiment #1.
Figure 15B:
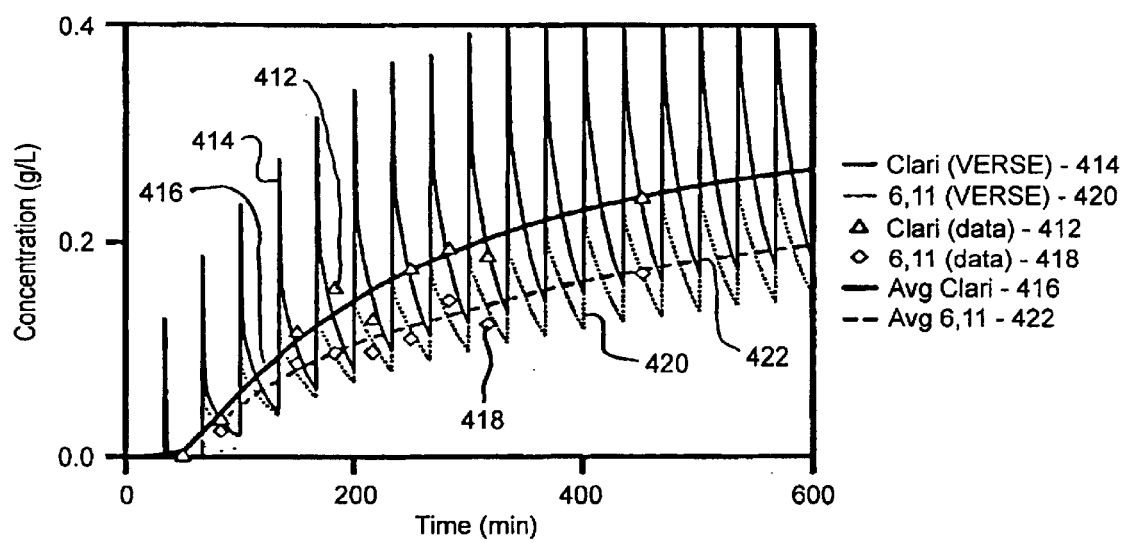
FIG. 15b shows the experimental and simulated histories for the Extract of Experiment #1.

SMB 300 was configured having four columns in a (1-1-1-1) zone configuration packed with 200–420 µm particles. The parameters for SMB Experiment #1 are shown in Table E. The optimal zone flow rates and switching time were optimized by solving the equations assuming solutes exhibiting linear adsorption isotherms and non-negligible mass transfer resistances, equations 8a–d and 12. The experiment was carried out in 467.6 minutes, allowing the system to make 14 switching time periods and approach a steady state elution profile. The results of samples taken from the Raffinate and Extract outlets are shown in FIGS. 15a and 15b. These samples were taken over entire switching time periods, so they represent the average concentration during their respective cycle. FIG. 15a shows the concentration of Clarithromycin and 6,11 in the Raffinate including Clarithromycin experimental data set 400, Clarithromycin simulated profile 402, Clarithromycin simulated average profile 404, 6,11 experimental data set 406, 6,11 simulated profile 408, 6,11 simulated average profile 410. FIG. 15b shows the concentration of Clarithromycin and 6,11 in the Extract including Clarithromycin experimental data set 412, Clarithromycin simulated profile 414, Clarithromycin simulated average 416, 6,11 experimental data set 418, 6,11 simulated profile 420, and 6,11 simulated average profile 422.

Figure 15C:
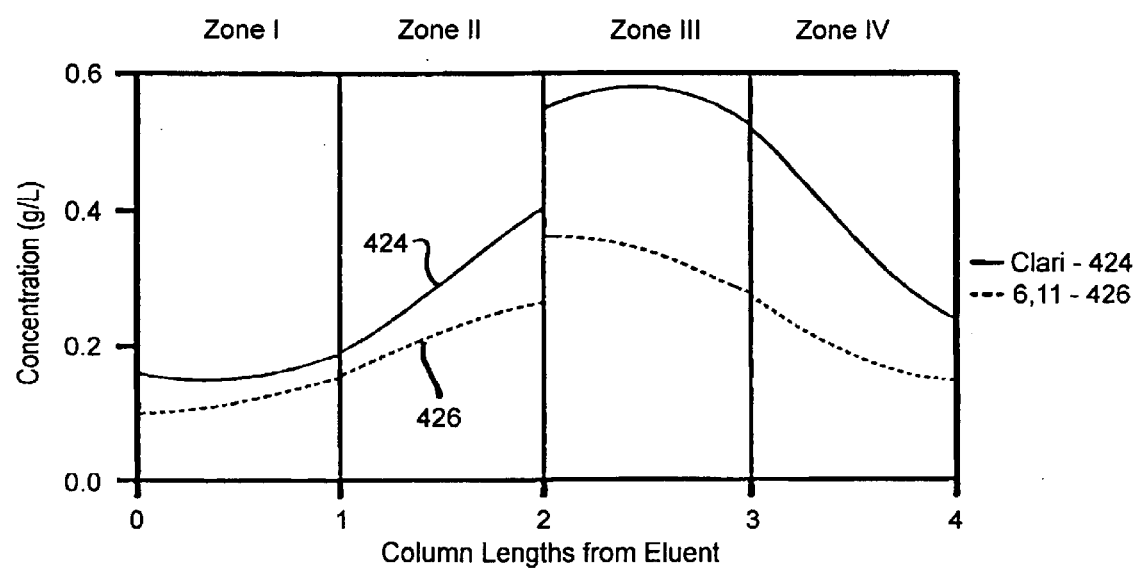
FIG. 15c shows the simulated column profiles for Experiment #1 at the end of the twentieth switching cycle.

FIG. 15c shows the four simulated column profiles, for Clarithromycin 424 and 6,11 426. From these it can be seen that the optimized zone flow rates and switching time were insufficient for keeping the Clarithromycin and 6,11 waves within their designated zones, causing overlapping throughout the system and eliminating most of the separation. The final results of this Experiment are shown in Table F. Though this Experiment did not yield sufficient separation of Clarithromycin and 6,11, it did confirm that the data from SMB system 300 and the VERSE simulations were fairly consistent with one another.

TABLE E

Parameters for Four Zone SMB Experiment #1

Description of System

Four 360 μm particle, 12.2 cm length columns, 1-1-1-1 column configuration

| | |
|---|---|
| Feed: | 1.78 g/L Clarithromycin |
| | 1.37 g/L 6,11 |

Flow Rates

| | |
|---|---|
| Feed = | 0.43 ml/min |
| Mobile Phase = | 1.68 ml/min |
| Raffinate = | 0.93 ml/min |
| Extract = | 1.18 ml/min |
| Zone I = | 5.08 ml/min |
| Zone II = | 3.90 ml/min |
| Zone III = | 4.33 ml/min |
| Zone IV = | 3.40 ml/min |
| Switching Time | 33.4 min |

TABLE F

Results for Four Zone SMB Experiment #1

| | Expected Results | | Experimental Results | |
|---|---|---|---|---|
| | Purity | Yield | Purity | Yield |
| Raffinate | 67.1% | 52.4% Raffinate | 62.7% | 54.9% |
| Extract | 41.9% | 57.1% Extract | 41.5% | 49.5% |

Four Zone SMB Experiment #2

SMB 300 was configured having four columns in a (1-1-1-1) configuration and being packed with 360 μm adsorbent particles. The zone flow rates and switching times were optimized from equations 17a–d and 18 for solutes exhibiting non-linear adsorption isotherms and non-negligible mass transfer resistances. Table G provides the parameters for Experiment #2.

Figure 16:
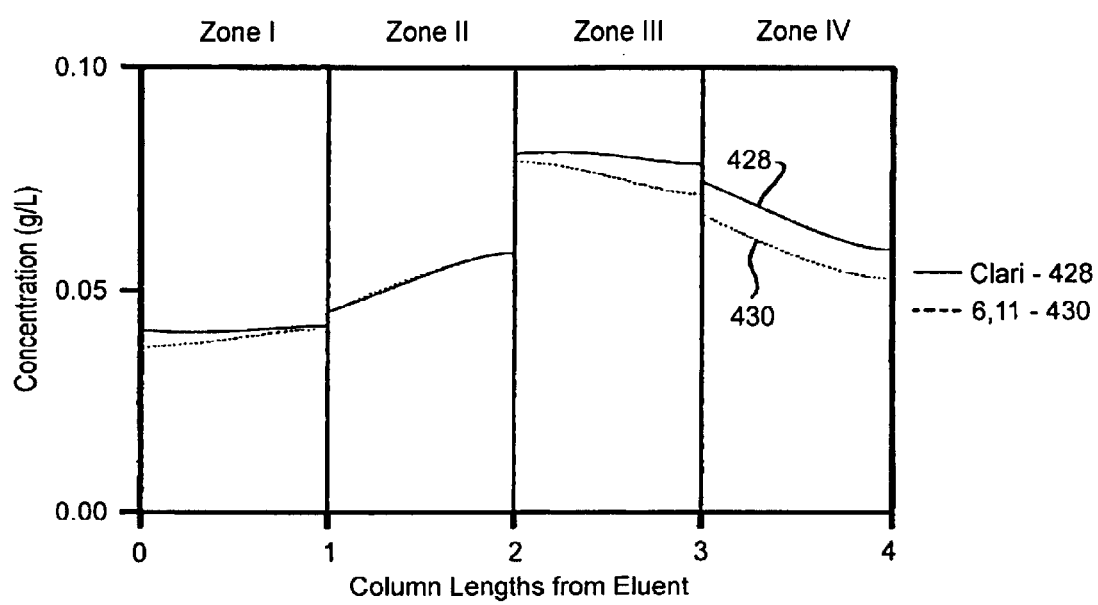
FIG. 16 shows the simulated column profiles for Experiment #2.

The expected results and the simulated column profiles for Clarithromycin 428 and 6,11 430 are shown in Table H and FIG. 16, respectively. Little separation was achieved with the setup of Experiment #2.

TABLE G

Parameters for Four Zone SMB Experiment #2

Description of System

Four 360 μm columns, 1-1-1-1 column configuration

| | |
|---|---|
| Feed: | 0.5 g/L Clarithromycin |
| | 0.5 g/L 6,11 |

Flow Rates

| | |
|---|---|
| Feed = | 0.2 ml/min |
| Mobile Phase = | 1.6 ml/min |
| Raffinate = | 0.5 ml/min |
| Extract = | 1.2 ml/min |

TABLE G-continued

Parameters for Four Zone SMB Experiment #2

| | |
|---|---|
| Zone I = | 5.2 ml/min |
| Zone II = | 4.0 ml/min |
| Zone III = | 4.2 ml/min |
| Zone IV = | 4.7 ml/min |
| Switching Time | 51.0 min |

TABLE H

Results for Four Zone SMB Experiment #2

| | Expected Results | | Experimental Results | |
|---|---|---|---|---|
| | Purity | Yield | Purity | Yield |
| Raffinate | 52.9% | 39.1% Raffinate | 62.7% | 54.9% |
| Extract | 50.2% | 63.9% Extract | 41.5% | 49.5% |

Four Zone SMB Experiment #3

Figure 17:
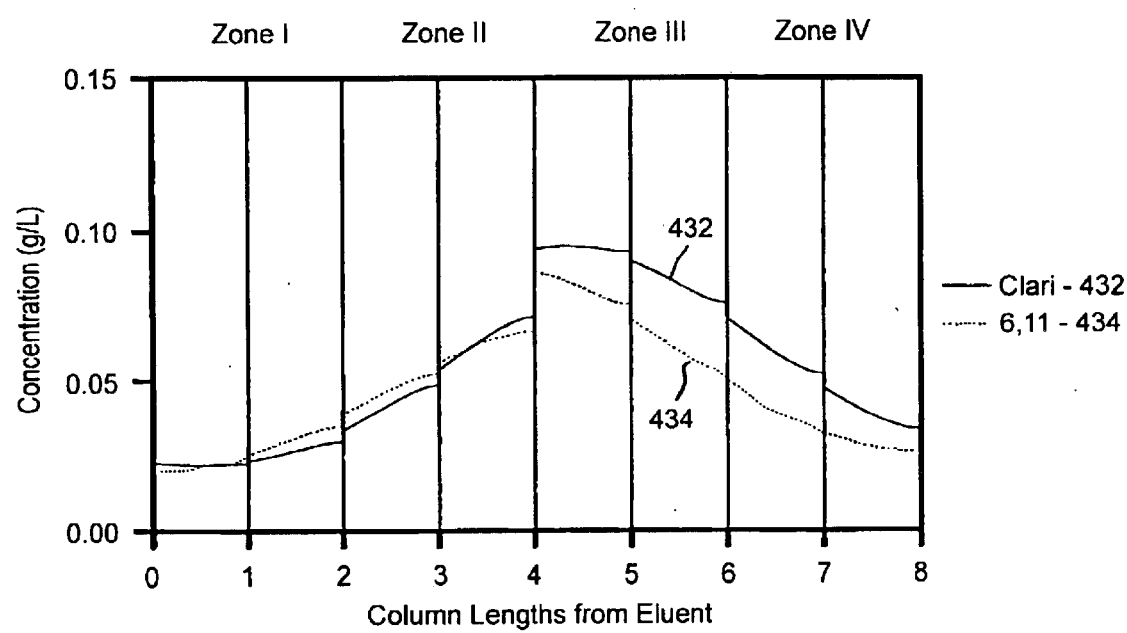
FIG. 17 shows the simulated column profiles for both Clarithromycin and 6,11 in Experiment #3.

SMB 300 was configured with eight columns in a (2-2-2-2) configuration and the columns were packed with 360 μm adsorbent particles. The zone flow rates and switching times were optimized from equations 17a–d and 18 for solutes exhibiting non-linear adsorption isotherms and non-negligible mass transfer resistances. The parameters for Experiment #3 are shown in Table I. As shown in Table J, the simulated results of Experiment #3 for the separation of Clarithromycin and 6,11 are a mild improvement over the results of Experiment #2. FIG. 17 shows the column profiles of Clarithromycin 432 and 6,11 434 for Experiment #3.

The lack of separation in both Experiments #2 and #3 may be attributed to slow pore diffusion in and out of the large adsorbent particles. Slow pore diffusion results in the spreading of the adsorption and desorption waves. This spreading reaches its limit at a certain length of a column called the mass transfer zone length. At this point, the adsorption and desorption waves keep a steady profile. The spreading limitation can be overcome by using columns having lengths longer than the mass transfer zone length of the adsorbent.

TABLE I

Parameters for Four Zone SMB Experiment #3

Description of System

Eight 360 μm columns, 2-2-2-2 column configuration

| | |
|---|---|
| Feed: | 0.5 g/L Clarithromycin |
| | 0.5 g/L 6,11 |

Flow Rates

| | |
|---|---|
| Feed = | 0.2 ml/min |
| Mobile Phase = | 1.5 ml/min |
| Raffinate = | 0.5 ml/min |
| Extract = | 1.2 ml/min |
| Zone I = | 5.1 ml/min |
| Zone II = | 3.9 ml/min |
| Zone III = | 4.1 ml/min |
| Zone IV = | 3.6 ml/min |
| Switching Time | 46.0 min |

TABLE J

Results for Four Zone SMB Experiment #3
Expected Results

| | Purity | Yield |
|---|---|---|
| Raffinate | 59.8% | 41.8% |
| Extract | 53.3% | 70.3% |

An alternative method of overcoming the spreading limitation is to reduce the particle size used in the columns. Reducing particle size results in a reduction of the mass transfer limitations and hence a reduction in the spreading of solute waves caused by pore diffusion. When the particle diameter is reduced, the distance the solute must diffuse in and out of the particle is reduced. Looking at Equation 9, decreasing the particle size results in an increase in $K_f$, the lumped mass transfer term. Turning to Equation 12, an increase in $K_f$ results in an increase in the possible purity for a given feed flow rate, $F^{Feed}$. Smaller particles make tighter packing easier (smaller $\epsilon_b$, as seen in Table B), increasing adsorption per solid volume. As such, decreasing the particle size increases the potential separation that can be achieved by a given packed bed volume. This is shown in Equation 12, wherein a decrease in $\epsilon_b$ results in an increase in the possible purity for a given feed flow rate. The remaining Four Zone SMB experiments were carried out using the smaller particle size, 38–150 microns. The remaining Four Zone SMB Experiments show that smaller particles are ideal for lab-scale SMB units.

Four Zone SMB Experiment #4

SMB 300 was configured with four columns in a (1-1-1-1) configuration and being packed with 38–150 $\mu$m adsorbent particles. The feed solution was changed to 0.41 g/L Clarithromycin and 0.15 g/L 6,11 dissolved in 60% volume Ethanol. The zone flow rates and switching time were optimized based on equations 21a–d and equation 22 for solutes exhibiting non-linear adsorption isotherms and non-negligible mass transfer resistances.

Since SMB 300 is a lab-scale system, the space between adjacent columns is often non-negligible and must be accounted for in determining the zone flow rates and switching time. The VERSE simulations included a 5 ml CSTR (continuously stirred tank reactor) volume before and after each column. This CSTR volume is not included in the equations 17a–d and 18, but is taken into account in the iteration for the switching time. As long as the VERSE simulation predicts accurate experimental results, the iteration step can be used to eliminate error caused by extra-column volume.

The parameters used for SMB Experiment #4 are shown in Table K. The expected results derived from simulation are shown in Table L. The Experiment was carried out for 10 cycles, or 685.0 minutes. The purity and yield of the two streams for the final cycle are shown in Table L. The purity of the Raffinate was higher than expected, but the yield of Clarithromycin was very low. Since the lost Clarithromycin must be present in the Extract, the Extract purity was very low. Although the yield was poor, this Experiment showed that the separation of Clarithromycin and 6,11 with SMB 300 was possible.

TABLE K

Parameters for Four Zone SMB Experiment #4

| Description of System | |
|---|---|
| Four 100 $\mu$m columns, 1-1-1-1 column configuration | |
| Feed: | 0.41 g/L Clarithromycin |
| | 0.15 g/L 6,11 |
| Flow Rates | |
| Feed = | 0.4 ml/min |
| Mobile Phase = | 1.1 ml/min |
| Raffinate = | 0.6 ml/min |
| Extract = | 0.9 ml/min |
| Zone I = | 3.5 ml/min |
| Zone II = | 2.6 ml/min |
| Zone III = | 3.0 ml/min |
| Zone IV = | 2.4 ml/min |
| Switching Time | 68.6 min |

TABLE L

Results for Four Zone SMB Experiment #4

| | Expected Results | | | Experimental Results | |
|---|---|---|---|---|---|
| | Purity | Yield | | Purity | Yield |
| Raffinate | 97.1% | 90.6% | Raffinate | ~99% | 13.9% |
| Extract | 80.4% | 93.5% | Extract | 40.1% | ~99% |

Four Zone SMB Experiment #5

SMB 300 was configured with four columns in a (1-1-1-1) configuration and being packed with 38–150 $\mu$m adsorbent particles. The zone flow rates and switching time were optimized based on equations 17a–d and equation 18 for solutes exhibiting non-linear adsorption isotherms and non-negligible mass transfer resistances. The concentrations of the feed were increased to 0.69 g/L Clarithromycin and 0.21 g/L 6,11. The operating parameters of Experiment #5 are given in Table M. The Experiment was carried out for 17 cycles, or 688.5 minutes, to more closely approach steady-state profiles. The expected purities and yields based on VERSE simulation are shown in Table N, along with the experimental purities and yields.

TABLE M

Parameters for Four Zone SMB Experiment #5

| Description of System | |
|---|---|
| Four 100 $\mu$m columns, 1-1-1-1 column configuration | |
| Feed: | 0.69 g/L Clarithromycin |
| | 0.21 g/L 6,11 |
| Flow Rates | |
| Feed = | 0.4 ml/min |
| Mobile Phase = | 2.1 ml/min |
| Raffinate = | 0.9 ml/min |
| Extract = | 1.6 ml/min |
| Zone I = | 6.1 ml/min |
| Zone II = | 4.5 ml/min |
| Zone III = | 4.9 ml/min |
| Zone IV = | 4.0 ml/min |
| Switching Time | 40.5 min |

TABLE N

Results for Four Zone SMB Experiment #5

| Expected Results | | | Experimental Results | | |
|---|---|---|---|---|---|
| | Purity | Yield | | Purity | Yield |
| Raffinate | 98.8% | 83.9% | Raffinate | 97.0% | 48.1% |
| Extract | 67.7% | 97.1% | Extract | 42.4% | 96.7% |

Figure 18A:
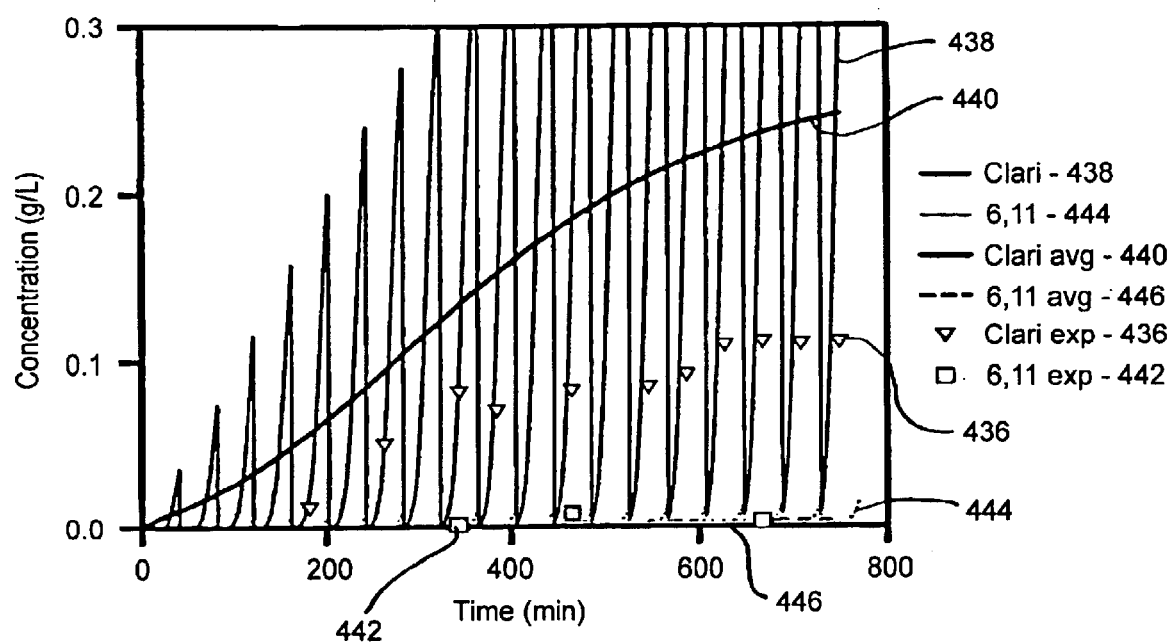
FIG. 18a shows the experimental and simulated histories for the Raffinate of Experiment #5.
Figure 18B:
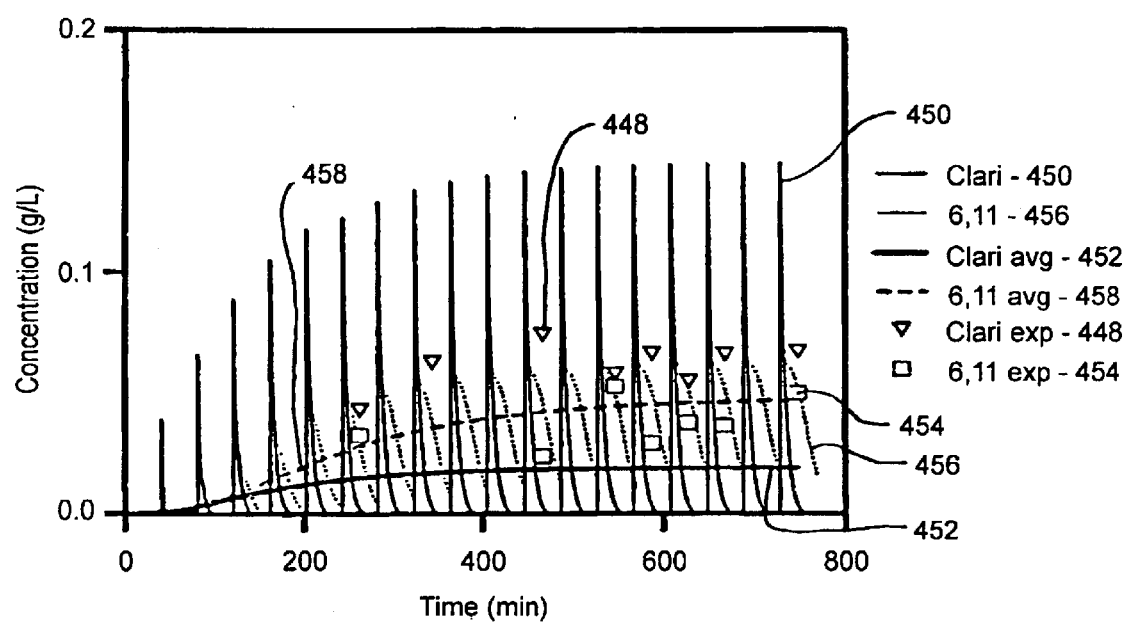
FIG. 18b shows the experimental and simulated histories of the Extract for Experiment #5.

Although the purity of the Clarithromycin product was close to the expected value, the yield was still 40% less than expected. The Raffinate and Extract data points for each cycle are graphed in FIGS. 18a and 18b along with the simulated elution profile and simulated average concentrations. FIG. 18a includes Clarithromycin experimental data set 436, Clarithromycin simulated profile 438, Clarithromycin average simulated profile 440, 6,11 experimental data set 442, 6,11 simulated profile 444, and 6,11 average simulated profile 446. FIG. 18b includes Clarithromycin experimental data set 448, Clarithromycin simulated profile 450, Clarithromycin average simulated profile 452, 6,11 experimental data set 454, 6,11 simulated profile 456, and simulated average profile 458.

Referring to Table N, the Raffinate had a purity close to the expected value, but the yield and concentration were lower than expected. One explanation for this is that the Clarithromycin solute wave did not travel as fast as expected, so a smaller portion of the Clarithromycin solute wave reached the Raffinate port. For the same reason, the remaining portion of the Clarithromycin solute wave would reach the Extract resulting in a higher than expected Clarithromycin concentration in the Extract.

The purities and yields from Experiment #5 suggest that the adsorption isotherm for Clarithromycin was inaccurate at the lower concentration range used in the Experiment. Since there were few adsorption data points at concentrations lower than 1 g/L, it was assumed that the isotherm only needed adjustment in this region, keeping the values at higher concentrations relatively the same. This way, the isotherm would support the new SMB experimental data while still fitting the original isotherm data points. This adjustment was made by increasing the linear coefficient, a, of the Clarithromycin isotherm, while also increasing the non-linear coefficient, b. The 6,11 isotherm was also changed. The $Q_{max}$, or adsorption capacity (see eq. 25), stayed the same for both the Clarithromycin and 6,11. The new isotherms are:

$$Q_{Clari} = \frac{40.27C}{1+0.26C} \quad (32)$$

$$Q_{6,11} = \frac{52.34C}{1+0.338C} \quad (33)$$

Figure 18C:
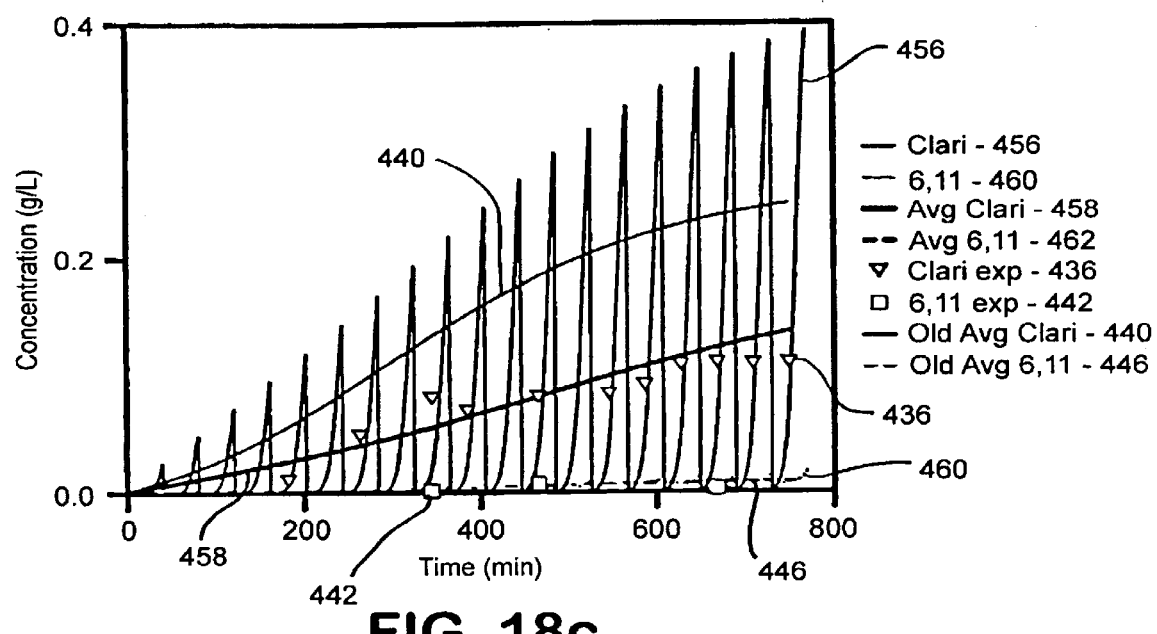
FIG. 18c shows the experimental profiles and revised simulated histories for Raffinate of Experiment #5.
Figure 18D:
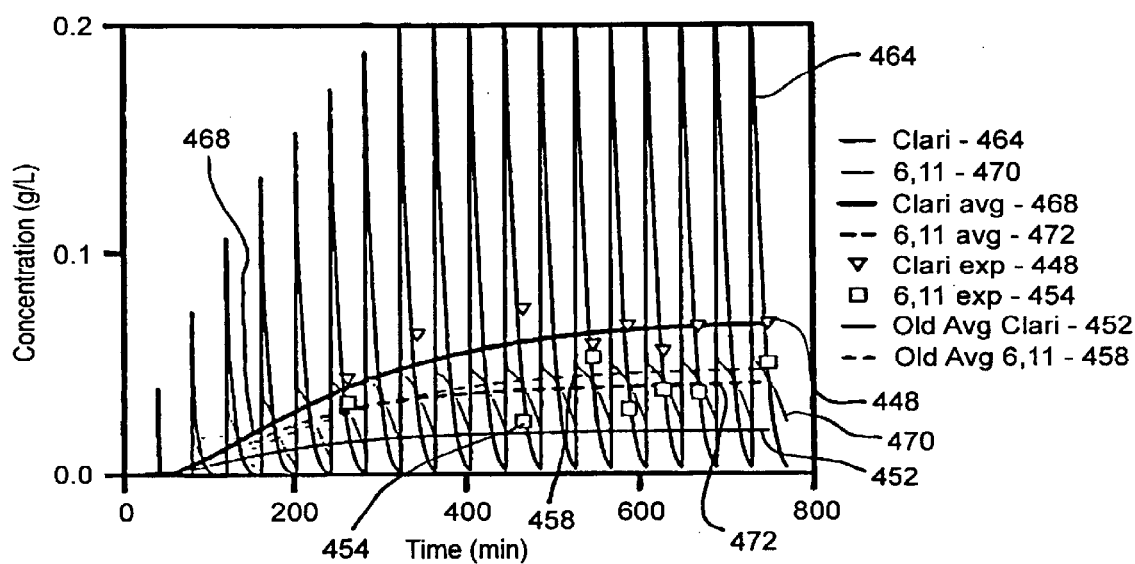
FIG. 18d shows the experimental profiles and revised simulated histories for the Extract of Experiment #5.

These new parameters were simulated under Experiment #5 operating conditions and the expected elution profiles are shown in FIGS. 18c and 18d against the experimental data sets 436, 442 and 448, 454, respectively. FIG. 18c corresponds to the Raffinate and shows the new simulated Clarithromycin 456 and the new average simulated Clarithromycin profile 458 the new 6,11 simulated profile 460, and the new simulated average 6,11 profile 462 profile 456. FIG. 18d corresponds to the Extract and shows the new simulated Clarithromycin profile 464, the new average Clarithromycin profile 468, the new simulated 6,11 profile 470 and the new average 6,11 profile 472. The new simulated results fit the experimental data well, supporting the isotherm parameters of equations 32 and 33. The new expected purities and yields are shown in Table O (Expected Results #2$^{nd}$ Run), and agree well with the experimental results shown in Table N.

TABLE O

Results for Four Zone SMB Experiment #5 - 2$^{nd}$ Run
Expected Results

| | Purity | Yield |
|---|---|---|
| Raffinate | 94.9% | 47.3% |
| Extract | 40.9% | 93.5% |

Four Zone SMB Experiment #6

The new isotherm values determined in Experiment #5 were used to derive parameters for a sixth experiment. SMB 300 was configured with four columns in a (1-1-1-1) configuration and being packed with 38–150 μm adsorbent particles. The zone flow rates and switching time were optimized based on equations 17a–d and equation 18 for solutes exhibiting non-linear adsorption isotherms and non-negligible mass transfer resistances. The parameters Experiment #6 are shown in Table P and the expected purities and yields are shown in Table Q. The feed concentrations and feed flow rate were kept the same as Experiment #5.

The small change in the isotherms resulted in a substantial change in the derived zone flow rates, increasing them dramatically. The Experiment was carried out for only 13 cycles due to operator error. Though this was not long enough to reach steady state, the trend of the outlet streams could be analyzed and evaluated. The experimental purities and yields of the outlet streams are shown in Table Q.

Figure 19A:
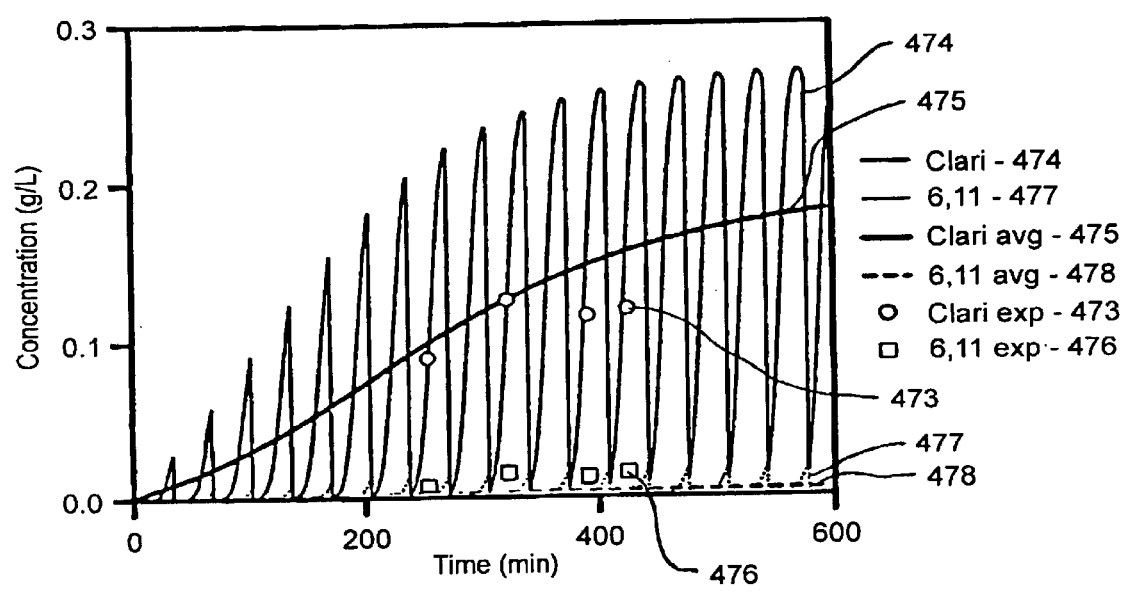
FIG. 19a shows the experimental and simulated histories for the Raffinate of Experiment #6.
Figure 19B:
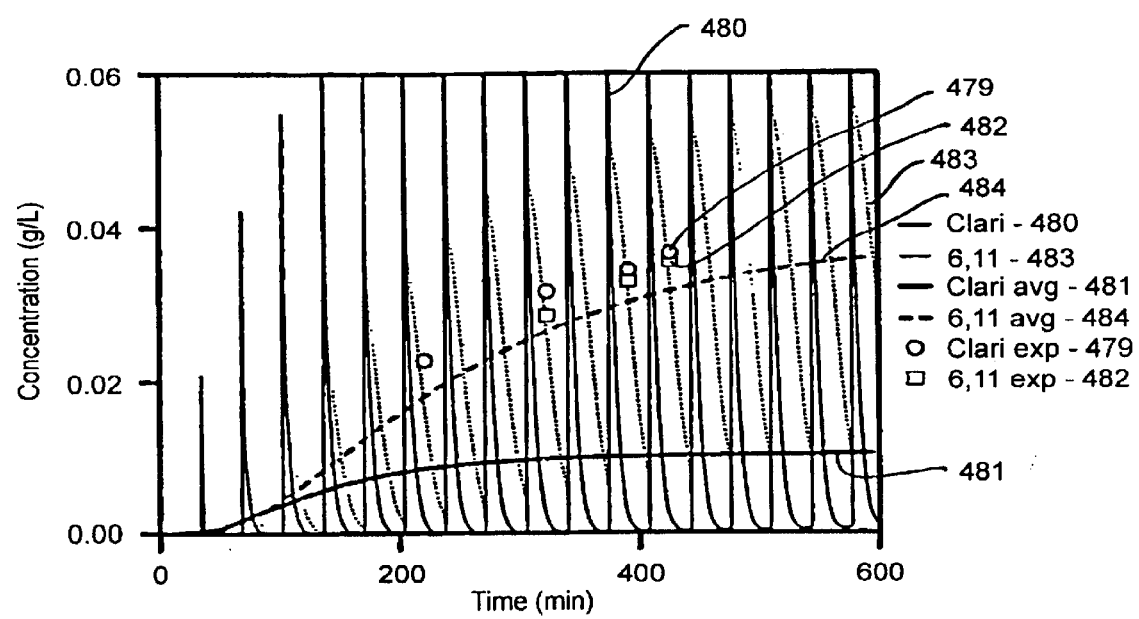
FIG. 19b shows the experimental and simulated histories for the Extract of Experiment #6.

The experimental data points are plotted against the expected elution profiles in FIGS. 19a and 19b.

TABLE P

Parameters for Four Zone SMB Experiment #6

| Description of System | |
|---|---|
| Four 100 μm columns, 1-1-1-1 column configuration | |
| Feed: | 0.69 g/L Clarithromycin |
| | 0.21 g/L 6,11 |
| Flow Rates | |
| Feed = | 0.4 ml/min |
| Mobile Phase = | 2.8 ml/min |
| Raffinate = | 1.3 ml/min |
| Extract = | 1.9 ml/min |
| Zone I = | 8.1 ml/min |
| Zone II = | 6.2 ml/min |
| Zone III = | 6.6 ml/min |
| Zone IV = | 5.3 ml/min |
| Switching Time | 34.0 min |

TABLE Q

Results for Four Zone SMB Experiment #6

| | Expected Results | | | Experimental Results | |
|---|---|---|---|---|---|
| | Purity | Yield | | Purity | Yield |
| Raffinate | 97.0% | 91.8% | Raffinate | 89.0% | 74.0% |
| Extract | 77.0% | 90.6% | Extract | 47.4% | 71.3% |

FIG. 19a, corresponding to the Raffinate, includes Clarithromycin experimental data set 473, Clarithromycin simulated profile 474, Clarithromycin average simulated profile 475, 6,11 experimental data 476, 6,11 simulated profile 477, and 6,11 simulated average profile 478. FIG. 19b, corresponding to the Extract, includes Clarithromycin experimental data set 479, Clarithromycin simulated profile 480, Clarithromycin average simulated profile 481, 6,11 experimental data 482, 6,11 simulated profile 483, and 6,11 simulated average profile 484. The Raffinate data points agree fairly well with expected average concentrations. The results of Experiment #6 are an improvement over Experiment #5. However, the purities were lower than expected and the Clarithromycin lost in the Extract was more than expected. Especially significant was the loss of purity of Clarithromycin in the Raffinate.

The results of Experiment #6 suggest that the increase in zone flow rates degraded the separation more than expected from just mass transfer limitations. This may be an indication that the SMB system, SMB 300, loses accuracy at higher flow rates.

One reason for this inaccuracy is the speed at which the valves are changed. The controller for the six rotary valves can only switch one valve at a time, taking about ten seconds for the whole set to change. Also, the manual valves have to be switched one at time, taking approximately five seconds to change configurations. While this switching may occur fast enough for slow flow rates, it could have a significant effect when flow rates are high, causing pressure increases and back-mixing. Another factor is the HPLC pumps used are not meant for high flow rate at low pressures and have a tendency to degrade, over time, in accuracy when used this way.

The Raffinate and Extract volumes were measured to determine the average flow rates of each. The Raffinate was found to average 1.4 ml/min, while the Extract averaged 1.8 ml/min. Therefore, the UPLC pump 308 was at least 0.1 ml/min slow. A simulation was performed wherein the HPLC pump 308 was 0.1 ml/min slower. This simulation showed that a slower flow rate degrades the results by decreasing the concentration of Clarithromycin and increasing the concentration of 6,11 present at the Raffinate. This is caused by insufficient flow in zone 52.

Four Zone SMB Experiment #7

In order to reduce the potential for error caused by the SMB system, the zone flow rates were reduced for the seventh SMB Experiment. This was accomplished by reducing the feed flow rate to 0.2 ml/min. Further, the potential for higher purity and yield was increased because the effects of mass transfer are lower at slower flow rates. The feed concentration and columns remained unchanged from Experiment #6. The zone flow rates and switching time were optimized based on equations 17a–d and equation 18 for solutes exhibiting non-linear adsorption isotherms and non-negligible mass transfer resistances. The parameters used in Experiment #7 are shown in Table R.

TABLE R

Parameters for Four Zone SMB Experiment #7

| Description of System | |
|---|---|
| Four 100 μm columns, 1-1-1-1 column configuration | |
| Feed: | 0.69 g/L Clarithromycin |
| | 0.21 g/L 6,11 |
| Flow Rates | |
| Feed = | 0.2 ml/min |
| Mobile Phase = | 1.4 ml/min |
| Raffinate = | 0.6 ml/min |
| Extract = | 1.0 ml/min |
| Zone I = | 4.0 ml/min |
| Zone II = | 3.0 ml/min |
| Zone III = | 3.2 ml/min |
| Zone IV = | 2.6 ml/min |
| Switching Time | 69.0 min |

Figure 20A:
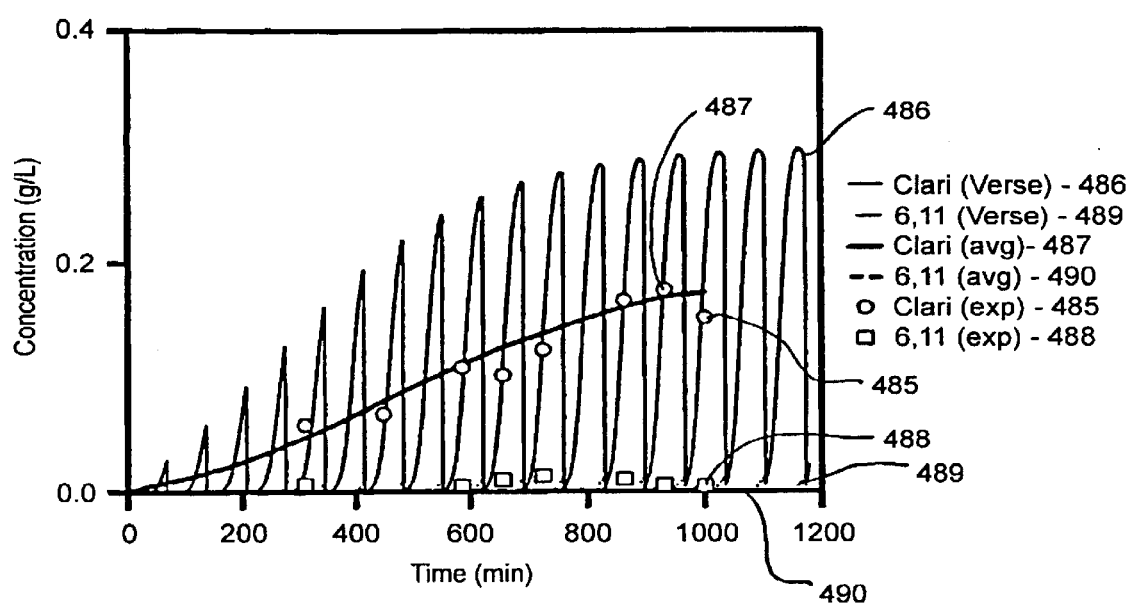
FIG. 20a shows the experimental and simulated histories for the Raffinate of Experiment #7.
Figure 20B:
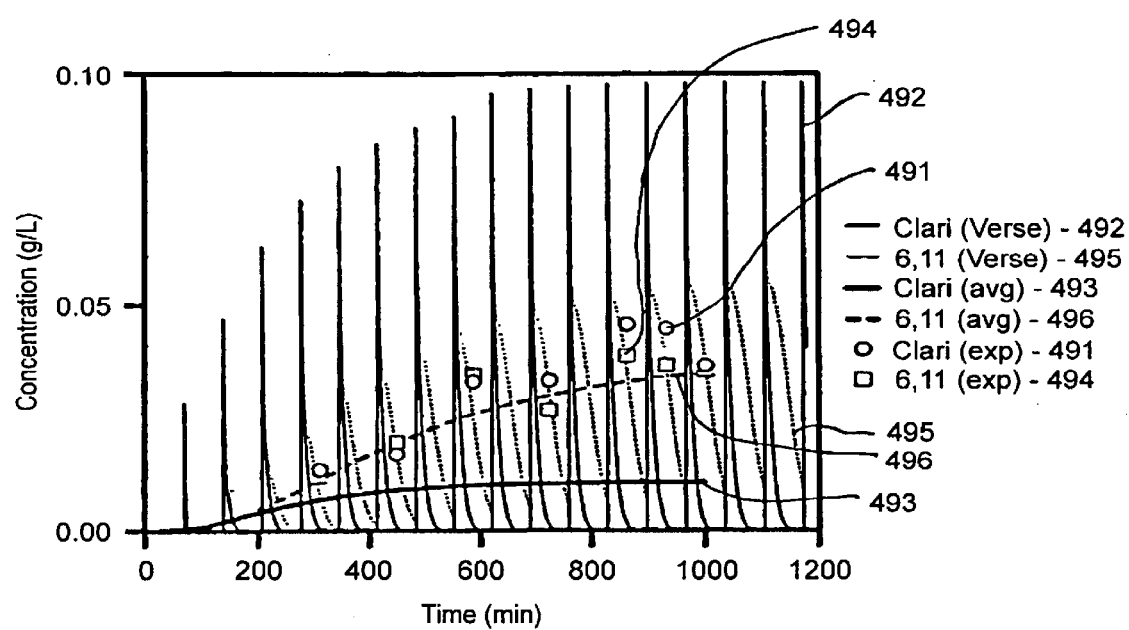
FIG. 20b shows the experimental and simulated histories for the Extract of Experiment #7.

The expected results are shown in Table S. The Experiment was carried out for 15 cycles or 1035 minutes. The results are graphed in FIGS. 20a and 20b and the experimental purities and yields are shown in Table S. FIG. 20a corresponds to the Raffinate and includes the Clarithromycin experimental data set 485, Clarithromycin simulated profile 486, Clarithromycin simulated average profile 486, 6,11 experimental data set 488, 6,11 simulated profile 489, 6,11 simulated average profile 490. FIG. 20b corresponds to the Extract and shows Clarithromycin experimental data set 491, Clarithromycin simulated profile 492, Clarithromycin simulated average profile 493, 6,11 experimental data set 494, 6,11 simulated profile 495, and 6,11 simulated average profile 496. The experimental and simulated data show good agreement for the Raffinate, but not for the Extract. The experimental purity of the Clarithromycin, 97%, was within 2.2% of the expected purity for Clarithromycin, but the Clarithromycin yield was 24% lower than expected. As can be seen in FIG. 20b, the amount of Clarithromycin in the Extract was about twice as large as expected, resulting in the lower yield. This indicated that there was likely still some error in the physical parameters used to describe and predict the SMB system.

TABLE S

Results for Four Zone SMB Experiment #7

| | Expected Results | | | Experimental Results | |
|---|---|---|---|---|---|
| | Purity | Yield | | Purity | Yield |
| Raffinate | 99.2% | 92.4% | Raffinate | 97.0% | 70.3% |
| Extract | 80.4% | 97.7% | Extract | 45.0% | 92.0% |

Four Zone SMB Experiment #8

One way to improve upon the results of Experiments 7 is to lengthen the separation zone of the SMB system, SMB 300, by adding columns. Two columns were added to the separation zones 54 and 56 to create a SMB having 1-2-2-1 column configuration. This configuration expands the separation zone without changing Zones I and IV, which are in effect guard columns to prevent overlapping. This is advantageous over a 2-2-2-2 configuration in that it requires less equipment and will have better adsorbent utilization.

Figure 21:
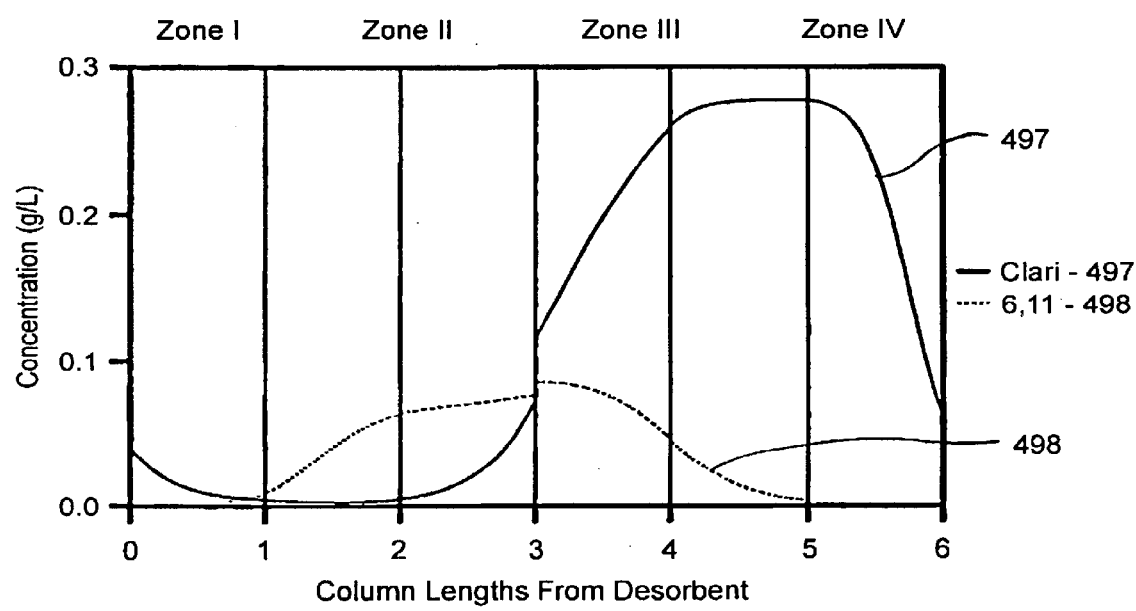
FIG. 21 shows the simulated column profiles for the six column simulated moving bed Experiment #7.

The zone flow rates and switching time were optimized based on equations 21a–d and equation 22 for solutes exhibiting non-linear adsorption isotherms and non-negligible mass transfer resistances. The parameters for Experiment #7 are shown in Table T. The expected results are shown in Table U. The expected Clarithromycin purity was 99.6% and the expected Clarithromycin yield was 98.7%, both significant improvements from the four-column system of Experiment 7. Simulated column profiles for Clarithromycin 497 and 6,11 498, are shown in FIG. 21.

TABLE T

Parameters for Four Zone SMB Experiment #8

Description of System

Six 100 μm columns,
1-2-2-1 column configuration

| | |
|---|---|
| Feed: | 0.69 g/L Clarithromycin |
| | 0.21 g/L 6,11 |

Flow Rates

| | |
|---|---|
| Feed = | 0.2 ml/min |
| Mobile Phase = | 1.3 ml/min |
| Raffinate = | 0.6 ml/min |
| Extract = | 0.9 ml/min |
| Zone I = | 3.8 ml/min |
| Zone II = | 2.9 ml/min |
| Zone III = | 3.1 ml/min |
| Zone IV = | 2.5 ml/min |
| Switching Time | 74.0 min |

TABLE U

Results for Four Zone SMB Experiment #8
Expected Results

| | Purity | Yield |
|---|---|---|
| Raffinate | 99.6% | 98.7% |
| Extract | 94.8% | 98.2% |

Four Zone SMB Experiment #9

Figure 22:
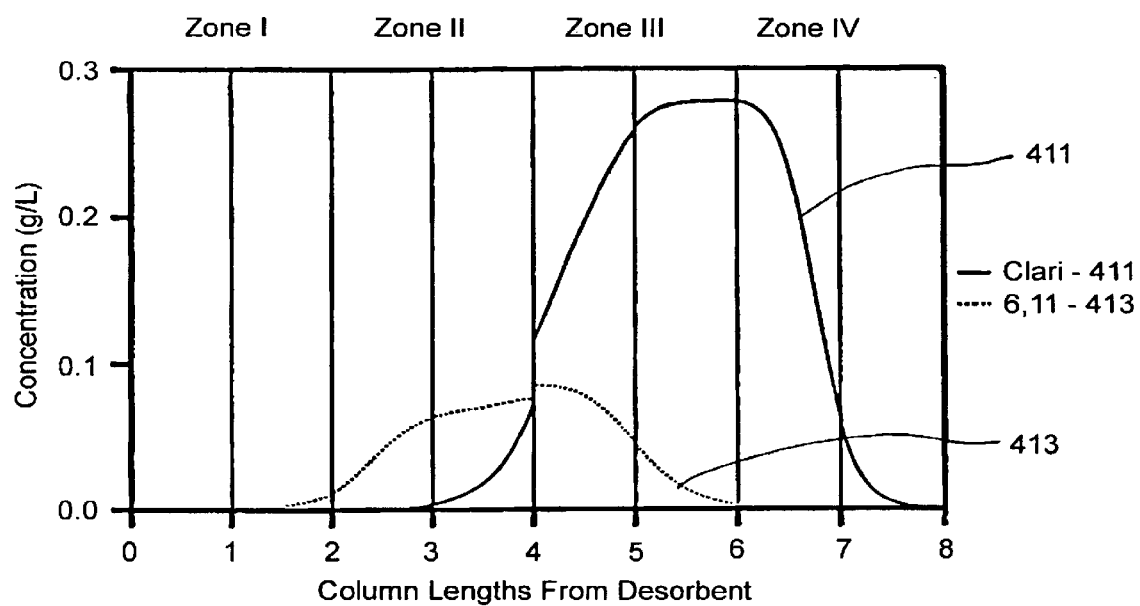
FIG. 22 shows the simulated column profiles for the eight column simulated moving bed system of Experiment #9.

Although the expected results from the six-column configuration in Experiment 8 are sufficient, an eight-column configuration of SMB 300 was configured and tested in order to determine if would be more advantageous. The zone flow rates and switching time were optimized based on equations 21a–d and equation 22 for solutes exhibiting non-linear adsorption isotherms and non-negligible mass transfer resistances. The parameters for Experiment #9 are given in Table V. The expected results are shown in Table W. The expected Clarithromycin purity improved to 99.9% with a 99.9% yield. The column profiles in FIG. 22 for Clarithromycin 411 and 6,11 413 show that the addition of the two columns has eliminated overlapping of the solutes in zones 52 and 58, which was prevalent in the six-column system shown in FIG. 21.

TABLE V

Parameters for Four Zone SMB Experiment #9

Description of System

Eight 100 μm columns,
2-2-2-2 column configuration

| | |
|---|---|
| Feed: | 0.69 g/L Clarithromycin |
| | 0.21 g/L 6,11 |

TABLE V-continued

Parameters for Four Zone SMB Experiment #9

Flow Rates

| | |
|---|---|
| Feed = | 0.2 ml/min |
| Mobile Phase = | 1.3 ml/min |
| Raffinate = | 0.6 ml/min |
| Extract = | 0.9 ml/min |
| Zone I = | 3.8 ml/min |
| Zone II = | 2.9 ml/min |
| Zone III = | 3.1 ml/min |
| Zone IV = | 2.5 ml/min |
| Switching Time | 76.0 min |

TABLE W

Expected Results for Four Zone SMB Experiment #9
Expected Results

| | Purity | Yield |
|---|---|---|
| Raffinate | 99.9% | 99.9% |
| Extract | 99.9% | 99.9% |

Figure 23A:
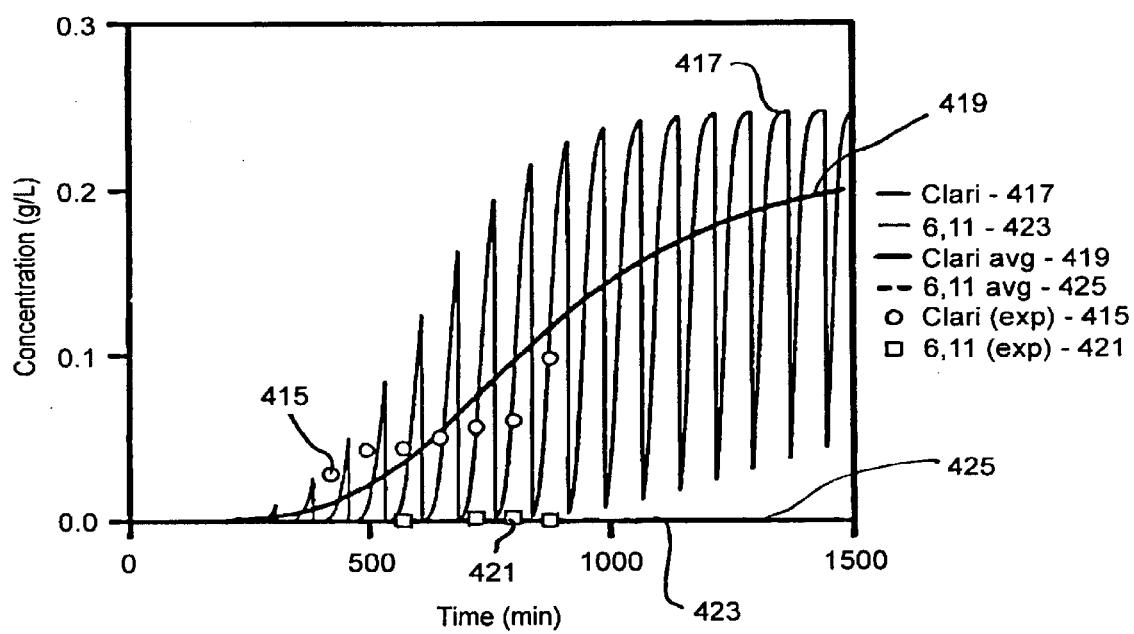
FIG. 23a shows the experimental and simulated histories for the Raffinate for Experiment #9.
Figure 23B:
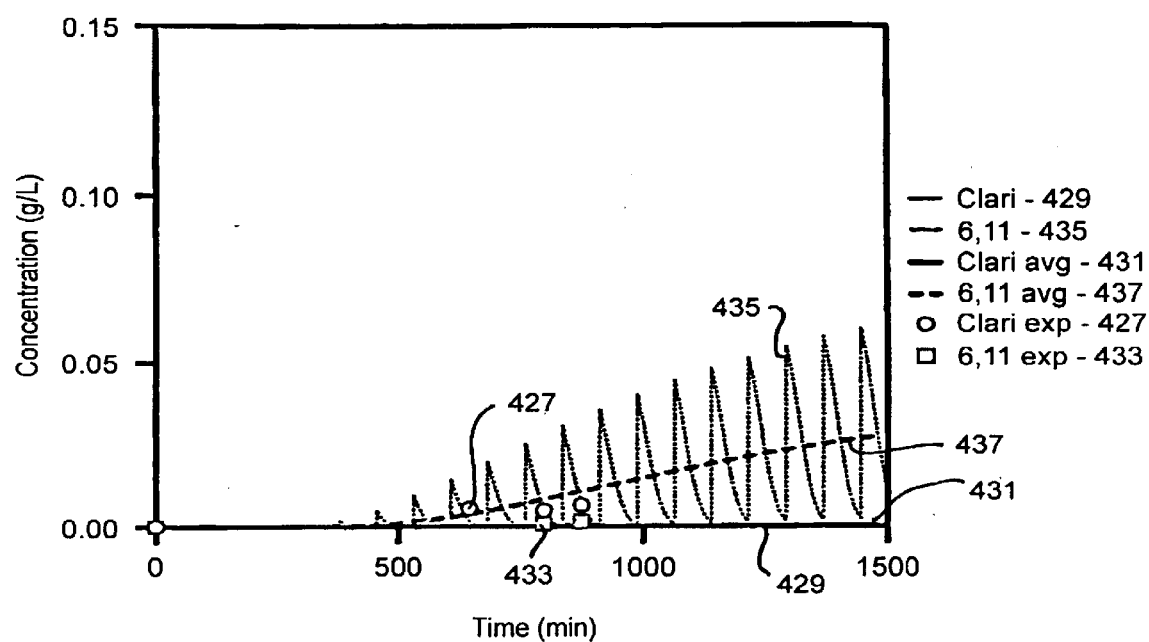
FIG. 23b shows the experimental and simulated histories for the Extract for Experiment #9.

An Experiment was carried out with SMB 300 using the parameters given in Table V. The Experiment was carried out for 12 cycles, or 912 minutes. The average Raffinate and Extract flow rates were 0.67 ml/min and 0.82 ml/min, respectively. Assuming a slow Pump 308 caused this error, zone I and IV flow rates were reduced when simulating the results. The experimental and simulated outlet profiles are shown in FIGS. 23a and 23b. FIG. 23a shows the flow from the Raffinate including Clarithromycin experimental data set 415, Clarithromycin simulated profile 417, Clarithromycin simulated average profile 419, 6,11 experimental data set 421, 6,11 simulated profile 423, and 6,11 simulated average profile 425. FIG. 23b shows the flow from the Extract including Clarithromycin experimental data set 427, Clarithromycin simulated profile 429, Clarithromycin simulated average profile 431, 6,11 experimental data set 433, 6,11 simulated profile 435, and 6,11 simulated average profile 437.

The experimental profiles are not well-developed because of the limited number of cycles and the long development time of the 8-column system. Also, it appears that the Clarithromycin profile in the Raffinate approaches a steady-state concentration that is both premature and low. In the Extract, the 6,11 profile has only begun to appear when the Experiment is stopped, much later than predicted. Although the results from the experimental data of Experiment #9 disagree with the simulated results, the purity and yield of the Clarithromycin product were both very high, as shown in Table X.

TABLE X

Experimental Results for Four Zone SMB Experiment #9
Experimental Results

| | Purity | Yield |
|---|---|---|
| Raffinate | 98.1% | 91.3% |
| Extract | Unknown | Unknown |

Four Zone SMB Experiment #10

Based upon the results of Experiment #9, the following changes were made for Experiment #10. First, a higher feed concentration was used to improve the accuracy and ease of HPLC analysis by providing a larger sample for testing. The feed flow rate was increased to 0.3 ml/min and the feed concentrations were increased to 1.10 g/L Clarithromycin and 0.56 g/L 6,11. Second, Experiment #10 should run for more cycles to ensure that steady-state conditions have been established. Experiment #10 was carried out for 20 cycles, or 1060 minutes. Third, SMB 300 should be reconfigured such that pumps 308 and 310 (HPLC pumps) are physically placed below the rest of the system (the columns and air traps) to reduce the possibly that air is present in the system and to stabilize the flow rates provided by HPLC pumps 308 and 310.

The zone flow rates and switching time were optimized based on equations 21a–d and equation 22 for solutes exhibiting non-linear adsorption isotherms and non-negligible mass transfer resistances. The parameters for Experiment #10 are shown in Table Y and the expected results are shown in Table Z.

Figure 24A:
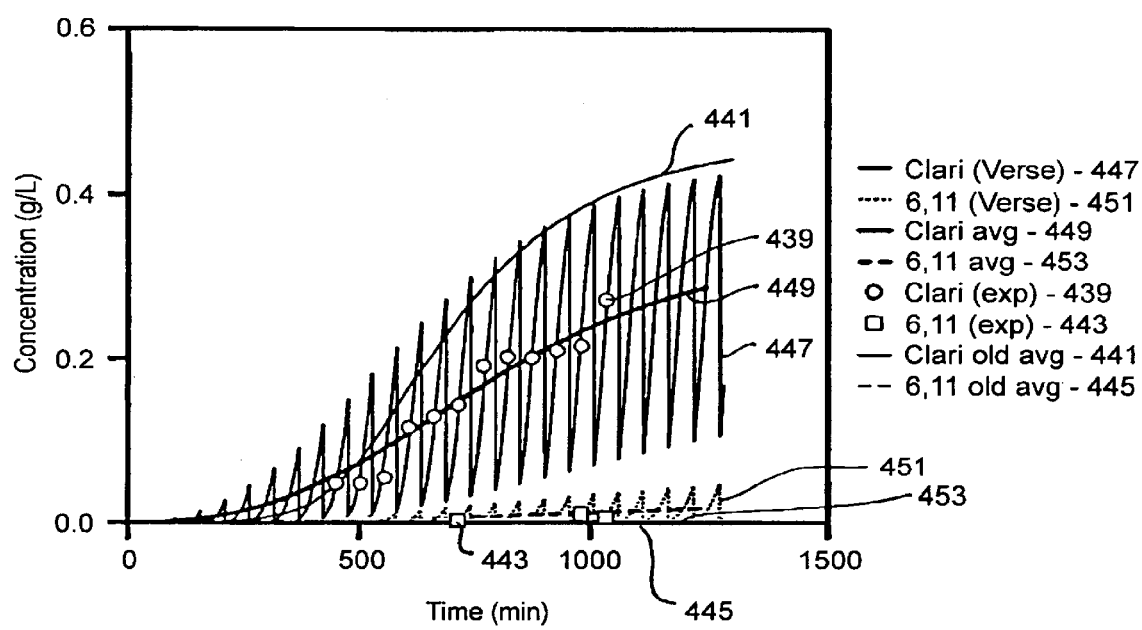
FIG. 24a shows the experimental and simulated histories for the Raffinate for Experiment #10.
Figure 24B:
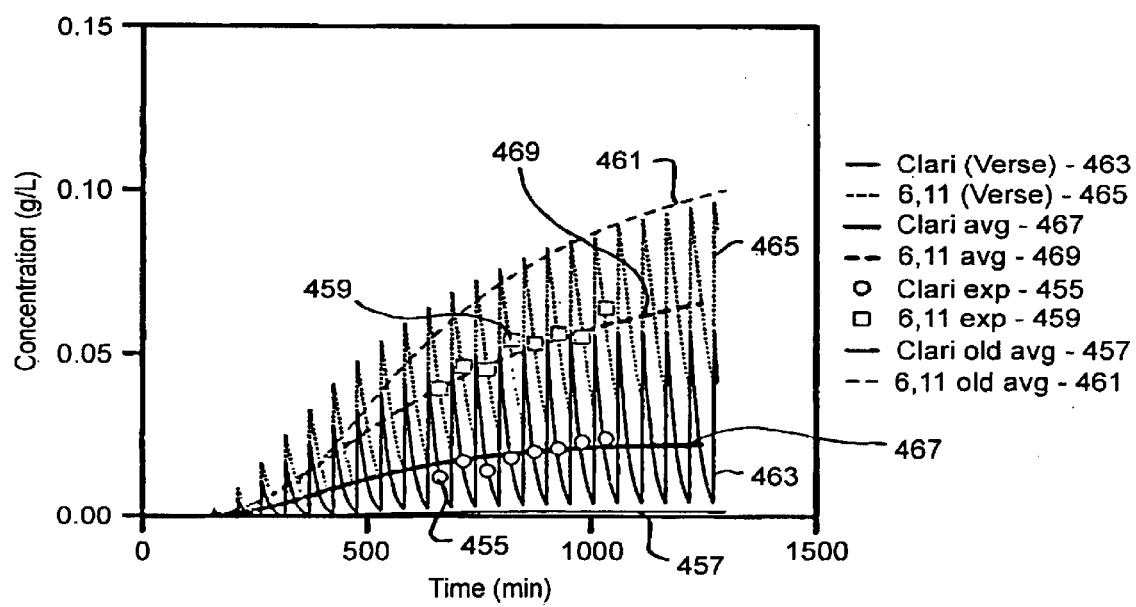
FIG. 24b shows the experimental and simulated histories for the Extract for Experiment #10.

Experimentally, the average outlet flow rates were determined to be 0.81 ml/min for the Raffinate and 1.17 ml/min for the Extract. HPLC pump 308 was assumed to be slow and the appropriate zone flow rates were decreased by 0.1 ml/min in the computer simulations. The experimental and simulated profiles are shown in FIGS. 24a and 24b.

The experimental results are shown in Table Z. FIG. 24a shows the flow from the Raffinate including Clarithromycin experimental data set 439, Clarithromycin simulated average profile 441, 6,11 experimental data set 443, and 6,11 simulated average profile 445. FIG. 24b shows the flow from the Extract including Clarithromycin experimental data set 455, Clarithromycin simulated profile 457, 6,11 experimental data set 459, and 6,11 simulated profile 461.

TABLE Y

Parameters for Four Zone SMB Experiment #10

Description of System

Eight 100 μm columns,
2-2-2-2 column configuration

| Feed: | 1.10 g/L Clarithromycin |
| | 0.56 g/L 6,11 |

Flow Rates

| Feed = | 0.3 ml/min |
| Mobile Phase = | 1.7 ml/min |
| Raffinate = | 0.7 ml/min |
| Extract = | 1.3 ml/min |
| Zone I = | 5.1 ml/min |
| Zone II = | 3.8 ml/min |
| Zone III = | 4.1 ml/min |
| Zone IV = | 3.4 ml/min |
| Switching Time | 53.0 min |

TABLE Z

Results for Four Zone SMB Experiment #10

| | Expected Results | | | Experimental Results | |
| --- | --- | --- | --- | --- | --- |
| | Purity | Yield | | Purity | Yield |
| Raffinate | 99.9% | 99.6% | Raffinate | 94.8% | 83.5% |
| Extract | 99.2% | 99.9% | Extract | 70.5% | 89.5% |

The purity and yield of the Clarithromycin product were high (94.8% and 83.5%, respectively), but were still lower than expected. Further, a larger than expected amount of Clarithromycin was lost in the Extract.

The simulation model was adjusted to better match the experimental data and to provide a more accurate model for future experiments. The CSTR volumes used previously were reduced to 2 ml and a multiplier was added to the Chung & Wen estimated axial dispersion coefficient. This multiplier was used to account for the extra-column axial dispersion caused by the volume between columns and the flow of solution through HPLC pumps 308 and 310. The preferred multiplier was found to be 40×.

The coefficients of the adsorption isotherms were adjusted to more closely approximate the experimental data. The coefficients were adjusted to increase the adsorption of Clarithromycin at lower concentrations by about 5% while maintaining the whole isotherm reasonably consistent with the frontal experimental data. The new coefficients result in the following isotherm for Clarithromycin:

$$Q_{clari} = \frac{a_i C}{1 + b_i C} = \frac{42.05 C}{1 + 0.30 C} \tag{34}$$

The adsorption isotherm for 6,11 was also adjusted:

$$Q_{6,11} = \frac{52.35 C}{1 + 0.37 C} \tag{35}$$

The above changes in the simulation model were tested against the experimental data in some of the preceding Experiments. In all cases an improved match was found between the experimental data and the simulation model. FIGS. 24a and 24b show the new simulated results for Experiment #10. FIG. 24a further shows the new Clarithromycin simulated profile 447, the new Clarithromycin simulated average profile 449, the new 6,11 simulated profile 451 and the new 6,11 simulated average profile 453. FIG. 24b further shows the new Clarithromycin simulated profile 463, the new Clarithromycin simulated average profile 465, the new 6,11 simulated profile 467 and the new 6,11 simulated average profile 469. As can be seen in FIGS. 24a–b, this new simulation agrees well with the experimental data, and predicts the experimental purity and yield well.

Four Zone SMB Experiment #11

Based upon the new isotherms and other parameters determined in Experiment #10, Experiment #11 was performed. The feed concentration in Experiment #11 was doubled to 2.0 g/L Clarithromycin and 0.55 g/L 6,11 in 60% Ethanol in order to ease HPLC analysis and to show that separation can be carried out at high concentrations, well within the non-linear range of the adsorption isotherms. The feed flow rate was set at 0.2 ml/min. The parameters for Experiment #11 are given in Table AA. The expected results are shown in Table BB. The Experiment was run for 25 cycles (1100 minutes).

TABLE AA

Parameters for Four Zone SMB Experiment #11

Description of System

Eight 100 μm columns,
2-2-2-2 column configuration

| Feed: | 2.0 g/L Clarithromycin |
| | 0.55 g/L 6, 11 |

TABLE AA-continued

Parameters for Four Zone SMB Experiment #11

Flow Rates

| | |
|---|---|
| Feed = | 0.2 ml/min |
| Mobile Phase = | 1.8 ml/min |
| Raffinate = | 0.8 ml/min |
| Extract = | 1.2 ml/min |
| Zone I = | 5.9 ml/min |
| Zone II = | 4.7 ml/min |
| Zone III = | 4.9 ml/min |
| Zone IV = | 4.1 ml/min |
| Switching Time | 44.0 min |

TABLE BB

Results for Four Zone SMB Experiment #11

| | Expected Results | | Experimental Results | |
|---|---|---|---|---|
| | Purity | Yield | | Purity | Yield |
| Raffinate | 95.2% | 91.3% | Raffinate | >98% | 89% |
| Extract | 65.9% | 81.7% | Extract | 64% | >86% |

Figure 25A:
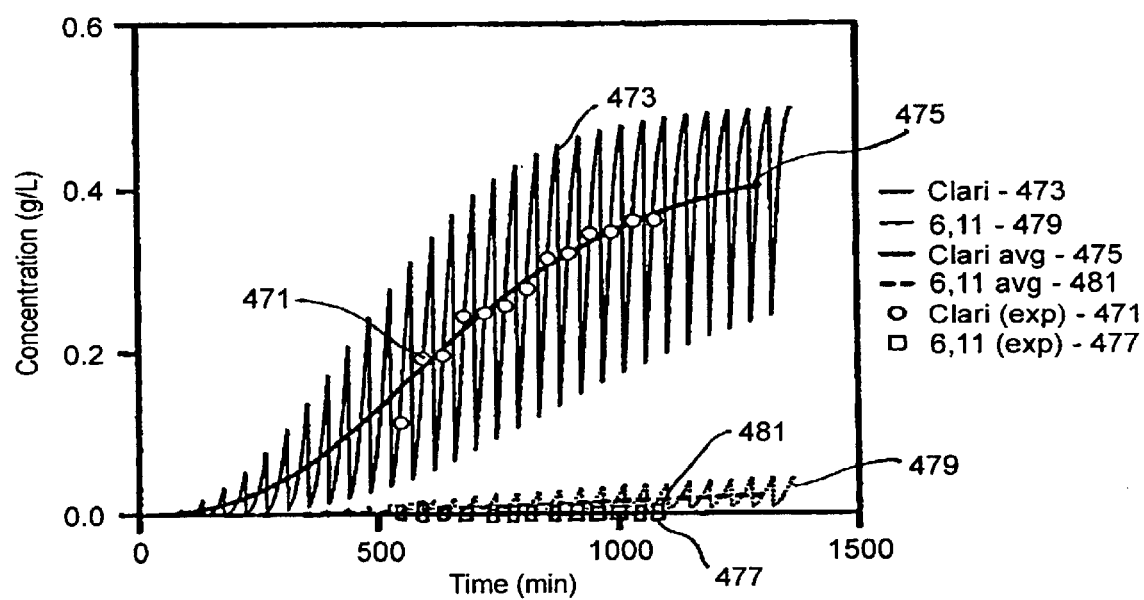
FIG. 25a shows the experimental and simulated histories for the Raffinate for Experiment #11.
Figure 25B:
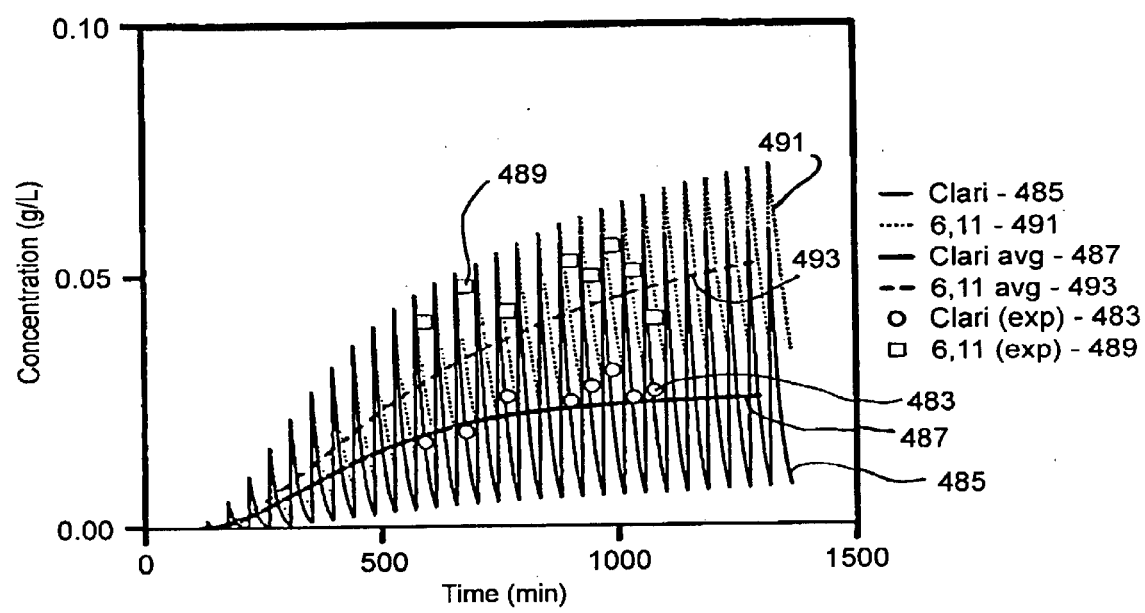
FIG. 25b shows the experimental and simulated histories for the Extract for Experiment #11.

The Experimental results are consistent with the Expected results. FIGS. 25a and 25b show that the experimental data for both the Raffinate and the Extract have good agreement with the expected results predicted by the computer simulation. FIG. 25a shows the flow from the Raffinate including the Clarithromycin experimental data set 471, the Clarithromycin simulated profile 473, the Clarithromycin simulated average profile 475, the 6,11 experimental data set 477, the 6,11 simulated profile 479 and the 6,11 simulated average profile 481. FIG. 25b shows the flow from the Extract including the Clarithromycin experimental data set 483, the Clarithromycin simulated profile 485, the Clarithromycin simulated average profile 487, the 6,11 experimental data set 489, the 6,11 simulated profile 491 and the 6,11 simulated average profile 493.

The major discrepancy between the experimental results and the simulation is the lack of 6,11 in the Raffinate and the greater than expected amount of 6,11 in the Extract, resulting in a higher Raffinate purity and higher Extract yield. These discrepancies suggest that the optimized zone flow rates and switching time might be too conservative.

The series of four zone SMB Experiments 1–11 demonstrate that a four zone SMB system may be used for the separation of a first component from a mixture containing both the first component and a second component, such as removal of 6,11 from Clarithromycin product. The zone flow rates and switching time for a SMB system are accurately optimized based on equations 21a–d and equation 22 for solutes exhibiting non-linear adsorption isotherms and non-negligible mass transfer resistances.

The results of Experiments 1–11 are used to optimize appropriate plant scale systems for the separation of Clarithromycin and 6,11. The plant scale system should be able to separate Clarithromycin and 6,11, meeting the purity and yield requirements while minimizing the cost of the separation. Solvent usage is the dominant cost factor in the separation of Clarithromycin and 6,11 with a four zone SMB.

The four zone Experiments 1–11 showed the viability of the first and second optimization methods described by equations 17 a–d, 18, 21 a–d, and 22 and the viability of the four zone SMB as a process for removing 6,11 from Clarithromycin. Based on the Experiments conducted with the five zone SMB system of the second embodiment, the third method for determining the optimal zone flow rates and optimal switching time is preferred relative to the first method and second method. Further based on the five zone SMB system of the second embodiment the following mobile phase-stationary phase systems are preferred: (A.) 60% by volume isopropyl alcohol and Dow Optipore Hydrophobic XUS-40323 adsorbent, (B.) 50% by volume isopropyl alcohol and Dow Optipore Hydrophobic XUS-40323 adsorbent, (C.) 50% by volume isopropyl alcohol and Amberlite XAD-16, (D.) 60% by volume ethanol and Dow Optipore Hydrophobic XUS-40323 adsorbent, (E.) 80% by volume methanol and Dow Optipore Hydrophobic XUS-40323 adsorbent, (F.) 75% by volume methanol and Dow Optipore Hydrophobic XUS-40323 adsorbent, and (G.) 85% by volume methanol and Dow Optipore Hydrophobic XUS-40323 adsorbent. In one variation the mobile phase used to separate Clarithromycin and 6,11 includes about 50 percent by volume to about 85 percent by volume of an organic solvent, such as either about 50 percent by volume isopropyl alcohol to about 60 by volume percent isopropyl alcohol, about 60 percent by volume ethanol to about 80 percent by volume ethanol, or about 75 percent by volume to about 85 percent by volume methanol.

For each mobile phase-stationary phase system, a plant-scale four zone SMB system was created to meet the production requirements of 60 g Clarithromycin/min at 90% purity and 95% yield. The plant-scale four zone simulated moving bed configuration was first set at 12 3-meter columns. These columns can be distributed throughout the four zones several different ways, but it is desirable to keep at least two columns in every zone. So the distribution of the remaining four columns must be optimized. It is also known that it is more advantageous to have more columns in the separation zones (54 and 56) than in the buffer zones (52 and 58). These two rules of thumb help to minimize the number of configurations that must be considered in order to determine the optimal column distribution. In one example, the columns are in a 3-4-3-2 zone configuration. The distribution of columns is the first of three optimal operating settings that must be determined when creating each plant-scale SMB system. The others are the feed flow rate and the feed concentrations. For each of these, a simple iteration process using the third method (the first and second methods could also be used) and comparing product cost is required to determine which values or set of values yields the lowest product cost. The iteration process for each operating setting requires an initial estimate of the optimal value(s) that is used to determine optimal zone flow rates using the third method. These zone flow rates are used to calculate the initial product cost. The value(s) is then changed, the zone flow rates recalculated, and the cost again estimated. Comparing these two costs will determine if an optimal value(s) has been acquired or if further iteration is required. Once these operating settings are known, the optimal zone flow rates and switching time were estimated using the third method. From these optimal operating conditions, the estimated product cost was calculated so that different systems and operating settings could be compared to determine the lowest-cost process.

In order to determine stationary phase requirements, the column diameter was determined from the required feed flow rate, which was then used to determine the volume of sorbent required and finally the cost of stationary phase per kilogram of purified product. For equipment costs, a plant-scale low-pressure simulated moving bed unit was assumed to cost $2,000,000 and to be depreciated over 7 years. For phobic XUS-40323 adsorbent, with a purification cost of $234/kg. Table CC is also useful for comparing the four zone SMB system with the five zone SMB system and the four zone SMB system described in the second embodiment of the present invention.

TABLE CC

Physical parameters and system parameters for plant-scale four zone system

| Solvent-sorbent system data | Case A | Case B | Case C | Case D | Case E | Case F | Case G |
|---|---|---|---|---|---|---|---|
| Mobile Phase | 60% IPA | 50% IPA | 60% EtOH | 50% IPA | 80% MeOH | 75% MeOH | 85% MeOH |
| Sorbent | Dow L323 | Dow L323 | Dow L323 | XAD-16 | Dow L323 | Dow L323 | Dow L323 |
| Fresh solvent Cost ($/L) | $ 0.667 | $ 0.667 | $ 0.552 | $ 0.667 | $ 0.277 | $ 0.277 | $ 0.277 |
| Net solvent cost ($/L)* | $ 0.133 | $ 0.133 | $ 0.111 | $ 0.133 | $ 0.0554 | $ 0.0554 | $ 0.0554 |
| Clari in mixture solubility | 2.23 | 1.06 | 1.60 | 1.06 | 2.46 | 1.90 | 2.70 |
| Selectivity ($a_2/a_1$) | 1.29 | 1.30 | 1.25 | 1.24 | 1.28 | 1.29 | 1.09 |
| Langmuir isotherm parameters (per solid volume mass) | $a_1 = 10.2$<br>$b_1 = 0.16$<br>$a_2 = 13.2$<br>$b_2 = 0.21$ | $a_1 = 24.0$<br>$b_1 = 0.30$<br>$a_2 = 1.20$<br>$b_2 = 0.44$ | $a_1 = 42.0$<br>$b_1 = 0.30$<br>$a_2 = 52.3$<br>$b_2 = 0.37$ | $a_1 = 21.0$<br>$b_1 = 0.32$<br>$a_2 = 26.1$<br>$b_2 = 0.40$ | $a_1 = 39.0$<br>$b_1 = 0.43$<br>$a_2 = 45.0$<br>$b_2 = 0.38$ | $a_1 = 81.3$<br>$b_1 = 0.635$<br>$a_2 = 105.2$<br>$b_2 = 1.05$ | $a_1 = 23.0$<br>$b_1 = 0.31$<br>$a_2 = 25.1$<br>$b_2 = 0.34$ |
| Plant scale system parameters | | | | | | | |
| Mode | SMB | SMB | SMB | SMB | SMB | SMB | SMB |
| Column diameter (m) | 2.20 | 2.74 | 2.65 | 3.02 | 3.66 | 2.67 | 7.07 |
| Column length (m) | 3.00 | 3.00 | 3.00 | 3.00 | 3.00 | 3.00 | 3.00 |
| Column configuration | 2-3-5-2 | 2-3-5-2 | 2-3-5-2 | 2-3-5-2 | 2-3-5-2 | 2-4-3-3 | 2-4-4-2 |
| Feed flow rate (L/min) | 26.9 | 56.6 | 37.5 | 56.6 | 26.9 | 31.58 | 22.2 |
| Feed Clari concentration (g/L) | 2.23 | 1.06 | 1.60 | 1.06 | 2.46 | 1.90 | 2.70 |
| Raffinate flow rate (L/min) | 27.9 | 54.9 | 46.9 | 64.8 | 74.7 | 43.7 | 87.9 |
| Desorbent flow rate (L/min) | 125.2 | 248.3 | 247 | 288 | 420 | 479 | 532 |
| Extract flow rate (L/min) | 124.2 | 250.0 | 238 | 280 | 370 | 467 | 466 |
| Zone II flow rate (1 min) | 252.7 | 404.7 | 626 | 569 | 880 | 388 | 2009 |
| Switching time (min) | 106.3 | 194.7 | 306.1 | 156.1 | 254.4 | 441.1 | 282.1 |
| Sorbent Cost ($/kg) | $ 10.8<br>(5%) | $ 16.8<br>(4%) | $ 15.7<br>(4%) | $ 20.4<br>(5%) | $ 30.0<br>(8%) | $ 15.9<br>(4%) | $ 112<br>(19%) |
| Equipment cost ($/kg)** | $ 10 | $ 10 | $ 10 | $ 10 | $ 10 | $ 10 | $ 10 |
| Organic Solvent Consumption (L/g) | 1.60 | 2.67 | 3.00 | 3.02 | 6.24 | 6.72 | 8.26 |
| Solvent Cost ($/kg) | $213<br>(91%) | $356<br>(93%) | $333<br>(93%) | $402<br>(93%) | $346<br>(90%) | $372<br>(93%) | $ 458<br>(79%) |
| Total Purification Cost ($/kg) | $234 | $382 | $358 | $432 | $386 | $398 | $ 579 |

*Based on 80% recycle recovery assumption (20% of solvent is fresh)
**Based on $2M low pressure SMB equipment depreciated over 7 years stationary phase costs, the organic solvent consumption (L/g product) was determined by adding the organic feed flow rate and organic desorbent flow rate then dividing by the production rate. The mobile phase cost was determined by estimating that 20% of mobile phase used would be fresh feed while the rest would by recycled. The fresh mobile phase costs used are given in Table CC. The total product cost was estimated as the sum of sorbent, equipment, and solvent costs. Water cost, labor cost, and utility cost were neglected. A summary of these plant-scale cost estimations is given in Table CC.

As can be seen from the plant-scale cost estimations, mobile phase cost is the major concern in the optimization of the four zone simulated moving bed systems, as it accounts for >80% of the production cost. The high mobile phase consumption of the four zone SMB systems is due to the low solubility of the solvents, the low selectivity of the sorbent-solvent systems, and the high affinity and high degree of non-linearity of their adsorption isotherms. The combination of all these factors determines the mobile phase consumption and production cost as estimated and shown for each system in Table CC. The most cost-efficient system is (A.) 60% isopropyl alcohol and Dow Optipore Hydrophobic XUS-40323 adsorbent, with a purification cost of SMB System Having a First and a Second Portion In a second embodiment, a five zone SMB system 500 and a four zone SMB system 800 are provided to separate a component from a mixture. In both five zone system 500 and four zone system 800, columns or at least portions of a column are cycled through two distinct portions, a first portion and a second portion, during a complete cycle of switching periods. For example, if there are eight columns, a first column is cycled completely through the first portion and the second portion after eight switching periods. Although both, five zone system 500 and four zone system 800 are shown with a certain number of columns packed with a stationary phase, it is to be understood that both the five zone system 500 and four zone system 800 can include a fewer or a greater number of columns. As explained in more detail below, the first portion of five zone system 500 and four zone system 800 is configured to treat the columns or portions of a columns present in the first portion and the second portion of five zone system 500 and four zone system 800 is configured to separate the desired component from the mixture.

The stationary phase used in five zone system 500 and four zone system 800 is chosen based upon the mobile phase to be used and the characteristics of the components in the mixture to be separated. It is within the scope of the present invention to employ sorbents as the stationary phase, including adsorbents and absorbents. Example adsorbents include adsorbents having one or more of the following mechanisms: hydrophobic interactions, ionic interactions, hydrogen bonds, π—π interactions, complex formation or ligand exchange, dipole interactions, and affinity interactions or guest-host interactions.

The mobile phase used in the five zone system 500 and the four zone system 800 is chosen based upon the stationary phase to be used and the characteristics of the components in the mixture to be separated. Example mobile phases include water or aqueous solutions, at least one organic solvent, supercritical fluids, or combinations thereof.

Figure 26:
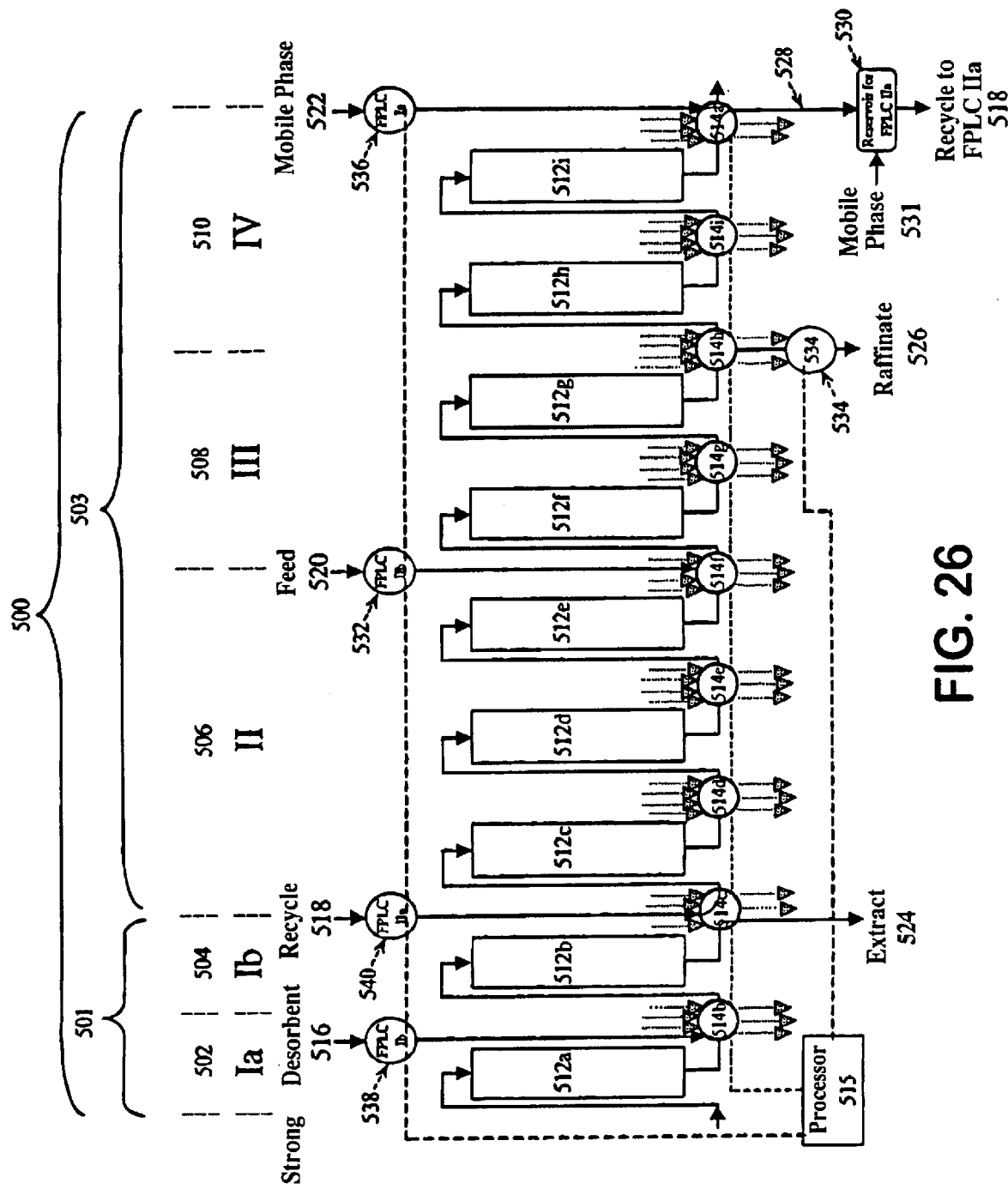
FIG. 26 is a diagrammatic representation of a five zone simulated moving bed of the present invention having a first portion configured to treat zones in the first portion and a second portion configured to recover the product, the first component, from the feed mixture.

Referring to FIG. 26, five zone SMB system 500 is shown. In one example of the second embodiment, a five zone SMB system is developed to separate Clarithromycin from a mixture including Clarithromycin and 6,11. Five zone SMB system 500 is preferred to the four zone SMB system 50, of the first embodiment for the separation of solutes exhibiting non-linear adsorption isotherms and non-negligible mass transfer resistances, such as the separation of Clarithromycin and 6,11, because the five zone SMB system 500 reduces the amount of solvent consumed during operation compared to the four zone SMB 50. Solvent usage is the major operation cost associated with the four zone SMB 50 for clarithromycin purification. The solvent consumption in the four zone system can be very large when the solutes to be separated exhibit high degrees of non-linearity in the pertinent adsorption isotherms of the solutes.

Referring to FIG. 26, five zone SMB 500 includes a first portion 501 including a first zone ($I_a$) 502 and a second zone ($I_b$) 504, and a second portion 503 including a third zone (II) 506, a fourth zone (III) 508, and a fifth zone (IV) 510. Each zone 502, 504, 506, 508, 510 includes at least one column or at least a portion of one or more columns. Five zone SMB system 500 is shown with nine columns 512*a*-I in a (1-1-3-2-2) zone configuration for zones 502, 504, 506, 508, 510. However, five zone system 500 may be configured with any number of columns suitable for creating five zones 502, 504, 506, 508, 510 and for facilitating the separation of a first component from a mixture including the first component and a second component.

As shown in FIG. 26, as a sample configuration of SMB 500, zone 502 includes column 512*a*, zone 504 includes column 512*b*, zone 506 includes columns 512*c*, 512*d*, 512*e*, zone 508 includes columns 512*f*, 512*g*, and zone 510 includes columns 512*h*, 512*i*. Each column 512*a–i* is connected to the preceding column of columns 512*a–i* through one of nine valves 514*a–i* and is connected to the following column of columns 512*a–i* through another of the nine valves 514*a–i*. In addition, each valve is connected to a strong desorbent inlet 516, a first mobile phase inlet 518, a feed inlet 520, a second mobile phase inlet 522, an Extract outlet 524, a Raffinate outlet 526, and an outlet 528 to a reservoir 530. As explained in more detail later, the flow from a first column of columns 512*a–i* is not always provided to a subsequent column 512*a–i*. For example, flow from the last column in first portion 501 does not flow to the first column in second portion 503 and flow from the last column in second portion 503 does not flow to the first column of first portion 501.

First portion 501 is configured to treat the columns of columns 512*a–i* located in first portion 501 to decrease the adsorptive strength of the second component or remove the second component from the apparatus 500. Various methods can be used to decrease the adsorptive affinity of the second component. Examples include affinity modulators and displacers. Example affinity modulators include the use of an acid wash, changes in pH of the mobile phase, change in the percentage of organic solvent present in the mobile phase, changes in the ionic strength of the mobile phase, and, for supercritical fluids, changes in temperature and/or pressure. Example displacers include competitive solutes that can displace the adsorbed second component.

As shown in FIG. 26, zones 502 and 504 comprise a two-zone strong desorbent carousel process for treating the columns of columns 512*a–i* located in first portion 501. Zone 502 is a solvent-exchange zone and zone 504 is an strong desorbent zone. The flow into solvent-exchange zone 502 is pure solvent from mobile phase inlet 522. The solvent-exchange zone 502 washes the strong desorbent out of each column that was previously washed with a strong desorbent-containing solvent in strong desorbent zone 504. The strong desorbent-containing solvent used in strong desorbent zone 504 is used to eliminate adsorption and to quickly wash out the desorption wave of 6,11 into Extract outlet 524. In alternative embodiments, the first portion treats the columns in the first portion to remove 6,11 by raising or lowering the pH of the mobile phase, increasing the percentage of organic solvent used in the mobile phase, increasing the temperature of the mobile phase or a combination thereof.

Zones 506, 508, 510 form a series of stationary phase-packed columns. In one variation, zones 506, 508, 510 form a continuous series (or ring). Flow into zone 506 includes flow from Mobile phase inlet 518. Flow into zone 508 includes flow from Feed stream 520 which is the solution containing the mixture of the components to be separated. In one example, feed stream 520 includes a crude mixture of Clarithromycin and 6,11 to be separated. Flow out of zone 508 includes Raffinate stream 526, which is used to remove the desired product, such as Clarithromycin which is less selectively adsorbed than 6,11. Flow out of zone 510 includes outlet stream 528 which flows into a reservoir 530. In one embodiment, the contents of reservoir 530 are combined with the pure solvent mobile phase stream 518 for flow into zone 506.

The six stream ports (Solvent Exchange 522, Strong Desorbent 516, Extract 524, Mobile phase 518 and 531, Feed 520, and Raffinate 526) are connected to valves 514*a–i* and using these valves can be positioned between any two columns, allowing for the movement of the series of ports in a cocurrent direction to mobile phase flow, generally in a direction 525 in FIG. 26, at periodic intervals. The switching time is chosen to create a simulated movement of the stationary phase in a direction 527 in FIG. 26, countercurrent to the direction of solvent flow, direction 525.

The proper determination of the five zone flow rates (and therefore the inlet and outlet flow rates) creates a separation region between Extract 524 and Raffinate 526 that spans zones 506 and 508 so that only the less selectively adsorbed component will exit out of Raffinate 526 and only the more selectively adsorbed component will exit out of Extract 524. The remaining zones 502, 504, 510 among other things act as buffer zones to prevent already-separated solutes from being remixed.

SMB system 500 has nine possible configurations, similar to the eight possible configurations of SMB system 300. FIG. 26 shows a first configuration of SMB system 500. In FIG. 26, feed inlet 520 is pumped through a pump 532 to valve 514*f* wherein it combines with the flow from column 512*e* for delivery to column 512*f*. Column 512*f* is the beginning column of the fourth zone 508. Flow from column 512f passes through valve 514g and is delivered to column 512g which is the last column in the fourth zone 508. Flow from column 512g passes into valve 514h wherein it is split into flow to pump 534 which is connected to Raffinate outlet 526 and flow to be delivered to column 512h.

Column 512h is the first column in fifth zone 510. Flow from column 512h passes through valve 514i and is delivered to column 512i which is the last column in zone 510. Flow from column 512i is passed through valve 514a to outlet 528 and ultimately to reservoir 530. Mobile phase inlet 522 is fed to pump 536 from which the mobile phase is fed through valve 514a to be delivered to column 512a which is the only column in first zone 502. Flow from column 512a passes to valve 514b where it is combined with the strong desorbent inlet 516 which is delivered to valve 514b through pump 538. Flow from valve 514b is delivered to column 512b which is the only column in second zone 504. Flow from column 512b passes through valve 514c to Extract outlet 524. Mobile phase inlet 518 is passed through valve 514c and delivered to column 512c which is the first column in the third zone 506. The flow to column 512c is not mixed with the flow from column 512b. Flow from column 512c is passed through valve 514d to column 512d. Flow from column 512d is passed through valve 514e and is delivered to column 512e which is the last column in third zone 506. As stated earlier, in the first configuration, flow from column 512e is combined with feed inlet 520 and delivered to column 512f.

FIGS. 27a–27i provide a representation of the flow through valve 514a for the nine different configurations of SMB 500. It should be noted that valve 514a is always connected to column 512a, column 512i, Strong Desorbent 516, Desorbent 518, Reservoir 530, Extract 524, Feed 520 and Raffinate 526 and that FIGS. 27a–i only show the connections that are active for the given position or configuration. Valves 514b–514i operate similar to valve 514a. It is contemplated that any suitable valve that includes ports for all of the above mentioned connections and that provides for maintaining two distinct flows, see FIG. 27a and FIG. 27c as examples, may be used with the present invention.

To create the flow system shown in FIGS. 27a–i each valve 514a–i must have the following ports: inlet from preceding column of columns 512a–i; outlet to subsequent column of columns 512a–i; inlet from Feed inlet 520; inlet 518 from combination of first Mobile phase inlet 531 and inlet from reservoir 530 (in one embodiment inlet 518 is comprised solely of first mobile phase inlet 531); outlet to Raffinate; inlet from second Mobile Phase inlet 522; inlet from Strong Desorbent inlet 516; outlet to reservoir 530; outlet to Extract 524.

Figure 27A:
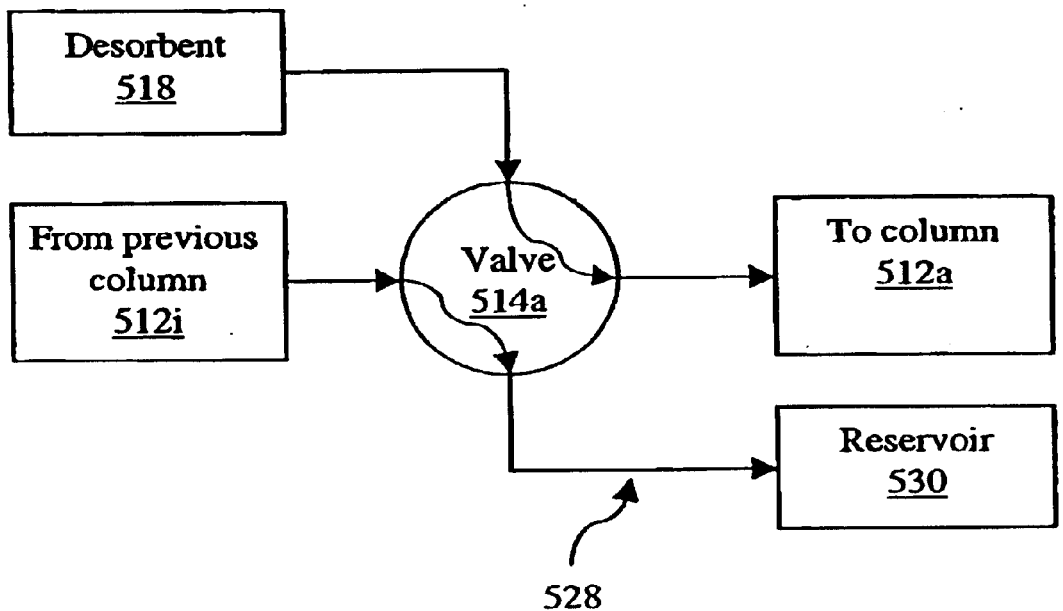
FIG. 27a is a diagrammatic representation of a first valve in the five zone simulated moving bed of FIG. 26 representing flow through the valve when the five zone simulated moving bed is in a first configuration.

FIG. 27a shows the configuration of valve 514a corresponding to the first configuration of SMB 500 as shown in FIG. 26. In the first configuration of SMB 500, valve 514a receives flow from column 512i, which is the last column in fifth zone 510, and passes that flow onto outlet 528 to reservoir 530. Also, valve 514a receives flow from inlet 522 and passes to column 512a. It should be noted that the flow from column 512i to reservoir 530 is maintained separate from the flow from inlet 522 to column 512a.

Figure 27B:
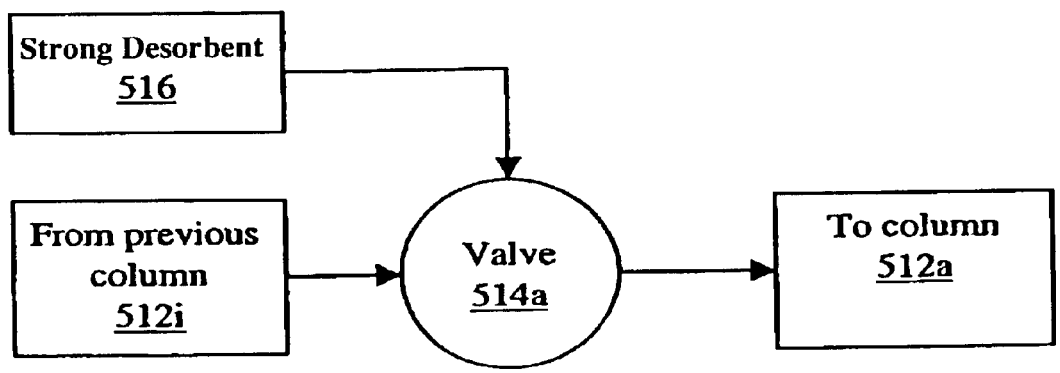
FIG. 27b is a diagrammatic representation of a first valve in the five zone simulated moving bed of FIG. 26 representing flow through the valve when the five zone simulated moving bed is in a second configuration.

In the second configuration of SMB 500, valve 514a, as shown in FIG. 27b, receives flow from column 512i which is the column in first zone 502 and strong desorbent inlet 516. The flow from column 512i and strong desorbent inlet 516 combine and are passed onto column 512a, which is the column in second zone 504.

Figure 27C:
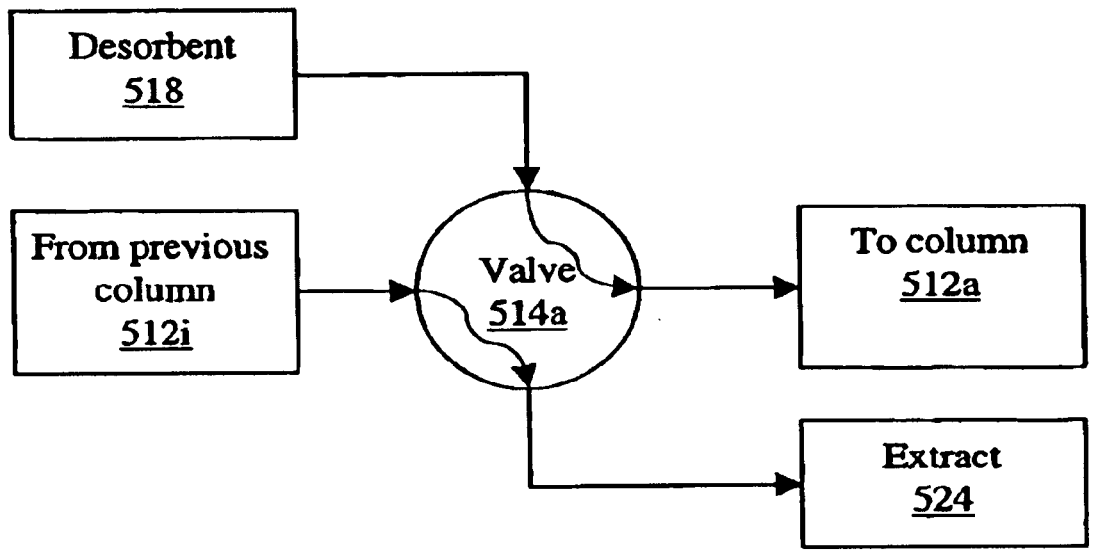
FIG. 27c is a diagrammatic representation of a first valve in the five zone simulated moving bed of FIG. 26 representing flow through the valve when the five zone simulated moving bed is in a third configuration.

In the third configuration of SMB 500, valve 514a, as shown in FIG. 27c, receives flow from column 512i, which is the column in zone 504, and passes it onto Extract outlet 524. Valve 514a further receives flow from Mobile phase inlet 518 and passes it onto column 512a, which is the first column in third zone 506. It should be noted that the flow from column 512i to Extract 524 is maintained separate from the flow from Mobile phase inlet to column 512a.

Figure 27D:
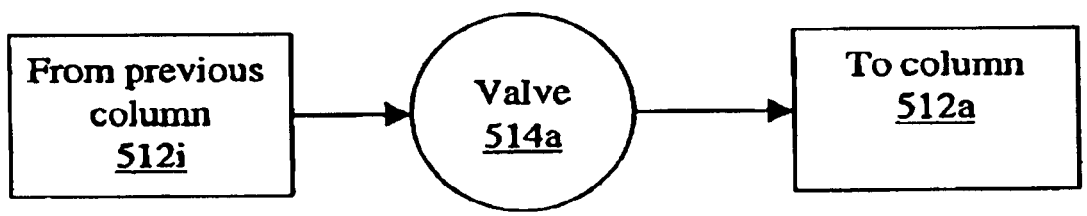
FIG. 27d is a diagrammatic representation of a first valve in the five zone simulated moving bed of FIG. 26 representing flow through the valve when the five zone simulated moving bed is in a fourth configuration.

In the fourth configuration of SMB 500, valve 514a, as shown in FIG. 27d, receives flow from column 512i, which is the first column in zone 506 and passes the flow onto column 512a, which is the second column in zone 506.

Figure 27E:
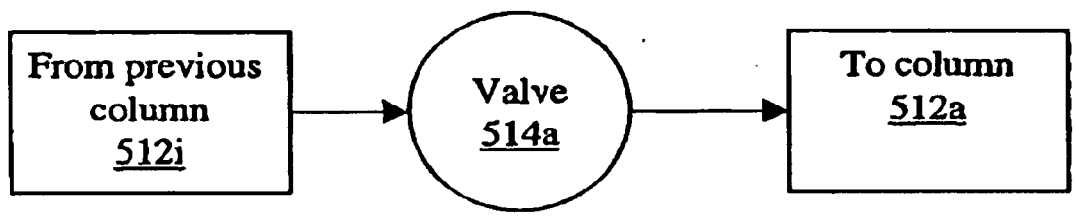
FIG. 27e is a diagrammatic representation of a first valve in the five zone simulated moving bed of FIG. 26 representing flow through the valve when the five zone simulated moving bed is in a fifth configuration.

In the fifth configuration of SMB 500, valve 514a, as shown in FIG. 27e, receives flow from column 512i, which is the second column in zone 506 and passes the flow onto column 512a, which is the last column in third zone 506.

Figure 27F:
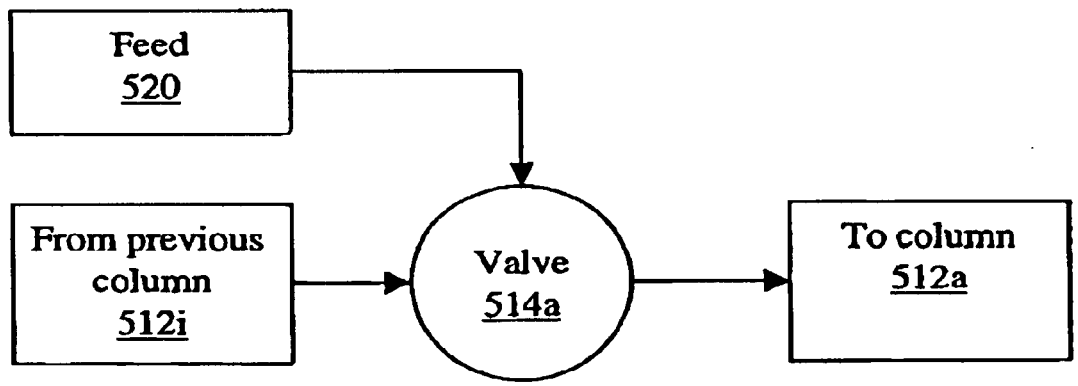
FIG. 27f is a diagrammatic representation of a first valve in the five zone simulated moving bed of FIG. 26 representing flow through the valve when the five zone simulated moving bed is in a sixth configuration.

In the sixth configuration of SMB 500, valve 514a, as shown in FIG. 27f, receives flow from column 512i, which is the last column in third zone 506 and receives flow from feed inlet. The flow from column 512i and feed inlet 520 are combined and the resultant flow is passed onto column 512a, which is the first column in fourth zone 508.

Figure 27G:
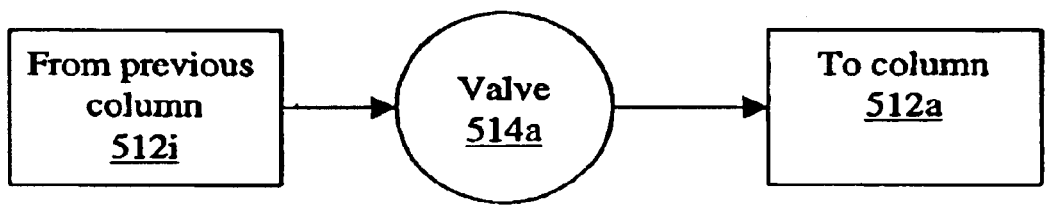
FIG. 27g is a diagrammatic representation of a first valve in the five zone simulated moving bed of FIG. 26 representing flow through the valve when the five zone simulated moving bed is in a seventh configuration.

In the seventh configuration of SMB 500, valve 514a, as shown in FIG. 27g, receives flow from column 512i, which is the first column in the fourth zone 508, and passes the flow onto column 512a, which is the last column in fourth zone 508.

Figure 27H:
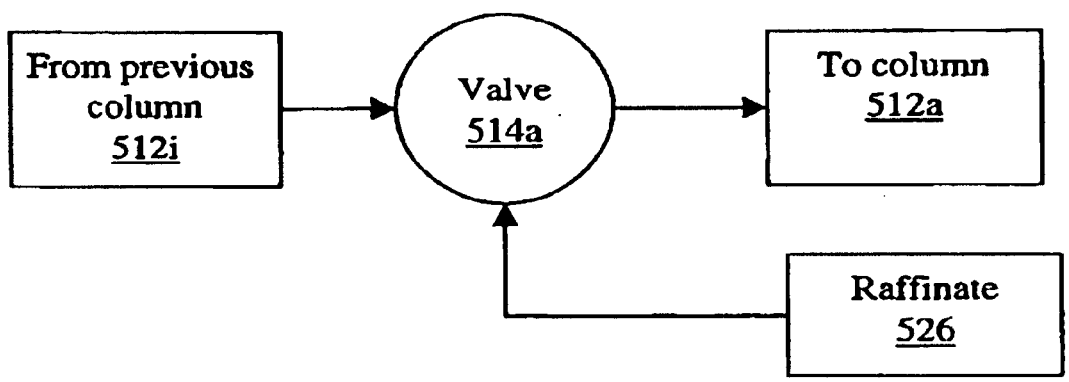
FIG. 27h is a diagrammatic representation of a first valve in the five zone simulated moving bed of FIG. 26 representing flow through the valve when the five zone simulated moving bed is in a eighth configuration.

In the eighth configuration of SMB 500, valve 514a, as shown in FIG. 27h, receives flow from column 512i, which is last column in fourth zone 508. The flow from column 512i is then split into flow to Raffinate outlet 526 and flow to column 512a, which is the first column in fifth zone 510.

Figure 27I:
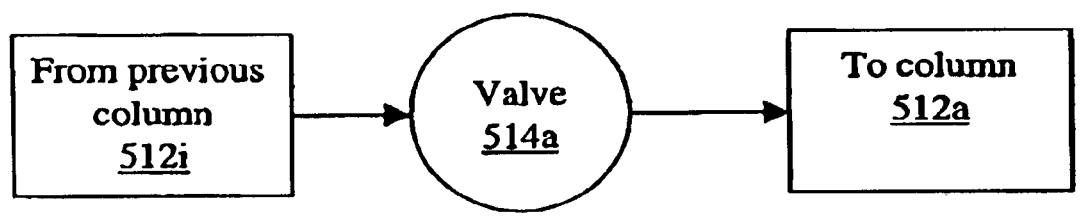
FIG. 27i is a diagrammatic representation of a first valve in the five zone simulated moving bed of FIG. 26 representing flow through the valve when the five zone simulated moving bed is in a ninth configuration.

In the ninth configuration of SMB 500, valve 514a, as shown in FIG. 27i, receives flow from column 512i, which is the first column in the fifth zone 510 and passes the flow onto column 512a, which is the last column in fifth zone 518.

The switching time and zone flow rates required for SMB 500 to facilitate the separation of a first component from a mixture including the first component and a second component are optimized from a set of equations developed as part of the present invention. This five zone SMB 500 can be used with solutes exhibiting linear adsorption isotherms and negligible mass transfer resistances, solutes exhibiting linear adsorption isotherms and non-negligible mass transfer resistances, solutes exhibiting non-linear adsorption isotherms and negligible mass transfer resistances, and solutes exhibiting non-linear adsorption isotherms and non-negligible mass transfer resistances, but is especially more efficient than a four zone SMB when the solutes to be separated exhibit highly non-linear adsorption isotherms.

In a first method of optimizing the zone flow rates and switching time, it is assumed that the solutes to be separated are solutes that exhibit non-linear adsorption isotherms and non-negligible mass transfer resistances. The zone flow rates and switching time in the first method are optimized in a similar manner to the determination of the optimal zone flow rates and optimal switching time for solutes exhibiting non-linear adsorption isotherms and non-negligible mass transfer resistances in the first method of the four zone SMB 50.

In a second method of determining the zone flow rates and switching time are optimized in a similar manner to the determination of the optimal zone flow rates and optimal switching time for solutes exhibiting non-linear adsorption isotherms and non-negligible mass transfer resistances in the second method of the four zone SMB 50.

Figure 28:
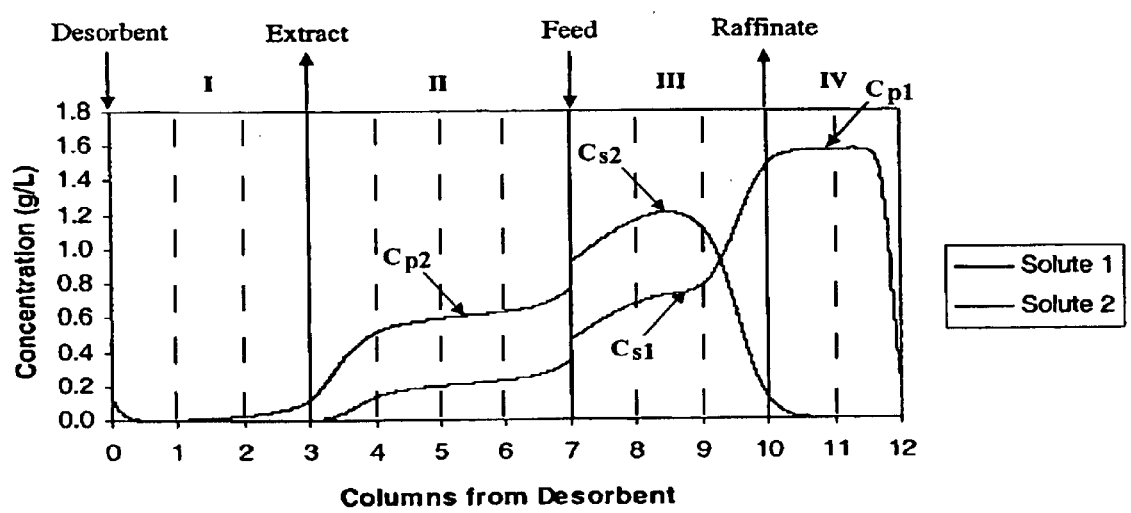
FIG. 28 shows the desired steady state standing waves of solutes in a four-zone SMB system exhibiting non-linear adsorption isotherms and non-negligible mass transfer resistances.

In a third method of determining the optimal zone flow rates and optimal switching time equations for the optimal zone flow rates and optimal switching time for five zone SMB system 500 are developed based on the assumption that the four plateau concentrations, the steady-state maximum concentrations of a non-linear system as shown in FIG. 28, can be used to find δ' terms for each zone which describe the relative adsorption or retention of each zone's designated standing wave. The δ' terms are assumed to be constant at steady state and are substituted for the linear δ terms in the linear adsorption isotherm, non-negligible mass transfer resistances equations 8a–d. The resultant equations consider both the effects of the non-linear adsorption isotherms and the mass transfer resistances of the solutes on the performance of SMB 500.

In a first example, the desired feed flow rate, $F^{feed}$, and purity requirements for both the Raffinate and the Extract are first designated. Based upon the feed flow rate, $F^{feed}$, and purity requirements the β terms in equations 10–11 are estimated. Next, the separation zone plateau concentrations must be calculated. These are the steady-state maximum concentrations found at the feed port. From the steady-state maximum concentrations the other two plateau concentrations are calculated as described in Mallmann et al (1998), the disclosure of which has been incorporated by reference. The four plateau concentrations, $C_{s1}$, $C_{s2}$, $C_{p1}$, and $C_{p2}$ are shown in FIG. 28 along with the standing wave column profiles for both the first component and the second component.

Since the concentrations of the first component and the second component are linearly related, $C_{p1}$ and $C_{p2}$ can be calculated from the equations:

$$c_1 = \gamma_+ c_2 + A_+ \tag{36}$$

$$c_1 = \gamma_- c_2 + A_- \tag{37}$$

where $$A_+ = \frac{a_1 - a_2}{a_2 b_1 + a_1 b_2 / \gamma_+} \tag{38}$$

$$A_- = \frac{a_1 - a_2}{a_2 b_1 + a_1 b_2 / \gamma_-} \tag{39}$$

where $a_i$ and $b_i$ are the linear and nonlinear adsorption coefficients of the Langmurian adsorption isotherm, respectively, for a given solute i, c1 and c2 are the concentrations of solute 1 and solute 2 at equilibrium with one another, $A_+$ and $A_-$ are terms defined by equations 38 and 39 and $\gamma_+$ and $\gamma_-$ are roots of the quadratic equation:

$$\frac{\partial q_2}{\partial c_1}\gamma^2 + \left(\frac{\partial q_2}{\partial c_2} - \frac{\partial q_1}{\partial c_1}\right)\gamma - \frac{\partial q_1}{\partial c_2} = 0 \tag{40}$$

derived by Mallmann et al (1998). Each term of this equation is a derivative of one of the adsorption isotherms, $q_1$ and $q_2$, of solute 1 and solute 2, evaluated at the feed port concentrations $C_{s1}$ and $C_{s2}$:

$$q_1 = \frac{a_1 C_{s1}}{1 + b_1 C_{s1} + b_2 C_{s2}} \tag{41}$$

$$q_2 = \frac{a_2 C_{s2}}{1 + b_1 C_{s1} + b_2 C_{s2}} \tag{42}$$

The second concentration plateau of the first component, $C_{p1}$, occurs when the concentration of the second component is zero, as seen in FIG. 28:

$$C_{p1} = c_1(c_2 = 0) \tag{43}$$

and the second concentration plateau of the second component occurs when the concentration of the first component is zero:

$$C_{p2} = c_2(c_1 = 0) \tag{44}$$

From equations 31 and 32, $C_{p1}$ and $C_{p2}$ are:

$$C_{p1} = A_- \tag{45}$$

$$C_{p2} = -\frac{A_+}{\gamma_+} \tag{46}$$

The next step is to calculate the δ' values of each zone. These terms are derived by comparing the equations 3a–d, 4, 5 for solutes exhibiting of linear adsorption isotherms and negligible mass transfer resistances for four zone SMB 50 with equations 15a–d and 16 for solutes exhibiting non-linear adsorption isotherms and negligible mass transfer resistances for four zone SMB 50. The equations for the δ' terms are:

$$\delta'^I = \varepsilon_p + (1 - \varepsilon_p)\frac{Dq_2}{Dc_2}\bigg|_{(0,0)} \tag{47a}$$

$$\delta'^{II} = \varepsilon_p + (1 - \varepsilon_p)\frac{Dq_1}{Dc_1}\bigg|_{(0,c_{p2})} \tag{47b}$$

$$\delta'^{III} = \varepsilon_p + (1 - \varepsilon_p)\frac{\Delta q_2}{\Delta c_2}\bigg|_{(c_{s1},c_{s2})} \tag{47c}$$

$$\delta'^{IV} = \varepsilon_p + (1 - \varepsilon_p)\frac{\Delta q_1}{\Delta c_1}\bigg|_{(c_{p1},c_0)} \tag{47d}$$

Once the δ' values are calculated from equations 47a–d, the δ' values are substituted into equations 18a–d for solutes exhibiting the linear adsorption isotherms and non-negligible mass transfer resistances for the four zone SMB 50 to optimize the zone flow rates.

$$u_0^I = (1 + P\delta'^I)v + \beta_2^I\left(\frac{E_{b_2}^I}{L^I} + \frac{Pv^2(\delta'^I)^2}{K_{f_2}^I L^I}\right) \tag{48a}$$

$$u_0^{II} = (1 + P\delta'^{II})v + \beta_1^{II}\left(\frac{E_{b_1}^{II}}{L^{II}} + \frac{Pv^2(\delta'^{II})^2}{K_{f_1}^{II} L^{II}}\right) \tag{48b}$$

$$u_0^{III} = (1 + P\delta'^{III})v - \beta_2^{III}\left(\frac{E_{b_2}^{III}}{L^{III}} + \frac{Pv^2(\delta'^{III})^2}{K_{f_2}^{III} L^{III}}\right) \tag{48c}$$

$$u_0^{IV} = (1 + P\delta'^{IV})v - \beta_1^{IV}\left(\frac{E_{b_1}^{IV}}{L^{IV}} + \frac{Pv^2(\delta'^{IV})^2}{K_{f_1}^{IV} L^{IV}}\right) \tag{48d}$$

where:

$$\frac{1}{K_f} = \frac{R^2}{15\varepsilon_p D_p} + \frac{R}{3k_f} \tag{49}$$

The $K_f$ term is the lumped mass transfer term, which includes the average particle radius, R, the film mass transfer coefficient, $k_f$, and the pore diffusivity, $D_p$. The $E_b$ term in the zone flow rate equations 13a–d is the axial dispersion coefficient, as determined from the Chung and Wen correlation. The solid movement velocity of the SMB system is derived from equation 6 and the substitution of equations 48b–c for into equations 8b–c.

$$\left(\frac{P\beta_2(\delta'^{III})^2}{K_{f_2}^{III}L^{III}} + \frac{P\beta_1(\delta'^{II})^2}{K_{f_1}^{II}L^{II}}\right)v^2 - P(\delta'^{III} - \delta'^{II})v + \frac{F^{feed}}{\varepsilon_b S} + \frac{\beta_2 E_{b_2}^{III}}{L^{III}} + \frac{\beta_1 E_{b_1}^{II}}{L^{II}} = 0 \quad (50)$$

The resultant equations do not provide a meaningful solution for every feed flow rate and purity conditions selected. As such, the next step is to determine if for a given feed flow rate and purity conditions, the δ' equations provide a meaningful solution.

Solution of this quadratic equation (50) is attainable only if:

$$P^2(\delta'^{III} - \delta'^{II})^2 - 4\left(\frac{P\beta_2(\delta'^{III})^2}{K_{f_2}^{III}L^{III}} + \frac{P\beta_1(\delta'^{II})^2}{K_{f_1}^{II}L^{II}}\right)\left(\frac{F^{feed}}{\varepsilon_b S} + \frac{\beta_2 E_{b_2}^{III}}{L^{III}} + \frac{\beta_1 E_{b_1}^{II}}{L^{II}}\right) \geq 0 \quad (51)$$

Given the lengths of zones 506 and 508, the porosity values of the adsorbent, the diameters of the columns, the values of the mass transfer parameters, and the desired purities and yields (the δ terms), equation 51 is used to determine the maximum feed flow rate by setting the left hand side equal to zero. The feed flow rate is used in equation 50 to determine the optimal v. The optimized v term is substituted into equations 48a–d to find the four optimized zone flow rates. Because the axial dispersion and film mass transfer coefficients of each zone depend upon the flow rate of a given zone, there is an interdependence between the zone flow rates and the mass transfer terms that must be dealt with through iteration.

The above equations 48a–d provide the flow rates for a four zone SMB system having zones I, II, III, IV, such as SMB 300. For a five-zone SMB system, such as SMB 500, the above zone flow rate for zone I is modified to optimize the flow rates of zones 502 ($I_a$) and 504 ($I_b$). For each zone 502 and 504 the $\delta'^I$ term is modified.

Zone 502 is required to wash strong desorbent introduced in zone 504 out of the present column before it reenters the continuous ring of zones 506, 508, 510 at the end of zone 510. The feed to zone 502 is pure solvent from mobile phase inlet 522. The wave velocity of strong desorbent being washed out in zone 502 is mainly dependent upon the bed volume of the column because the strong desorbent introduced into the column while the column was in zone 504 does not readily adsorb to the adsorbent. Therefore, the zone flow rate required to completely wash out the strong desorbent from zone 502 in a single switching time period depends mainly upon the bed volume and mass transfer resistances of the bed. Without the adsorption term, $\delta'^I$ from equation 47a becomes:

$$\delta'^{Ia} = \varepsilon_p \quad (52)$$

and the minimal zone flow rate of zone 502 is:

$$u_0^{Ia} = (1 + P\delta'^{Ia})v + \beta_2^I\left(\frac{E_{b_2}^I}{L^I} + \frac{Pv^2(\varepsilon_p)^2}{K_{f_2}^I L^I}\right) \quad (53)$$

Since equation 53 gives the minimal zone flow rate for zone 502 a larger flow rate for zone 502 is acceptable.

Strong Desorbent zone 504 is used to wash the second component, the more selectivity retained solute, desorption wave out into Extract outlet 524. It is desired to completely wash the second component out of the column in zone 504.

Figure 29:
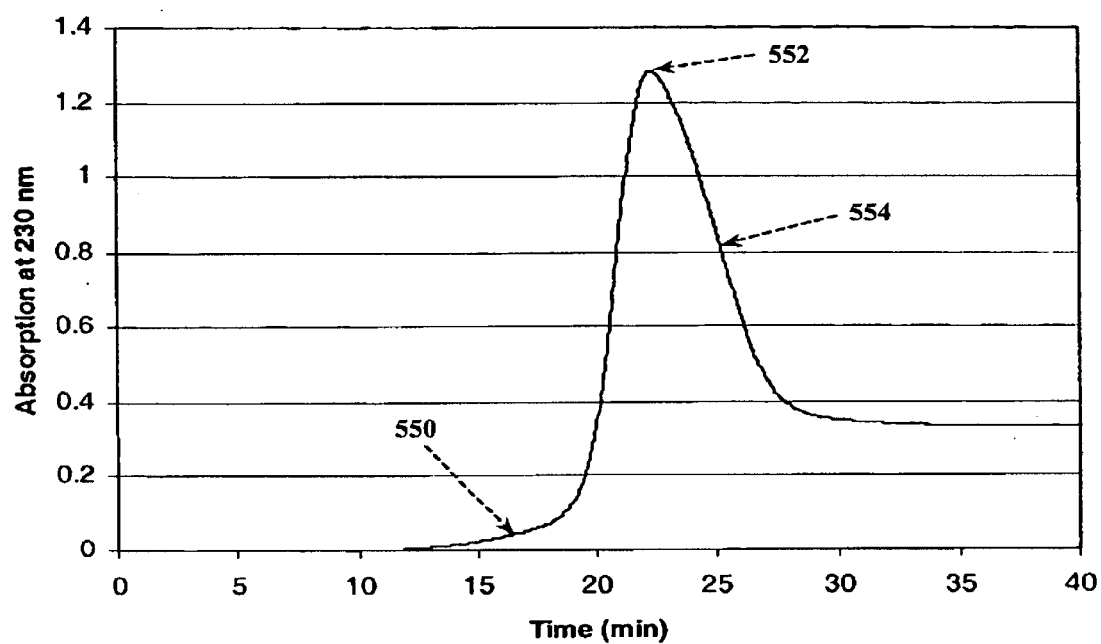
FIG. 29 shows an example of the acid breakthrough from a column.

When the strong desorbent is added to the column, the adsorption of the second component to the adsorbent is greatly reduced and is mostly linear in behavior. FIG. 29 shows an example stream flowing from the column in zone 504. In this example, the strong desorbent is a high concentration of acetic acid added to the mobile phase. The acid breakthroughs 550 is immediately followed by a pulse 552 of the second component leaving the column. The retention time of this peak 552 associated with the second component is predicted using an experimentally-determined linear adsorption isotherm coefficient, of the second component in the strong desorbent, $a_2^{strong\ desorbent}$, which is substituted into equations 3a and 4 to determine the zone flow rate required for the pulse's peak to reach the end of the column in one switching time period:

$$u_0^{Ib} = \left(1 + P\delta_2^{strongdesorbent}\right)v \quad (54)$$

But to wash out the entire pulse, there must be enough flow to wash out the spreading second half of pulse 552. Spreading 554 after pulse 552 is caused by mass transfer resistances. Therefore, the amount of spreading 554 is characteristic for a given packed column and flow conditions and can be easily experimentally determined from a single-column experiment. First, a single column is equilibriated with the second component or solute. Second, a strong desorbent is fed into the column at an appropriate flow rate. By monitoring the eluent, the time required for the second component pulse to completely wash out is determined. The mass transfer zone length is determined from the experimentally determined peak retention time and the flow rate by the following relation:

$$L_{mtz} = (t_{wash} - t_{peak})u_0 \quad (55)$$

The zone flow rate required in zone 504 to completely wash out the desorbed second component is:

$$u_0^{Ib} = \left(1 + P\delta_2^{strongdesorbent}\right)v + \frac{L_{mtz}v}{L} \quad (56)$$

Based upon the zone flow rate in zone 504, the strong desorbent zone flow rate required is optimized.

The required strong desorbent concentration for use in zone 504 is optimized by experimental study. However, the strong desorbent inlet 516 must have a higher strong desorbent concentration than the required strong desorbent concentration because the strong desorbent inlet 516 is combined with flow from zone 502 through valve 514b which will dilute the strong desorbent concentration of the strong desorbent inlet 516. The following relation is used to optimize the strong desorbent concentration for use in the five zone SMB system, when the strong desorbent is acid in this example:

$$C_{acid}^{acidwashfeed} = \frac{C_{acid}^{lb} F^{lb}}{F^{acidwashfeed}} \tag{57}$$

where $C^{lb}_{acid}$ is the acid concentration desired for optimal acid elution in zone 504, $F^{lb}$ is the flow rate of zone 504, $F^{acidwashfeed}$ is the acid wash feed flow rate at inlet 516, and $C^{acidwashfeed}_{acid}$ is the concentration of acid required for the acid wash feed. Similar calculations would have to be carried out for different types of strong desorbents.

The strong desorbent concentration resulting from the mixing of flow from zone $I_a$ and strong desorbent feed inlet 516 is not constant during the operation of the SMB. As such, equation 57 is used to insure the minimum strong desorbent concentration required. During a given period, the concentration of strong desorbent in zone 504 may be higher because of strong desorbent washing out of zone 502. This is acceptable because a higher strong desorbent concentration speeds up the desorption wave of the second component and increase the solubility of the second component.

Using the modifications to the $\delta'^I$ terms for zones 502 and 504 allows for the estimation of the optimal flow conditions for the five zone SMB. The zone flow rates for the five zone SMB system are:

$$u_0^{Ia} = (1 + P\varepsilon_p)v + \beta_2^I \left( \frac{E_{b_2}^I}{L^I} + \frac{Pv^2(\varepsilon_p)^2}{K_{f_2}^I L^I} \right) \tag{58a}$$

$$u_0^{Ib} = (1 + P\delta_2^{strongdesorbent})v + \frac{L_{mtz}v}{L} \tag{58b}$$

$$u_0^{II} = (1 + P\delta'^{II})v + \beta_1^{II} \left( \frac{E_{b_1}^{II}}{L^{II}} + \frac{Pv^2(\delta'^{II})^2}{K_{f_1}^{II} L^{II}} \right) \tag{58c}$$

$$u_0^{III} = (1 + P\delta'^{III})v - \beta_2^{III} \left( \frac{E_{b_2}^{III}}{L^{III}} + \frac{Pv^2(\delta'^{III})^2}{K_{f_2}^{III} L^{III}} \right) \tag{58d}$$

$$u_0^{IV} = (1 + P\delta'^{IV})v - \beta_1^{IV} \left( \frac{E_{b_1}^{IV}}{L^{IV}} + \frac{Pv^2(\delta'^{IV})^2}{K_{f_1}^{IV} L^{IV}} \right) \tag{58e}$$

Mobile phase inlet stream 518 contains pure solvent and combines with flow from reservoir 530 to produce the zone 506 flow rate. Its required flow rate is optimized by the flow rates of zones 510 and 506 to be:

$$F^D = S\varepsilon_b = (u_0^{II} - u_0^{IV}) \tag{59}$$

The Mobile phase inlet stream 518 flow rate can be either positive or negative. A positive value corresponds to pure solvent being fed into zone 506. A negative value corresponds to pure solvent flowing out of the reservoir and out of the system before entering zone 506. Therefore, inlet stream 518 becomes an outlet stream. If the flow rate is a negative value the excess solvent may be recycled to the Solvent Exchange feed 522 of zone 502. In summary, if the zone 510 flow rate is less than the zone 506 flow rate, a makeup inlet stream is required. If zone 510 flow rate is higher, then an outlet stream containing pure solvent is required.

In one variation of the third method, the $\delta'$ term describing the relative velocity of the second diffuse wave in equation 47b requiring a zero concentration of the first component is too conservative for determining the most efficient SMB zone flow rates and switching time. In SMB systems having mass transfer effects and diffuse wave spreading, a certain amount of the less-adsorbed solute, the first component, is inevitably lost. Therefore, it is too conservative to designate the "standing" point on the solute 1 desorption wave the zero concentration point at the very end of the wave. Rather, another point along the desorption wave is made standing to provide the desired yield with lower solvent consumption. Otherwise, using the conservative approach (zero concentration point standing) leads to an under-utilization of zone 506, a greater dilution of the product concentration, and a lower maximum feed flow rate, leading to a higher-than-necessary solvent consumption.

The $\delta'$ term is corrected by making another point on the second component wave to be standing in zone 506. This changes the concentration point for the $\delta'$ term:

$$\text{Zone II: } (\alpha_1{}''C_{s1}, C_{p2}) \tag{60}$$

where $\alpha$ is a percentage used to control what point on the first component diffuse wave is made standing in zone 506. Equation 47b then becomes:

$$\delta'^{II} = \varepsilon_p + (1 - \varepsilon_p) \frac{Dq_1}{Dc_1} \Big|_{(\alpha_1^{II} c_{s1}, c_{p2})} \tag{61}$$

It has been found that an $\alpha$ value in the range of about 20% to about 30% is adequate to correct for the conservative assumption mentioned above, but the $\alpha$ term may be modified based on the desired purity, desired yield, and desired solvent consumption requirements. Increasing the $\alpha$ term will lower solvent usage at the sacrifice of purity of the second component at the Extract and yield of the first component at the Raffinate. Decreasing the $\alpha$ term will increase the purity of the second component at the Extract and the yield of the first component at the Raffinate and the amount of solvent used.

The addition of the a term in equation 61 requires a change to be made to the calculation of the concentration plateau of the second component present in zone II, $C_{p2}$ given in equation 46. The calculation of $C_{p2}$ is at the following conditions:

$$C_{p2} = c_2(c_1 = \alpha_1{}''c_{s1}) \tag{62}$$

resulting in $C_{p2}$ being:

$$C_{p2} = \frac{-A_+ + \alpha_1^{II}}{\gamma_+} \tag{63}$$

Once the $C_{p2}$ and $\delta'^{II}$ are calculated using Equations 63 and 61, the rest of the system calculations are carried out as before. The optimal zone flow rates and switching time for five zone SMB 500 are optimized from equations 58a–e using an iterative process. A similar iterative process can be used to optimize the zone flow rates and switching time for the four zone SMB system of the first embodiment. To calculate accurate $\delta'$ terms and use them to optimize the zone flow rates and switching time, the plateau concentrations at steady-state, shown in FIG. 28, must be accurately estimated. The secondary plateaus designated by $C_{p1}$ and $C_{p2}$ are calculated from the feed port plateaus $C_{s1}$ and $C_{s2}$ as described above (equations 45 and 63). Once the plateau concentrations $C_{p1}$, $C_{p2}$, $C_{s1}$, and $C_{s2}$ are optimized the $\beta$ terms are calculated. From the $\beta$ terms, the zone flow rates and switching time are calculated.

But the feed port plateaus $C_{s1}$ and $C_{s2}$ are not easy to predict and are themselves dependent on the zone flow rates used. Therefore, the concentration plateaus $C_{s1}$ and $C_{s2}$ are optimized through an iterative process. The iterative process is required because the operating parameters of the SMB determine the degree of dilution of the feed port plateau concentrations and the optimal operating parameters of the SMB are themselves dependent on the feed port plateau concentrations.

Figure 30:
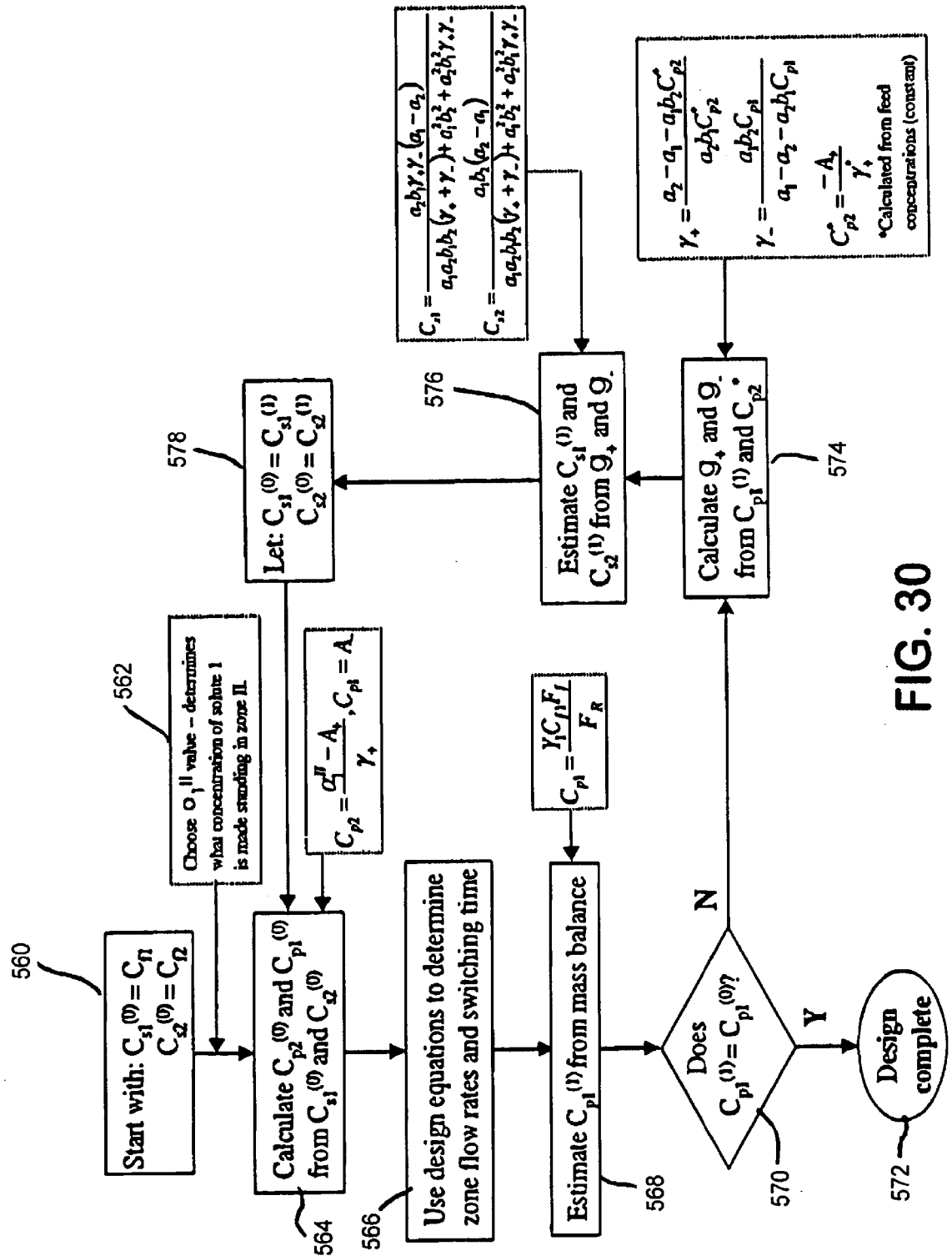
FIG. 30 is a representation of an iterative process for determining the optimal zone flow rates and switching time.

Referring to FIG. 30, a preferred iterative process is shown. The following constants are required for the iterative process: the feed flow rate ($F_f$), the feed concentrations ($C_{f1}$ and $C_{f2}$), the number of columns, column length, column configuration, the chosen $\alpha_1^{II}$ value, the desired purity, and the desired yield. All of the above constant parameters will have optimal values for a given system. Further, the adsorption properties of the adsorbent and solutes, porosity values of the adsorbent, particle size of the adsorbent and mass transfer properties of the column and solutes must be known.

A first step 560 of the iteration process is to start with values of $C_{s1}^{(0)}$ and $C_{s2}^{(0)}$ equal to the feed concentrations, $C_{f1}$ and $C_{f2}$. A value for $\alpha$ is chosen in step 562. If the feed concentrations, $C_{f1}$ and $C_{f2}$, are not known the initial values require an educated estimation. From these initial values, the initial values of $C_{p1}^{(0)}$ and $C_{p2}^{(0)}$ are calculated using equations 63 and 45:

$$C_{p2}^{(0)} = \frac{\alpha_1^{II} - A_+}{\gamma_+} \quad (65a)$$

$$C_{pl}^{(0)} = A_- \quad (65b)$$

by the above equations in step 564. The set of plateau concentration values are entered into the equations to optimize a set of zone flow rates and switching time, in step 566. Then a mass balance is used to predict $C_{p1}$, in step 568, wherein it is assumed that the average concentration of the first component at Raffinate outlet 526 will be equal to $C_{p1}$. The predicted $C_{p1}$ is:

$$C_{pl}^{(1)} = \frac{Y_1 C_{fl} F_f}{F_R} \quad (66)$$

where $Y_1$ is the expected yield of the first component and $F_R$ is the flow rate of Raffinate outlet 526. The values for $C_{p1}^{(0)}$ and $C_{p1}^{(1)}$ are compared to see if they are equal in step 570. If the values for $C_{p1}^{(0)}$ and $C_{p1}^{(1)}$ are equal, the iteration process is complete, as shown by 572.

If the values for $C_{p1}^{(0)}$ and $C_{p1}^{(1)}$ are not equal, new $C_{s1}$ and $C_{s2}$ values are calculated from $C_{p1}^{(1)}$ and $C_{p2}^*$. $C_{p2}^*$ is the theoretical value of the second component plateau concentration in zone 506 if the plateau concentration is only dependent upon the feed concentrations $C_{f1}$ and $C_{f2}$. It is assumed that the feed plateau concentrations $C_{s1}$ and $C_{s2}$ will retain the same relative values and therefore keep the resulting $C_{p2}$ plateau concentration constant. Since it is desired to calculate $C_{s1}$ and $C_{s2}$ from $C_{p2}$, the portion of the $C_{p2}$ value determined by the standing point of the first component in equation 58 is left out. Therefore, $C_{p2}^*$ is calculated using:

$$C_{p2}^* = \frac{-A_+}{\gamma_+^*} \quad (67)$$

where:

$$\gamma_+^* = \frac{-\left(\frac{\partial q_2}{\partial c_2} - \frac{\partial q_1}{\partial c_1}\right) - \sqrt{\left(\frac{\partial q_2}{\partial c_2} - \frac{\partial q_1}{\partial c_1}\right)^2 - 4\left(\frac{\partial q_2}{\partial c_1}\right)\left(-\frac{\partial q_1}{\partial c_2}\right)}}{2\frac{\partial q_2}{\partial c_1}} \quad (68)$$

evaluated at $C_1 = C_{f1}$ and $C_2 = C_{f2}$. The $\gamma$ terms are calculated from $C_{p1}^{(1)}$ and $C_{p2}^*$ in step 574.

$$\gamma_+ = \frac{a_2 - a_1 - a_1 b_2 C_{p2}^*}{a_2 b_1 C_{p2}^*} \quad (69)$$

$$\gamma_- = \frac{a_1 b_2 C_{pl}}{a_1 - a_2 - a_2 b_1 C_{pl}} \quad (70)$$

$C_{s1}$ and $C_{s2}$ are then calculated from these $\gamma$ terms in step 576:

$$C_{s1}^{(1)} = \frac{a_2 b_1 \gamma_+ \gamma_- (a_1 - a_2)}{a_1 a_2 b_1 b_2 (\gamma_+ + \gamma_-) + a_1^2 b_2^2 + a_2^2 b_1^2 \gamma_+ \gamma_-} \quad (71)$$

$$C_{s2}^{(1)} = \frac{a_1 b_2 (a_2 - a_1)}{a_1 a_2 b_1 b_2 (\gamma_+ + \gamma_-) + a_1^2 b_2^2 + a_2^2 b_1^2 \gamma_+ \gamma_-} \quad (72)$$

These values will be different than the previous $C_{s1}^{(0)}$ and $C_{s2}^{(0)}$ values. In step 578, the old values for $C_{s1}^{(0)}$ and $C_{s2}^{(0)}$ are replaced with the calculated values for $C_{s1}^{(1)}$ and $C_{s2}^{(1)}$.

$$C_{s1}^{(0)} = C_{s1}^{(1)} \quad (73)$$

$$C_{s2}^{(0)} = C_{s2}^{(1)} \quad (74)$$

The iteration loop is started over again with step 564 and the new values for $C_{s1}^{(0)}$ and $C_{s2}^{(0)}$. The iteration loop is repeated until $C_{p1}^{(1)}$ is equal to $C_{p1}^{(0)}$.

Having calculated the required plateau concentrations, the $\beta$ terms, the zone flow rates and the switching time are calculated. Modifications can be made to the above system to more closely approximate each individual five zone SMB system and the components or solutes to be separated.

For instance, when using SMB systems in which the relative size of the columns and the connecting tubing and pump volumes is such that significant additional retention time and extra-column axial dispersion is introduced an additional adjustment is made to the system equations to account for the additional retention time and extra-column axial dispersion. The additional retention time and axial dispersion is due to the substantial amount of extra-column volume between the columns in the system. Extra-column volume is the dead volume between each column that must be traversed in addition to the column void. If this extra volume is of sufficient size, it will have a detrimental effect upon the function of the SMB if not taken into account. Typically, substantial extra-volume space is present in lab-scale SMB systems.

This extra-column volume effectively increases the retention of the solute wave in each column, therefore each δ' term is modified to include this increase in retention:

$$\delta'^I = \varepsilon_p + (1-\varepsilon_p)\frac{Dq_2}{Dc_2}\Big|_{(0,0)} + \frac{V_{CSTR}}{P} \qquad (75a)$$

$$\delta'^{II} = \varepsilon_p + (1-\varepsilon_p)\frac{Dq_1}{Dc_1}\Big|_{(\alpha_1^{II} c_{s1}, c_{p2})} + \frac{V_{CSTR}}{P} \qquad (75b)$$

$$\delta'^{III} = \varepsilon_p + (1-\varepsilon_p)\frac{\Delta q_2}{\Delta c_2}\Big|_{(c_{s1}, c_{s2})} + \frac{V_{CSTR}}{P} \qquad (75c)$$

$$\delta'^{IV} = \varepsilon_p + (1-\varepsilon_p)\frac{\Delta q_1}{\Delta c_1}\Big|_{(c_{p1}, c_0)} + \frac{V_{CSTR}}{P} \qquad (75d)$$

The substitution of equations 75a–d into equations 48a–d provides the zone flow rates and switching time for four-zone SMB systems having substantial extra-volume space. For the five zone SMB system, equation 75a is replaced by the $\delta'$ terms for zones 502 and 504, with the added volume term:

$$\delta'^{Ia} = \varepsilon_p + \frac{V_{CSTR}}{P} \qquad (75e)$$

$$\delta'^{Ib} = \varepsilon_p + (1-\varepsilon_p)a_2^{acid} + \frac{V_{CSTR}}{P} \qquad (75f)$$

In summary, the zone flow rates and switching time for the four zone SMB are determined by substituting equations 75a–d into equations 48a–d and 50. For the five-zone SMB, the zone 502 and 504 flow rates are calculated differently, so equations 75a and 48a are replaced with equations 75e and 75f plugged into equations 53 and 54, respectively, to give the optimal zone 502 and 504 flow rates. The zone 506, 508, 510 flow rates and switching time calculations are identical to the four zone SMB values.

In another variation of the third method for the four zone SMB system, the first embodiment, or the five zone SMB system, the second embodiment, are simplified based on assumptions involving the mass transfer terms in zones 508 and 510. In zones 508 and 510, the solute waves are adsorption waves and the solute concentration is increasing in the upstream direction. Because of the Langmuirian nature of the adsorption isotherms, the solute adsorption strength decreases with increasing concentration so the solute will move faster at higher concentration. The faster-moving upper section of the solute wave is constantly catching up to the lower section of the solute wave, reducing the spreading caused by mass transfer resistance. Therefore, the mass transfer corrections required for these zones are overestimated. The overestimation is most prevalent when the column length is much longer than the mass transfer zone length of the system. The mass transfer zone length is the minimal length of packed bed over which a spreading wave will reach its maximum spreading width.

Due to the diminishing of the mass transfer effects in zones 508 and 510, the mass transfer terms in zones 508 and 510 are reduced or completely ignored in this variation. The reduction or elimination of these mass transfer terms in zones 508 and 510 reduces the solvent consumption of the SMB system, further optimizing the SMB system. Removing the mass transfer terms results in the following flow rate equations for zones 508 and 510:

$$u_0^{III} = (1 + P\delta'^{III})v \qquad (77)$$

$$u_0^{IV} = (1 + P\delta'^{IV})v \qquad (78)$$

The quadratic equation for solid movement velocity becomes:

$$\left(\frac{P\beta_1(\delta'^{III})^2}{K_{f_1}^{II} L^{II}}\right)v^2 - P(\delta'^{III} - \delta'^{II})v + \frac{F^{feed}}{\varepsilon_b S} + \frac{\beta_1 E_{b_1}^{II}}{L^{II}} = 0 \qquad (79)$$

For the special case of the 5-zone SMB, it may not be desirable to remove the mass transfer term from the zone 510 flow rate equation. This is because of the difference in column order and system structure. In a four zone SMB, the first adsorption wave of solute 1 can be standing in zone IV on an average basis, but the very front of the wave will still enter zone I. This is not a problem, because this part of the wave will return to zone IV at the end of the period. But for the 5-zone SMB, any amount of solute 1 that leaves zone IV will be lost in the extract rather than returning to zone IV at the end of the switching time period. Therefore, the conservative system including the mass transfer terms may be preferable in some cases, and the removal of the mass transfer terms to reduce solvent consumption should be done on a case-by-case basis.

Several optimal plant-scale systems were determined for various mobile phase and adsorbent combinations, with the zone flow rates and switching times calculated by the equations developed above. Table DD gives each solvent-sorbent system along with the required adsorption parameters, mass transfer parameters, and physical packed column parameters, which were estimated through experimentation. Using the system method and the experimentally-determined physical properties, an optimal plant-scale system was created for each mobile phase-adsorbent system to show the potential for the five zone SMB system to be used to meet production requirements of feed (60 g/min), final purity (90%), and final yield (95%). The plant scale flow rates in both the first embodiment and the second embodiment are determined by multiplying the flow rates $u^1$ by $S\epsilon_b$, wherein S is the cross-sectional area of the column and $\epsilon_b$ is the interparticle porosity of the adsorbent.

The preferred mobile phase-stationary phase combinations are shown in Table DD. In one variation the mobile phase used to separate Clarithromycin and 6,11 includes about 50 percent by volume to about 85 percent by volume of an organic solvent, such as either about 50 percent by volume isopropyl alcohol to about 60 percent by volume isopropyl alcohol, about 60 percent by volume to about 80 percent by volume of ethanol, or about 75 percent by volume to about 85 percent by volume methanol.

TABLE DD

| Solvent-sorbents system data | Case A | Case B | Case C | Case D | Case E | Case F | Case G |
|---|---|---|---|---|---|---|---|
| Physical parameters and system parameters for plant-scale five zone system | | | | | | | |
| Mobile Phase | 60% IPA | 50% IPA | 60% EtOH | 50% IPA | 80% MeOH | 75% MeOH | 85% MeOH |
| Sorbent | Dow L323 | Dow L323 | Dow L323 | XAD-16 | Dow L323 | Dow L323 | Dow L323 |
| Fresh solvent cost ($/L) | $ 0.667 | $ 0.667 | $ 0.552 | $ 0.667 | $ 0.277 | $ 0.277 | $ 0.277 |
| Net solvent cost ($/L)* | $ 0.133 | $ 0.133 | $ 0.111 | $ 0.133 | $ 0.0554 | $ 0.0554 | $ 0.0554 |
| Clari in mixture solubility | 2.23 | 1.06 | 1.60 | 1.06 | 2.46 | 1.90 | 2.70 |
| Selectivity ($a_2/a_1$) | 1.29 | 1.30 | 1.25 | 1.24 | 1.28 | 1.32 | 1.09 |
| Langmuir isotherm parameters (per solid volume mass) | $a_1 = 10.2$ $b_1 = 0.16$ $a_2 = 13.20$ $b_2\ 0.21$ | $a_1 = 24.0$ $b_1 = 0.30$ $a_2 = 31.20$ $b_2 = 0.44$ | $a_1 = 42.0$ $b_1 = 0.30$ $a_2 = 52.3$ $b_2 = 0.37$ | $a_1 = 21.0$ $b_1 = 0.32$ $a_2 = 26.1$ $b_2 = 0.40$ | $a_1 = 39.0$ $b_1 = 0.43$ $a_2 = 45.0$ $b_2 = 0.38$ | $a_1 = 79.8$ $b_1 = 0.60$ $a_2 = 105.2$ $b_2 = 1.05$ | $a_1 = 23.0$ $b_1 = 0.31$ $a_2 = 25.1$ $b_2 = 0.34$ |
| Plant scale system parameters | | | | | | | |
| Mode | SMB | SMB | SMB | SMB | SMB | SMB | SMB |
| Column diameter (m) | 2.08 | 2.52 | 2.37 | 2.91 | 3.48 | 1.99 | 7.07 |
| Column length (m) | 3.00 | 3.00 | 3.00 | 3.00 | 3.00 | 3.00 | 3.00 |
| Column configuration | 1-1-4-4-2 | 1-1-4-4-2 | 1-1-4-4-2 | 1-1-4-4-2 | 1-1-4-4-2 | 1-1-4-3-3 | 1-1-4-4-2 |
| Feed flow rate (L/min) | 26.9 | 56.6 | 37.5 | 56.6 | 26.9 | 35.3 | 22.2 |
| Feed Clari concentration (g/L) | 2.23 | 1.06 | 1.60 | 1.06 | 2.46 | 1.70 | 2.70 |
| Raffinate flow rate (L/min) | 27.9 | 55.3 | 47.8 | 64.5 | 72.8 | 44.7 | 87.9 |
| Make-tip flow rate (L/min) | 1.0 | -1.2 | 10.3 | 7.8 | 48.4 | 9.4 | 65.7 |
| Extract/acid wash flow rate (L/min) | 110 | 93.1 | 55.7 | 141 | 126 | 35.6 | 427 |
| Zone II flow rate (L/min) | 253 | 407 | 392 | 569 | 871 | 362 | 2009 |
| Switching time (min) | 94.6 | 164.6 | 242.9 | 145.5 | 255.3 | 267.0 | 282.1 |
| Sorbent Cost ($/kg) | $ 10 (5%) | $ 14 (7%) | $ 13 (9%) | $ 19 (7%) | $ 30 (15%) | $ 9 (12%) | $ 112 (20%) |
| Equipment Cost ($/kg)** | $ 10 | $ 10 | $ 10 | $ 10 | $ 10 | $ 10 | $ 10 |
| Organic Solvent Consumption (L/g) | 1.45 | 1.30 | 1.09 | 1.80 | 2.79 | 1.06 | 7.67 |
| Solvent Cost ($/kg) | $193 (91%) | $173 (88%) | $121 (85%) | $239 (89%) | $155 (79%) | $ 59 (76%) | $ 425 (78%) |
| Total Purification Cost ($/kg) | $213 | $197 | $143 | $268 | $195 | $ 77 | $ 547 |

*Based on 80% recycle recovery assumption (20% of solvent is fresh)
**Based on $2M low pressure SMB equipment depreciated over 7 years The adsorbent Dow Optipore Hydrophobic XUS-40323 (L323) is produced by Dow Chemical (Midland, Mich.). The adsorbent Amberlite XAD-16 is produced by Rohm and Haas (Philadelphia, Pa.). The mobile phases consist of a given % volume of an organic solvent and the remainder % volume water. The isopropyl alcohol (IPA) is HPLC grade produced by Mallinckrodt located in Paris, Ky. The methanol (MeOH) is IPLC grade produced by Mallinckrodt located in Paris, Ky. The Ethanol is 200 proof produced by Mallinckrodt located in Paris, Ky. The water is distilled and deionized produced by a Millipore filtration system located at Purdue University in West Lafayette, Ind.

The isotherms parameters were determined experimentally for both Clarithromycin and 6,11. Each isotherm had the following Langmuir-type form:

$$Q_{6\text{-}O\text{-}methylerythromycinA} = \frac{a_{6\text{-}O\text{-}methyl} C_{6\text{-}O\text{-}methyl}}{1 + b_{6\text{-}O\text{-}methyl} C_{6\text{-}O\text{-}methyl} + b_{6,11\text{-}O\text{-}methyl} C_{6,11\text{-}O\text{-}methyl}} \quad (80)$$

$$Q_{6,11\text{-}O\text{-}methylerythromycinA} = \frac{a_{6,11\text{-}O\text{-}methyl} C_{6,11\text{-}O\text{-}methyl}}{1 + b_{6\text{-}O\text{-}methyl} C_{6\text{-}O\text{-}methyl} + b_{6,11\text{-}O\text{-}methyl} C_{6,11\text{-}O\text{-}methyl}} \quad (81)$$

where $C_i$ is the concentration of solute i present (g solute/L mobile phase) and $Q_i$ is the adsorption of species i (g solute i/g adsorbent). Terms a and b are the linear and non-linear adsorption isotherm coefficients, respectively. The values of the isotherm constants are found by fitting Equations 80 and 81 to experimental data. The estimated values for each chromatography system are shown in Table DD.

The solubility data for each system tested in Table DD, was determined by the following method. First, a measured amount of dry crude mixture (39.3% clari, 37.5% 6,11, and 23.2% other impurities) was added to a measured volume of the mobile phase solvent being used for the particular test case and the mixture was stirred. Heat was added while the mixture was being stirred because dissolution of Clarithromycin and 6,11 is very slow at room temperature. The solution temperature was allowed to approach the boiling temperature of the solvent. The solution was held constant at that temperature until no more solid material was present in the mixture (complete dissolution). The heat source was removed and the mixture was allowed to cool to room temperature (24 C.) while stirring for at least 48 hours. This cooling period insures that no super-saturation occurs. If the Clarithromycin and 6,11 did not precipitate out of the solution the solute concentrations were determined by mass balance and/or HPLC analysis. In order to determine the absolute limit, the amount of dry solid added to the solvent is increased and the experiment carried out again. This process is repeated until the solid starts to precipitate out during the cooling period indicating that the solubility limit had been breached. Then HPLC analysis is used to determine the solubility limit from the final solution concentrations.

The physical parameters used in the plant scale-up systems for deriving the optimal zone flow rates and switching time were estimated. An optimal SMB system is one that provides the required production rate, purity, and yield at the lowest cost. These physical parameters include the feed composition, the feed flow rate, column diameter, column length, particle diameter, the number of columns, and column configuration. Since the column diameter can be freely changed to meet production requirements as long as the linear zone velocities, $u_{Os}$, are kept constant, the column diameter is first given a small value to make flow rate values more convenient for computer simulations. The particle diameter is preferably small but is limited by the pressure drop and commercial availability. Typically, a longer column is preferred in SMB systems in order to minimize mass transfer effects. However, both the pressure drop and the physical plant size limit the length of the column. The feed composition, or the concentrations of the adsorbed species in the feed, is an important determinant of solvent consumption and sorbent utilization when optimizing the operating parameters of the SMB process. The maximum feed concentration, determined by the solubility limit of the solvent, will yield the highest sorbent utilization and is optimal for a linear system. But for nonlinear systems, there will be an optimal set of feed concentrations, determined by relative solvent consumption and sorbent utilization. This is one of many parameters that have to be optimized by developing several sets of optimal designs and pinpointing the optimal value of that parameter. Other parameters that must be treated this way are the feed flow rate, the number of columns, and the column configuration (the placement of columns).

Once initial parameters have been chosen, the maximum feed flow rate is determined using equation 51. Maximizing the feed flow rate gives the system its highest adsorbent utilization, or throughput, which reduces the adsorbent and equipment costs. However, the maximum feed flow rate may not be the optimal one for a given set of purity and yield requirements, because solvent consumption may be lower at certain feed flow rates and solvent consumption is the most important cost factor. Therefore, the optimal feed flow rate is not necessarily the maximum feed flow rate. The maximum pressure drop in the system is estimated using the Blake-Kozeny equation:

$$\Delta P = \frac{150 \mu F L}{S(2R)^2} \frac{(1-\varepsilon_b)^2}{\varepsilon_b^3} \tag{82}$$

where $\mu$ is the mobile phase viscosity, F is the flow rate in a given zone, L is the zone length, S is the cross-sectional area of the columns and R is the particle radius. This equation is appropriate for laminar flow, Reynolds numbers less than 10, and void fractions less than 0.5. The maximum pressure drop of the system must be found to be within the limitations of the five zone SMB system for the given system to be acceptable. If the pressure drop is found to be within system limitations, the column lengths and number of columns in each zone can be increased to further optimize the process. For Table DD, it was assumed the maximum practical column length was 3.0 meters.

Once the desired column length, feed flow rate, particle size, and feed composition are known, it is also desired to optimize the total number of columns used and their distribution (configuration) within the SMB system (among zones 502, 504, 506, 508, and 510 for the five zone SMB). This step in the optimization is guided by a number of guidelines. For zones 504 and 506, in first portion 501 one column per zone or one portion of a column is preferred. For zones 506, 508, 510 in second portion 503, in the five zone SMB system a minimum of two columns or portions of a column per zone is preferred. For a particular separation, there will be a maximum number of columns that will be considered practical. Further, zone 506 which involves the most difficult and important separation is preferred to have the largest number of columns or portions of a column. Once the feed flow rate, feed composition, column length, number of columns, and column configuration have all been optimized and the particle diameter and preliminary column diameter set, the optimal system parameters are calculated from equations 58a–e and 50. Once the optimal parameters are determined for a given system, the column diameter and feed flow rate can be proportionately increased (scaled up) to meet the throughput requirements while keeping the linear velocities in each zone constant. Once the diameter and flow rates have been scaled up, the adsorbent and solvent requirements are determined and a cost per mass product is determined.

For each of the cases A, B, C, D, E, F, G shown in Table DD, an optimal scale-up system for the SNB process was found using a target throughput of 60 g/min, a target purity of 90%, and a target yield of 95%. The smallest particle diameter for the adsorbents that is commercially available is 360 microns. In order to facilitate easy comparison between the plant-scale and lab-scale simulated moving bed and computer simulation, the preliminary column diameter was set at 1.5 cm. The column length was set at 3.0 meters. In practice, this length of column will require two partition/distribution plates to be installed in each column in order to reduce adsorbent attrition caused by weight in a long column.

Using the aforementioned method for determining the zone flow rates and switching time for a five zone SMB, the optimal zone flow rates and switching time of a twelve-column simulated moving bed were developed for each chromatography system in Table DD. Equations 58a–e and 50 provided the optimal zone flow rates and switching time and a ox correction term (30%) and the plateau concentration iteration procedure described above were used for calculating the $\delta'$ terms. These optimal operating parameters are summarized in the Table DD.

Table DD shows the optimal column dimensions, column configuration, feed flow rate, feed concentration, mobile phase flow rates, and outlet flow rates required for each mobile phase-stationary phase system. The estimated stationary phase cost, equipment cost, and mobile phase cost are also shown. In order to determine stationary phase requirements, the column diameter was determined from the required feed flow rate, which was then used to determine the volume of stationary phase required and finally the cost of stationary phase per kilogram of purified product. For equipment costs, a plant-scale low-pressure simulated moving bed unit was assumed to cost $2,000,000 and to be depreciated over 7 years. For mobile phase costs, the organic solvent consumption (L/g product) was determined by adding the organic feed flow rate and organic mobile phase flow rate together, then dividing by the production rate. The solvent cost was estimated by assuming that 20% of solvent used would be fresh feed while the rest would by recycled. The fresh solvent costs used are also given in Table DD. Finally, the total product cost is given as the sum of stationary phase, equipment, and mobile phase costs. Water cost, labor cost, and utility cost were neglected.

As can be seen from the plant-scale cost estimations in Table DD, mobile phase cost is the major concern for optimization of these simulated moving bed systems, as it accounts for greater than 80% of the production cost. The high solvent consumption of these systems is due to the low solubility of the solvents, the low selectivity of the adsorbent-solvent systems, and the high affinity and high degree of non-linearity of the adsorption isotherms of the solutes. The most cost-efficient system is (F) with a solvent/adsorbent combination of 75% by volume methanol and Optipore adsorbent. The estimated purification cost of Clarithromycin for system E is $77/kg.

Figure 31A:
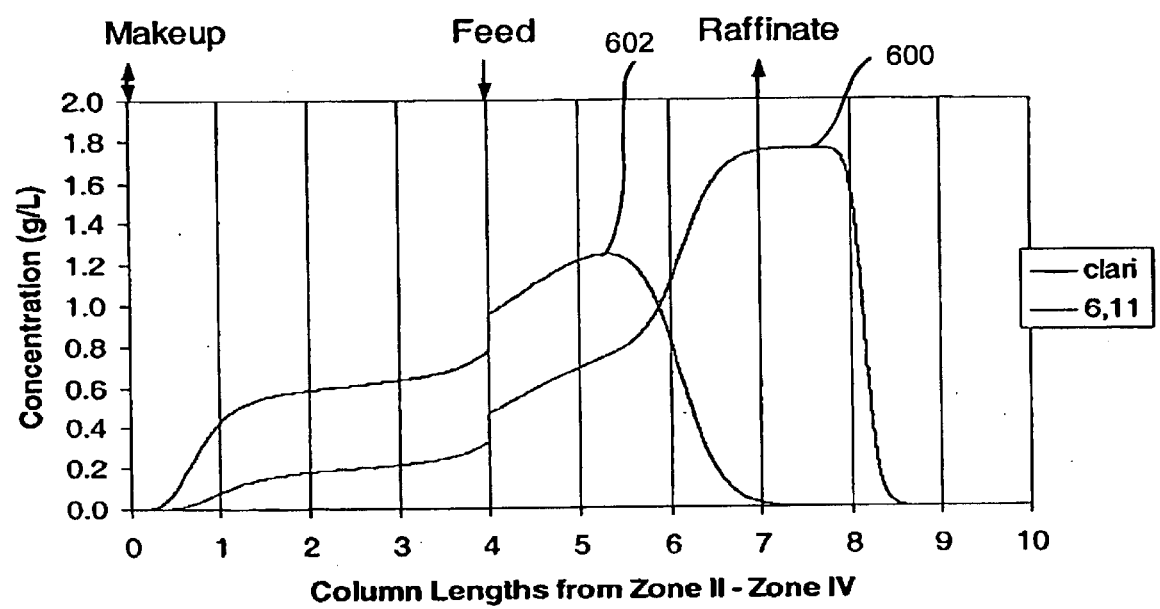
FIG. 31a shows the simulated standing wave column profiles of the five zone simulated moving bed of FIG. 26 at the end of the $140^{th}$ switching period.
Figure 31B:
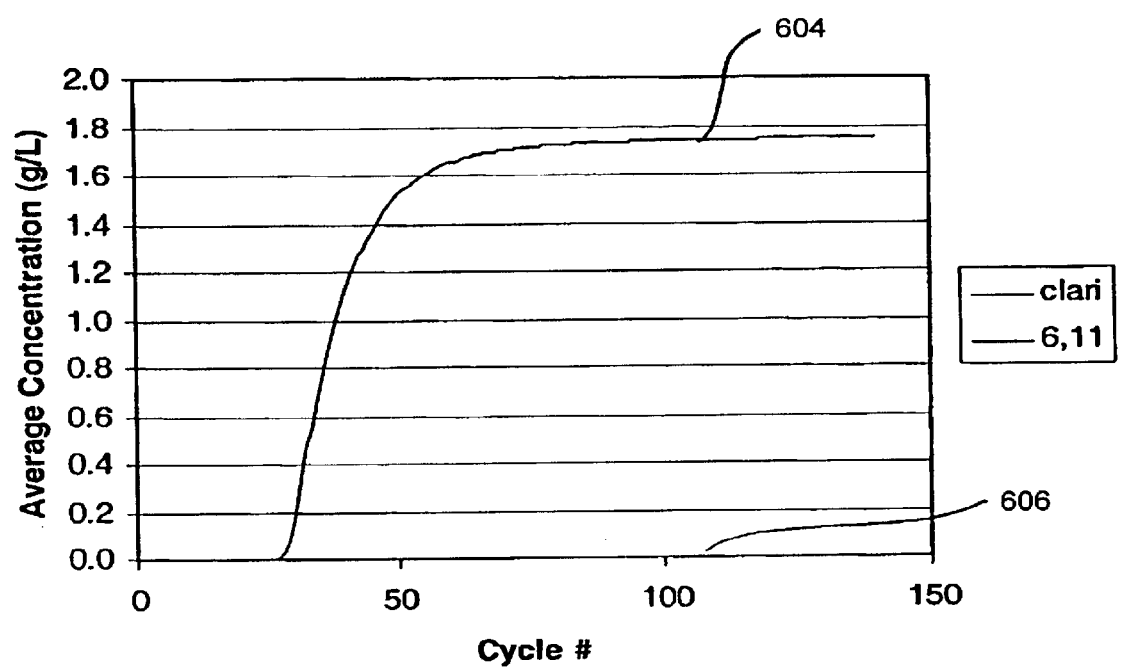
FIG. 31b shows the simulated Raffinate history of the five zone simulated moving bed of FIG. 26.

The parameters for the 80% by volume methanol and Optipore adsorbent (Case E in Table DD) were simulated using the VERSE program described. FIGS. 31a and 31b show the simulation results. FIG. 31a shows the column profiles for Clarithromycin 600 and 6,11 602 from zones 506, 508, 510 at the end of the $140^{th}$ switching time period. FIG. 31b shows the Raffinate history for Clarithromycin 604 and 6,11 606, plotting average concentration versus switching time period. The expected purity and yield for both Clarithromycin and 6,11 are shown in Table EE.

TABLE EE

Simulated results for Case E

|  | Avg. $C_{clari}$ | Avg $C_{6,11}$ | Purity | Yield |
|---|---|---|---|---|
| Raffinate | 1.75 g/L | 0.004 g/L | 99.8% | 89.9% |
| Extract* | 0.099 g/L | 1.39 g/L | 93.4% | 99.9% |

*estimated from mass balance

The 80% by volume methanol and Optipore adsorbent 5 zone SMB system was tested using a lab-scale SMB system. The lab-scale experiment serves to validate the experimentally-determined adsorption parameters of the system along with other properties such as mass transfer constants and porosities.

The lab scale system used is SMB 500 shown in FIGS. 26 and 27a–i. SMB 500 is controlled by a software program executed by a processor 515. The software program, in one embodiment, requires the zone flow rates and switching time from the equations for solutes to be provided to the software, including the zone flow rates and switching time for solutes exhibiting non-linear adsorption isotherms and non-negligible mass transfer resistances to be provided to the software. In another embodiment, the software program includes code to solve the zone flow rates and switching time equations for solutes including the zone flow rates and switching time for solutes exhibiting non-linear adsorption isotherms and non-negligible mass transfer resistances to optimize the zone flow rates and switching time. The software is used to control the valve positions for each period and requires the switching time to entered in order to change the valve positions to their proper order among the columns at the end of each switching time period. In one embodiment, the software program is written in the software package, LabView available from National Instruments located at Austin, Tex.

Columns 512a–i are 12.2 cm in length and 1.5 cm in diameter. Columns 512a–i are made of glass and are Model No. Omnifit 64120 available from Alltech located in Deerfield, Ill. Columns 512a–i are packed with the Optipore adsorbent, having particle sizes in the range of 38–150 mm in diameter. According to the product sheet for the Optipore adsorbent, the intraparticle porosity of this adsorbent is 0.664.

Columns 512a–i were packed with the adsorbent by using a degassed slurry consisting of the mobile phase and the clean adsorbent. The slurry was added to the empty columns 512a–i slowly in order to allow for uniform packing. To insure that the packing of all nine columns 512a–i was uniform, porosity tests were run for each column 512a–i. The porosity tests consisted of introducing a 0.5 ml pulse of concentrated blue dextran available from Sigma Chemical located in St. Louis, Mo., into each column 512a–i and monitoring the flow from the column using a photodiode array detector Model No. Waters 990, available from Waters located in Milford, Mass., at 620 nm. The retention time of each pulse was then determined. Because blue dextran does not adsorb and is too large due to its very high molecular weight to enter the pores of the adsorbent, the retention time of blue dextran is used to calculate the interparticle porosity of a packed column. Columns that did not exhibit similar results were emptied and repacked until all nine columns 512a–i exhibited similar porosity characteristics. The porosity values for each column 512a–i is shown in Table FF. The average interparticle porosity is 0.396.

TABLE FF

Porosity of columns used in lab scale SMB system

| Col. No. | 512a | 512b | 512c | 512d | 512e | 512f | 512g | 512h | 512i | Avg. |
|---|---|---|---|---|---|---|---|---|---|---|
| $\epsilon_b$ | 0.362 | 0.411 | 0.421 | 0.376 | 0.397 | 0.411 | 0.383 | 0.401 | 0.398 | 0.396 |

Four LPLC (low pressure liquid chromatography) pumps (model number P-500 produced by Pharmacia Fine Chemicals in Chicago, Ill.) and one HPLC (high pressure liquid chromatography) pump (model number Waters 510 HPLC pump produced by Waters in Milford, Mass.) are used to provide the 5 different zone flow rates of the five zone SMB system. Three FPLC pumps 532, 536, 538 provide the following feed flows: Feed 520, Mobile Phase 522, and Strong Desorbent 516, respectively. The fourth FPLC pump 540 is used to feed pure solvent into zone 506, providing the zone 506 flow rate. In one variation, the pure solvent is recycled flow from zone 510 with a make-up flow provided by an additional pump. Because of the technical difficulties involved in the lab-scale experiments it was decided that the flow between zones 510 and 506 would not be recycled directly, but the outlet flow from zone 510 would be fed into reservoir 530 containing the zone 506 feed solvent 518. Because the outlet flow from zone 510 should be free of both Clarithromycin and 6,11, this is a reasonable substitution. This also allows for direct measurement of the Zone 510 flow rate to insure that the pumps 532, 534, 536, 538, 540 are operating properly. Though this recycle of flow is important in the conservation of solvent and the overall efficiency of the SMB, it is not important to the development of the solute concentration profiles and the separation of Clarithromycin and 6,11. Therefore, as long as the recycled solvent is monitored periodically through HPLC analysis, it is valid to treat any experimental results as if recycle were instantaneous. For this reason five zone SMB Experiments #1–4 had a 4.0 L reservoir into which the recycle flow from Zone 510 entered. This reservoir then served as the source of Zone 502 and Zone 506 feed and was assumed to be essentially pure solvent (that is, any impurities present would not effect the adsorption behavior of Clarithromycin or 6,11). Fresh solvent was regularly added to make up for solvent exiting the system and to keep the reservoir volume fairly constant. However, because of suspected recycle effects and the possibility of contamination, mobile phase inlet 522 was used as the sole source of the solvent exchange feed (Zone 502). HPLC pump 534 provides the flow rate for Raffinate 526, the product outlet stream. The combination of pumps 532, 534, 536, 538, 540 provides the five zone flow rates, four inlet flow rates, and two outlet flow rates required by the five-zone SMB system.

Before the columns are installed in the system, all of the lines connecting the columns and the inlets and outlets are washed with pure 80% methanol and each column is washed with first 80% methanol with acetic acid and then pure 80% methanol, both at 1.5 ml/min for 30 minutes. After the columns are installed, each pump is calibrated under operating conditions to insure that the flow rates are accurate.

In addition to the assembly of the physical system 500, the maximum feed concentration allowed by solubility must be known to optimize the operating parameters with the non-linear, non-equilibrium equations. The solubility was determined in the manner described earlier. Next, the optimal feed concentration was determined and was created by diluting the maximum feed concentration solution. The optimal feed calculation is carried out in the same manner as for the plant scale systems described above. The final optimal system is limited by the limitations of the lab-scale system.

At a base level, the number of columns and column lengths of the lab scale system are different than the plant scale system. Further, the flow rates of pumps 532, 534, 536, 538, 540 have limited ranges and accuracy. Pumps 532, 536, 538 and 540 have a range of –0.01 to 9.99 ml/min with an accuracy of 0.01 ml/min. Pump 534 has a range of –0.1 to 9.9 ml/min with an accuracy of 0.1 ml/min. Due to the limitations of the lab-scale system, the purity and yield of the lab scale system will not likely match the plant scale purity and yield. However, the lab scale system will provide a measurement of the applicability of the method used to optimize the zone flow rates and switching time.

The number of columns and column configuration used for the lab scale SMB experiments were different than the plant scale system. The lab scale system has nine columns 512a–i in a 1-1-3-2-2 configuration. Zones 502 and 504 are in the first portion separate from zones 506, 508 and 510 in the second portion and are used for the washing steps. As such, only one column is used for each zone 502 and 504. In the second portion, zones 506, 508, and 510, a minimum of two columns are used in each zone 506, 508, 510. Zone 506 includes an extra column to increase the overall length of zone 506 wherein the most difficult separation of Clarithromycin and 6,11 occurs. By using this extra column to increase the length of zone 506 the maximum possible Clarithromycin yield at the Raffinate is increased. As shown in FIG. 26, the final configuration is 1-1-3-2-2. the desired purity was set to at least 95% and the desired yield was set at least 90% for use in the equations to determine the optimal zone flow rates and switching time. As discussed before, the desired yield and purity are used to estimate the $\beta$ terms.

The optimal feed concentrations of the lab scale system were determined for several different dilutions of the feed solution to determine an optimal set of concentrations. For each feed concentration, the maximum feed flow rate, $F^{feed}$, was optimized and the corresponding zone flow rates and switching time were found using equations 58a–e and 50. The zone flow rates and switching time were simulated using the VERSE simulation program. These simulations were used to predict the product purity, product yield, and run time required for steady-state operation. Based upon the simulations the most optimal systems were tested with the lab scale system 500.

As stated earlier the zone flow rates must fall within the range and accuracy of the pumps 532, 534, 536, 538, 540 of SMB 500. Once the operating parameters of the lab-scale experiment were optimized, the mixture for the Feed inlet 520, the solution for the Strong Desorbent inlet 516, the solution for the Mobile phase inlet 518 and the solution for the Mobile Phase inlet 522 were prepared. The mixture for Feed inlet 520 was diluted to the optimized concentrations and analyzed by HPLC to insure accuracy. The solutions for Mobile phase inlet 518 and 522 were pure 80% methanol. The solution for Strong Desorbent inlet 516 was 12 ml/L acetic acid in 80% methanol. It is preferred that the concentration of the acetic acid be 3 g/L in zone 504. Alternatively, other weak acids can be used instead of acetic acid. Processor 515 controls the switching time, and the initial order of the columns by controlling the valve positions. In one embodiment, the switching time, order of the columns, and valve positions for each period are entered into a program being executed by processor 515. In another embodiment, processor 515 calculates the optimal zone flow rates and optimal switching time. In another embodiment, the processor calculates the optimal zone flow rates and optimal switching time for subsequent switching periods based upon the purity and yield results of prior switching periods. Therefore, the processor in one embodiment includes a feedback loop to optimize the zone flow rates and switching time based upon the current results of the five zone SMB system.

To start the experiment, Strong desorbent inlet 516, Mobile phase inlet 518, Feed inlet 520, mobile phase inlet 522, and Raffinate outlet 526 and the respective pumps 538, 540, 532, 536, 534 are activated simultaneously. The outlet flows are collected on a per-step time (switching period) basis. These include the Extract outlet 524, the Raffinate outlet 526, and the zone 510 outlet 528. After each switching period, these collected flows are each measured for total volume and sampled for later HPLC analysis. Samples are stored in test tubes with plastic lock-caps to prevent evaporation. The total volume for each outlet is used to determine the average outlet flow rate. These flow rates are compared with the expected flow rates to determine pump accuracy and predict experimental results using the VERSE simulation program.

Five Zone SMB Experiment #1

The feed solutions for Experiment #1 were prepared by mixing 5.6 g dry crude (39.3% clari, 37.5% 6,11, 23.2% other) Clarithromycin and 6,11 with 1000 ml of 80% methanol. This mixture was then heated to about 70° C. and stirred until it was a clear solution. The solution was allowed to cool to room temperature and stirred for fifteen hours. Finally, this solution was filtered to remove any remaining solids and the volume measured to insure there was not significant evaporation. This final solution was analyzed by HPLC to determine the maximum feed concentration. This analysis indicated that the concentrations were 2.19 g/L Clarithromycin and 2.74 g/L 6,11. These values are within the solubility limit determined by previous solubility tests to be 2.46 g/L Clarithromycin and 3.03 g/L 6,11.

For Experiment #1, the following adsorption isotherms were used, based on the current adsorption isotherm data derived from single-column frontal tests:

$$Q_{clari} = \frac{38.0 C_{clari}}{1 + 0.31 C_{clari}} \quad (83)$$

$$Q_{6,11} = \frac{48.5 C_{6,11}}{1 + 0.44 C_{6,11}} \quad (84)$$

Based upon the equations 58a–e and 50, it was determined that the feed concentration should be diluted 2×. At 2× dilution, the predicted purity and yield of Clarithromycin was estimated to be greater than 95% and the feed flow rate and zone flow rates were within the limitations of SMB 500. At higher concentrations, the maximum feed flow rate would be too low and/or the zone flow rates too high.

The resulting calculations based on 2× dilution (using plateau concentration iteration and equation 51) indicated that 0.17 ml/min was the maximum feed flow rate to be used. The parameters for Experiment #1 are summarized in Table GG. The low set yield of 80.0% was found to actually result in a higher VERSE-simulated yield, but this was probably due to a miscalculation in the feed concentrations discussed below in connection with the Experimental results. The extra-column volume of 2.0 ml is an estimate of the dead volume present between each column. The axial dispersion factor is an estimated correction to the Chung and Wen correlation used to calculate the axial dispersion coefficient. The relatively large amount of dead volume, connections, and valves compared to column volume in the lab-scale system creates a larger amount of axial dispersion that must be taken into account. The factor 20× was used based on past experience with lab-scale systems.

TABLE GG

Experimental parameters for Experiment #1

| | |
|---|---|
| Feed flow rate | 0.17 ml/min |
| Particle radius | 50 μm |
| Raffinate impurity | 15% ($\beta_2^{III}$ = 1.87) |
| Extract impurity | 15% ($\beta_1^{II}$ = 1.68) |
| α correction factor | 20% |
| Set yield | 80% |
| Extra-column volume | 2.0 ml |
| Axial dispersion factor | 20 × |

TABLE HH

Expected and Experimental Results for Experiment #1

| Flow Rates | Original Design (ml/min) | Adjusted Design (ml/min) | Experimental (ml/min) |
|---|---|---|---|
| Zone 502 | 0.290 | 0.30 | |
| Zone 504 | 0.534 | 0.60 | |
| Zone 506 | 2.790 | 2.79 | |
| Zone 508 | 2.960 | 2.96 | |
| Zone 510 | 2.698 | 2.60 | 2.605 |
| Strong desorbent 516 | 0.244 | 0.30 | |
| Extract 524 | 0.534 | 0.60 | 0.60 |
| Mobile phase 518 | 0.092 | 0.19 | |
| Feed 520 | 0.170 | 0.17 | |
| Raffinate 526 | 0.262 | 0.36 | 0.37 |
| Switching time | 59.5 min | 59.5 min | 59.5 min |

The flow rates optimized with equations 58a–e and 50 are shown in Table HH in the column headed Original Design. These flow rates were simulated for 140 switching time periods using the VERSE simulation program. From this simulation, a Clarithromycin purity of 99.1% and Clarithromycin yield of 91.8% is predicted at steady-state. The second column in Table HH entitled Adjusted System provides the parameters of the Original system to accommodate the requirements (constraints) of SMB 500. All the flow rates were rounded to the accuracy of the appropriate pumps. Further, the Raffinate and Strong Desorbent flow rates were increased. The Raffinate flow rate was increased by 37% to increase Clarithromycin yield and lessen the chance of the Clarithromycin adsorption wave reaching zone 506. The Strong Desorbent and Mobile Phase flow rates were increased 12.4% and 3.4%, respectively, to insure the columns in the first portion, zones 502 and 504, were completely washed and that acid concentration in zone 504 was always at least 3 ml/L. The parameters in the Adjusted System column were simulated in the VERSE simulation program to determine the expected results of the experimental run. From this simulation, the expected purity and yield of the Clarithromycin product is 97.3% and 97.5% after 140 switching time periods. The simulated column profile and simulated raffinate history are shown in FIGS. 31*a* and 31*b*, respectively.

This simulation was experimentally tested with SMB 500 for 51 switching time periods. The average outlet flow rates for the first 46 switching time periods are shown in Table HH in the column entitled Experimental. Only the first 46 switching periods were considered for the average because the switching time was increased by five minutes to 64.5 minutes for switching periods 47–51. As seen in Table NH, the average experimental flow rates were fairly accurate compared with the simulated flow rates.

Figure 32A:
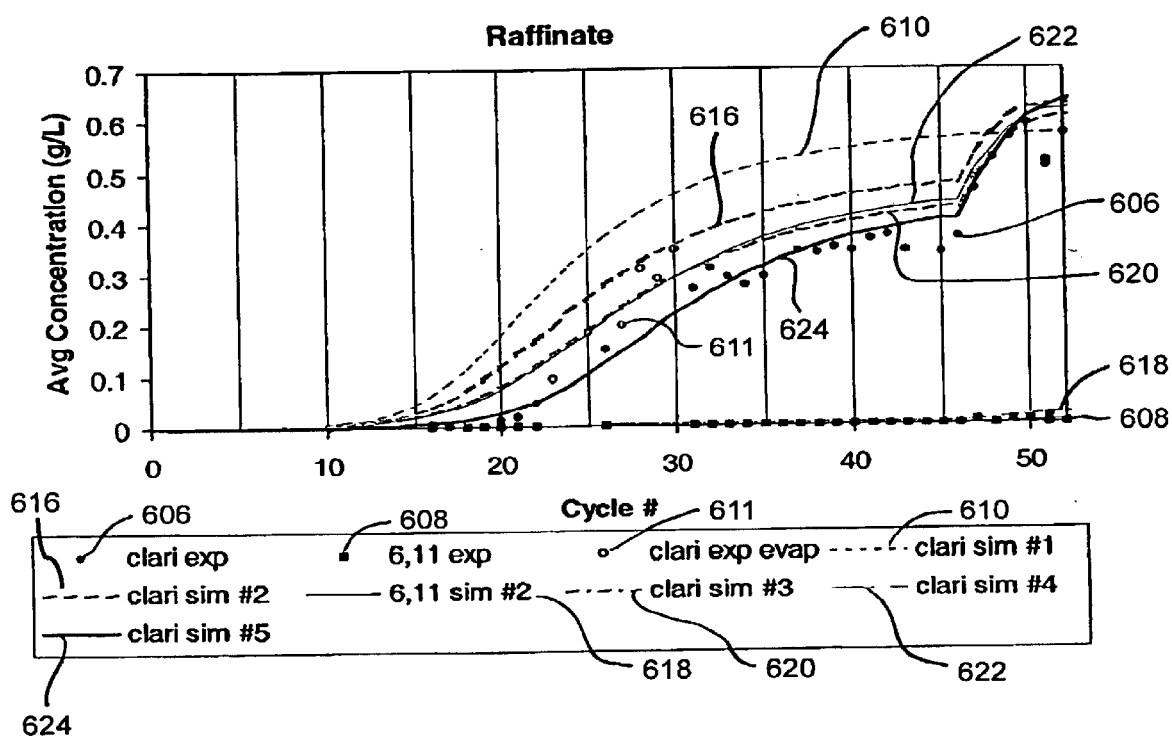
FIG. 32a shows the experimental and simulated histories for the Raffinate for Experiment #1 of the five zone simulated moving bed of FIG. 26.
Figure 32B:
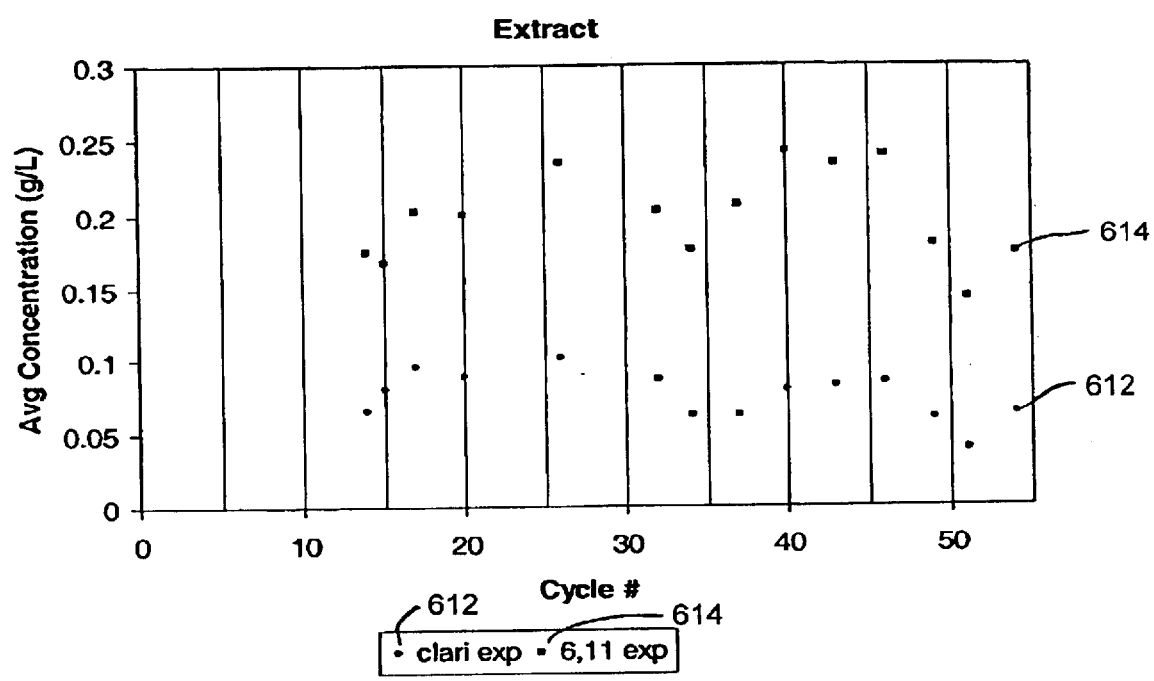
FIG. 32b shows the experimental and simulated histories for the Extract for Experiment #1 of the five zone simulated moving bed of FIG. 26.

The experimental and expected results for Raffinate 526 and Extract 524 are shown in FIGS. 32*a* and 32*b*. FIG. 32*a* shows the flow from Raffinate 526 including Clarithromycin experimental data set 606, 6,11 experimental data set 608, and the Clarithromycin simulated profile 610. FIG. 32*a* also include Clarithromycin samples 611 which were inaccurate due to evaporation of solvent before testing for concentration. FIG. 32*b* shows the flow from Extract 524 including the Clarithromycin experimental data 612 and the 6,11 experimental data 614. At the 46$^{th}$ switching time period, the purity of Clarithromycin from Raffinate 526 is very high (~100%), with 6,11 concentrations at Raffinate 526 nearly zero throughout. However, the yield for the Clarithromycin at Raffinate 526 after 46 switching time periods is only about 71%, compared to the expected 97.5%.

As shown in FIGS. 32*a–b*, the experimental average concentrations of Clarithromycin at Raffinate 526 were much lower than simulated curve 610 while the concentrations of Clarithromycin at Extract 524 were higher than expected. HPLC analysis of the samples from Raffinate 526 and Extract 524 taken before switching time period #46 showed that experimental results for yield and purity did not match the predicted results. This indicates that the Clarithromycin was not completely reaching Raffinate 526 because it was more retained than predicted, resulting in a significant amount of Clarithromycin being lost in Extract 524. The HPLC analysis further showed that the 6,11 concentration was not as high as the mass balance calculations suggested. It was determined that the extract data were only marginally useful, because acetic acid breaks down both Clarithromycin and 6,11. The switching time for switching periods 47–51 was increased by 5 minutes to 64.5 minutes to see the effect on the Raffinate. As can be seen in FIG. 32*a*, the experimental data for Clarithromycin in switching cycles 47–51 better approximates the simulated curve 610, indicating that a longer switching period results in more Clarithromycin reaching Raffinate 526 and an increase in yield.

The results of the HPLC analysis suggest two possible errors. First, the feed concentrations were lower than expected. Second, the adsorption of the Clarithromycin was stronger than expected. A review of the experimental results showed that there were two errors made in the calculation of the feed concentrations for Experiment #1. First, the concentrations entered into the system equations were 1.23 g/L Clarithromycin and 1.57 g/L 6,11, the values corresponding to a 2× dilution in the solubility limits. But the actual feed concentrations were a 2× dilution of 2.19 g/L Clarithromycin and 2.74 g/L 6,11, as determined by HPLC analysis. Second, the $C_{p2}^*$ value used in the plateau concentration iteration to optimize the zone flow rates and switching time corresponded to the maximum feed concentrations not the diluted (actual) feed concentrations.

The feed concentration values were corrected and the system was simulated a second time. The resulting Clarithromycin simulation curve 616 and the resulting 6,11 simulation curve 618 are shown in FIG. 32*a*. Simulation curve 616 still does not accurately reflect the experimental data, even though the two switching times (first one for cycles 1–46 and the second one for cycles 47–51) were included in the simulation.

The discrepancy between the experimental data and second simulation curve 616 suggests that corrections to the adsorption isotherms for Clarithromycin and 6,11 are required. One indication of the need to recalculate the adsorption isotherms is that the mass balance of 6,11 did not agree with the determined feed concentration. One reason for this is that the strong acid used to wash the columns of SMB system 500 destroys some of the 6,11. Another reason is that the 6,11 concentration in the adsorption experiments was overestimated by HPLC analysis. It was determined that the HPLC response factor of 6,11 was 1.31, much greater than Clarithromycin (1.00). That is, a given concentration of 6,11 will have an HPLC peak area 1.31 times that of a Clarithromycin sample of equal concentration. Therefore, the concentrations of 6,11 had up to this point been overestimated. As such, the actual feed concentrations for Experiment #1 were 1.10 g/L Clarithromycin and 1.05 g/L 6,11.

Using these corrected feed concentrations, a third simulation was conducted resulting in Clarithromycin simulation curve 620 shown in FIG. 32*a*. Simulation curve 620 has a closer fit to the experimental data than simulation curves 610 and 616. However, the expected steady-state concentration of Clarithromycin in Raffinate 526 is still higher than the experimental results. This suggests that either the CSTR volume is inaccurate or the adsorption of one or both of Clarithromycin and 6,11 is stronger than expected. The CSTR volume was believed to be within the range of the actual values for SMB 500. As such, the adsorption isotherm for one or both of Clarithromycin and 6,11 needed to be recalculated. The Clarithromycin adsorption isotherm has been extensively tested and believed to be fairly accurate, as such the adsorption isotherm for 6,11 is reevaluated.

The 6,11 isotherm was developed using solutions that contained significant amounts of Clarithromycin, 5–15%. The 6,11 isotherm was previously created with the assumption that the solution contained only pure 6,11. A more accurate isotherm for 6,11 should account for the amount of Clarithromycin present in the solution.

Only one frontal was detected during the frontal experiments for the 6,11 isotherm, due to the similarity between Clarithromycin and 6,11. However, the recorded frontal was actually two frontals, one attributable to 6,11 and one attributable to Clarithromycin. Therefore the adsorption is governed by the following relationship including, $Q_{tot}$:

$$u = \frac{L}{t_{r,total}} = \frac{v}{1 + \frac{1-\varepsilon_b}{\varepsilon_b}\varepsilon_p K_d + \frac{1-\varepsilon_b}{\varepsilon_b}(1-\varepsilon_p)\frac{\Delta Q_{total}}{\Delta C_{total}}} \quad (85)$$

The adsorption of 6,11 can be determined from the total adsorption:

$$Q_{tot} = Q_{clari} + Q_{6,11} \quad (86)$$

It is required that the isotherm constants $a_{6,11}$ and $b_{6,11}$ be estimated from the adsorption data. Because the Clarithromycin concentration is a variable in determining the total adsorption, it is required to expand Equation 81 and derive a line equation having the form of y=mx+b. By putting the isotherm equation in a linear form allows a linear regression analysis to estimate the 6,11 isotherm constants. The expansion of Equation 81 yields:

$$Q_{tot} = \frac{a_{clari}C_{clari} + a_{6,11}C_{6,11}}{1 + b_{clari}C_{clari} + b_{6,11}C_{6,11}} \quad (87)$$

Among the terms of Equation 87, $a_{6,11}$ and $b_{6,11}$ are unknown constants. $Q_{tot}$, $C_{clari}$, and $C_{6,11}$ are variables, but only two are independent. The linear form of Equation 87 is provided below as Equation 90:

$$(1 + b_{clari}C_{clari} + b_{6,11}C_{6,11})Q_{tot} = a_{clari}C_{clari} + a_{6,11}C_{6,11} \quad (88)$$

$$(1 + b_{clari}C_{clari})\frac{Q_{tot}}{C_{6,11}} + b_{6,11}Q_{tot} = \frac{a_{clari}C_{clari}}{C_{6,11}} + a_{6,11} \quad (89)$$

$$\frac{(1 + b_{clari}C_{clari})Q_{tot} - a_{clari}C_{clari}}{C_{6,11}} = -b_{6,11}Q_{tot} + a_{6,11} \quad (90)$$

In Equation 90 the x and y variables are defined as:

$$y = \frac{(1 + b_{clari}C_{clari})Q_{tot} - a_{clari}C_{clari}}{C_{6,11}} \quad (91)$$

$$x = -Q_{tot} \quad (92)$$

The slope and y-intercept from Equation 90 are defined as:

$$A = b_{6,11} \quad (93)$$

$$B = a_{6,11} \quad (94)$$

Data from the frontal experiments was tabulated and the terms x and y from each solute frontal were calculated.

Using a regression analysis $a_{6,11}$ and $b_{6,11}$ were determined to be 48.22 and 0.456, respectively. The resultant isotherm for 6,11 is:

$$Q_{6,11} = \frac{48.22 C_{6,11}}{1 + 0.456 C_{6,11}} \quad (95)$$

Using this new isotherm, the 6,11 Experiment #1 was simulated a fourth time using the corrected isotherm values, as shown by Clarithromycin simulation curve 622 in FIG. 32a. Simulation curve 622 shows little change from simulation curve 620. As such, this inaccuracy in the 6,11 isotherm does not completely explain the difference between the simulation 622 and the experimental data 606.

The CSTR volume was increased to 5 ml and the Experiment #1 was simulated for a fifth time, resulting in simulation curve 624 shown in FIG. 32a. Simulation curve 624 shows good agreement with experimental data 606. At this point, it appeared that the CSTR volume between each column was larger than expected or adsorption strength was larger than expected.

Five Zone SMB Experiment #2

Unless otherwise stated, the same parameters were used in Experiment #2 as in Experiment #1. The feed solution was created by adding 2.8 g dry crude Clarithromycin and 6,11 to 1.0 L 80% methanol and using the same heating and cooling steps as used in Experiment #1. This provides the same feed concentration as used in Experiment #1, 1.10 g/L Clarithromycin and 1.05 g/L 6,11, based on mass balance and the corrected HPLC analysis method. In addition, the adsorption isotherms were modified because of additional single-column adsorption data:

$$Q_{clari} = \frac{37.7 C_{clari}}{1 + 0.31 C_{clari}} \quad (96)$$

$$Q_{6,11} = \frac{47.0 C_{6,11}}{1 + 0.43 C_{6,11}} \quad (97)$$

The isotherms in equations 96 and 97 have a lower selectivity. The lower selectivity resulted in a lower maximum feed flow rate: 0.15 ml/min. Also, the target purity and yield of Clarithromycin at Raffinate 526 were lowered to 95% each. The resulting operating parameters are shown in Table II in the column entitled Original Design. Simulation of these operating parameters predicted a Clarithromycin purity of 98.9% at Raffinate 256 and a Clarithromycin yield of 94.1% at Raffinate 256.

TABLE II

Operating Parameters for Experiment #2

| Flow Rates | Original Design (ml/min) | Adjusted Design (ml/min) | Experiment #2 (ml/min) |
|---|---|---|---|
| Zone 502 | 0.284 | 0.30 | |
| Zone 504 | 0.356 | 0.40 | |
| Zone 506 | 2.687 | 2.69 | |
| Zone 508 | 2.837 | 2.84 | |
| Zone 510 | 2.564 | 2.53 | 2.55 |
| Strong Desorbent | 0.072 | 0.10 | |
| Extract | 0.356 | 0.40 | 0.45 |
| Mobile phase | 0.123 | 0.16 | |
| Feed | 0.150 | 0.15 | |
| Raffinate | 0.273 | 0.31 | 0.31 |
| Switching time | 60.9 min | 60.9 min | 60.9 min |

The Original System was modified to meet the accuracy of the SMB system 500. The adjusted parameters are given in Table II in the column entitled Adjusted Design. Simulation of the adjusted parameters predicted Clarithromycin purity of 98.8% at Raffinate 256 and Clarithromycin yield of 94.8% at Raffinate 256. The expected output of Raffinate 256 for the Adjusted parameters is shown in FIG. 33 as Clarithromycin simulation curve 626 and 6,11 simulation curve 628.

The parameters for the Adjusted System were tested with SMB 500. Before the actual Experiment was performed, the SMB 500 columns were washed first with an acidic 80% methanol solution followed by a pure 80% methanol solution. Pumps 532, 534, 536, 538, 540 were calibrated with all columns 512a–i installed and valves 514a–i set for column configuration #1, shown in FIG. 26. SMB 500 was calibrated by measuring the time taken for a particular outlet flow to fill up a 25 ml volumetric flask. Valve switching was not initiated during this calibration step, so any effects the valve switching would have on the average flow rate, such as pressure fluctuations, were not considered.

Figure 33:
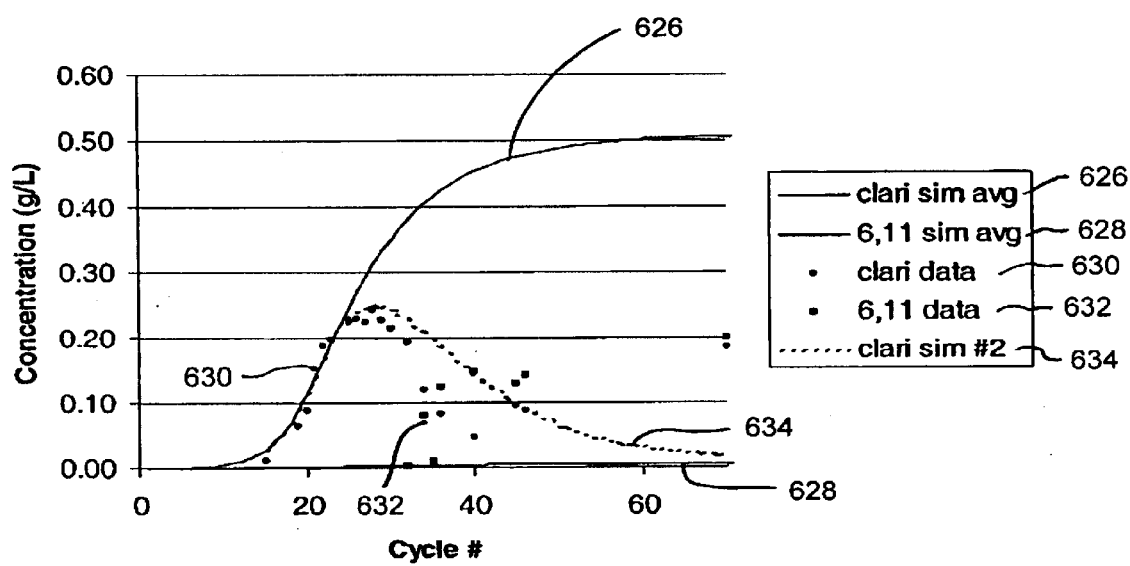
FIG. 33 shows the Experiment and simulated histories for the Raffinate for Experiment #2 of the five zone simulated moving bed of FIG. 26.

Experiment #2 was run for 70 switching time periods, as shown in FIG. 33. FIG. 33 includes Clarithromycin experimental data set 630 and 6,11 experimental data set 632. However, the Raffinate history developed as expected for only 23 switching time periods. Raffinate history for switching time periods greater than the $23^{rd}$ switching period deviated from the expected Raffinate history. It was discovered subsequent to the $23^{rd}$ switching period that pump 540 stopped functioning properly and needed to be repaired. Pump 540 was replaced.

A second simulation of Experiment #2 was carried out under the assumption that pump 540 stopped functioning after the $23^{rd}$ switching period. The resultant Clarithromycin simulation curve 634, in FIG. 33, shows agreement with experimental data 630.

Five Zone SMB Experiment #3

Experiment #2 conditions were used again once pump 540 was replaced for Experiment #3. Experiment #3 was run for 158 switching time periods, but several adjustments were made to the flow conditions throughout due to inaccurate flow rates and indications by preliminary data from Raffinate 526. During switching time periods #1–86, it was discovered that pump 540, the pump providing the feed into Zone 506, was behaving erratically. Adjustments were regularly made to correct for this, but flow was too inconsistent to provide consistent data.

Figure 34:
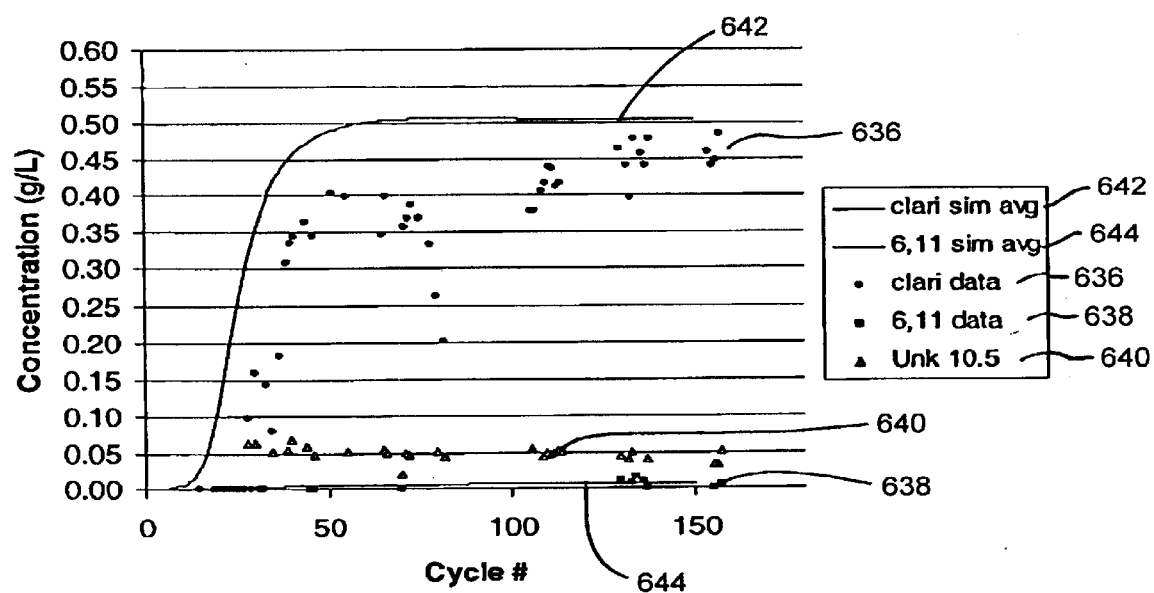
FIG. 34 shows the experimental and simulated histories for the Raffinate for Experiment #3 of the five zone simulated moving bed of FIG. 26.

FIG. 34 includes Clarithromycin experimental data 636, 6,11 experimental data 638, and Unknown 10.5 (so named for the time (10.5 minutes) at which the unknown peak occurs in HPLC analysis at 2 ml/min) experimental data 640. The Unknown 10.5 experimental data 640 represents a further impurity in Raffinate 526. This impurity should be removed from the Clarithromycin by a subsequent crystallization.

It was discovered during Experiment #3 that the previous method of flow rate measurement was inaccurate. The flow rate must be measured over an entire switching period to get an accurate average flow rate because of the inherent pressure changes caused by the valve switching at the beginning of each switching time period. Further observation of this flow discrepancy found that pump 540 was leaking through the plunger seals when system pressure reached its highest levels. This was most likely the source of the flow irregularities and the extreme fall in zone 510 flow rate before period #86. This loss of flow resulted in the fall in Clarithromycin concentration at the Raffinate 526 as seen in FIG. 34. Therefore, the process was stopped after switching time period #86, pump 540 replaced, and the process was started again with a more reliable pump in place.

The new pump 540 resulted in a more consistent flow rate for zone 510. Once this flow rate was correct, the process was allowed to reach steady-state, as shown by the Raffinate history shown in FIG. 34. However, the steady-state Clarithromycin concentration was lower than expected, as shown in Table JJ and FIG. 34; compare Clarithromycin simulated profile 642 and 6,11 simulated profile 644 to experimental data at period #s 87–109. In order to increase this concentration and therefore the yield of the process, the pump 540 flow rate was increased slowly, allowing time for steady-state to be reached at each new flow rate. The flow rates of both zone 510 and Raffinate 526 were measured during each of these periods. The flow rates, average Clarithromycin concentration at steady state, Clarithromycin purity, and Clarithromycin yield during each of these periods is shown in Table JJ. The final pump 540 flow rate increase (switching time periods #138–158) had the highest Clarithromycin yield (86.8%) at Raffinate 526 with no loss in Clarithromycin purity at Raffinate 526 (99.9%), as shown in Table JJ. The experimental run was ended after 158 switching time periods.

periods subsequent to the replacement of pump 540 (switching time periods #87–158) are useful because they can be reproduced by bringing computer simulations of the process to steady-state at the appropriate flow conditions. These sets of steady-state concentrations, combined with the final column profile concentration data from simulation of the final flow conditions, were used to determine corrections that needed to be made to increase Clarithromycin yield at Raffinate 526 and improve the accuracy of the optimal flow conditions and the VERSE-simulated prediction.

Based on the results from the first 3 SMB Experiments, it appears that the adsorption of Clarithromycin and 6,11 is stronger than estimated from the single-column experimental data. Besides inaccurate adsorption isotherm data, the simulated curves 656, 658 and experimental data sets 646, 648 profile results shown in FIG. 35 suggest several possible corrections. First of all, the experimental data suggests a profile that is much sharper than the simulated profile. That is, the spreading of the waves is much more subdued than anticipated. The Clarithromycin adsorption frontal of zone 510 never reaches the last column in the second portion, column 512i in the first configuration shown in FIG. 26. Further, the multiple concentration profiles appear to be more developed than the simulation results, which suggests less axial dispersion. As such, it appears that the 20× factor added to the Chung and Wen axial dispersion coefficient was unnecessary. Second, the extra-column volume (between each column) is much less than 5 ml and may be insignificant (<0.5 ml), based on measurements made of these volumes. Therefore, the CSTR volume cannot be used to explain the experimental results.

TABLE JJ

Experimental Results for Five Zone SMB Experiment #3

| Cycles | Avg. Zone 510 Flow (ml/min) | Avg. Raffinate Flow (ml/min) | Avg. Zone 506 Flow (ml/min) | Avg. Raffinate Clarithromycin Concentration (g/L) | Avg. Clarithromycin Purity at Raffinate (%) | Avg. Clarithromycin Yield at Raffinate (%) |
|---|---|---|---|---|---|---|
| 1–86 | Varied | 0.302 | Varied | Varied | 99.9% | 73.2%* |
| 87–109 | 2.54 | 0.309 | 2.70 | 0.405 | 99.9% | 75.8% |
| 110–114 | 2.58 | 0.309 | 2.74 | 0.427 | 99.9% | 80.1% |
| 115–137 | 2.59 | 0.303 | 2.74 | 0.460 | 97.8% | 84.5% |
| 138–158 | 2.61 | 0.304 | 2.76 | 0.471 | 99.9% | 86.8% |

*best yield when concentration plateau is fully developed (cycles #51–55)

Figure 35:
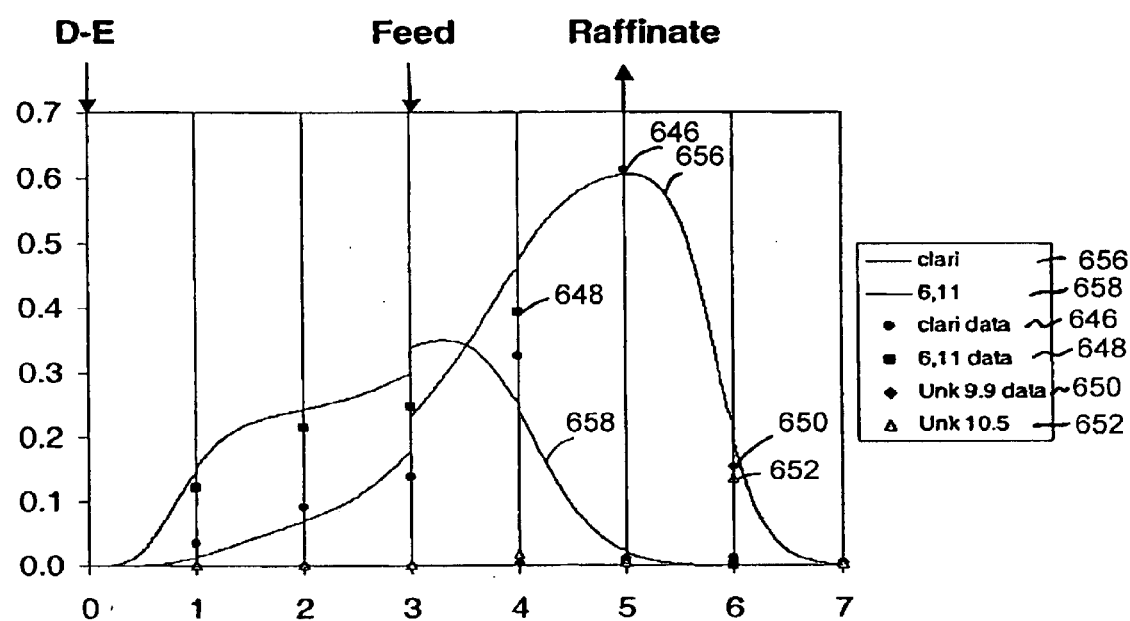
FIG. 35 shows the experimental and simulated column profiles at steady state for Experiment #3 of the five zone simulated moving bed of FIG. 26.

In order to get column profile data at steady-state, small samples were taken from the outlets of the seven columns 512c–i in the second portion 503 of SMB 500 at the end of the 158th switching time period. FIG. 35 shows the experimental concentration data from these samples for Clarithromycin 646, 6,11 648 and two unknowns 650 and 652 versus the simulated column profiles for Clarithromycin 656 and 6,11 658 at the end of a steady-state switching time period. The unknowns were other solutes present in the crude mixture. Their inclusion in FIGS. 34 and 35 serves to show their presence and their relative concentration and retention in the SMB 500 process, but their concentrations are not included in the calculation of purity because it is assumed that they can be easily removed when the product is crystallized. The column profile data for Clarithromycin and 6,11, 646 and 648, show disagreement with the simulated profiles, 656 and 658.

Because of the erratic flow rate of zone 510 due to pump 540 the data from switching time periods #1–86 is not useful. However, data corresponding to the switching time But these corrections do not explain the apparent increase in adsorption of both Clarithromycin and 6,11. The experimental profile data and additional VERSE simulations are used to more-accurately estimate the apparent Clarithromycin and 6,11 isotherms beyond simply increasing the a-terms of the adsorption isotherms. Several important observations from FIG. 35 help to make this determination. First of all, the front Clarithromycin concentration plateau creates a sharp "hump" at the front of the profile, so the Clarithromycin concentration in column 512h in FIG. 26 has a sharp decrease from $C_{p1}$ to nearly zero to create the first adsorption frontal. On the other side of this hump there is another sharp wave so that the Clarithromycin concentration at the end of column 512d in FIG. 35 is much lower than $C_{p1}$. The second observation is a 6,11 "hump" created by the $C_{s2}$ concentration plateau that is more concentrated and further to the right in the second portion. Both of these behaviors suggest higher $b_i$ values for both the Clarithromycin and 6,11 isotherms.

Another important observation is that there appears to be some adsorption activity by some of the unknowns. Unknowns 650, 652, appear to have enough affinity that they are captured just in front of the Clarithromycin adsorption frontal in zone 510. This resulted in both unknowns 650 and 652 becoming more concentrated and eventually removed at the Raffinate outlet stream. The presence of these unknowns may be significant because of the pH-dependence that the adsorption of both Clarithromycin and 6,11 is known to have.

Figure 36A:
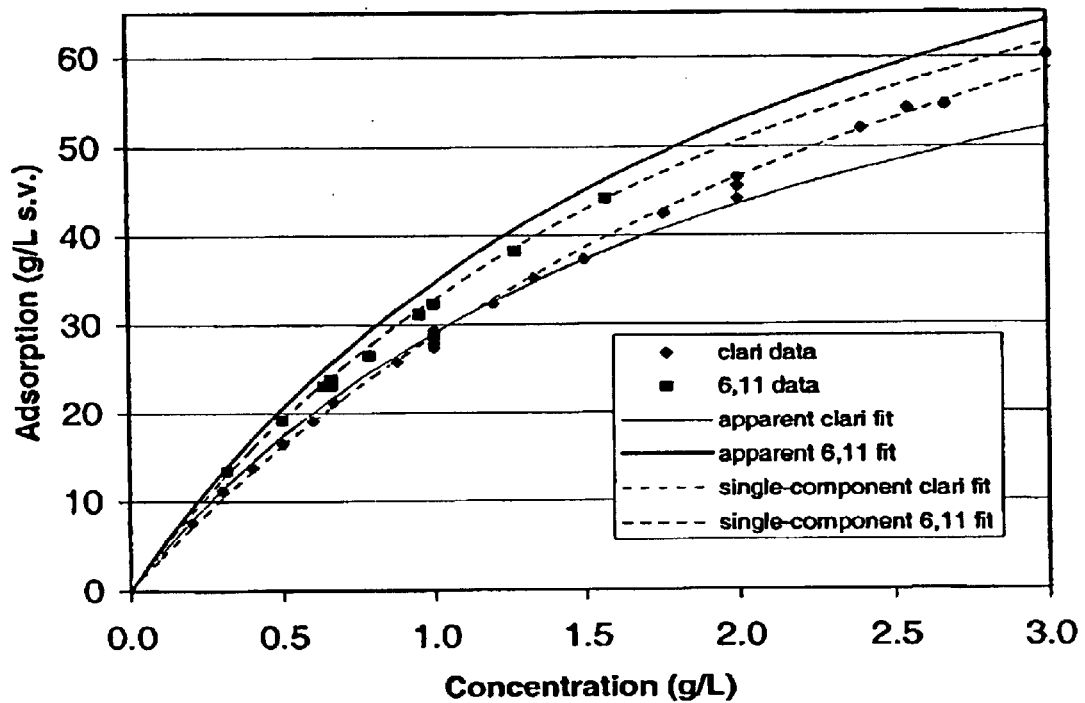
FIG. 36a shows the apparent isotherm fit from 80% methanol/L-323 lab-scale SMB Experiment #3 and single-component isotherm fits.
Figure 36B:
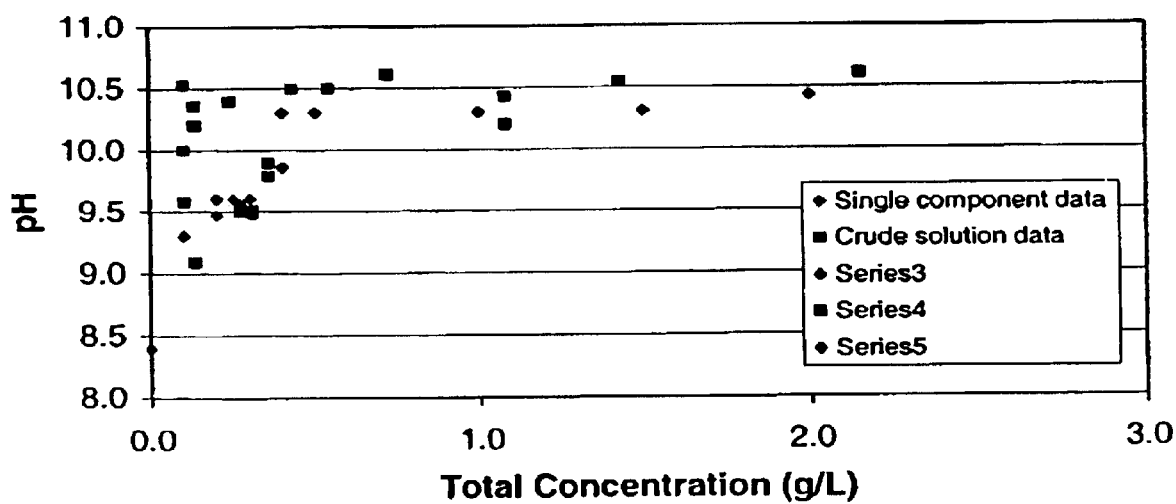
FIG. 36b shows pH data from pure Clarithromycin in 80% methanol solutions and a mixture of Clarithromycin and 6,11 in 80% methanol solutions.

Using this information the single-component adsorption isotherms of Clarithromycin and 6,11, the simulated axial dispersion factor, and simulated extra-column volume were all modified to fit the experimental data. The axial dispersion factor was reduced to 1×, indicating that the Chung and Wen correlation is adequate. The extra-column volume was reduced to 1.0 ml. The apparent adsorption isotherms used to fit the data are shown in FIGS. 36a and 36b. These new isotherms are:

$$Q_{clari} = \frac{43.5 C_{clari}}{1 + 0.50 C_{clari}} \quad (98)$$

$$Q_{6,11} = \frac{50.5 C_{6,11}}{1 + 0.455 C_{6,11}} \quad (99)$$

These new isotherms represent the apparent change in adsorption behavior during the SMB process. In addition to increasing the adsorption strength, the nonlinearity of both isotherms is significantly increased and the selectivity between Clarithromycin and 6,11 is significantly decreased. This may be due to unpredictable interaction between Clarithromycin and 6,11 or due to effects caused by the additional impurities. The pH of the feed solution was tested and showed an increase in pH over pure Clarithromycin in 80% methanol of 0.1. An increase in pH is known to result in an increase in the adsorption strength of Clarithromycin and 6,11. This indicates that the presence of other unknowns increases the pH and may account for the increase in adsorption apparent in the SMB 500 experimental results.

Figure 37:
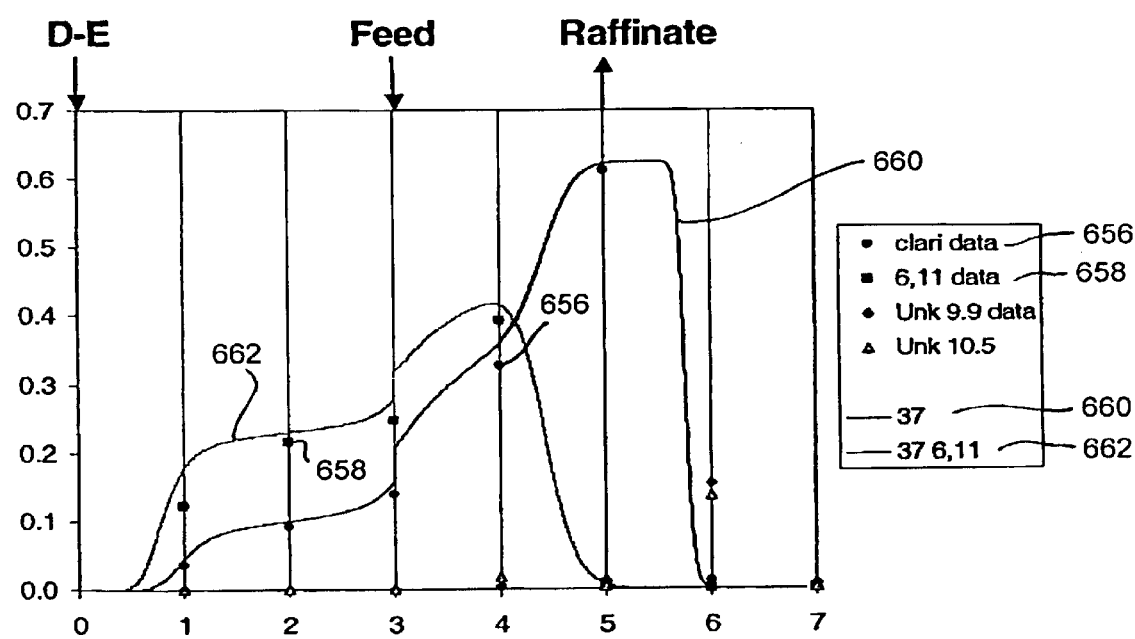
FIG. 37 shows the experimental and adjusted simulated column profiles at steady state for Experiment #3 of the five zone simulated moving bed of FIG. 26.

Either way, these new conditions were simulated and the resulting steady-state column profile is shown in FIG. 37. FIG. 37 shows the Clarithromycin experimental data 646, the 6,11 experimental data 648, Clarithromycin simulated profile 660 and 6,11 simulated profile 662.

This simulated data shows a much better fit with the experimental data, but it is desired that the prediction be even more accurate. Further fitting and simulation will be required for accuracy to be increased.

In addition to the final conditions simulated and shown in FIG. 37, the steady-state Raffinate concentrations from all periods of different flow conditions of Experiment #3 are shown in Table KK. These results show a significant improvement in prediction of the lab-scale results.

TABLE KK

Comparison of Simulated and Experimental Results for Five Zone SMB Experiment #3

| Cycles | Experimental Average Raffinate Clarithromycin Concentration (g/L) | Average Yield (%) | Simulated Average Raffinate Clarithromycin Concentration (g/L) | Average Yield (%) |
|---|---|---|---|---|
| 87–109 | 0.405 | 75.8% | 0.417 | 78.0% |
| 110–114 | 0.427 | 80.1% | 0.445 | 83.5% |
| 115–137 | 0.460 | 84.5% | 0.455 | 83.6% |
| 138–158 | 0.471 | 86.8% | 0.473 | 87.2% |

Five Zone SMB Experiment #4

Figure 38:
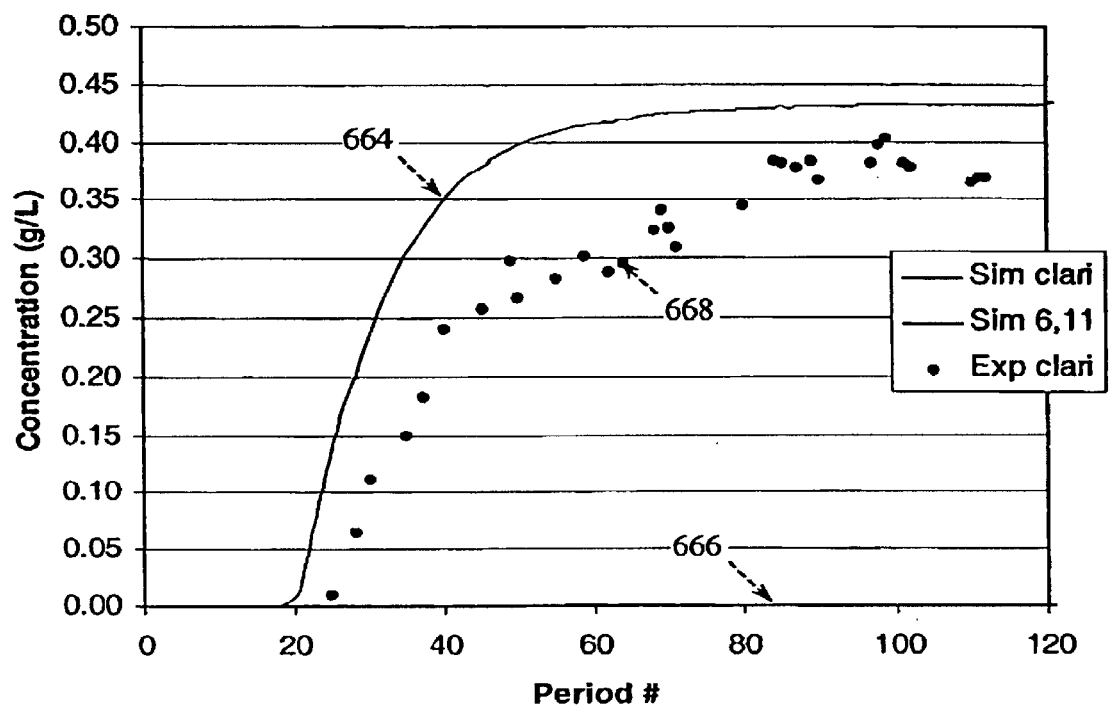
FIG. 38 shows the experimental and simulated histories for the Raffinate for Experiment #4 of the five zone simulated moving bed of FIG. 26.

For Experiment #4, the adsorption isotherms (eqs. 98–99) were used to optimize the zone flow rates and switching time with equations 58a–e and 50 and the plateau concentration iteration method outlined above. The α value used to adjust $C_{p2}$ was 25% and the set yield used in the iteration was 85%. Otherwise, the set parameters were the same as before. Because of the reduced selectivity and the limitations of the experimental SMB system 500, it was determined that the maximum feed flow rate was 0.10 ml/min. The operating parameters derived are shown in Table LL. As before, the flow rates were rounded to the accuracy of the experimental SMB system 500 pumps. Simulation of the parameters predicted a purity of 99.8% and a yield of 94.7% after 150 switching time periods. The simulated and experimental Raffinate 526 histories are shown in FIG. 38. This history shows once again a late breakthrough of Clarithromycin, indicating stronger-than-expected adsorption. This stronger adsorption led to a lower initial yield than expected.

Table MM summarizes the flow conditions and estimated yields that occurred during the experiment. Initially, LPLC pump 540, which provides the zone 506 flow rate, was adjusted during the experimental run in order to keep the measured flow close to the desired value (2.99 ml/min). When it became apparent that the Clarithromycin concentration profile was moving slower than expected, resulting in a low yield, it was decided to slowly increase the LPLC pump 540 flow rate to observe the changes in purity and yield. From periods #68 to #103, the zone 506 flow rate was increased from 2.99 ml/min to 3.12 ml/min. This did not change the purity, which remained nearly 100%, but did increase the average yield from 66% to 85%. Assuming that the column profiles had reached steady-state after the last flow rate change, all flow was stopped at the end of period #113 and small samples were taken from each column in order to analyze them for a column profile. The resulting column profile is shown in FIG. 39a.

Figure 39A:
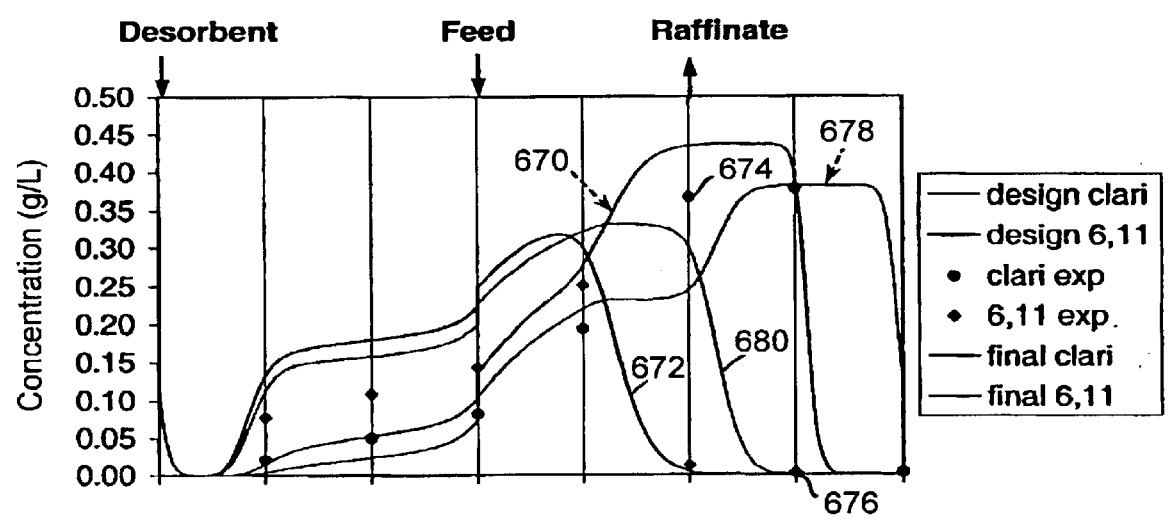
FIG. 39a shows column profiles at steady-state for five zone SMB Experiment #4 at the end of the $113^{th}$ switching time period including "Design" (profiles from simulation of original design to steady-state), "Final" (profiles from simulation of final flow rates to steady-state) and Experimental data collected from outlets of each column at end of the $113^{th}$ switching time period.
Figure 39B:
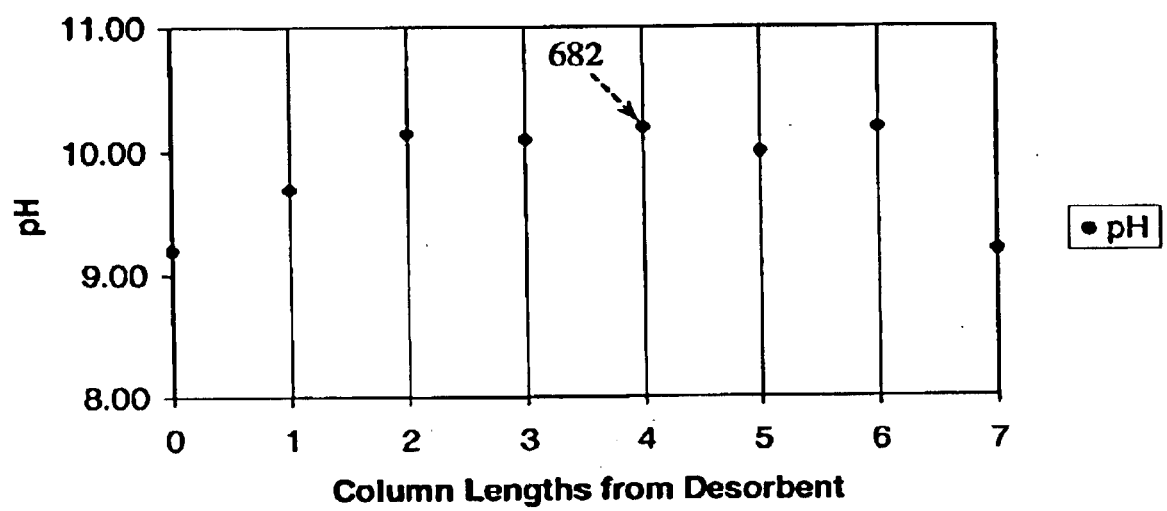
FIG. 39b shows the pHs of each sample at the end of the $113^{th}$ switching time period.

In FIG. 39a, the experimental Clarithromycin concentrations 674 and experimental 6,11 concentrations 676 are shown. Also shown are the simulated Clarithromycin concentration profile 670 and simulated 6,11 concentration profile 672 shown at the end of period #113 and simulating the original operating parameters given in Table LL. In addition, the final experimental operating parameters, shown in Table MM, were simulated, and the simulated Clarithromycin concentration profile 678 and the simulated 6,11 concentration profile 680 are also shown at the end of period #113. The pH 682 of each column sample was measured and is also shown in FIG. 39b. These results indicate that the adsorption isotherms (eqs. 98 and 99) used for the experimental system do not accurately predict the experimental results, and these adsorption isotherms need to be modified to reflect the apparent adsorption behavior within SMB system 500.

TABLE LL

Five Zone SMB Experiment #4 Operating Parameters

| Flow Rates | Original Design (ml/mm) | Adjusted Design (ml/mm) |
|---|---|---|
| Zone 502 | 0.282 | 0.45 |
| Zone 504 | 0.354 | 0.60 |
| Zone 506 | 2.990 | 2.99 |
| Zone 508 | 3.090 | 3.09 |
| Zone 510 | 2.849 | 2.85 |
| Strong Desorbent 516 | 0.072 | 0.15 |
| Extract 524 | 0.354 | 0.60 |
| Mobile phase 522 | 0.282 | 0.45 |
| Feed | 0.100 | 0.10 |
| Raffinate | 0.241 | 0.24 |
| Switching time | 61.2 min | 61.2 min |

TABLE MM

Experimental Results for Five Zone SMB Experiment #4

| Cycles | Avg. Zone 510 Flow (ml/min) | Avg. Raffinate Flow (ml/min) | Avg. Zone 506 Flow (ml/min) | Avg. Raffinate Clarithromycin Concentration (g/L) | Avg. Clarithromycin Purity at Raffinate (%) | Avg. Clarithromycin Yield at Raffinate (%) |
|---|---|---|---|---|---|---|
| 1–28 | 2.87 | 0.253 | 3.025 | | | |
| 29–68 | 2.85 | 0.240 | 2.99 | 0.296 | 99.9% | 64.6% |
| 69–71 | 2.86 | 0.245 | 3.005 | 0.318 | 99.9% | 70.8% |
| 72–86 | 2.88 | 0.240 | 3.02 | 0.384 | 99.9% | 83.8% |
| 87–92 | 2.92 | 0.240 | 3.06 | 0.376 | 99.9% | 81.9% |
| 93–102 | 2.94 | 0.253 | 3.08 | 0.389 | 99.9% | 89.4% |
| 103–113 | 2.97 | 0.252 | 3.12 | 0.370 | 99.9% | 84.8% |

Five Zone SMB Experiment #5

From the results of Experiments #3 and #4, it was apparent that the adsorption isotherms given in equations 98 and 99 do not accurately predict the actual behavior with SMB system 500. From the steady-state profile data (FIGS. 37 and 39) from these two Experiments, VERSE simulations were used to estimate the following set of Langmuir isotherms:

$$Q_{clari} = \frac{49.1 C_{clari}}{1 + 0.75 C_{clari}} \quad (100)$$

$$Q_{6,11} = \frac{58.2 C_{6,11}}{1 + 1.00 C_{6,11}} \quad (101)$$

Figure 40:
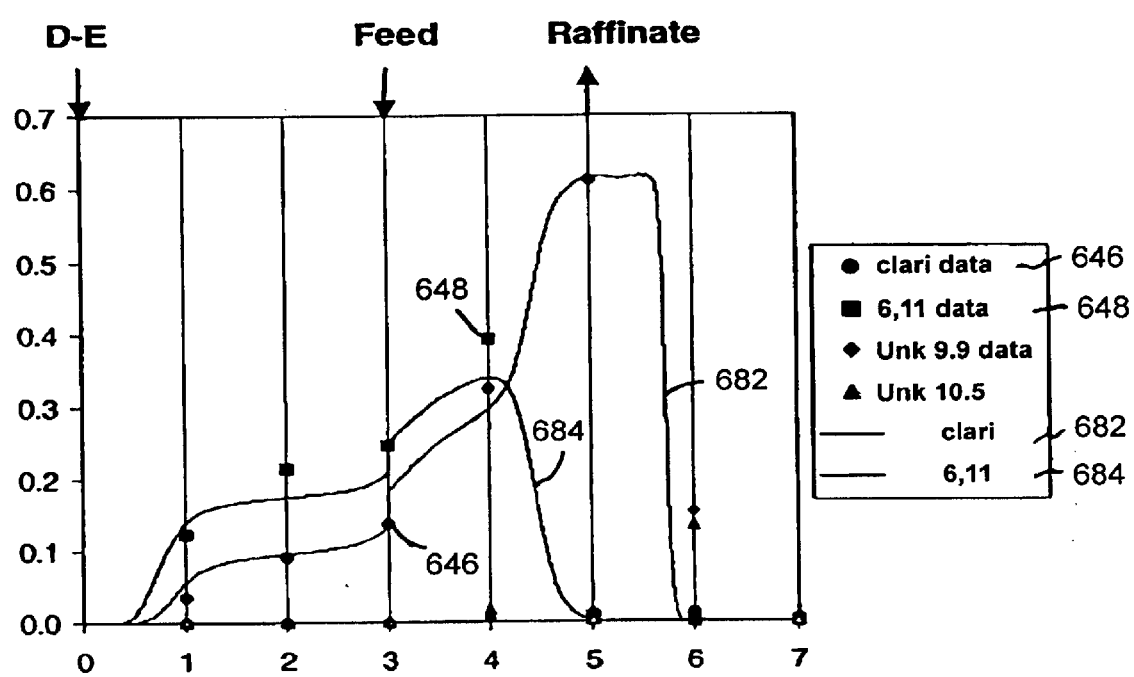
FIG. 40 shows the revised simulated column profiles at steady-state for five zone SMB Experiment #3.
Figure 41:
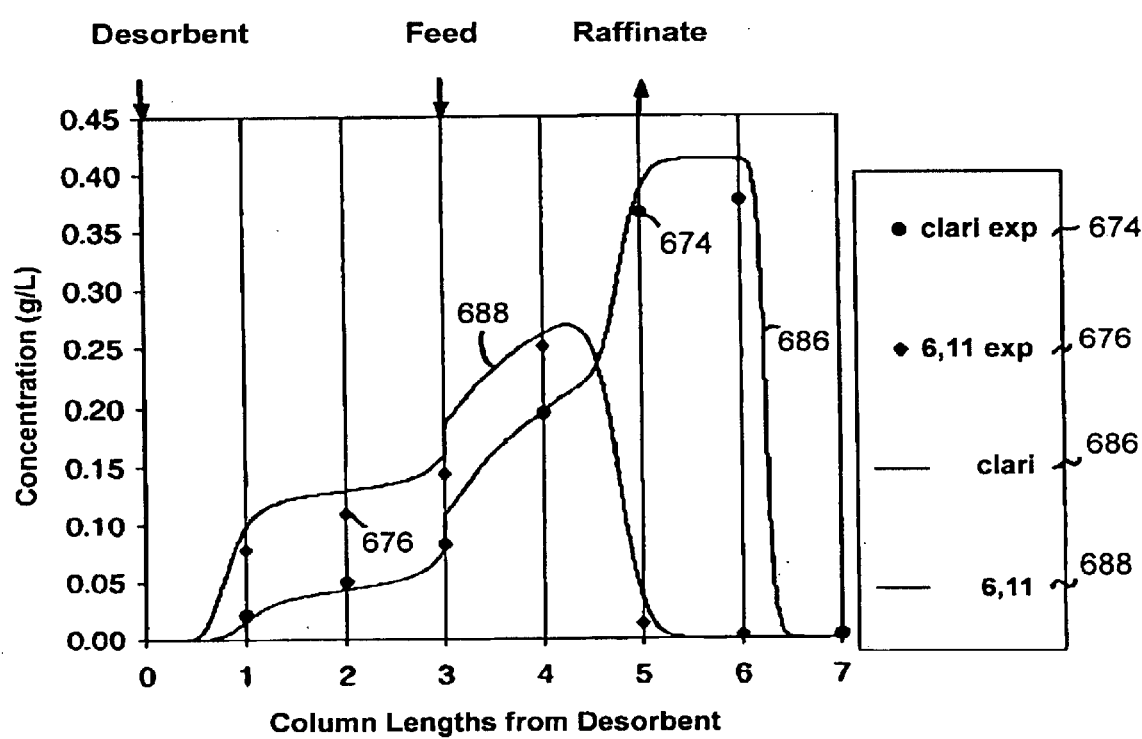
FIG. 41 shows the revised simulated column profiles at steady-state for five zone SMB Experiment #4.

The final conditions of both Experiments were simulated to steady state using these isotherms and their end-of-period profiles were graphed against experimental data in FIGS. 40 and 41. FIG. 40 shows good agreement between the simulation of Experiment #3 and the experimental data. Final raffinate concentration was also well-predicted for Experiment #3. FIG. 41 shows that the prediction of the Experiment #4 profile is not as accurate, but is significantly improved from the prediction shown in FIG. 39. This disagreement suggests that adsorption was even stronger in Experiment #4, which is acceptable because the concentrations present at steady-state are much lower for Experiment #4 than Experiment #3, and it is theorized that adsorption strength at these low concentrations is much stronger, to the point that it cannot be predicted by the same Langmuir adsorption isotherms. Both of these Experiments show a divergence from the single-component Langmuir adsorption isotherm data. This stronger adsorption appears to be due to the very low plateau concentrations present, leading to an adsorption behavior unique to a given concentration range. Experiment #5 aimed to recreate the concentration range of Experiment #3 in order to recreate its adsorption behavior. Therefore, the same feed concentrations and feed flow rate were used in Experiment #5 as were used in Experiment #3.

Figure 42:
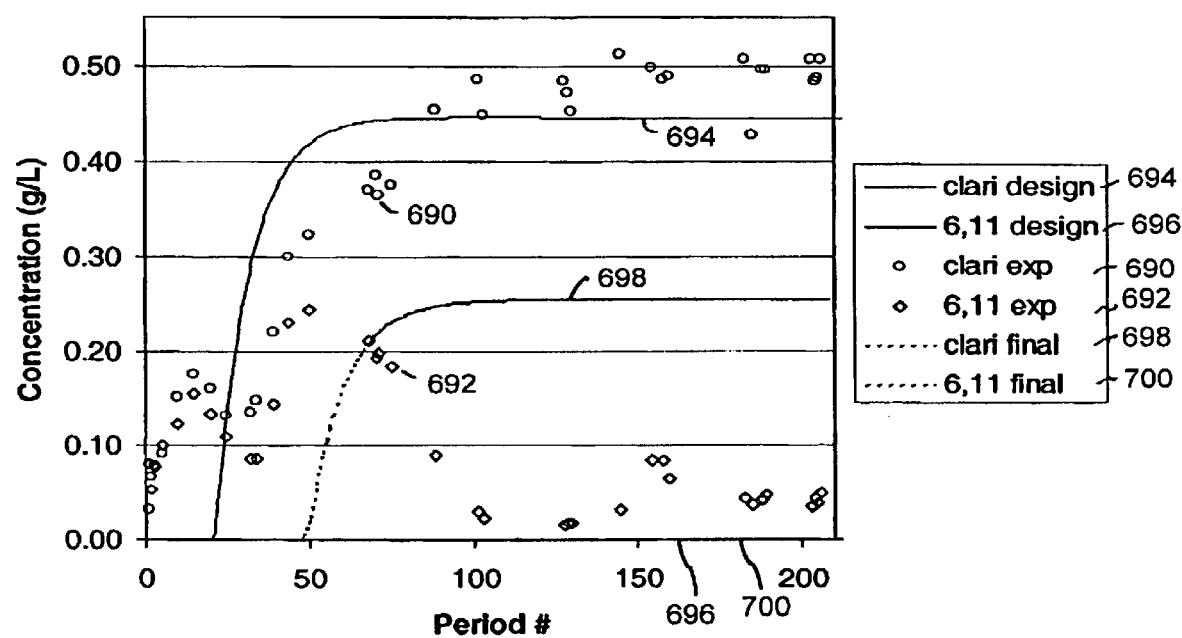
FIG. 42 shows the raffinate histories for the five zone SMB Experiment #5 including simulated flow at original operating conditions, simulated flow at experimental final operating conditions, and experimental flow.

The isotherms of equations 100 and 101 were used to optimize operating parameters for Experiment #5 and SMB system 500. Equations 58a–e and 50 were again used in combination with the plateau concentration iteration method outlined before. The feed flow rate was set to 0.15 ml/min and the feed concentration was 1.10 g/L Clarithromycin and 1.05 g/L 6,11. The α value used was 30% and the set yield was 90%. The optimal operating conditions, before and after adjustment for the accuracy of the pumps, are shown in Table NN. The adjusted system was simulated using VERSE. The predicted steady-state purity was 99.6% and the predicted steady-state yield was 88.8%. The simulated raffinate histories of Clarithromycin (694) and 6,11 (696) are shown in FIG. 42.

TABLE NN

Five Zone SMB Experiment #5 Operating Parameters

| Flow Rates | Original Design (ml/min) | Adjusted Design (ml/min) |
|---|---|---|
| Zone 502 | 0.350 | 0.50 |
| Zone 504 | 0.440 | 0.67 |
| Zone 506 | 3.560 | 3.56 |
| Zone 508 | 3.710 | 3.71 |
| Zone 510 | 3.430 | 3.38 |
| Strong Desorbent 516 | 0.090 | 0.17 |
| Extract 524 | 0.440 | 0.67 |
| Mobile phase 522 | 0.350 | 0.50 |
| Mobile phase 531 | 0.130 | 0.18 |
| Feed | 0.150 | 0.15 |
| Raffinate | 0.280 | 0.33 |
| Switching time | 49.3 min | 50.0 min |

As before, the system was washed and the five pumps calibrated for the flow conditions. The crude solution was made as before, and had concentrations of 1.10 g/L Clarithromycin and 1.05 g/L 6,11 in 80% methanol.

The Experiment was started under the calibrated flow conditions. Unlike the prior Experiments, the reservoir 530 volume between zones 510 and 506 was kept very small (~200 ml), while fresh solvent was added periodically to act as mobile phase inlet 531. The zone 510 outlet flow rate was still measured periodically by measuring the volume over one switching time period, but the measured volume was returned to the reservoir so that is was still recycled.

Early HPLC analysis of the raffinate samples showed early breakthrough of Clarithromycin and a large amount of the 6,11 impurity, as seen in FIG. 42. In addition to this large amount of impurity, early sampling and analysis of the reservoir revealed that some Clarithromycin was exiting zone 510 and entering zone 506, from where it was ultimately lost, resulting in a lower yield. Because of the apparent faster speeds of the component profiles, the zone 506, 508, and 510 zone flow rates were decreased several times over the course of the Experiment in order to improve the purity and yield. This was done by adjusting LPLC pump 540. The measured zone flow rates for the entire Experiment are shown in Table OO. The final conditions resulted in a Clarithromycin purity of 92.2% and a Clarithromycin yield of 91.7%.

The Experiment was ended at the end of the $207^{th}$ switching time period, and small samples were taken from each column in order to determine the steady-state column profiles. Although the purity was lower than desired, the yield was significantly higher than predicted. However, the preliminary simulations based on the isotherms of equations 95 and 96 did not show good agreement with the raffinate history. FIG. 42 shows the predicted raffinate history for Clarithromycin 694 and 6,11 696 based on the operating conditions. Also shown are the predicted histories for Clarithromycin 698 and 6,11 700 based on the final operating conditions. The experimental data for Clarithromycin 690 and 6,11 692 are also shown. The Clarithromycin and 6,11 profiles moved much faster than expected, causing the Clarithromycin adsorption wave to overshoot the raffinate port 526 and the 6,11 adsorption wave to reach the raffinate port 526. Further, as indicated by the very early breakthrough of small amounts of Clarithromycin 690 and 6,11 692, the columns were apparently not clean. As the zone flow rates in the second portion 503 of the SMB (zones 506, 508, and 510) were slowed, the Clarithromycin adsorption wave was brought back to a standing condition in zone 510 and the 6,11 concentration in the raffinate 526 was reduced.

The final conditions led to the best overall purity and yield. From the predicted history of Clarithromycin 698 and 6,11 700, equations 100 and 101 do not provide adequate prediction of the adsorption behavior for Experiment #5.

In reviewing the results of Experiments #3–5, it was noticed that Experiment #5 showed very different behavior than Experiments #3 and #4, but the only significantly different operating procedure was the use of a much smaller reservoir 530 for recycling from zone 510 to 506. Experiments #3 and #4 appear to have very strong adsorption at the lowest concentrations, while Experiment #5 does not. The reservoir 530 used in Experiment #5 was 10–16 times smaller than that of Experiments #3 and 4, so any impurities that were present in the reservoir were recycled at much higher concentrations in Experiment #5. Therefore, it is possible that the recycled impurities participated in competitive adsorption in zone 506, reducing the strength of Clarithromycin and 6,11 adsorption. Due to the presence of the recycled impurities some control or feedback procedure may be required.

Further study of Experiments #3 and #4 found that they are both more accurately simulated using BiLangmuir-type adsorption isotherms, because these isotherms allow for very strong adsorption at very low concentrations. The following isotherms were found to accurately predict the raffinate and profile results for both Experiments #3 and #4:

TABLE OO

Experimental Results for Five Zone SMB Experiment #5

| Cycles | Avg. Zone 510 Flow (ml/min) | Avg. Raffinate Flow (ml/min) | Avg. Zone 506 Flow (ml/min) | Avg. Raffinate Clarithromycin Concentration (g/L) | Avg. Clarithromycin Purity at Raffinate (%) | Avg. Clarithromycin Yield at Raffinate (%) |
|---|---|---|---|---|---|---|
| 1–47 | 3.40 | 0.326 | 3.58 | 0.299 | 56.6% | 59.1% |
| 48–73 | 3.36 | 0.324 | 3.53 | 0.374 | 65.7% | 73.4% |
| 74–93 | 3.24 | 0.328 | 3.42 | 0.453 | 98.1% | 90.1% |
| 94–104 | 3.18 | 0.316 | 3.35 | 0.468 | 95.5% | 89.6% |
| 105–161 | 3.16 | 0.312 | 3.32 | 0.491 | 86.3% | 92.8% |
| 162–186 | 3.10 | 0.306 | 3.26 | 0.495 | 91.7% | 91.8% |
| 187–189 | 3.09 | 0.304 | 3.24 | | | |
| 190–207 | 3.055 | 0.305 | 3.21 | 0.496 | 92.2% | 91.7% |

Figure 43:
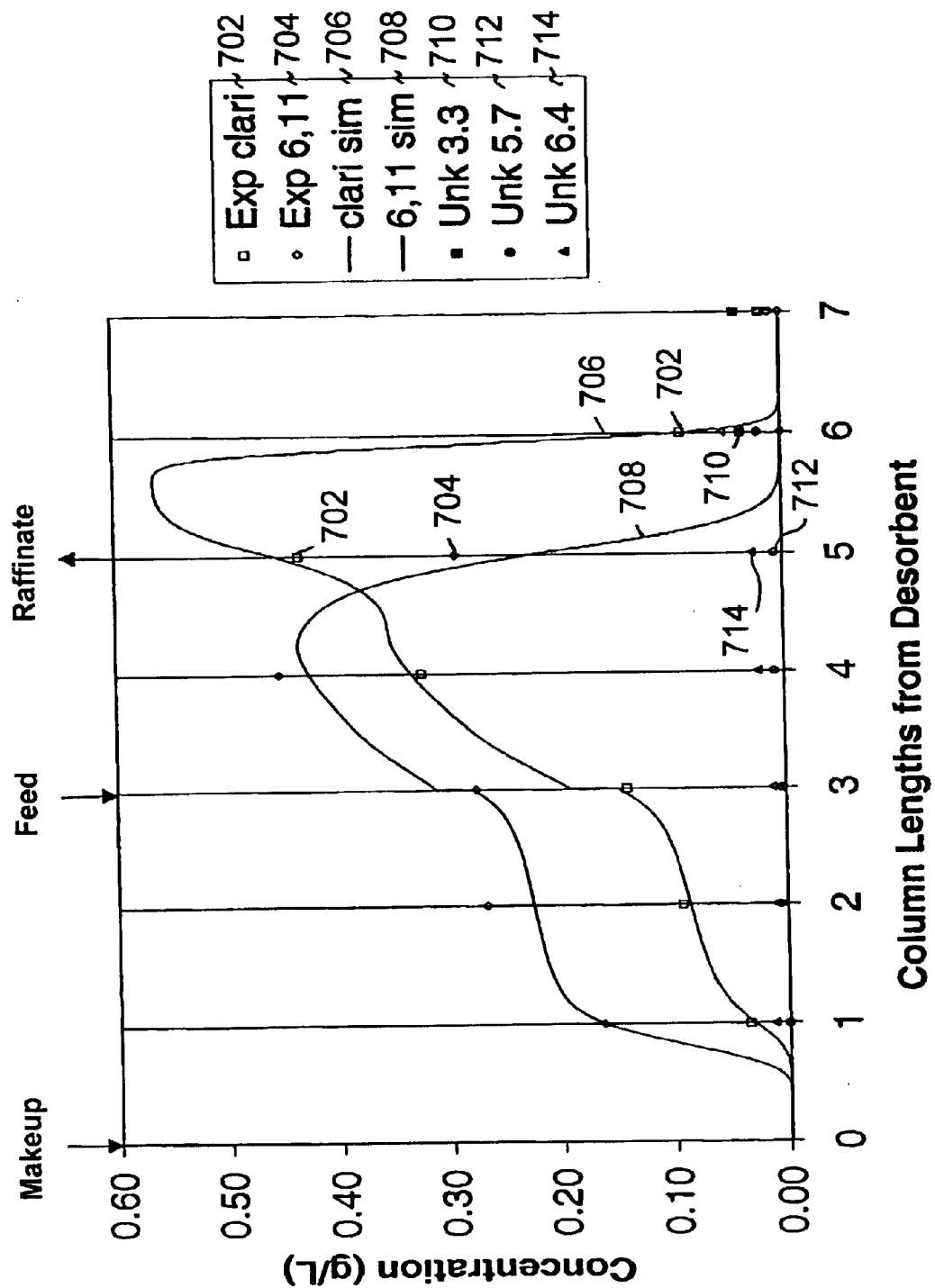
FIG. 43 shows the simulated and experimental column profiles at steady-state for five zone SMB Experiment #5.
Figure 44:
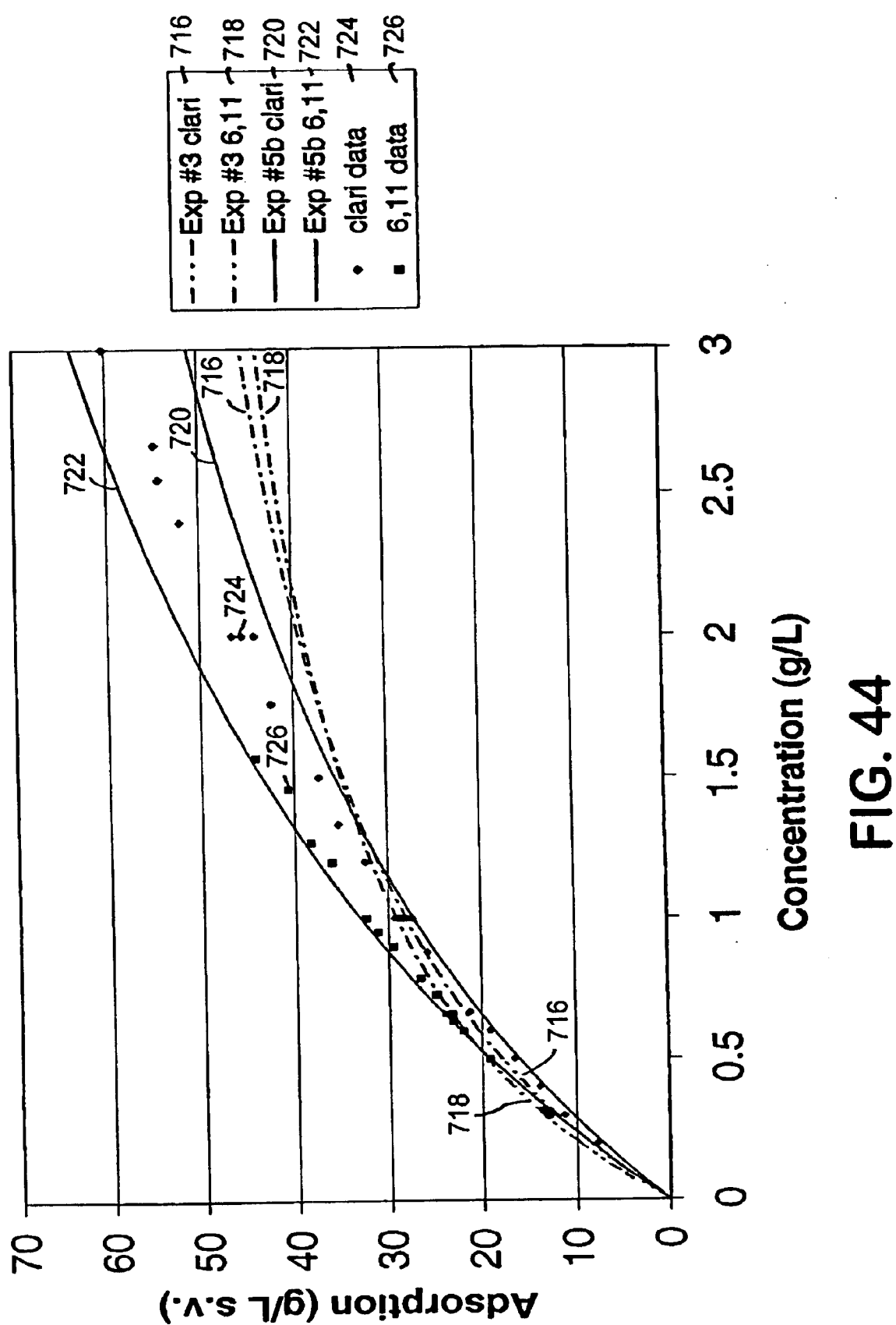
FIG. 44 shows the apparent adsorption isotherms based on five zone SMB Experiment #3, the apparent adsorption isotherms based on five zone SMB Experiment #5, and the single component isotherm data.

The column profile samples were taken at the end of switching time period #207 and were analyzed by HPLC. The resulting profile data is shown in FIG. 43, including the concentrations of Clarithromycin (702), 6,11 (704) and the three most prominent unknowns (710, 712, and 714). As before, the raffinate and profile data were used to determine the apparent adsorption isotherms. The following isotherms:

$$Q_{clari} = \frac{39.0 C_{clari}}{1 + 0.43 C_{clari}} \quad (102)$$

$$Q_{6,11} = \frac{45.0 C_{6,11}}{1 + 0.38 C_{6,11}} \quad (103)$$

were found to accurately predict both the final raffinate 526 concentrations and the column profile concentrations. FIG. 43 shows the simulated profiles based on equations 102 and 103. FIG. 44 compares these two isotherms (720 and 722) with the previous isotherms based on Experiment #3 (716 and 718) and the single-component isotherm data (724 and 726). These new isotherms are significantly closer to the single-component isotherm data.

$$Q_{clari} = \frac{28.5 C_{clari}}{1 + 0.21 C_{clari}} + \frac{32.0 C_{clari}}{1 + 4.8 C_{clari}} \quad (104)$$

$$Q_{6,11} = \frac{34.0 C_{6,11}}{1 + 0.245 C_{6,11}} + \frac{36.0 C_{6,11}}{1 + 6.0 C_{6,11}} \quad (105)$$

Figure 45:
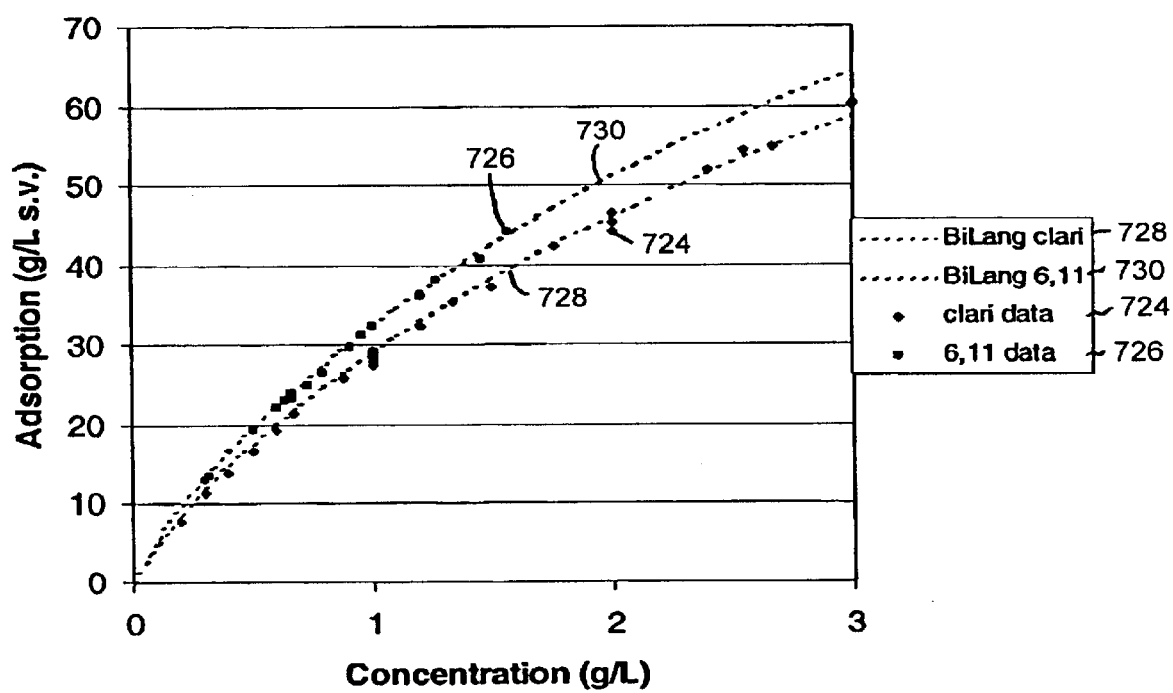
FIG. 45 shows the apparent BiLangmuir adsorption isotherms for the five zone SMB Experiments #3 and #4 versus the single component isotherm data.

As seen in FIG. 45, these two isotherms (728 and 730) agree well with the single component isotherm data (724 and 726), unlike equations 100 and 101. The second term of these equations accounts for the very high adsorption strength at low concentrations, and it is believed that the recycling impurities greatly reduce this term, in effect reducing equations 104 and 105 to equation 102 and 103. These apparent recycling effects are actually beneficial, because the Langmuir behavior of equations 102 and 103 leads to lower solvent consumption and higher possible yield than equations 104 and 105.

Five Zone SMB Experiment #6

Figure 46:
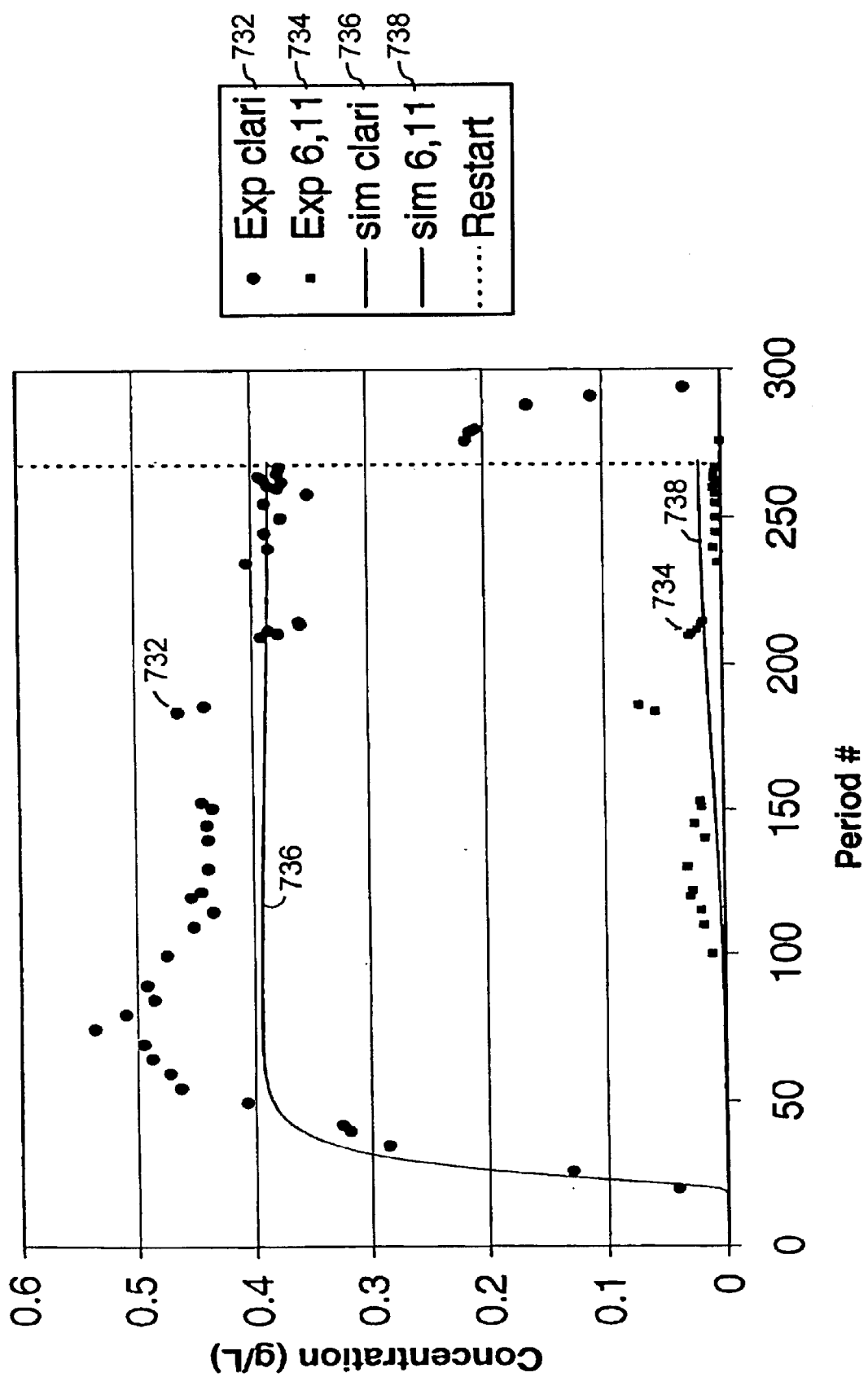
FIG. 46 shows the simulated and experimental raffinate histories for five zone SMB Experiment #6.
Figure 47:
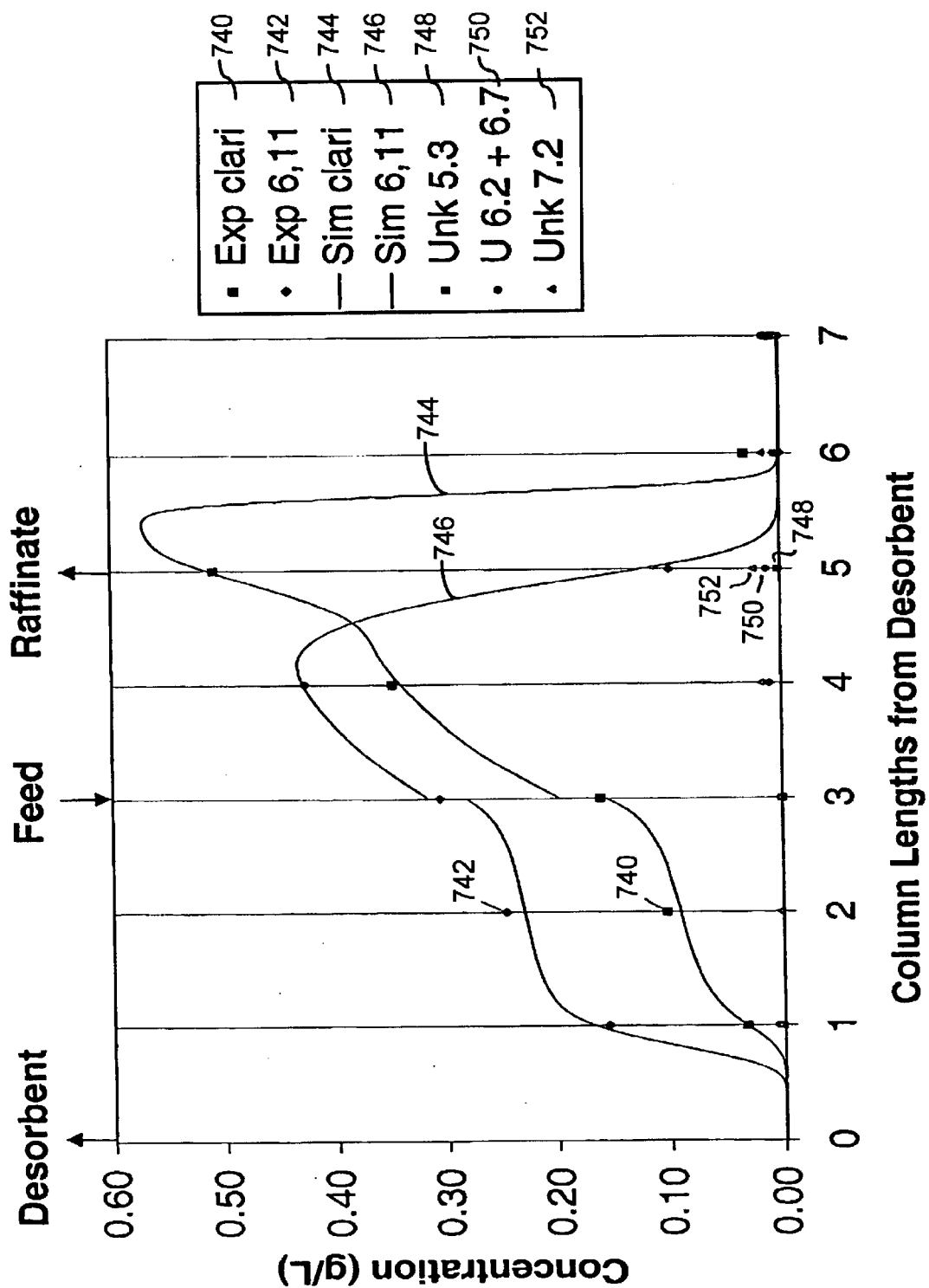
FIG. 47 shows the simulated and experimental column profiles at steady-state for five zone SMB Experiment #6.

In order to show that the results of five zone SMB Experiment #5 are reproducible and are not history-dependent, another experiment using the final operating conditions of Experiment #5 was carried out. Five zone SMB Experiment #6 was carried out using the final operating conditions of Experiment #5, as given in Table PP, starting with a clean SMB system 500. The actual flow conditions of Experiment #6 are given in Table QQ. Note that the only significant changes in flow conditions were due to changes in the raffinate 526 flow. This was due to erratic behavior by the HPLC pump 534 and attempts to improve purity and yield by increasing the raffinate 526 flow. Therefore, different periods during the Experiment had different average raffinate flows, which apparently determined purity and yield. Note that the lowest raffinate flow rate yielded the lowest purity and yield. This is apparently due to the amount of impurity recycled from zone 510 to zone 506 will depend on the raffinate flow rate. The slightly lower zone 506 flow rate of Experiment #6 resulted in a final purity and yield which was better than Experiment #5. However, the isotherms derived from Experiment #5 (equations 102 and 103) still accurately predict the final raffinate history conditions, as seen in FIG. 46. At the end of switching time period 268, the Experiment was stopped and small samples taken from the ends of each column. The resulting column profiles (732 and 734), shown in FIG. 47, agree well with profiles simulated using these isotherms (736 and 738). Therefore, SMB Experiment #6 shows the reproducibility of the Experiment #5 results.

In order to more accurately determine the effects of the recycling impurities, the operating conditions were resumed at the beginning of switching time period 269 without washing, so that Experiment #6 could be continued. The reservoir 530 was removed and the recycle flow from zone 510 to zone 506 was replaced by an outlet to be collected as a waste stream after 510 and an inlet into zone 506 containing only pure mobile phase. As can be seen in FIG. 46, the raffinate 526 concentrations of both Clarithromycin (732) and 6,11 (734) fell after period #268, further indicating that the recycle of impurities diminishes the relative adsorption strength of Clarithromycin and 6,11, as described in equations 102 and 103.

TABLE PP

Five Zone SMB Experiment #6 Operating Parameters

| Flow Rates | Final Exp #5 Conditions (ml/min) |
|---|---|
| Zone 502 | 0.50 |
| Zone 504 | 0.67 |
| Zone 506 | 3.21 |
| Zone 508 | 3.36 |
| Zone 510 | 3.05 |
| Strong Desorbent 516 | 0.17 |
| Extract 524 | 0.67 |
| Mobile phase 522 | 0.50 |
| Mobile phase 531 | 0.16 |
| Feed | 0.15 |
| Raffinate | 0.31 |
| Switching time | 50.0 min |

TABLE QQ

Experimental Results for Five Zone SMB Experiment #6

| Cycles | Avg. Zone 510 Flow (ml/min) | Avg. Raffinate Flow (ml/min) | Avg. Zone 506 Flow (ml/min) | Avg. Raffinate Clarithromycin Concentration (g/L) | Avg. Clarithromycin Purity at Raffinate (%) | Avg. Clarithromycin Yield at Raffinate (%) |
|---|---|---|---|---|---|---|
| 1–73 | 3.04 | 0.296 | 3.19 | 0.492 | 100% | 88.3% |
| 74–156 | 3.01 | 0.333 | 3.19 | 0.440 | 95.9% | 88.8% |
| 157–189 | 3.05 | 0.290 | 3.19 | 0.453 | 87.6% | 79.6% |
| 190–229 | 2.96 | 0.382 | 3.19 | 0.374 | 96.1% | 86.6% |
| 230–268 | 2.94 | 0.398 | 3.19 | 0.384 | 98.7% | 92.6% |
| 269–295* | 2.94 | 0.398 | 3.19 | 0.031 | 100% | 7.5% |

*no recycle from zone 510 to zone 506

Five Zone SMB Experiment #7

Experiment #7 was conducted to determine if the adsorption behavior of Clarithromycin and 6,11 in a SMB system as described by equations 102 and 103 is reproducible. If it is, then equations 102 and 103 can be used to determine optimal conditions for a plant scale 4-zone or 5-zone SMB process. If not, a control scheme, such as a feedback system, will be required to adjust the zone flow rates while monitoring the process, as was done in Experiments 3, 4, and 5, in order to arrive at the desired purity and yield.

Figure 48:
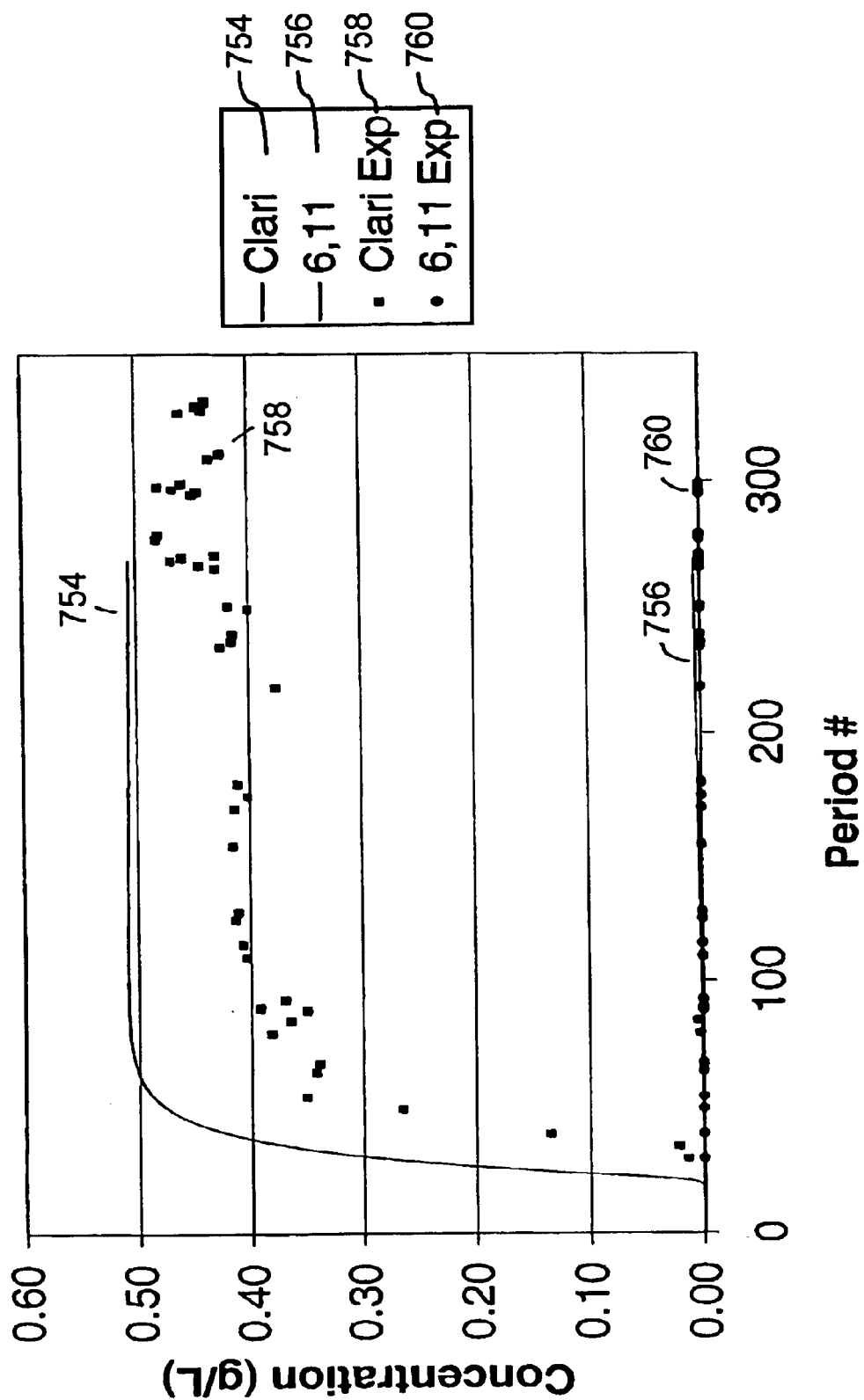
FIG. 48 shows the simulated and experimental raffinate histories for five zone SMB Experiment #7.

The reproducibility is thought to be dependent on the sensitivity of adsorption behavior to the concentration levels of the recycled impurities. For the optimization of Experiment #7 operating parameters, the same feed concentrations, feed flow rate, and SMB system 500 were used as for Experiment #5. The α value used was 30.0% and the set yield used for the plateau concentration iteration was 90.0%. Using the iteration scheme and equations 58a–e and 50 as before, the optimal operating parameters shown in Table RR were calculated. These parameters were adjusted for the SMB system 500, as also shown in Table RR. VERSE simulations using the isotherms of equations 102 and 103 predicted a product purity of 98.9% and a product yield of 92.0%. The predicted raffinate history is shown in FIG. 48.

TABLE RR

Five Zone SMB Experiment #7 Operating Parameters

| Flow Rates | Original Design (ml/min) | Adjusted Design (ml/min) |
|---|---|---|
| Zone 502 | 0.363 | 0.50 |
| Zone 504 | 0.456 | 0.67 |
| Zone 506 | 3.332 | 3.33 |
| Zone 508 | 3.482 | 3.48 |
| Zone 510 | 3.218 | 3.18 |
| Strong Desorbent 516 | 0.093 | 0.17 |

TABLE RR-continued

Five Zone SMB Experiment #7 Operating Parameters

| Flow Rates | Original Design (ml/min) | Adjusted Design (ml/min) |
|---|---|---|
| Extract 524 | 0.456 | 0.67 |
| Mobile phase 522 | 0.363 | 0.50 |
| Mobile phase 531 | 0.114 | 0.15 |
| Feed | 0.150 | 0.15 |
| Raffinate | 0.264 | 0.30 |
| Switching time | 47.5 min | 48.0 min |

Before operation of this Experiment, the SMB system 500 was thoroughly washed as before. The measured flow rate conditions and experimental results are given in Table SS. The raffinate 526 history data for Clarithromycin 758 and 6,11 760 are shown in FIG. 48. As can be seen in FIG. 48, breakthrough of the Clarithromycin 758 into the raffinate 526 was later than predicted by the simulation (754), and the predicted yield was not reached during the first 223 switching time periods. Also, no apparent 6,11 760 concentration was found. In order to increase the to Clarithromycin yield, LPLC pump 540 flow was increased four separate times, each time allowing enough switching time periods to pass by to reach a new steady state. These changes in flow conditions are shown in Table SS, which also shows the steady-state purity and yield resulting from each set of conditions. The final flow conditions occurred during periods 313–333, and resulted in the highest yield, 91.2%. Still no 6,11 was evident in the raffinate 526 outlet stream. Although the final yield was close to the predicted yield, the final Clarithromycin concentration 760 does not match the predicted Clarithromycin concentration 754 because the raffinate flow was higher than originally designed.

Figure 49:
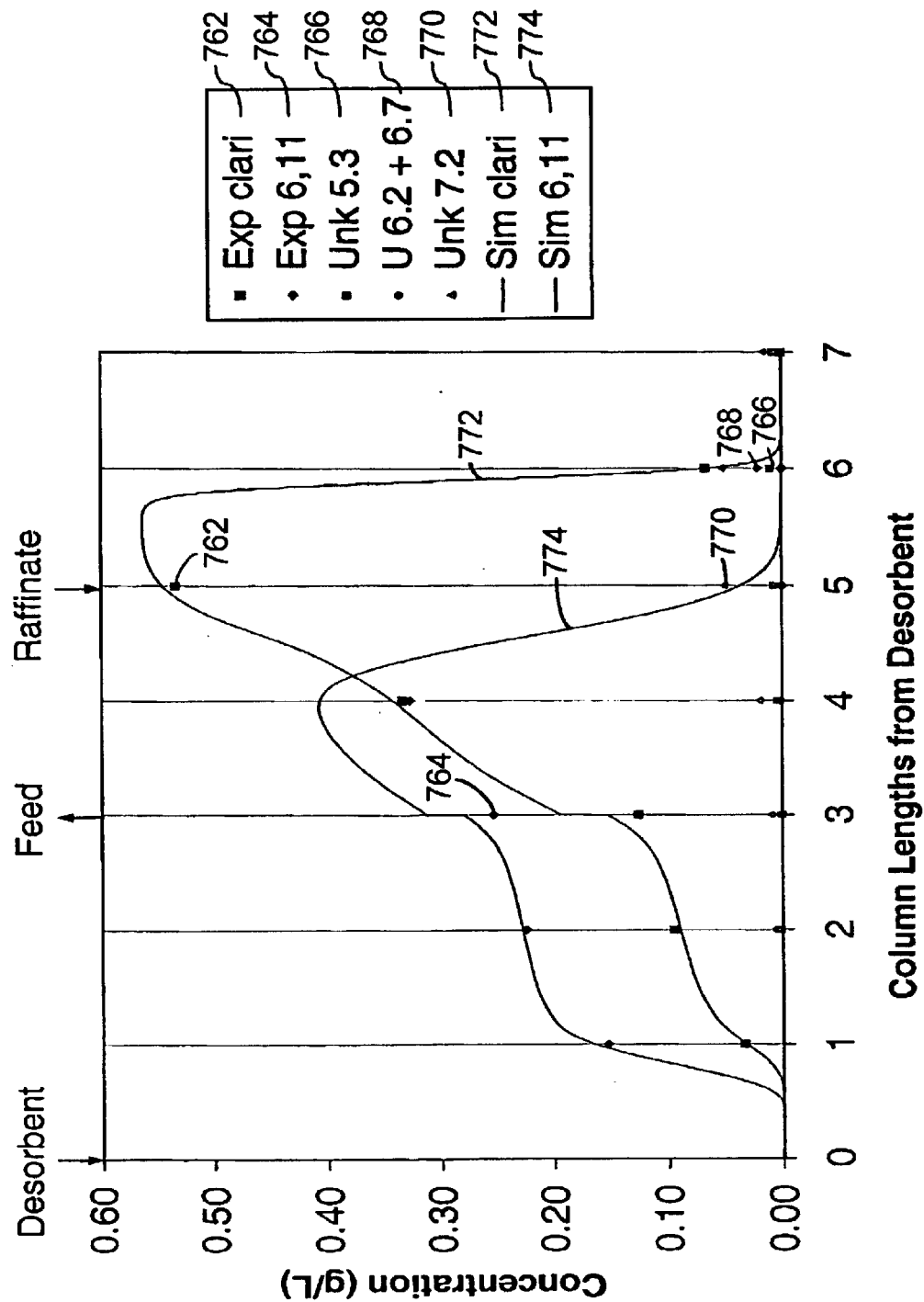
FIG. 49 shows the simulated and experimental column profiles at steady-state for five zone SMB Experiment #7.
Figure 50:
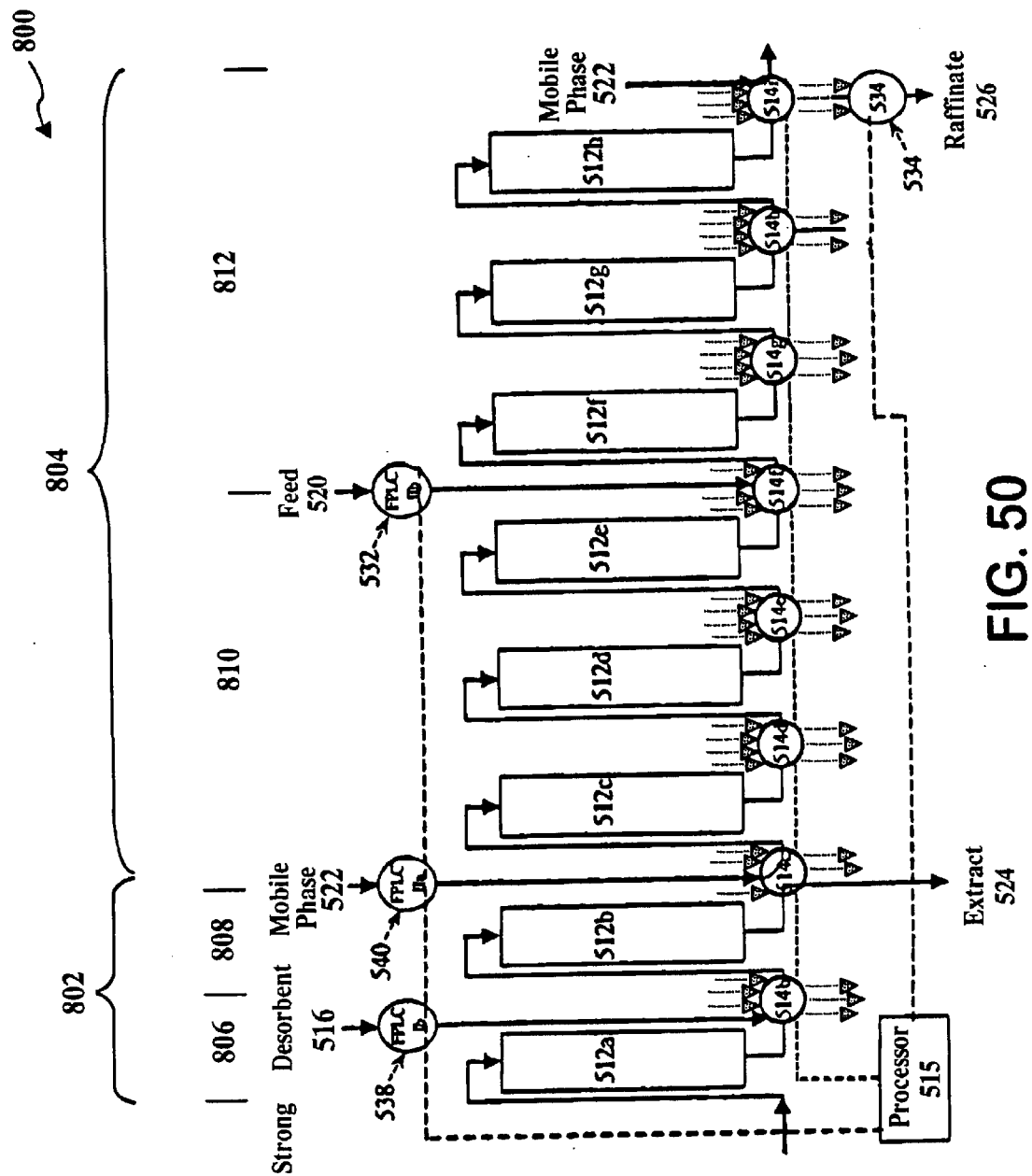
FIG. 50 is a diagrammatic representation of a four zone simulated moving bed of the present invention having a first portion configured to treat zones in the first portion and a second portion configured to recover the product, the first component, from the feed mixture.

At the end of the $333^{rd}$ switching time period, small samples were taken from the end of each column in order to find the final steady-state column profile. FIG. 49 shows the Clarithromycin 762, 6,11 764, and unknowns (766–770) data from these samples. Also shown are the predicted column profiles (772 and 774) from simulation of the original operating conditions and isotherm equations 102 and 103. These data points match the simulated profiles well, even though the zone flow rate conditions were modified. The only discrepancy is that the 6,11 profile 774 does not appear to be as far downstream as expected.

rities. However, Experiment #7 shows that it is possible to determine an optimal parameters set from the estimated adsorption isotherms of equations 102 and 103 and to use that optimal parameter set as the starting conditions for a SMB process. Thereafter, monitoring of the raffinate outlet stream 526 with a feedback system is used to modify the zone flow rates of zones 506, 508, and 510 to increase purity or yield as needed. As such, a feedback loop is used to modify the optimal zone flow rates and switching time during the operation of the SMB system. In one embodiment, the feedback loop is carried out by processor 515.

Thus, a control mechanism can be formulated in order to reach and maintain the desired purity and yield while allowing the process to run continuously. The small 3.0% increase in pump 540 flow resulted in a yield increase of 15.5% during Experiment #7. It should also be noted that these zone flow rate changes within the SMB ring 503 do not result in a change in solvent consumption, as long as all three zone flow rates are changed by the same amount, as was the case in Experiment #7. Therefore, the third method of equations 58a–e and 50 is shown to be a viable method for determining the optimal operating conditions of the SMB processes, even though some control or feedback procedure may be required during the process run. Also, any cost estimation based on these conditions will remain accurate after any zone flow rate changes, so preliminary cost predictions used to determine the relative viability of similar processes (as shown in Table DD) are valid.

In one variation of the second embodiment, a four zone simulated moving bed system 800 is provided. In general four zone system 800 functions and is configured the same as five zone system 500. As such, like numerals are used to refer to like components, such as columns 512*a–h* and valves 514*b–i*.

Four zone system 800 includes a first portion 802 and a second portion 804. First portion 802 includes a first zone 806 and a second zone 808. First and second zones 806 and 808 function similar to zones 502 and 504 of five zone system 500. Zones 806 and 808 are configured to treat the columns present in zones 806 and 808 to decrease the adsorptive strength of the sorbent for the second component

TABLE SS

Experimental Results for Five Zone SMB Experiment #7

| Cycles | Avg. Zone 510 Flow (ml/min) | Avg. Raffinate Flow (ml/min) | Avg. Zone 506 Flow (ml/min) | Avg. Raffinate Clarithromycin Concentration (g/L) | Avg. Clarithromycin Purity at Raffinate (%) | Avg. Clarithromycin Yield at Raffinate (%) |
|---|---|---|---|---|---|---|
| 1–223 | 3.15 | 0.332 | 3.33 | 0.376 | 99.9% | 75.7% |
| 224–242 | 3.18 | 0.295 | 3.33 | 0.419 | 99.9% | 74.9% |
| 243–252 | 3.18 | 0.322 | 3.35 | 0.410 | 99.9% | 80.0% |
| 253–273 | 3.20 | 0.315 | 3.37 | 0.451 | 99.9% | 86.1% |
| 274–312 | 3.22 | 0.337 | 3.41 | 0.430 | 99.9% | 87.8% |
| 313–333 | 3.24 | 0.338 | 3.43 | 0.445 | 99.9% | 91.2% |

Based on the results of these Experiments the precise prediction and optimal parameters of the 5-zone SMB process with a single set of optimal zone flow rates and switching time is difficult because of the small variations in effective adsorption strength caused by the recycled impuor to remove the second component from first portion 802. Second portion 804 includes two zones 810 and 812. Zones 810 and 812 are configured to separate the first component from the feed 520 and zones 810 and 812 function similar to zones 506 and 508 of five zone system 500.

Four zone system 800 differs from five zone system 500 in that zone 510 in five zone system 500 is not present in four zone system 800. Zone 510 in five zone system 500 recovers the mobile phase used and passes the mobile phase into reservoir 530 for subsequent recycling back into zone 506. In four zone system 800, the mobile phase exits out Raffinate 526 along with the recovered first component and is not recycled back to zone 810. As such, four zone system 800 has fewer components than five zone system 500, but has increased mobile phase consumption. Four zone system 800 is preferable in situations wherein mobile phase cost is not a driving concern in the separation, such as when the mobile phase is water.

Batch Elution System

Figure 51:
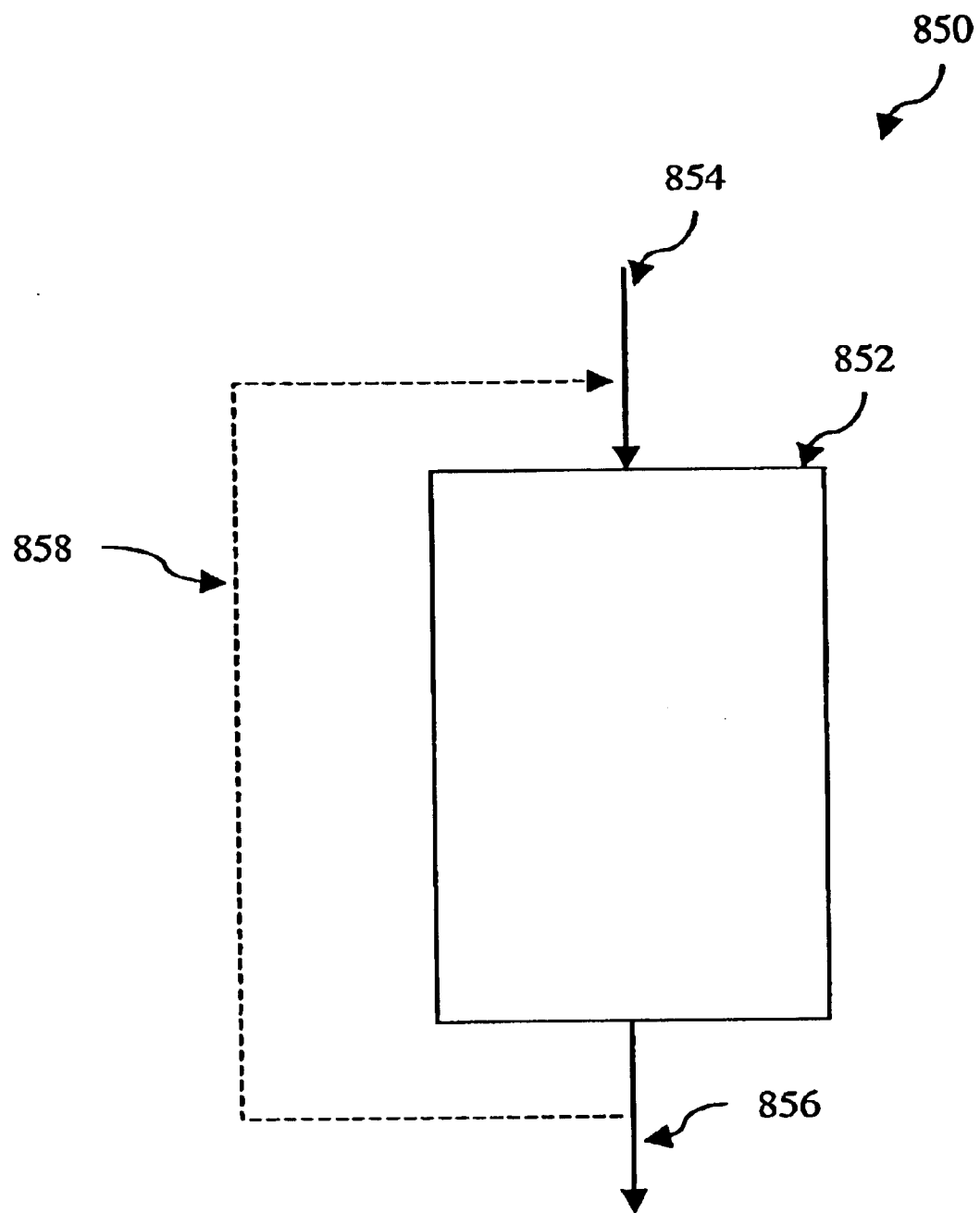
FIG. 51 is a diagrammatic representation of a conventional batch elution system.

In a third embodiment of the present invention, Clarithromycin is separated from 6,11 given a mixture of the two with a batch elution system. Referring to FIG. 51, a diagrammatic representation of a batch elution system 850 is shown. Batch elution system 850 includes at least one column 852 packed with an adsorbent having a greater affinity for 6,11 than Clarithromycin for a given solution of Clarithromycin, 6,11 and mobile phase. Column 852 includes an inlet 854 configured to provide flow to column 852 and an outlet 856 configured to allow flow to exit column 852. As explained in more detail below, at times at least a portion of the flow exiting column 852 through outlet 856 is reintroduced into column 852 at inlet 854 through a recycle loop 858.

Batch elution system 850 is configured to separate Clarithromycin and 6,11 given a mixture of the two in individual batches not in a continuous run as is the case in the four zone simulated moving bed and the five zone simulated moving bed. As such, batch elution system 850 in a first separation step, separates the Clarithromycin and 6,11 and in a first treatment step, the stationary phase is treated to remove 6,11 from the adsorbent. Batch system 850 then separates subsequent batches of Clarithromycin and 6,11 in subsequent separation steps and subsequent treatment steps.

During the separation step, inlet 854 provides a continuous feed of the mobile phase to column 852. A mixture of Clarithromycin, 6,11 and corresponding mobile phase is combined with the mobile phase feed and provided to column 852 through inlet 854. Since the 6,11 has a higher affinity for the adsorbent packed in column 852, 6,11 moves more slowly through column 852 and is more readily adsorbed to the adsorbent than Clarithromycin. As such, outlet 856 produces a flow consisting primarily of mobile phase and Clarithromycin which has been separated from 6,11 due to the interaction between 6,11 and the adsorbent in column 852.

The separation step is continued until the Clarithromycin in the batch has been given sufficient time to pass through column 852, based in part upon the migration velocity of Clarithromycin through the adsorbent. The separation time is limited in part by the migration velocity of 6,11 through the adsorbent. As such, not all of the Clarithromycin in a given batch can be recovered as purified Clarithromycin. The solution of unpurified Clarithromycin (Clarithromycin and 6,11) can be recycled through recycle loop 858 and saved for subsequent batches.

The separation step is followed by a treatment step wherein the 6,11 retained by the adsorbent is removed from column 852. In its, simplest form the treatment step involves the passing of pure mobile phase through the column for a sufficient time until most of the 6,11 in column 852 has been removed from column 852. In one variation, a mobile phase change is used to reduce affinity of the adsorbent for 6,11. By reducing the affinity of the adsorbent, the 6,11 present in column 852 is more readily removed from column 852, thereby reducing the amount of mobile phase required in the treatment step. The reduction in the affinity of the adsorbent for 6,11 can be accomplished by one or a combination of the following: an increase or decrease in pH of the mobile phase, an increase in percentage of organic solvent in the mobile phase, and an increase in temperature of the mobile phase. Once the treatment step is completed, the mobile phase supplied to column 852 is returned back to the mobile phase of the separation step thereby once again increasing the affinity of the adsorbent for 6,11.

Suitable mobile phase and stationary phases for use with batch elution system 850 are the mobile phase and stationary phases used with the four zone simulated moving bed of the present invention and the five zone simulated moving bed of the present invention. As such, preferred mobile phases include an organic solvent and preferred adsorbents include hydrophobic adsorbents including a reversed phase absorbent. In one variation, the following adsorbent and mobile phase combinations are preferred 60% by volume isopropyl alcohol and Dow Optipore Hydrophobic XUS-40323 adsorbent, 50% by volume isopropyl alcohol and Dow Optipore Hydrophobic XUS-40323 adsorbent, 50% by volume isopropyl alcohol and Amberlite XAD-16, 60% by volume ethanol and Dow Optipore Hydrophobic XUS-40323 adsorbent, 80% by volume methanol and Dow Optipore Hydrophobic XUS-40323 adsorbent, 75% by volume methanol and Dow Optipore Hydrophobic XUS-40323 adsorbent, and 85% by volume methanol and Dow Optipore Hydrophobic XUS-40323 adsorbent. In another variation, the mobile phase used to separate Clarithromycin and 6,11 includes about 50 percent by volume to about 85 percent by volume of an organic solvent, such as either about 50 percent by volume isopropyl alcohol to about 60 percent by volume isopropyl alcohol, about 60 percent by volume to about 80 percent by volume ethanol, or about 75 percent by volume to about 85 percent by volume methanol.

Although, batch elution system 850 can effectively separate Clarithromycin and 6,11 using the mobile phase and adsorbent combinations given, it should be noted that the four zone simulated moving bed of the present invention and the five zone simulated moving bed of the present invention are preferred because they allow for continuous separation and they typically require at least four times less solvent.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected.

We claim:

1. An apparatus for separating a first component from a mixture containing the first component and a second component, the apparatus comprising:

at least one column packed with a stationary phase having a greater affinity for the second component and having a first and second inlet coupled to the column and a first and second outlet coupled to the column, the at least one column being separated into a first portion and a second portion, the first portion including a first and a second zone connected together in series and the second portion including at least a third zone and a fourth zone connected together in series;

a first pump coupled to the first inlet and configured to provide the mixture to the second portion;

a second pump coupled to the second inlet and configured to provide at least one solution to the first portion to remove the second component from the stationary phase; and a processor configured to control the flow rates of the first pump, the second pump, and the zones within the first portion and the second portion to facilitate the separation of the first component and the second component so that the first component exits the first outlet which is coupled to the second portion and the second component exits the second outlet which is coupled to the first portion, wherein the first component and the second component exhibit non-linear adsorption isotherms and non-negligible mass transfer resistances and wherein the first component is Clarithromycin and the second component is 6,11-O-methyl erythromycin A.

2. The apparatus of claim 1, wherein the second portion includes a fifth zone and the apparatus comprises at least five columns, a first column located in the first zone, a second column located in the second zone, a third column located in the third zone, a fourth column located in the fourth zone and a fifth column located in the fifth zone.

3. The apparatus of claim 2, wherein the first inlet is coupled to the fourth column located in the fourth zone, the second inlet is coupled to the second column located in the second zone, the first outlet is coupled to the fourth column located in the fourth zone, and the second outlet is coupled to the second column located in the second zone.

4. The apparatus of claim 3, wherein the processor after a first predetermined switching interval changes of the position of each column so that the first column is located in the fifth zone, the second column is located in the first zone, the third column is located in the second zone, the fourth column is located in the third zone, and the fifth column is located in the fourth zone and wherein the first inlet is coupled to the fifth column located in the fourth zone, the second inlet is coupled to the third column located in the second zone, the first outlet is coupled to the fifth column located in the fourth zone, and the second outlet is coupled to the third column located in the second zone.

5. The apparatus of claim 4, wherein the processor after a second predetermined switching interval changes of the position of each column so that the first column is located in the fourth zone, the second column is located in the fifth zone, the third column is located in the first zone, the fourth column is located in the second zone, and the fifth column is located in the third zone and wherein the first inlet is coupled to the first column located in the fourth zone, the second inlet is coupled to the fourth column located in the second zone, the first outlet is coupled to the first column located in the fourth zone, and the second outlet is coupled to the fourth column located in the second zone.

6. The apparatus of claim 4, wherein the processor through an iterative process optimizes the switching interval.

7. An apparatus for separating a first component from a mixture containing the first component and a second component, the apparatus comprising:

at least one column packed with a stationary phase having a greater affinity for the second component and having a first and second inlet coupled to the column and a first and second outlet coupled to the column, the at least one column being separated into a first portion and a second portion, the first portion including a first and a second zone connected together in series and the second portion including at least a third zone and a fourth zone connected together in series, wherein the second portion includes a fifth zone and the apparatus comprises at least five columns, a first column located in the first zone, a second column located in the second zone, a third column located in the third zone, a fourth column located in the fourth zone and a fifth column located in the fifth zone;

a first pump coupled to the first inlet and configured to provide the mixture to the second portion;

a second pump coupled to the second inlet and configured to provide at least one solution to the first portion to remove the second component from the stationary phase; and a processor configured to control the flow rates of the first pump, the second pump, and the zones within the first portion and the second portion to facilitate the separation of the first component and the second component so that the first component exits the first outlet which is coupled to the second portion and the second component exits the second outlet which is coupled to the first portion, wherein the first component and the second component exhibit non-linear adsorption isotherms and non-negligible mass transfer resistances and wherein the first component is Clarithromycin and the second component is 6,11-O-methyl erythromycin A.

8. An apparatus for separating a first component from a mixture containing the first component and a second component, the apparatus comprising:

at least one column packed with a stationary phase having a greater affinity for the second component and having a first and second inlet coupled to the column and a first and second outlet coupled to the column, the at least one column being separated into a first portion and a second portion, the first portion including a first and a second zone connected together in series and the second portion including at least a third zone and a fourth zone connected together in series, wherein the second portion includes a fifth zone and the apparatus comprises at least five columns, a first column located in the first zone, a second column located in the second zone, a third column located in the third zone, a fourth column located in the fourth zone and a fifth column located in the fifth zone, the first inlet is coupled to the fourth column located in the fourth zone, the second inlet is coupled to the second column located in the second zone, the first outlet is coupled to the fourth column located in the fourth zone, and the second outlet is coupled to the second column located in the second zone;

a first pump coupled to the first inlet and configured to provide the mixture to the second portion;

a second pump coupled to the second inlet and configured to provide at least one solution to the first portion to remove the second component from the stationary phase; and a processor configured to control the flow rates of the first pump, the second pump, and the zones within the first portion and the second portion to facilitate the separation of the first component and the second component so that the first component exits the first outlet which is coupled to the second portion and the second component exits the second outlet which is coupled to the first portion, wherein the first component and the second component exhibit non-linear adsorption isotherms and non-negligible mass transfer resistances and wherein the first component is Clarithromycin and the second component is 6,11-O-methyl erythromycin A.

9. An apparatus for separating a first component from a mixture containing the first component and a second component, the apparatus comprising:

at least one column packed with a stationary phase having a greater affinity for the second component and having a first and second inlet coupled to the column and a first and second outlet coupled to the column, the at least one column being separated into a first portion and a second portion, the first portion including a first and a second zone connected together in series and the second portion including at least a third zone and a fourth zone connected together in series, wherein the second portion includes a fifth zone and the apparatus comprises at least five columns, a first column located in the first zone, a second column located in the second zone, a third column located in the third zone, a fourth column located in the fourth zone and a fifth column located in the fifth zone, the first inlet is coupled to the fourth column located in the fourth zone, the second inlet is coupled to the second column located in the second zone, the first outlet is coupled to the fourth column located in the fourth zone, and the second outlet is coupled to the second column located in the second zone;

a first pump coupled to the first inlet and configured to provide the mixture to the second portion;

a second pump coupled to the second inlet and configured to provide at least one solution to the first portion to remove the second component from the stationary phase; and a processor configured to control the flow rates of the first pump, the second pump, and the zones within the first portion and the second portion to facilitate the separation of the first component and the second component so that the first component exits the first outlet which is coupled to the second portion and the second component exits the second outlet which is coupled to the first portion, the processor after a first predetermined switching interval changes of the position of each column so that the first column is located in the fifth zone, the second column is located in the first zone, the third column is located in the second zone, the fourth column is located in the third zone, and the fifth column is located in the fourth zone and wherein the first inlet is coupled to the fifth column located in the fourth zone, the second inlet is coupled to the third column located in the second zone, the first outlet is coupled to the fifth column located in the fourth zone, and the second outlet is coupled to the third column located in the second zone, wherein the first component and the second component exhibit non-linear adsorption isotherms and non-negligible mass transfer resistances and wherein the first component is Clarithromycin and the second component is 6,11-O-methyl erythromycin A.

10. An apparatus for separating a first component from a mixture containing the first component and a second component, the apparatus comprising:

at least one column packed with a stationary phase having a greater affinity for the second component and having a first and second inlet coupled to the column and a first and second outlet coupled to the column, the at least one column being separated into a first portion and a second portion, the first portion including a first and a second zone connected together in series and the second portion including at least a third zone and a fourth zone connected together in series, wherein the second portion includes a fifth zone and the apparatus comprises at least five columns, a first column located in the first zone, a second column located in the second zone, a third column located in the third zone, a fourth column located in the fourth zone and a fifth column located in the fifth zone, the first inlet is coupled to the fourth column located in the fourth zone, the second inlet is coupled to the second column located in the second zone, the first outlet is coupled to the fourth column located in the fourth zone, and the second outlet is coupled to the second column located in the second zone;

a first pump coupled to the first inlet and configured to provide the mixture to the second portion;

a second pump coupled to the second inlet and configured to provide at least one solution to the first portion to remove the second component from the stationary phase; and a processor configured to control the flow rates of the first pump, the second pump, and the zones within the first portion and the second portion to facilitate the separation of the first component and the second component so that the first component exits the first outlet which is coupled to the second portion and the second component exits the second outlet which is coupled to the first portion, the processor after a first predetermined switching interval changes of the position of each column so that the first column is located in the fifth zone, the second column is located in the first zone, the third column is located in the second zone, the fourth column is located in the third zone, and the fifth column is located in the fourth zone and wherein the first inlet is coupled to the fifth column located in the fourth zone, the second inlet is coupled to the third column located in the second zone, the first outlet is coupled to the fifth column located in the fourth zone, and the second outlet is coupled to the third column located in the second zone, wherein the processor through an iterative process optimizes the switching interval, the first component and the second component exhibit non-linear adsorption isotherms and non-negligible mass transfer resistances and wherein the first component is Clarithromycin and the second component is 6,11-O-methyl erythromycin A.

11. The apparatus of claim 7, wherein the first inlet is coupled to the fourth column located in the fourth zone, the second inlet is coupled to the second column located in the second zone, the first outlet is coupled to the fourth column located in the fourth zone, and the second outlet is coupled to the second column located in the second zone.

12. The apparatus of claim 11, wherein the processor after a first predetermined switching interval changes of the position of each column so that the first column is located in the fifth zone, the second column is located in the first zone, the third column is located in the second zone, the fourth column is located in the third zone, and the fifth column is located in the fourth zone and wherein the first inlet is coupled to the fifth column located in the fourth zone, the second inlet is coupled to the third column located in the second zone, the first outlet is coupled to the fifth column located in the fourth zone, and the second outlet is coupled to the third column located in the second zone.

13. The apparatus of claim 12, wherein the processor after a second predetermined switching interval changes of the position of each column so that the first column is located in the fourth zone, the second column is located in the fifth zone, the third column is located in the first zone, the fourth column is located in the second zone, and the fifth column is located in the third zone and wherein the first inlet is coupled to the first column located in the fourth zone, the second inlet is coupled to the fourth column located in the second zone, the first outlet is coupled to the first column located in the fourth zone, and the second outlet is coupled to the fourth column located in the second zone.

14. The apparatus of claim 12, wherein the processor through an iterative process optimizes the switching interval.

15. The apparatus of claim 8, wherein the processor after a first predetermined switching interval changes of the position of each column so that the first column is located in the fifth zone, the second column is located in the first zone, the third column is located in the second zone, the fourth column is located in the third zone, and the fifth column is located in the fourth zone and wherein the first inlet is coupled to the fifth column located in the fourth zone, the second inlet is coupled to the third column located in the second zone, the first outlet is coupled to the fifth column located in the fourth zone, and the second outlet is coupled to the third column located in the second zone.

16. The apparatus of claim 15, wherein the processor after a second predetermined switching interval changes of the position of each column so that the first column is located in the fourth zone, the second column is located in the fifth zone, the third column is located in the first zone, the fourth column is located in the second zone, and the fifth column is located in the third zone and wherein the first inlet is coupled to the first column located in the fourth zone, the second inlet is coupled to the fourth column located in the second zone, the first outlet is coupled to the first column located in the fourth zone, and the second outlet is coupled to the fourth column located in the second zone.

17. The apparatus of claim 15, wherein the processor through an iterative process optimizes the switching interval.

18. The apparatus of claim 9, wherein the processor after a second predetermined switching interval changes of the position of each column so that the first column is located in the fourth zone, the second column is located in the fifth zone, the third column is located in the first zone, the fourth column is located in the second zone, and the fifth column is located in the third zone and wherein the first inlet is coupled to the first column located in the fourth zone, the second inlet is coupled to the fourth column located in the second zone, the first outlet is coupled to the first column located in the fourth zone, and the second outlet is coupled to the fourth column located in the second zone.

19. The apparatus of claim 9, wherein the processor through an iterative process optimizes the switching interval.

20. The apparatus of claim 10, wherein the processor after a second predetermined switching interval changes of the position of each column so that the first column is located in the fourth zone, the second column is located in the fifth zone, the third column is located in the first zone, the fourth column is located in the second zone, and the fifth column is located in the third zone and wherein the first inlet is coupled to the first column located in the fourth zone, the second inlet is coupled to the fourth column located in the second zone, the first outlet is coupled to the first column located in the fourth zone, and the second outlet is coupled to the fourth column located in the second zone.

* * * * *